US008846891B2

(12) United States Patent
Prento et al.

(10) Patent No.: US 8,846,891 B2
(45) Date of Patent: Sep. 30, 2014

(54) INFECTIOUS GENOTYPE 1A, 1B, 2A, 2B, 3A, 5A, 6A AND 7A HEPATITIS C VIRUS LACKING THE HYPERVARIABLE REGION 1 (HVR1)

(75) Inventors: Jannick Prento, Bronshoj (DK); Judith M. Gottwein, Frederiksberg (DK); Troels Kasper Hoyer Scheel, Copenhagen NV (DK); Tanja Bertelsen Jensen, Frederiksberg C (DK); Jens Bukh, Praesto (DK)

(73) Assignees: Hvidovre Hospital, Hvidovre (DK); Kobenhavns Universitet, Copenhagen K (DK)

(*) Notice: Subject to any disclaimer, the term of this patent is extended or adjusted under 35 U.S.C. 154(b) by 530 days.

(21) Appl. No.: 13/060,533

(22) PCT Filed: Aug. 7, 2009

(86) PCT No.: PCT/DK2009/050197

§ 371 (c)(1),
(2), (4) Date: Aug. 10, 2011

(87) PCT Pub. No.: WO2010/022727

PCT Pub. Date: Mar. 4, 2010

(65) Prior Publication Data

US 2012/0003719 A1 Jan. 5, 2012

(30) Foreign Application Priority Data

| | | |
|---|---|---|
| Aug. 28, 2008 | (DK) | 2008 01186 |
| Aug. 29, 2008 | (EP) | 08163289 |
| Mar. 6, 2009 | (DK) | 2009 00307 |

(51) Int. Cl.

| | |
|---|---|
| ***C12N 7/00*** | (2006.01) |
| ***C12N 5/10*** | (2006.01) |
| ***C12N 15/51*** | (2006.01) |
| ***A61K 39/29*** | (2006.01) |
| ***C07K 14/005*** | (2006.01) |
| *A61K 39/00* | (2006.01) |

(52) U.S. Cl.

CPC ........... *C12N 7/00* (2013.01); *A61K 2039/5254* (2013.01); *A61K 39/29* (2013.01); *C12N 2770/24234* (2013.01); *C12N 2770/24222* (2013.01); *C07K 14/005* (2013.01); *C12N 2770/24261* (2013.01)

USPC ...................... 536/23.72; 435/235.1; 435/370

(58) Field of Classification Search

CPC . A61K 39/29; A61K 2039/5254; C12N 7/00; C12N 2770/24222; C12N 2770/24234; C12N 2770/24261; C07K 14/005

See application file for complete search history.

(56) References Cited

U.S. PATENT DOCUMENTS

| | | | | |
|---|---|---|---|---|
| 2006/0210969 | A1* | 9/2006 | Rice et al. | 435/5 |
| 2007/0073039 | A1 | 3/2007 | Chisari | |

FOREIGN PATENT DOCUMENTS

| | | | |
|---|---|---|---|
| WO | 2006/096459 | A2 | 9/2006 |
| WO | 2007/041487 | A2 | 4/2007 |
| WO | 2008/125117 | A1 | 10/2008 |
| WO | 2008/125119 | A1 | 10/2008 |
| WO | 2008/141651 | A1 | 11/2008 |
| WO | 2009/080052 | A1 | 7/2009 |
| WO | 2009/080053 | A1 | 7/2009 |
| WO | 2010/017818 | A1 | 2/2010 |
| WO | 2010/017819 | A1 | 2/2010 |

OTHER PUBLICATIONS

Scheel et al. Development of JFH1-based Cell Culture Systems for Hepatitis C Virus Genotype 4a and Evidence for Cross-Genotype Neutralization. Proceedings of the National Academy of Science of USA, Jan. 22, 2008, vol. 105, No. 3, pp. 997-1002.*

Roccasecca et al. Binding of the hepatitis C virus E2 glycoprotein to CD81 is strain specific and is modulated by a complex interplay. Journal of Virology, 2003, vol. 77, p. 1856-1867.*

Forns et al., "Hepatitis C Virus Lacking the Hypervariable Region 1 of the Second Envelope Protein is Infectious and Causes Acute Resolving or Persistent Infection in Chimpanzees", PNAS, Nov. 21, 2000, pp. 13318-13323, vol. 97, No. 24.

Mondelli et al., Antiviral Res., 2001, pp. 153-159, vol. 52.

Ray et al., "Hypervariable Region 1 Sequence Stability During Hepatitis C Virus Replication in Chimpanzees", Journal of Virology, Apr. 2000, pp. 3058-3066, vol. 74, No. 7.

Scarselli et al., "The Human Scavenger Receptor Class B Type I is a Novel Candidate Receptor for the Hepatitis C Virus", The EMBO Journal, 2002, pp. 5017-5025, vol. 21, No. 19, European Molecular Biology Organization.

Steinmann et al., "Hepatitis C Virus p7 Protein is Crucial for Assembly and Release of Infectious Virions", PLoS Pathogens, Jul. 2007, pp. 962-971, vol. 3, Issue 7.

Appel et al., "Essential Role of Domain III of Nonstructural Protein 5A for Hepatitis C Virus Infectious Particle Assembly", PLOS Pathogens, Mar. 28, 2008, Article No. e1000035, vol. 4, No. 3.

(Continued)

*Primary Examiner* — Louise Humphrey

(74) *Attorney, Agent, or Firm* — Thompson Coburn LLP; Charles P. Romano

(57) ABSTRACT

The present inventors used the previously developed H77/JFH $1_{T27OOC,A4O8OT}$ (1a/2a), J4/JFH $_{1T2996C,A4827T,\Delta HVRI}$ (1b/2a), J6/JFH $_{1\Delta HVRI}$ (2a/2a), J8/JFH $1_{\Delta HVRI}$ (2b/2a), S52/JFH $1_{T27i8G,\tau 7i6oc}$ (3a/2a), SA13/JFH $1_{C34O5G,A3696G}$ (5a/2a) and HK6a/JFH $1T_{1389c,A1590G}$ (6a/2a) constructs for the deletion of Hypervariable Region 1 (HVR1) to construct viable, JFH 1 (genotype 2a) based, genomes. The present inventors serially passaged the viruses in cell culture obtaining relatively high HCV RNA titers and infectivity titers. Sequence analysis of the viruses identified mutations adapting H77/JFH $1_{T27OOC,A4O8OT,\Delta HVR1}$ (1a/2a), J8/JFH $_{1\Delta HVR1}$ (2b/2a), S52/JFH $1_{T2718G,T716OC,\Delta HVR1}$ (3a/2a) and J4/JFH $1_{T2996C,A4827T,\Delta HVR1}$ (1b/2a) to the HVR1 deletion.

6 Claims, 16 Drawing Sheets

(56) References Cited

OTHER PUBLICATIONS

International Search Report and Written Opinion for Corresponding Priority PCT/DK2009/050197 dated Dec. 8, 2009.

Prentoe et al., "HCV Entry Related Studies", Abstract Booklet, 4th Smogen Summer Symposium on Virology, Aug. 2008, retrieved from the Internet Jan. 2009, http://sahlgrenska.se/upload/SU/omrade__medot/labmed/virologen/ SmoAb2008.pdf?epslanguage=sv>.

Suzuki, "Novel Chimeric Hepatitis C Viral Genome Comprising Nucleic Acid Encoding Epitope Tag Peptide at Hypervariable Region 1 of E2 Protein, Useful as Vaccine for Preventing or Treating Hepatitis-C Viral Infection", Database WPI Week 200914, Thomson Scientific, London, GB, AN 2009-E03534.

Pietschmann et al., "Construction and Characterization of Infectious Intragenotypic and Intergenotypic Hepatitis C Virus Chimeras", Proceedings of the National Academy of Science of USA, May 9, 2006, pp. 7408-7413, vol. 103, No. 19, National Academy of Science, Washington D.C.

* cited by examiner

INFECTIOUS GENOTYPE 1A, 1B, 2A, 2B, 3A, 5A, 6A AND 7A HEPATITIS C VIRUS LACKING THE HYPERVARIABLE REGION 1 (HVR1)

CROSS-REFERENCE TO RELATED APPLICATIONS

The present application is a National Stage application of International Patent Application No PCT/DK2009/050197, filed Aug. 7, 2009, which is incorporated herein by reference in its entirety and which claims the benefit of Denmark Application No. PA200801186, filed Aug. 28, 2008, European Application No. EP 08163289.5, filed Aug. 29, 2008 and Denmark Application No. DK PA200900307 filed Mar. 6, 2009.

INCORPORATION OF SEQUENCE LISTING

A computer readable form of the Sequence Listing named "66146_90587_SEQ_LST.txt" and which is 469330 bytes in size, is electronically filed herewith and herein incorporated by reference in its entirety. This Sequence Listing consists of SEQ ID NOs: 1-24.

TECHNICAL FIELD OF THE INVENTION

This invention provides infectious recombinant hepatitis C viruses (HCV) lacking the Hypervariable Region 1 (HVR1), and vectors, cells and animals comprising the same. The present invention provides methods of producing the infectious recombinant HCV lacking HVR1, and their use in identifying anti-HCV therapeutics including use in development of vaccines and diagnostics, as well as sequences of HCV associated with HCV pathogenesis.

BACKGROUND OF THE INVENTION

Hepatitis C virus (HCV) is one of the most widespread infectious diseases in the world. About 170 million people are infected with HCV worldwide with a yearly incidence of 3-4 million. While the acute phase of infection is mostly asymptomatic, the majority of acutely infected individuals develop chronic hepatitis and is at increased risk of developing liver cirrhosis and hepatocellular carcinoma. Thus, HCV infection is a major contributor to end-stage liver disease and in developed countries to liver transplantation.

HCV is a small, enveloped virus classified as a member of the Flaviviridae family. Its genome consists of a 9.6 kb single stranded RNA of positive polarity composed of 5' and 3' untranslated regions (UTRs) and one long open reading frame (ORF) encoding a polyprotein, which is co- and post-translationally cleaved and thus yields the structural (Core, E1, E2), p7 and nonstructural (NS2, NS3, NS4A, NS4B, NS5A, NS5B) proteins.

HCV isolates from around the world exhibit significant genetic heterogeneity. At least 7 major HCV genotypes (genotypes 1-7) have been identified, which differ by 31-33% at the nucleotide level. In addition, there are numerous subtypes (a, b, c, etc.).

Since its discovery in 1989, research on HCV has been hampered by the lack of appropriate cell culture systems allowing for research on the complete viral life cycle as well as new therapeutics and vaccines.

In 2001, a genotype 2a isolate (JFH1) was described (Kato et al., 2001), which yielded high RNA titers in the replicon system without adaptive mutations (Kato et al., 2003).

A major breakthrough occurred in 2005, when formation of infectious viral particles was reported after transfection of RNA transcripts from the JFH1 full-length consensus cDNA clone into Huh7 cells (Wakita et al., 2005) (Zhong et al., 2005).

At the same time, Lindenbach et al. demonstrated that the intragenotypic 2a/2a recombinant genome (J6/JFH1), in which the structural genes (C, E1, E2), p7 and NS2 of JFH1 were replaced by the respective genes of clone J6CF, produced infectious viral particles in Huh7.5 cells (a cell line derived from bulk Huh7 cells) with an accelerated kinetic (Lindenbach et al., 2005). Cell culture derived J6/JFH viruses were apparently fully viable in vivo. Recently the inventors of the present invention developed robust JFH1-based cell culture systems with genotype specific C-NS2 for HCV genotype 1a, 1b, 2b, 3a, 4a, 5a, 6a and 7a.

A part of the structural gene E2, which is present in all of these genotypes, is the Hypervariable Region 1 (HVR1). HVR1 is generally defined as the N-terminal 26-27 amino acids (aa) of the HCV protein E2 and is marked by the highest variability in the entire HCV genome—even higher than that of the other two HCV hypervariable regions: HVR2 and HVR3.

The region is easy to recognize in spite of the high variability due to several conserved residues within the sequence. It has previously been demonstrated that specific targeting of HVR1 by the adaptive immune system of the host likely causes the high variability of HVR1 (Manzin et al. 2000 and Ray et al. 1999).

The inferred immunogenic properties of HVR1, together with the fact that HVR1 specific antibodies are persistently found in patients chronically infected with HCV (Cerino et al. 1997), suggests that an HVR1 specific immune response occurs during an HCV infection, but does not in itself allow clearance of the viral infection.

It has been suggested that HVR1 acts as an immunological decoy by drawing the attention of the immune system away from less immunogenic, but ultimately more effective epitopes outside of HVR1 (Mondelli et al. 2001). This hypothesis is based on the assumption that HVR1 is not crucial for virus-host interactions since it is difficult to imagine how immune responses targeting HVR1 would not interfere with such interactions.

Thus, the proposed interaction of HVR1 with the HCV receptor Scavenger Receptor class B type I (SR-BI) (Scarselli et al. 2002) made the "immunological decoy" hypothesis less likely.

Steinmann et al. have used the HCV intragenotypic recombinant virus, Jc1 (2a/2a) showing that in this specific case HVR1 deletion was tolerated (Steinmann et al., 2007). Like the J6/JFH (2a/2a) virus used by the inventors the Jc1 (2a/2a) virus consists of J6 and JFH1 sequence that has been spliced, but the genotype-junction is at a different location in the HCV genome. As will be shown in the detailed description, viability of HVR1 deleted virus depends greatly on the virus isolates and as such the outcome of HVR1 deletion from J6/JFH could not have been predicted by these earlier observations.

SUMMARY OF THE INVENTION

In the present application the inventors used the previously developed H77/JFH1$_{T2700C,A4080T}$ (1a/2a), J4/JFH1$_{T2996C,A4827T}$ (1b/2a), J6/JFH1 (2a/2a), J8/JFH1 (2b/2a), S52/JFH1$_{T2718G,T7160C}$ (3a/2a), ED43/JFH1$_{A2819G,A3269T}$ (4a/2a), SA13/JFH1$_{C3405G,A3696G}$ (5a/2a) and HK6a/JFH1$_{T1389C,A1590G}$ (6a/2a) constructs for the deletion of Hypervariable Region 1 (HVR1). After HVR1 deletion, in transfection experiments, viral spread was achieved for recombinants: H77/JFH1$_{T2700C,A4080T}$ (1a/2a), J4/JFH1$_{T2996C,A4827T}$ (1b/2a), J6/JFH1 (2a/2a), J8/JFH1 (2b/2a), S52/JFH1$_{T2718G,T7160C}$ (3a/2a), SA13JFH1$_{C3405G,A3696G}$ (5a/2a) and HK6a/JFH1$_{T1389C,A1590G}$ (6a/2a).

The present inventors serially passaged the H77/JFH1$_{T2700C,A4080T,\Delta HVR1}$ (1a/2a), J4/JFH1$_{T2996C,A4827T,\Delta HVR1}$ (1b/2a), J6/JFH1$_{\Delta HVR1}$ (2a/2a), J8/JFH1$_{\Delta HVR1}$ (2b/2a), S52/JFH1$_{T2718G,T7160C,\Delta HVR1}$ (3a/2a), SA13/JFH1$_{C3405G,A3696G,\Delta HVR1}$ (5a/2a) and HK6a/JFH1$_{T1389C,A1590G,\Delta HVR1}$ (6a/2a) virus in cell culture, obtained high HCV RNA titers and infectivity titers and identified and tested additional mutations adapting H77/JFH1$_{T2700C,A4080T,\Delta HVR1}$ (1a/2a), J8/JFH1$_{\Delta HVR1}$ (2b/2a) and S52/JFH1$_{T2718G,T7160C,\Delta HVR1}$ (3a/2a) to the HVR1 deletion. The present inventors also identified a number of other mutations in the envelope proteins for H77/JFH1$_{T2700C,A4080T,\Delta HVR1}$ (1a/2a), J4/JFH1$_{T2996C,A4827T,\Delta HVR1}$ (1b/2a) and J8/JFH1$_{\Delta HVR1}$ (2b/2a) that are likely candidates to have a similar adapting effect.

For several JFH1-based recombinants of the different HCV genotypes, several adaptive mutations or combinations thereof were found to confer efficient growth kinetics in cell culture. It is likely, that recombinants containing such adaptive mutations, different from the ones described above, would also be viable after deletion of HVR1.

These HVR1 deleted viruses potentially allow for developing strategies for raising non-HVR1 based immune responses in patients as well as raising and testing antibodies against non-HVR1 epitopes. Thus, HVR1 deleted viruses may be used as antigens in inactivated virus vaccines. These vaccine development efforts could be targeted at both a prophylactic vaccine, which may be used for immunization of the general population in high prevalence-/incidence countries and for individuals at risk (medical staff, intravenous drug users) in lower prevalence-/incidence countries as well as a therapeutic vaccine, which may be used in HCV infected individuals.

In addition, HVR1 deleted viruses may be used for raising neutralizing antibodies in laboratory animals, which could later be humanized for use in immunotherapy. These neutralizing antibodies mainly find use as post-exposure prophylaxis e.g. after needle-stick injuries in the medical sector and in conjunction with liver transplantation of individuals with HCV induced end-stage liver disease.

Cell culture systems employing HVR1 deleted viruses may also be used directly to screen these antibodies for neutralizing effect across genotypes. The use of the HVR1 deleted viruses in conjunction with the parental virus (otherwise identical non-HVR1 deleted construct) would allow the determination of whether HVR1 has any relevance for the neutralizing effect of the given antibody. This use of HVR1 deleted viruses in conjunction with the parental viruses could also be used as a prognostic tool in infected patients by making it possible to assess how much of a patients antibody response is directed against HVR1 and may thus contribute to individualized patient treatment.

Finally the invention is useful for basic research on the importance and function of HVR1. Thus the developed systems can be used for studies on virus-host interactions including interaction with host receptors. Such studies could help define the HCV protein region of interaction with the host, and thus potentially aid in development of entry inhibitors.

Thus, one aspect of the invention relates to a replicating RNA comprising the structural gene E2 from human hepatitis C virus, wherein said the structural gene E2 comprises a deletion of at least part of HVR1.

In another aspect the present invention relates to a composition comprising a nucleic acid molecule according to the present invention, a cassette vector for cloning viral genomes, methods for producing a cell which replicates strain H77/JFH1$_{T2700C,A4080T,\Delta HVR1}$ (1a/2a), J4/JFH1$_{T2996C,A4827T,\Delta HVR1}$ (1b/2a), J6/JFH1$_{\Delta HVR1}$ (2a/2a), J8/JFH1$_{\Delta HVR1}$ (2b/2a), S52/JFH1$_{T2718G,T7160C,\Delta HVR1}$ (3a/2a), SA13/JFH1$_{C3405G,A3696G,\Delta HVR1}$ (5a/2a), HK6a/JFH1$_{T1389C,A1590G,\Delta HVR1}$ (6a/2a) or QC69/JFH1$_{\Delta HVR1}$ (7a/2a) RNA and cells obtainable there from.

In a further aspect the present invention relates to methods for producing a hepatitis C virus particle and methods for in vitro producing a hepatitis C virus infected cell.

In a last aspect the present invention relates to methods for screening an anti-hepatitis C virus substance, hepatitis C vaccines comprising a hepatitis C virus particle, methods for producing a hepatitis C virus vaccine and antibodies against hepatitis C virus.

Figure 1:
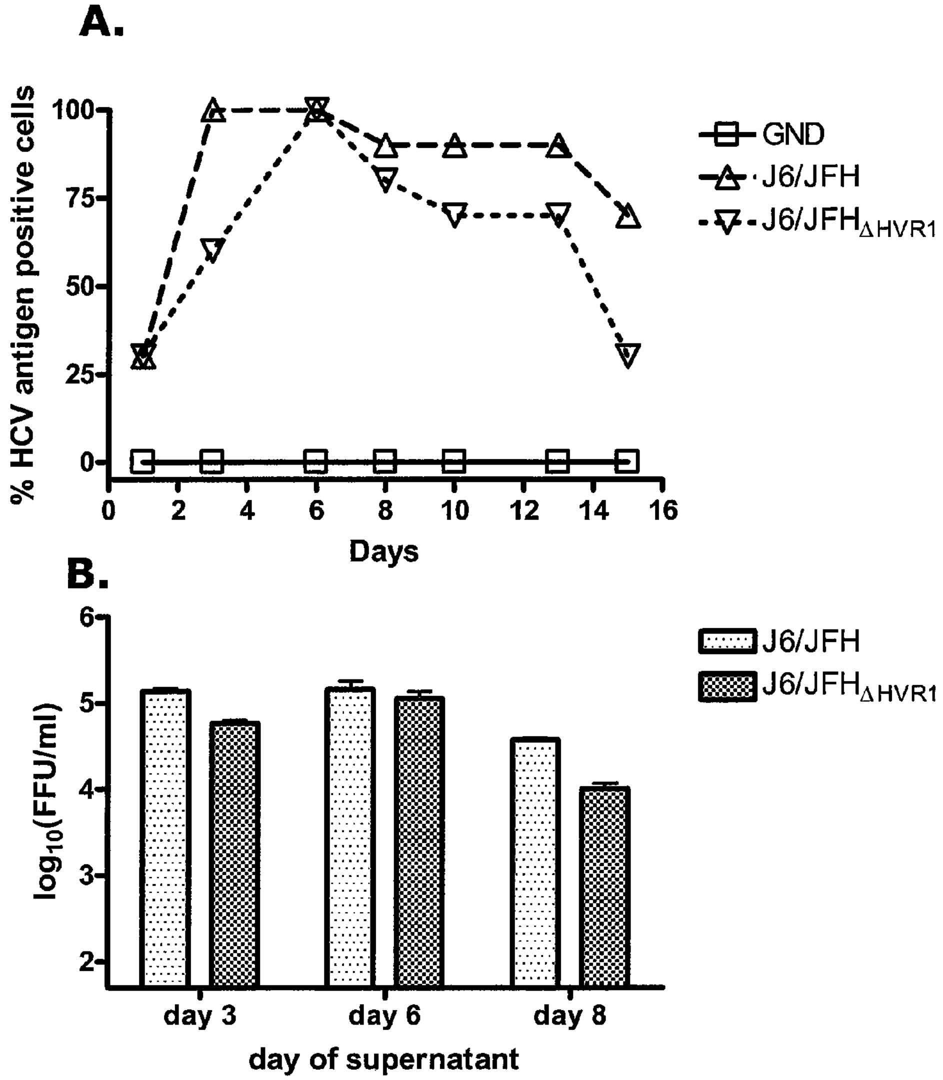
FIG. 1 shows transfection of J6/JFH with and without HVR1.

The present invention will now be described in more detail in the following.

DETAILED DESCRIPTION OF THE INVENTION

The present inventors advantageously provide hepatitis C virus (HCV) nucleotide sequences capable of replication, expression of functional HCV proteins and infection in vitro for development of antiviral therapeutics and prophylactics as well as diagnostics and prognostics.

The present inventors developed H77/JFH1$_{T2700C,A4080T}$ (1a/2a), J4/JFH1$_{T2996C,A4827T,}$ (1b/2a), J6/JFH (2a/2a), J8/JFH1 (2b/2a), S52/JFH1$_{T2718G,T7160C}$ (3a/2a), SA13/JFH1$_{C3405G,A3696G}$ (5a/2a) and HK6a/JFH1$_{T1389C,A1590G}$ (6a/2a). These HCV recombinant viruses were used for the deletion of Hypervariable Region 1 (HVR1) to construct viable, JFH1-based genomes. This potentially allows for developing strategies for raising non-HVR1 based immune responses in patients as well as raising and testing antibodies against non-HVR1 epitopes.

As is generally done within the art, all numerical references to specific mutations in a given genome (nucleic acid or amino acid) refers to numbering of the relevant reference sequence and therefore mutation numbers are not altered by deletions or insertions. More specifically, the HVR1 deletion of 78 or 81 nucleotides, corresponding to 26 or 27 amino acids, does not alter the downstream numbering of mutations. All references to specific mutations have been annotated according to this. Tables 1, 2, 3 and 4 list the coding envelope mutations identified for this application and are all numbered as described in this paragraph.

In the present context a HCV strain containing adaptive mutations and/or deletions is written with these adaptive mutations and deletions in subscript i.e. a strain S52/JFH1 with cell culture adaptive mutations T2718G, T7160C and deletion of HVR1 (ΔHVR1) is denoted as S52/JFH1$_{T2718G,T7160C,\Delta HVR1}$ (3a/2a). If such strain acquires additional adaptive mutations that relate to the HVR1 deletion such adaptive mutations are written in subscript parenthesis i.e. a S52/JFH1$_{T2718G,T7160C,\Delta HVR1}$ (3a/2a) acquiring a C1446T adaptive mutation is denoted as S52/JFH1$_{(C1446T),T2718G,T7160C,\Delta HVR1}$ (3a/2a).

In the present context the terms "non-HVR1 epitopes", "reference strains lacking HVR1", "ΔHVR1", and "deletion of HVR1" refer to an HCV genotype 1a, 1b, 2a, 2b, 3a, 4a, 5a, 6a or 7a in which the structural gene E2 has a deletion of at least part of HVR1.

In the present context the term "genotype" is to be understood in accordance with Simmonds et al. 2005—i.e. the term "genotype" relate to the presently 7 identified major HCV genotypes.

In the present context the term "subtype" is to be understood in accordance with Simmonds et al. 2005—in relation to e.g. genotype 1, this means, the presently identified subtypes indicated by lower-case letters; e.g. 1a, 1b etc. (Simmonds et al., 2005).

In the present context the term "isolate" or "strain" is to be understood in accordance with Simmonds et al. 2005. Many different isolates/strains exist within a given genotype and subtype. An example of this is the H77 isolate/strain which is genotype 1, subtype a (abbreviated 1a) The terms "isolate" and "strain" are used herein interchangeably.

Nucleic Acid Molecules (cDNA Clones and RNA Transcripts)

In a broad aspect, the present invention is directed to genetically engineered hepatitis C virus (HCV) encoded by nucleic acid sequences such as complementary DNA (cDNA) sequences and replicating RNA comprising the structural gene E2 from HCV, wherein the structural gene E2 comprises a deletion of at least part of HVR1.

Thus in one embodiment, the present invention relates to a replicating RNA comprising the structural gene E2 for human hepatitis C virus, wherein said structural gene E2 comprises a deletion of at least part of HVR1.

In another embodiment the human hepatitis C virus is selected from the group consisting of strain H77/JFH1$_{T2700C,A4080T,\Delta HVR1}$ (1a/2a), J4/JFH1$_{T2996C,A4827T,\Delta HVR1}$ (1b/2a), J6/JFH1$_{\Delta HVR1}$ (2a/2a), J8/JFH1$_{\Delta HVR1}$ (2b/2a), S52/JFH1$_{T2718G,T7160C,\Delta HVR1}$ (3a/2a), SA13/JFH1$_{C3405G,A3696G,\Delta HVR1}$ (5a/2a), HK6a/JFH1$_{T1389C,A1590G,\Delta HVR1}$ (6a/2a) and QC69/JFH1$_{\Delta HVR1}$ (7a/2a).

In yet another embodiment the replicating RNA further comprises the structural genes (Core, E1 & E2), p7 and the non-structural gene NS2 of genotypes 1a, 1b, 2a, 2b, 3a, 4a, 5a, 6a or 7a, and the non-structural genes NS3, NS4A, NS4B, NS5A and NS5B from the human hepatitis C virus genotype 2a strain JFH1.

Deletion of at least part of HVR1 is to be understood as a deletion of an amino acid or amino acids N-terminally in HCV protein E2. N-terminally being defined as the first 30 amino acids in the E2 protein, such as the first 29 amino acids, e.g. the first 28 amino acids, such as the first 27 amino acids, e.g. the first 26 amino acids, such as the first 25 amino acids, e.g. the first 24 amino acids, such as the first 23 amino acids, e.g. the first 22 amino acids, such as the first 21 amino acids, e.g. the first 20 amino acids, such as the first 19 amino acids, e.g. the first 18 amino acids, such as the first 17 amino acids, e.g. the first 16 amino acids, such as the first 15 amino acids, e.g. the first 14 amino acids, such as the first 13 amino acids, e.g. the first 12 amino acids, such as the first 11 amino acids, e.g. the first 10 amino acids, such as the first 9 amino acids, e.g. the first 8 amino acids, such as the first 7 amino acids, e.g. the first 6 amino acids, such as the first 5 amino acids, e.g. the first 4 amino acids, such as the first 3 amino acids, e.g. the first 2 amino acids, such as the first amino acid of the E2 protein. This deletion could be of 26-27 amino acids as the one described here, but since the HVR1 epitopes recognized by the immune system could conceivably be located anywhere in the HVR1 sequence it is possible that smaller or larger deletions not yet attempted would yield very similar result.

Thus, in one embodiment of the present invention the deletion may be of 30 amino acids, e.g. of 29 amino acids, such as of 28 amino acids, e.g. of 27 amino acids, such as of 26 amino acids, e.g. of 25 amino acids, such as of 25 amino acids, e.g. of 23 amino acids, such as of 22 amino acids, e.g. of 21 amino acids, such as of 20 amino acids, e.g. of 19 amino acids, such as of 18 amino acids, e.g. of 17 amino acids, such as of 16 amino acids, e.g. of 15 amino acids, such as of 14 amino acids, e.g. of 13 amino acids, such as of 12 amino acids, e.g. of 11 amino acids, such as of 10 amino acids, e.g. of 9 amino acids, such as of 8 amino acids, e.g. of 7 amino acids, such as of 6 amino acids, e.g. of 5 amino acids, such as of 4 amino acids, e.g. of 3 amino acids, such as of 2 amino acids, e.g. of 1 amino acid. As described under the possible effects of an HVR1 deletion of the HCV virus. This deletion could by of a single amino acid anywhere in the first 30 amino acids of E2 or it could be of multiple amino acids anywhere in this sequence.

A replicating RNA is to be understood as a RNA inside an appropriate cell which can maintain its own replication, i.e. copying itself, by the help of endogenous encoded protein and/or cellular factors such as proteins and RNA.

The structural gene E2 is to be understood as a HCV protein incorporated in the virus particle. This HCV protein is generally believed to be encoded as the third protein in the aforementioned polyprotein of HCV. The two upstream proteins being Core and E1.

The invention provides isolated nucleic acid molecules encoding infectious recombinant HCV genomes, of which nucleic acid comprises intra- and intergenotypic HCV genomes.

In one embodiment, the intra- or inter-genotypic HCV genomes comprises sequences encoding structural genes (Core, E1 and E2) comprising a deletion of at least part of HVR1 of E2, p7, the non-structural gene NS2 from a first HCV strain, and sequences encoding the non-structural genes NS3, NS4A, NS4B, NS5A, NS5B from a second HCV strain In one embodiment, the first HCV strain and the second HCV strain are from different genotypes.

In one embodiment, the first HCV strain is strain $H77_{\Delta HVR1}$, $J4_{\Delta HVR1}$, $J6_{\Delta HVR1}$, $J8_{\Delta HVR1}$, $S52_{\Delta HVR1}$, $SA13_{\Delta HVR1}$, $HK6a_{\Delta HVR1}$ and $QC69_{\Delta HVR1}$, and in another embodiment, the second HCV strain is strain JFH1.

The construction of all HVR1 deleted HCV virus coding plasmids was done by standard cloning techniques by the inventors. The N-terminal HVR1 deletions performed in HCV gene E2 was of 81 nucleotides encoding 27 amino acids in the case of genotypes 1a, 2a, 3a, 4a, 5a and 7a and of 78 nucleotides encoding 26 amino acids in the case of 6a. N-terminally are here defined as the first 30 amino acids in the E2 protein such as the first 29 amino acids, e.g. the first 28 amino acids, such as the first 27 amino acids, e.g. the first 26 amino acids, such as the first 25 amino acids, e.g. the first 24 amino acids, such as the first 23 amino acids, e.g. the first 22 amino acids, such as the first 21 amino acids, e.g. the first amino acids, such as the first 19 amino acids, e.g. the first 18 amino acids, such as the first 17 amino acids, e.g. the first 16 amino acids, such as the first 15 amino acids, e.g. the first 14 amino acids, such as the first 13 amino acids, e.g. the first 12 amino acids, such as the first 11 amino acids, e.g. the first 10 amino acids, such as the first 9 amino acids, e.g. the first 8 amino acids, such as the first 7 amino acids, e.g. the first 6 amino acids, such as the first 5 amino acids, e.g. the first 4 amino acids, such as the first 3 amino acids, e.g. the first 2 amino acids, such as the first amino acid in the E2 protein.

Since the HVR1 epitopes recognized by the immune system could conceivably be located anywhere in the HVR1 sequence it is possible that smaller or larger deletions not yet attempted would yield very similar result as the ones described and also offer many of the same advantages in both neutralizing antibody production as well as vaccine development. It has been reported by Kato (1992) that HVR1 was shorter for genotype 1a and we therefore tested whether a shorter deletion of 21 aa would yield a viable virus in the case of genotype 1a. This turned out not to be the case. As described under the possible effects of an HVR1 deletion of the HCV virus, this deletion could be of a single amino acid anywhere in the first 30 amino acids of E2 or it could be of multiple amino acids anywhere in this sequence.

In one embodiment, the HCV nucleic acid molecules of the present invention comprises the nucleic acid sequences (cDNA) of $H77/JFH1_{T2700C,A4080T,\Delta HVR1}$ (SEQ ID NO: 7), $J6/JFH_{\Delta HVR1}$ (SEQ ID NO: 8), $S52/JFH1_{T2718G,T7160C,\Delta HVR1}$ (SEQ ID NO: 9), $ED43/JFH1_{A2819G,A3269T,\Delta HVR1}$ (SEQ ID NO: 10), $SA13/JFH1_{C3405G,A3696G,\Delta HVR1}$ (SEQ ID NO: 11) or $HK6a/JFH1_{T1389C,A1590G,\Delta HVR1}$ (SEQ ID NO: 12), $J4/JFH1_{T2996C,A4827T,\Delta HVR1}$ (SEQ ID NO: 19) and $J8/JFH1_{\Delta HVR1}$ (SEQ ID NO: 20). This deletion of HVR1 can be performed in all HCV constructs functioning in cell culture. Thus in another embodiment, the HCV nucleic acid sequence has 90% sequence identity to the strains mentioned above.

In one embodiment the nucleic acid molecule comprises the nucleic acid molecule with a sequence identity of at least 90% to that of sequence SEQ ID NO: 7, SEQ ID NO: 8, SEQ ID NO: 9, SEQ ID NO: 10, SEQ ID NO: 11, SEQ ID NO: 12, SEQ ID NO: 19 or SEQ ID NO: 20.

In another embodiment, the nucleic acid comprises a sequence sharing at least 90% identity with that set forth in SEQ ID NO: 7, SEQ ID NO: 8, SEQ ID NO: 9, SEQ ID NO: 10, SEQ ID NO: 11, SEQ ID NO: 12, SEQ ID NO: 19 or SEQ ID NO: 20, such as 90% identity, 91% identity, 92% identity, 93% identity, 94% identity, 95% identity, 96% identity, 97% identity, 98% identity, or 99% identity.

Sequence Identity

As commonly defined "identity" is here defined as sequence identity between genes or proteins at the nucleotide or amino acid level, respectively.

Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

One may manually align the sequences and count the number of identical amino acids. Alternatively, alignment of two sequences for the determination of percent identity may be accomplished using a mathematical algorithm. Such an algorithm is incorporated into the NBLAST and XBLAST programs (Altschul et al., 1990). BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention. To obtain gapped alignments for comparison purposes, Gapped BLAST may be utilised. Alternatively, PSI-Blast may be used to perform an iterated search which detects distant relationships between molecules. When utilising the NBLAST, XBLAST, and Gapped BLAST programs, the default parameters of the respective programs may be used. See http://www.ncbi.nlm.nih.gov. Alternatively, sequence identity may be calculated after the sequences have been aligned e.g. by the BLAST program in the EMBL database (www.ncbi.nlm.gov/cgi-bin/BLAST). Generally, the default settings with respect to e.g. "scoring matrix" and "gap penalty" may be used for alignment. In the context of the present invention, the BLASTN and PSI BLAST default settings may be advantageous.

In another embodiment the sequence identity is calculated on the sequence of the Core, E1, E2, p7 and NS2 the first HCV strain such as but not limited to H77, $H77_{\Delta HVR1}$, J4, $J4_{4\Delta HVR1}$, J6, $J6_{\Delta HVR1}$, J8, $J8_{\Delta HVR1}$, S52, $S52_{\Delta HVR1}$, SA13, $SA13_{\Delta HVR1}$, HK6a, $HK6a_{\Delta HVR1}$, QC69 and $QC69_{\Delta HVR1}$.

In another embodiment the sequence identity is calculated on the sequence of the 5' UTR, NS3, NS4A, NS4B, NS5A, NS5B and 3' UTR of JFH1.

The percent identity between two sequences may be determined using techniques similar to those described above, with or without allowing gaps. In calculating percent identity, only exact matches are counted.

It should be noted that while SEQ ID NO: 7, SEQ ID NO: 8, SEQ ID NO: 9, SEQ ID NO: 10, SEQ ID NO: 11 SEQ ID NO: 12, SEQ ID NO: 19 and SEQ ID NO: 20 are DNA sequences, the present invention contemplates the corresponding RNA sequence, and DNA and RNA complementary sequences as well.

In a further embodiment, a region from an HCV isolate is substituted for a corresponding region, e.g., of an HCV nucleic acid having a sequence of SEQ ID SEQ ID NO: 7, SEQ ID NO: 8, SEQ ID NO: 9, SEQ ID NO: 10, SEQ ID NO: 11, SEQ ID NO: 12, SEQ ID NO: 19 or SEQ ID NO: 20.

In another embodiment, the HCV nucleic acids is a DNA that codes on expression or after in vitro transcription for a replication-competent HCV RNA genome, or is itself a replication-competent HCV RNA genome.

In one embodiment, the HCV nucleic acid of the invention has a full-length sequence as depicted in or corresponding to SEQ ID NO: 7, SEQ ID NO: 8, SEQ ID NO: 9, SEQ ID NO: 10, SEQ ID NO: 11, SEQ ID NO: 12, SEQ ID NO: 19 or SEQ ID NO: 20. Various modifications for example of the 5' and 3' UTR are also contemplated by the invention. In another embodiment, the nucleic acid further comprises a reporter gene, which, in one embodiment, is a gene encoding neomycin phosphotransferase, Renilla luciferase, secreted alkaline phosphatase (SEAP), Gaussia luciferase or fluorescent proteins, such as enhanced green fluorescent protein (EGFP).

Naturally, as noted above, the HCV nucleic acid sequence of the invention is selected from the group consisting of double stranded DNA, positive-sense cDNA, or negative-sense cDNA, or positive-sense RNA or negative-sense RNA or double stranded RNA. Thus, where particular sequences of nucleic acids of the invention are set forth, both DNA and corresponding RNA are intended, including positive and negative strands thereof.

In a further embodiment, the nucleic acid sequence of SEQ ID NO: 7, SEQ ID NO: 8, SEQ ID NO: 9, SEQ ID NO: 10, SEQ ID NO: 11, SEQ ID NO: 12, SEQ ID NO: 19 or SEQ ID NO: 20 or the said nucleic acid sequence with any mutation described in this document is obtained by any other means than what is described above.

In an embodiment, the complementary DNAs (cDNA) provided by the present invention encodes human hepatitis C virus of strain:

H77/$JFH1_{T2700C,A4080T,\Delta HVR1}$ (1a/2a), J4/$JFH1_{T2996C,A4827T,\Delta HVR1}$ (1b/2a) J6/$JFH_{\Delta HVR1}$ (2a/2a), J8/$JFH1_{\Delta HVR1}$ (2b/2a), S52/$JFH1_{T2718G,T7160C,\Delta HVR1}$ (3a/2a), ED43/$JFH1_{A2819G,A3269T,\Delta HVR1}$ (4a/2a), SA13/$JFH1_{C3405G,A3696G,\Delta HVR1}$ (5a/2a), HK6a/$JFH1_{T1389C,A1590G,\Delta HVR1}$ (6a/2a) or QC69/$JFH1_{\Delta HVR1}$ (7a/2a)

wherein said molecule is capable of expressing said virus, when transfected into cells, and further capable of infectivity in vivo wherein H77/$JFH1_{T2700C,A4080T,\Delta HVR1}$ (1a/2a) encodes the amino acid sequence with a sequence identity of at least 90% to that of SEQ ID NO: 1, wherein J4/$JFH1_{T2996C,A4827T,\Delta HVR1}$ (1b/2a) encodes the amino acid sequence with a sequence identity of at least 90% to that of SEQ ID NO: 22 wherein J6/$JFH1_{\Delta HVR1}$ (2a/2a) encodes the amino acid sequence with a sequence identity of at least 90% to that of SEQ ID NO: 2, wherein J8/$JFH1_{\Delta HVR1}$ (2b/2a) encodes the amino acid sequence with a sequence identity of at least 90% to that of SEQ ID NO: 23 wherein S52/$JFH1_{T2718G,T7160C,\Delta HVR1}$ (3a/2a) encodes the amino acid sequence with a sequence identity of at least 90% to that of SEQ ID NO: 3, wherein ED43/$JFH1_{A2819G,A3269T,\Delta HVR1}$ (4a/2a) encodes the amino acid sequence with a sequence identity of at least 90% to that of SEQ ID NO: 4, wherein SA13/$JFH1_{C3405G,A3696G,\Delta HVR1}$ (5a/2a) encodes the amino acid sequence with a sequence identity of at least 90% to that of SEQ ID NO: 5 and, wherein HK6a/$JFH1_{T1389C,A1590G,\Delta HVR1}$ (6a/2a) encodes the amino acid sequence with a sequence identity of at least 90% to that of SEQ ID NO: 6.

In another embodiment, the amino acid sequences comprises a sequence sharing at least 90% identity with that set forth in SEQ ID NO: 1, SEQ ID NO: 2, SEQ ID NO: 3, SEQ ID NO: 4, SEQ ID NO: 5, SEQ ID NO: 6, SEQ ID NO: 22 or SEQ ID NO: 23 such as 91% identity, 92% identity, 93% identity, 94% identity, 95% identity, 96% identity, 97% identity, 98% identity, or 99% identity.

It should be understood that a sequence identity of at least 90%, such as 90% identity, 91% identity, 92% identity, 93% identity, 94% identity, 95% identity, 96% identity, 97% identity, 98% identity, or 99% identity applies to all sequences disclosed in the present application.

In an embodiment of the present invention H77/$JFH1_{T2700C,A4080T,\Delta HVR1}$ (1a/2a) comprises the nucleic acid sequence with a sequence identity of at least 90% to that of SEQ ID NO: 7.

In a further embodiment of the present invention J4/$JFH1_{T2996C,A4827T,\Delta HVR1}$ (1b/2a) comprises the nucleic acid sequence with a sequence identity of at least 90% to that of SEQ ID NO: 19.

In yet an embodiment of the present invention J6/$JFH1_{\Delta HVR1}$ (2a/2a) comprises the nucleic acid sequence with a sequence identity of at least 90% to that of SEQ ID NO: 8.

In another embodiment of the present invention J8/$JFH1_{\Delta HVR1}$ (2b/2a) comprises the nucleic acid sequence with a sequence identity of at least 90% to that of SEQ ID NO: 20.

In a further embodiment of the present invention S52/$JFH1_{T2718G,T7160C,\Delta HVR1}$ (3a/2a) comprises the nucleic acid sequence with a sequence identity of at least 90% to that of SEQ ID NO: 9.

In yet an embodiment of the present invention ED43/$JFH1_{A2819G,A3269T,\Delta HVR1}$ (4a/2a) comprises the nucleic acid sequence with a sequence identity of at least 90% to that of SEQ ID NO: 10.

In another embodiment of the present invention SA13/$JFH1_{C3405G,A3696G,\Delta HVR1}$ (5a/2a) comprises the nucleic acid sequence with a sequence identity of at least 90% to that of SEQ ID NO: 11.

In a further embodiment of the present invention HK6a/JFH1$_{T1389C,A1590G,\Delta HVR1}$ (6a/2a) comprises the nucleic acid sequence with a sequence identity of at least 90% to that of SEQ ID NO: 12.

According to various aspects of the invention, HCV nucleic acid, including the polyprotein coding region, can be mutated or engineered to produce variants or derivatives with, e.g., silent mutations, conservative mutations, etc. In a further preferred aspect, silent nucleotide changes in the polyprotein coding regions (i.e., variations of the second or third base of a codon that encodes the same amino acid) are incorporated as markers of specific HCV clones.

Thus, one aspect of the present invention relates to any of the amino acid sequences disclosed herein, such as but not limited to SEQ ID NOs: 1, 2, 3, 4, 5, 6, 22 and 23.

Nucleic acid molecules according to the present invention may be inserted in a plasmid vector for translation of the corresponding HCV RNA. Thus, the HCV DNA may comprise a promoter 5' of the 5'-UTR on positive-sense DNA, whereby transcription of template DNA from the promoter produces replication-competent RNA. The promoter can be selected from the group consisting of a eukaryotic promoter, yeast promoter, plant promoter, bacterial promoter, or viral promoter.

In one embodiment the present invention provides a cassette vector for cloning viral genomes, comprising, inserted therein, the nucleic acid sequence according to the invention and having an active promoter upstream thereof.

HVR1 Deletion

Deletion of HVR1 may and may not affect infectivity of HCV in vitro and in vivo. It may affect the type of immune response generated by a suitable host upon infection with HCV lacking HVR1. It may affect the epitopes targeted by the immune system of the suitable host. It may affect outcome of an HCV infection of a suitable host. If HVR1 deletion has an effect on this outcome this effect could be reduced pathogenicity of HCV, reduced titers of HCV in the blood and/or soft tissues of the suitable host, higher occurrence of spontaneous clearance of the infection. It may render the virus more susceptible to treatment of both a prophylactic as well as a therapeutic nature. All the above-mentioned possibilities may differ between the individual genotypes. They may be more severe for particular genotypes than for others. Some of the above considerations may not apply to particular genotypes, but may still hold true for others. Deletion of amino acids downstream of HVR1 either with or without a concurrent deletion of HVR1 may have effects similar to the possibilities described above. If multiple amino acids immediately downstream of HVR1 are deleted then at some point the virus will likely become non-infectious as is described for J6/JFH$_{\Delta HVR1}$ (2a/2a) in example 2. In example 2 additional amino acids are removed and upon the removal of a total of 30 N-terminal amino acids in E2 the virus becomes non-infectious.

HVR1 may be deleted by fusion PCR, standard cloning techniques or by commercially available kits.

The present inventors indicate a decoy function of HVR1, and add credence to this hypothesis by the following findings: Most HCV genotypes retain in vitro infectivity after HVR1 deletion that in some cases rivals that of the parental virus (original non-HVR1 deleted). These data support the hypothesis of a decoy function of HVR1 since they show that HVR1 is not required for viral infectivity.

Adaptive Mutations

Adapted mutants of a HCV-cDNA construct or HCV-RNA full-length genome with improved abilities to generate infectious viral particles in cell culture compared to the original HCV-cDNA construct or the original HCV-RNA full-length genome are characterized in that they are obtainable by a method in which the type and number of mutations in a cell culture adapted HCV-RNA genome are determined through sequence analysis and sequence comparison and these mutations are introduced into a HCV-cDNA construct, particularly a HCV-cDNA construct according to the present invention, or into an (isolated) HCV-RNA full-length genome, either by site-directed mutagenesis, or by exchange of DNA fragments containing the relevant mutations.

The adaptive mutations present in the constructs prior to HVR1 deletion for the following recombinant viruses: H77/JFH1$_{T2700C,A4080T}$ (1a/2a), J4/JFH1$_{T2996C,A4827T}$ (1b/2a), S52/JFH1$_{T2718G,T7160C}$ (3a/2a), SA13/JFH1$_{C3405G,A3696G}$ (5a/2a) and HK6a/JFH1$_{T1389C,A1590G}$ (6a/2a) are the basis for the viability of these constructs in the cell culture system. They adapt the virus thereby improving the infection capacity of the given HCV recombinant. In the case of J6/JFH (2a/2a) and J8/JFH1 (2b/2a) the viruses did not require mutations adapting them to spread in cell culture. These viruses were the specific basis for the generation of the HVR1 deleted viruses, but any HCV genome able to replicate in cell culture would very likely have served. The main point being that in order to investigate the effect of an HVR1 deletion on infectivity, the virus has to be infectious to begin with (meaning before deletion of HVR1).

The degree of infectivity is described elsewhere in this document (examples 1 and 3 and Table 5). By using the aforementioned specific recombinant viruses, cell culture adapted and as such viable, the inventors generated and serially passaged HCV recombinants of the following HVR1 deleted constructs: H77/JFH1$_{T2700C,A4080T,\Delta HVR1}$ (1a/2a), J4/JFH1$_{T2996C,A4827T,\Delta HVR1}$ (1b/2a), J6/JFH1$_{\Delta HVR1}$ (2a/2a), J8/JFH1$_{\Delta HVR1}$ (2b/2a), S52/JFH1$_{T2718G,T7160C,\Delta HVR1}$ (3a/2a), SA13/JFH1$_{C3405G,A3696G,\Delta HVR1}$ (5a/2a) and HK6a/JFH1$_{T1389C,A1590G,\Delta HVR1}$ (6a/2a). Of these H77/JFH1$_{T2700C,A4080T,\Delta HVR1}$ (1a/2a), J4/JFH1$_{T2996C,A4827T,\Delta HVR1}$ (1b/2a), J8/JFH1$_{\Delta HVR1}$ (2b/2a) and S52/JFH1$_{T2718G,T7160C,\Delta HVR1}$ (3a/2a) acquired additional coding mutations in HCV genes E1 and E2 either in transfection or in serial passages (see example 3 and tables 1-4).

The identified coding envelope mutations were A1122G, T1383G, T1421C, A1628G, A1671G, A1766G, T2385A and C2538T for H77/JFH1$_{T2700C,A4080T,\Delta HVR1}$ A1236G, C1428T, A1643C, A2066G, G2225G and G2468C for J4/JFH1$_{T2996C,A4827T,\Delta HVR1}$ (1b/2a), C1571G, T1572G, T1574A, A1580G, A1652T and A1941C for J8/JFH1$_{\Delta HVR1,T1574A}$ (2b/2a), and finally C1446T for S52/JFH1$_{T2718G,T7160C,\Delta HVR1}$ (3a/2a). Of these A1122G, A1671G, A1766G, C2538T, T1574A and C1446T were tested in reverse genetic studies by engineering the mutations into the original HVR1 deleted constructs. All were found to improve infectivity of the respective HVR1 deleted viruses. More specifically it was possible to increase kinetics, infectivity titers and viral spread by introducing A1122G, A1671G, A1766G and C2538T into H77/JFH1$_{T2700C,A4080T,\Delta HVR1}$ singly or in combinations of two, T1574A into J8/JFH1$_{\Delta HVR1}$ and C1446T into S52/JFH1$_{T2718G,T7160C,\Delta HVR1}$.

The present inventors here report adaptive mutations following deletion of HVR1 in the structural E1 or E2 domain, which allow efficient formation and release of viral particles in cell culture. Other adaptive mutations in either E1 or E2 serving the same purpose, that purpose being the adaptation of HVR1 deleted virus, are expected to exist and a number of putative adaptive mutations are listed in table 1-4 (in the present context termed merely adaptive mutations). Thus the present invention relates to these specific as well as of yet unknown adaptive mutations with similar HVR1 adapting capabilities in the present use as well as use in other strains by changing equivalent positions of such genomes to the adapted nucleotide or amino acid described.

In the present invention, the adaptive mutations that are of importance are mutations relating to the deletion of HVR1. The deletion of at least part of HVR1 in combination with these adaptive mutations could potentially be transferred to any HCV construct viable in cell culture and after the transfer still be viable.

A group of preferred HCV-cDNA constructs with the ability to release viral particles in cell culture, which are consequently highly suitable for practical use, are characterized in that they contain one, several or all of the nucleic acid changes listed below and/or one or several or all of the following amino acid exchanges.

It should be understood that any feature and/or aspect discussed above in connection with the mutations according to the invention apply by analogy to both single mutation and any combination of the mutations.

One embodiment of the present invention relates to adaptive mutations, wherein the adaptive mutation is a mutation that can be observed by clonal or direct sequencing of recovered replicating genomes of SEQ ID NOs: 16, 17, 18 and 21.

In a further embodiment, the present invention relates to nucleic acid molecules according to the present invention, wherein said molecule comprises one or more adaptive mutations in the envelope genes E1 or E2, singly or in combination.

In one embodiment the present invention relates to a replicating RNA comprising the structural gene E2 from human hepatitis C virus, wherein the structural gene E2 comprises a deletion of at least part of HVR1, wherein the human hepatitis C virus is selected from the group consisting of strain H77/JFH1$_{T2700C,A4080T,\Delta HVR1}$ (1a/2a), J4/JFH1$_{T2996C,A4827T,\Delta HVR1}$ (1b/2a), J6/JFH1$_{\Delta HVR1}$ (2a/2a), J8/JFH 1$_{\Delta HVR1}$ (2b/2a), S52/JFH1$_{T2718G,T7160C,\Delta HVR1}$ (3a/2a), ED43/JFH1$_{A2819G,A3269T,\Delta HVR1}$ (4a/2a), SA13/JFH1$_{C3405G,A3696G,\Delta HVR1}$ (5a/2a), HK6a/JFH1$_{T1389C,A1590G,\Delta HVR1}$ (6a/2a) and QC69/JFH1$_{\Delta HVR1}$ (7a/2a) and wherein the replicating RNA comprises the structural genes (Core, E1 & E2), p7 and the non-structural gene NS2 of genotypes 1a, 1b, 2a, 2b, 3a, 4a, 5a or 6a, and the non-structural genes NS3, NS4A, NS4B, NS5A and NS5B from the human hepatitis C virus genotype 2a strain JFH1.

In yet an embodiment the present invention pertains to an isolated nucleic acid molecule, which encodes human hepatitis C virus of strain: H77/JFH1$_{T2700C,A4080T,\Delta HVR1}$ (1a/2a), J4/JFH1$_{T2996C,A4827T,\Delta HVR1}$ (1b/2a), J6/JFH1$_{\Delta HVR1}$ (2a/2a), J8/JFH1$_{\Delta HVR1}$ (2b/2a), S52/JFH1$_{T2718G,T7160C,\Delta HVR1}$ (3a/2a), SA13/JFH1$_{C3405G,A3696G,\Delta HVR1}$ (5a/2a), HK6a/JFH1$_{T1389C,A1590G,\Delta HVR1}$ (6a/2a) or QC69/JFH1$_{\Delta HVR1}$ (7a/2a)

wherein said molecule is capable of expressing said virus, when transfected into cells, and wherein H77/JFH1$_{T2700C,A4080T,\Delta HVR1}$ (1a/2a) encodes the amino acid sequence with a sequence identity of at least 90% to that of SEQ ID NO: 1, wherein J4/JFH1$_{T2996C,A4827T,\Delta HVR1}$ (1b/2a) encodes the amino acid sequence with a sequence identity of at least 90% to that of SEQ ID NO: 22, wherein J6/JFH1$_{\Delta HVR1}$ (2a/2a) encodes the amino acid sequence with a sequence identity of at least 90% to that of SEQ ID NO: 2, wherein J8/JFH1$_{\Delta HVR1}$ (2b/2a) encodes the amino acid sequence with a sequence identity of at least 90% to that of SEQ ID NO: 23, wherein S52/JFH1$_{T2718G,T7160C,\Delta HVR1}$ (3a/2a) encodes the amino acid sequence with a sequence identity of at least 90% to that of SEQ ID NO: 3, wherein SA13/JFH1$_{C3405G,A3696G,\Delta HVR1}$ (5a/2a) encodes the amino acid sequence with a sequence identity of at least 90% to that of SEQ ID NO: 5 and, wherein HK6a/JFH1$_{T1389C,A1590G,\Delta HVR1}$ (6a/2a) encodes the amino acid sequence with a sequence identity of at least 90% to that of SEQ ID NO: 6.

In a further embodiment H77/JFH1$_{T2700C,A4080T,\Delta HVR1}$ (1a/2a) comprises the nucleic acid sequence with a sequence identity of at least 90% to that of SEQ ID NO: 7.

In yet an embodiment J4/JFH1$_{T2996C,A4827T,\Delta HVR1}$ (1b/2a) comprises the nucleic acid sequence with a sequence identity of at least 90% to that of SEQ ID NO: 19.

In an embodiment J6/JFH1$_{\Delta HVR1}$ (2a/2a) comprises the nucleic acid sequence with a sequence identity of at least 90% to that of SEQ ID NO: 8.

In a still further embodiment J8/JFH1$_{\Delta HVR1}$ (2b/2a) comprises the nucleic acid sequence with a sequence identity of at least 90% to that of SEQ ID NO: 20.

In yet an embodiment S52/JFH1$_{T2718G,T7160C,\Delta HVR1}$ (3a/2a) comprises the nucleic acid sequence with a sequence identity of at least 90% to that of SEQ ID NO: 9.

In an embodiment SA13/JFH1$_{C3405G,A3696G,\Delta HVR1}$ (5a/2a) comprises the nucleic acid sequence with a sequence identity of at least 90% to that of SEQ ID NO: 11.

In a still further embodiment HK6a/JFH1$_{T1389C,A1590G,\Delta HVR1}$ (6a/2a) comprises the nucleic acid sequence with a sequence identity of at least 90% to that of SEQ ID NO: 12.

Furthermore the present invention pertains to a nucleic acid molecule wherein H77/JFH1$_{T2700C,A4080T,\Delta HVR1}$ (1a/2a), J4/JFH1$_{T2996C,A4827T,\Delta HVR1}$ (1b/2a), J6/JFH$_{\Delta HVR1}$ (2a/2a), J8/JFH1$_{\Delta HVR1}$ (2b/2a), S52/JFH1$_{T2718G,T7160C,\Delta HVR1}$ (3a/2a), SA13/JFH1$_{C3405G,A3696G,\Delta HVR1}$ (5a/2a), HK6a/JFH1$_{T1389C,A1590G,\Delta HVR1}$ (6a/2a) and/or QC69/JFH1$_{\Delta HVR1}$ (7a/2a) comprises one or more adaptive mutations in HCV proteins E1 and E2.

In one embodiment the one or more adaptive mutations in H77/JFH1$_{T2700C,A4080T,\Delta HVR1}$ (1a/2a) is at least one of the replacements of the first said nucleotide of SEQ ID NO: 7 by the following said nucleotide selected from the group consisting of A1122G, A1671G, A1766G and C2538T.

In another embodiment the one or more adaptive mutations in H77/JFH1$_{T2700C,A4080T,\Delta HVR1}$ (1a/2a) is at least one of the replacements of the first said nucleotide of SEQ ID NO: 7 by the following said nucleotide selected from the group consisting of T1383G, T1421C, A1628G and T2385A.

In one embodiment the one or more adaptive mutations in H77/JFH1$_{T2700C,A4080T,\Delta HVR1}$ (1a/2a) is at least one of the replacements of the first said nucleotide of SEQ ID NO: 7 by the following said nucleotide selected from the group consisting of A1122G, A1671G, A1766G, C2538T, T1383G, T1421C, A1628G and T2385A.

In a further embodiment the one or more adaptive mutations in H77/JFH1$_{V787A,Q1247L,\Delta HVR1}$ (1a/2a) is at least one of the replacements of the first said amino acid of SEQ ID NO: 1 by the following said amino acid selected from the group consisting of H261R, Q444R, N476D and S733F.

In yet an embodiment the one or more adaptive mutations in H77/JFH1$_{V787A,Q1247L,\Delta HVR1}$ (1a/2a) is at least one of the replacements of the first said amino acid of SEQ ID NO: 1 by the following said amino acid selected from the group consisting of I348S, Y361H, N430D and L682Q.

In a further embodiment the one or more adaptive mutations in H77/JFH1$_{V787A,Q1247L,\Delta HVR1}$ (1a/2a) is at least one of the replacements of the first said amino acid of SEQ ID NO:

1 by the following said amino acid selected from the group consisting of H261R, Q444R, N476D, S733F, I348S, Y361H, N430D and L682Q.

In a still further embodiment the one or more adaptive mutations in J4/JFH1$_{T2996C,A4827T,\Delta HVR1}$ (1b/2a) is at least one of the replacements of the first said nucleotide of SEQ ID NO: 19 by the following said nucleotide selected from the group consisting of A1236G, C1428T, A1643C, A2066G, G2225A and G2468C.

In an embodiment the one or more adaptive mutations in J4/JFH1$_{F886L,Q1496L\Delta HVR1}$ (1b/2a) is at least one of the replacements of the first said amino acid of SEQ ID NO: 22 by the following said amino acid selected from the group consisting of E299G, S363F, T435P, N576D, V629I and V710L.

In a further embodiment the one or more adaptive mutations in J8/JFH1$_{\Delta HVR1}$ (2b/2a) is at least one of the replacements of the first said nucleotide of SEQ ID NO: 20 by the following said nucleotide selected from the group consisting of T1574A.

In yet an embodiment the one or more adaptive mutations in J8/JFH1$_{\Delta HVR1}$ (2b/2a) is at least one of the replacements of the first said nucleotide of SEQ ID NO: 20 by the following said nucleotide selected from the group consisting of C1571G, T1572G, A1580G, A1652T and A1941C.

In a further embodiment the one or more adaptive mutations in J8/JFH1$_{\Delta HVR1}$ (2b/2a) is at least one of the replacements of the first said nucleotide of SEQ ID NO: 20 by the following said nucleotide selected from the group consisting of T1574A, C1571G, T1572G, A1580G, A1652T and A1941C.

In a still further embodiment the one or more adaptive mutations in J8/JFH1$_{\Delta HVR1}$ (2b/2a) is at least one of the replacements of the first said amino acid of SEQ ID NO: 23 by the following said amino acid selected from the group consisting of Y412N.

In an embodiment the one or more adaptive mutations in J8/JFH1$_{\Delta HVR1}$ (2b/2a) is at least one of the replacements of the first said amino acid of SEQ ID NO: 23 by the following said amino acid selected from the group consisting of L411V, L411R, I414V, M438L and N534T.

In a still further embodiment the one or more adaptive mutations in J8/JFH1$_{\Delta HVR1}$ (2b/2a) is at least one of the replacements of the first said amino acid of SEQ ID NO: 23 by the following said amino acid selected from the group consisting of Y412N, L411V, L411R, I414V, M438L and N534T.

In yet an embodiment the one or more adaptive mutations strain S52/JFH1$_{T2718G,T7160C,\Delta HVR1}$ (3a/2a) is at least one of the replacements of the first said nucleotide of SEQ ID NO: 9 by the following said nucleotide selected from the group consisting of C1446T.

In a further embodiment the one or more adaptive mutations in S52/JFH1$_{I793S,S2274P,\Delta HVR1}$ (3a/2a) is at least one of the replacements of the first said amino acid of SEQ ID NO: 3 by the following said amino acid from the group consisting of A369V.

In a further embodiment the invention relates to an isolated nucleic acid molecule, which encodes human hepatitis C virus of strain H77/JFH1$_{V787A,Q1247L,\Delta HVR1}$ (1a/2a), wherein the molecule is capable of expressing said virus, when transfected into cells, and wherein H77/JFH1$_{V787A,Q1247L,\Delta HVR1}$ (1a/2a) encodes the amino acid sequence with a sequence identity of at least 90% to that of SEQ ID NO: 1, and the adaptive mutation in H77/JFH1$_{V787A,Q1247L,\Delta HVR1}$ (1a/2a) is at least one of the replacements of the first said amino acid at the said position of H77/JFH1$_{V787A,Q1247L}$ in SEQ ID NO: 1 by the following said amino acid selected from the group consisting of H261R, Q444R, N476D and S733F.

In one embodiment the present invention pertains to an isolated nucleic acid molecule which encodes human hepatitis C virus of strain H77/JFH1$_{V787A,Q1247L,\Delta HVR1}$, wherein said molecule:

(i) is capable of expressing said virus when transfected into cells,
(ii) is capable of infectivity in vivo,
(iii) encodes the amino acid sequence with a sequence identity of at least 90% to that of SEQ ID NO: 1, which
(iv) comprises at least one adaptive mutation in the amino acid sequence of E1 or E2 selected from the group consisting of H261R, Q444R, N476D and S733F.

In one embodiment the present invention pertains to an isolated nucleic acid molecule which encodes human hepatitis C virus of strain H77/JFH1$_{V787A,Q1247L,\Delta HVR1}$ wherein said molecule:

(i) is capable of expressing said virus when transfected into cells,
(ii) is capable of infectivity in vivo,
(iii) encodes the amino acid sequence with a sequence identity of at least 90% to that of SEQ ID NO: 1, which
(iv) comprises at least one adaptive mutation in the amino acid sequence of E1 or E2 selected from the group consisting of I348S, Y361H, N430D and L682Q.

In one embodiment the amino acid sequence of SEQ ID NO: 1 comprises at least one adaptive mutation in the amino acid sequence of E1 or E2 selected from the group consisting of I348S, Y361H, N430D, L682Q, H261R, Q444R, N476D and S733F.

In particular the amino acid sequence H77/JFH1$_{(H261R,Q444R),V787A,Q1247L,\Delta HVR1}$ (1a/2a) SEQ ID NO: 13 and H77/JFH1$_{(N476D,S733F),V787A,Q1247L,\Delta HVR1}$ (1a/2a) SEQ ID NO: 14.

One embodiment of the invention relates to an isolated nucleic acid molecule, which encodes human hepatitis C virus of strain H77/JFH1$_{T2700C,A4080T,\Delta HVR1}$ (1a/2a), wherein the molecule is capable of expressing said virus, when transfected into cells, and wherein H77/JFH1$_{T2700C,A4080T,\Delta HVR1}$ (1a/2a) is encoded by the nucleotide sequence with a sequence identity of at least 90% to that of SEQ ID NO: 7, and the adaptive mutation in H77/JFH1$_{T2700C,A4080T,\Delta HVR1}$ (1a/2a) is at least one of the replacements of the first said nucleotide at the said position of SEQ ID NO: 7 by the following said nucleotide selected from the group consisting of A1122G, A1671G, A1766G and C2538T. In particular the nucleotide sequence H77/JFH1$_{(A1122G,A1671G),T2700C,A4080T,\Delta HVR1}$ (1a/2a) SEQ ID NO: 16 and H77/JFH1$_{(A1766G,C2538T),T2700C,A4080T,\Delta HVR1}$ (1a/2a) SEQ ID NO: 17.

In one embodiment the present invention pertains to an isolated nucleic acid molecule which encodes human hepatitis C virus of strain H77/JFH1$_{V87A,Q1247L,\Delta HVR1}$ wherein said molecule:

(i) is capable of expressing said virus when transfected into cells,
(ii) is capable of infectivity in vivo,
(iii) encodes the nucleic acid sequence with a sequence identity of at least 90% to that of SEQ ID NO: 7, which
(iv) comprises at least one adaptive mutation in the nucleic acid sequence of E1 or E2 selected from the group consisting of A1122G, A1671G, A1766G and C2538T.

In one embodiment the present invention pertains to an isolated nucleic acid molecule which encodes human hepatitis C virus of strain H77/JFH1$_{V787A,Q1247L,\Delta HVR1}$ wherein said molecule:

(i) is capable of expressing said virus when transfected into cells,
(ii) is capable of infectivity in vivo, (iii) encodes the nucleic acid sequence with a sequence identity of at least 90% to that of SEQ ID NO: 7, which (iv) comprises at least one adaptive mutation in the nucleic acid sequence of E1 or E2 selected from the group consisting of T1383G, T1421C, A1628G and T2385A.

In one embodiment the nucleic acid sequence of SEQ ID NO: 7 comprises at least one adaptive mutation in the nucleic acid sequence of E1 or E2 selected from the group consisting of A1122G, A1671G, A1766G, C2538T T1383G, T1421C, A1628G and T2385A.

One embodiment of the invention relates to an isolated nucleic acid molecule, which encodes human hepatitis C virus of strain J8/JFH1$_{\Delta HVR1}$ (2b/2a), wherein the molecule is capable of expressing said virus, when transfected into cells, and wherein J8/JFH1$_{\Delta HVR1}$ (2b/2a) encodes the amino acid sequence with a sequence identity of at least 90% to that of SEQ ID NO: 23, and the adaptive mutation in J8/JFH1$_{\Delta HVR1}$ (2b/2a) is at least one of the replacements of the first said amino acid at the said position of SEQ ID NO: 23 by the following said amino acid selected from the group consisting of Y412N. In particular the amino acid sequence J8/JFH1$_{(Y412N),\Delta HVR1}$ (2b/2a), SEQ ID NO: 24.

In one embodiment the present invention pertains to an isolated nucleic acid molecule which encodes human hepatitis C virus of strain J8/JFH1$_{\Delta HVR1}$ (2b/2a), wherein said molecule:

(i) is capable of expressing said virus when transfected into cells, (ii) is capable of infectivity in vivo, (iii) encodes the amino acid sequence with a sequence identity of at least 90% to that of SEQ ID NO: 23, which (iv) comprises at least one adaptive mutation in the amino acid sequence of E1 or E2 selected from the group consisting of Y412N.

In one embodiment the present invention pertains to an isolated nucleic acid molecule which encodes human hepatitis C virus of strain J8/JFH1$_{\Delta HVR1}$ (2b/2a), wherein said molecule:

(i) is capable of expressing said virus when transfected into cells, (ii) is capable of infectivity in vivo, (iii) encodes the amino acid sequence with a sequence identity of at least 90% to that of SEQ ID NO: 23, which (iv) comprises at least one adaptive mutation in the amino acid sequence of E1 or E2 selected from the group consisting of L411V, L411R, I414V, M438L and N534T.

In one embodiment the amino acid sequence of SEQ ID NO: 23 comprises at least one adaptive mutation in the amino acid sequence of E1 or E2 selected from the group consisting of Y412N, L411V, L411R, I414V, M438L and N534T.

One embodiment of the invention relates to an isolated nucleic acid molecule, which encodes human hepatitis C virus of strain J8/JFH1$_{\Delta HVR1}$ (2b/2a), wherein the molecule is capable of expressing said virus, when transfected into cells, and wherein J8/JFH1$_{\Delta HVR1}$ (2b/2a) is encoded by the nucleotide sequence with a sequence identity of at least 90% to that of SEQ ID NO: 20, and the adaptive mutation in J8/JFH1$_{\Delta HVR1}$ (2b/2a) is at least one of the replacements of the first said nucleotide at the said position of SEQ ID NO: 20 by the following said nucleotide selected from the group consisting of T1574A. In particular the nucleotide sequence J8/JFH1$_{(T1574A),\Delta HVR1}$ (2b/2a) SEQ ID NO: 21.

In one embodiment the present invention pertains to an isolated nucleic acid molecule which encodes human hepatitis C virus of strain J8/JFH1$_{\Delta HVR1}$ (2b/2a), wherein said molecule:

(i) is capable of expressing said virus when transfected into cells, (ii) is capable of infectivity in vivo, (iii) encodes the nucleic acid sequence with a sequence identity of at least 90% to that of SEQ ID NO: 20, which (iv) comprises at least one adaptive mutation in the nucleic acid sequence of E1 or E2 selected from the group consisting of T1574A.

In one embodiment the present invention pertains to an isolated nucleic acid molecule which encodes human hepatitis C virus of strain J8/JFH1$_{\Delta HVR1}$ (2b/2a), wherein said molecule:

(i) is capable of expressing said virus when transfected into cells, (ii) is capable of infectivity in vivo, (iii) encodes the nucleic acid sequence with a sequence identity of at least 90% to that of SEQ ID NO: 20, which (iv) comprises at least one adaptive mutation in the nucleic acid sequence of E1 or E2 selected from the group consisting of C1571G, T1572G, A1580G, A1652T and A1941C.

In one embodiment the nucleic acid sequence of SEQ ID NO: 20 comprises at least one adaptive mutation in the nucleic acid sequence of E1 or E2 selected from the group consisting of T1574A, C1571G, T1572G, A1580G, A1652T and A1941C.

One embodiment of the invention relates to an isolated nucleic acid molecule, which encodes human hepatitis C virus of strain S52/JFH1$_{T2718G,T7160C,\Delta HVR1}$ (3a/2a), wherein the molecule is capable of expressing said virus, when transfected into cells, and wherein S52/JFH1$_{T2718G,T7160C,\Delta HVR1}$ (3a/2a) encodes the amino acid sequence with a sequence identity of at least 90% to that of SEQ ID NO: 3, and the adaptive mutation in S52/JFH1$_{T2718G,T7160C,\Delta HVR1}$ is at least one of the replacements of the first said amino acid at the said position of SEQ ID NO: 3 by the following said amino acid selected from the group consisting of A369V. In particular the amino acid sequence S52/JFH1$_{(A369V),I793S,S2274P,\Delta HVR1}$ (3a/2a), SEQ ID NO: 15.

In one embodiment the present invention pertains to an isolated nucleic acid molecule which encodes human hepatitis C virus of strain S52/JFH1$_{T2718G,T7160C,\Delta HVR1}$ wherein said molecule:

(i) is capable of expressing said virus when transfected into cells, (ii) is capable of infectivity in vivo, (iii) encodes the amino acid sequence with a sequence identity of at least 90% to that of SEQ ID NO: 3, which (iv) comprises at least one adaptive mutation in the amino acid sequence of E1 or E2 selected from the group consisting of A369V.

One embodiment of the invention relates to an isolated nucleic acid molecule, which encodes human hepatitis C virus of strain S52/JFH1$_{T2718G,T7160C,\Delta HVR1}$ (3a/2a), wherein the molecule is capable of expressing said virus, when transfected into cells, and wherein S52/JFH1$_{T2718G,T7160C,\Delta HVR1}$ (3a/2a) is encoded by the nucleotide sequence with a sequence identity of at least 90% to that of SEQ ID NO: 9, and the adaptive mutation in S52/JFH1$_{T2718G,T7160C,\Delta HVR1}$ is at least one of the replacements of the first said nucleotide at the said position of SEQ ID NO: 9 by the following said nucleotide selected from the group consisting of C1446T. In particular the nucleotide sequence S52/JFH1$_{(C1446T),T2718G,T7160C,\Delta HVR1}$ (3a/2a), SEQ ID NO: 18.

In one embodiment the present invention pertains to an isolated nucleic acid molecule which encodes human hepatitis C virus of strain S52/JFH1$_{T2718G,T7160C,\Delta HVR1}$, wherein said molecule:

(i) is capable of expressing said virus when transfected into cells, (ii) is capable of infectivity in vivo, (iii) encodes the nucleic acid sequence with a sequence identity of at least 90% to that of SEQ ID NO: 9, which (iv) comprises at least one adaptive mutation in the nucleic acid sequence of E1 or E2 selected from the group consisting of C1446T.

In another embodiment all the amino acid changes observed herein are provided by the present application. The skilled addressee can easily obtain the same amino acid change by mutating another base of the codon and hence all means of obtaining the given amino acid sequence is intended.

Finally, it would be interesting to elucidate the mechanism of action of the identified mutations. It is most likely, that they compensate for deletion of HVR1, facilitating the restoration of a fully functional E2 protein. In principle they might enable efficient intergenotypic protein interaction and/or lead to improvement of protein function independent of these intergenotypic interactions, for example by influencing interactions with host cell proteins.

HVR1 Deleted JFH1-Based Recombinants of Genotype 4a

E2 protein deleted of HVR1 is expressed in the ED43/JFH1$_{A2819G,A3269T,\Delta HVR1}$ (4a/2a) transfected cells and as such recombinant protein could be purified from this and used for the stated purposes of prophylactic and therapeutic vaccine development in spite of the great attenuation of the virus upon HVR1 deletion. The present inventors investigated if a shorter, 21 aa deletion of N-terminal aa of E2 would allow for less attenuation. This was not the case (see example 4 for details).

HVR1 deleted JFH1-based recombinants of genotype 7aIt is likely that QC69/JFH1$_{\Delta HVR1}$ (7a/2a) with a deletion of at least part of HVR1 will be or adapt to being viable like it has here been described for H77/JFH1$_{T2700C,A4080T,\Delta HVR1}$ (1a/2a), J4/JFH1$_{T2996C,A4827T,\Delta HVR1}$ (1b/2a), J6/JFH1$_{\Delta HVR1}$ (2a/2a), J8/JFH1$_{\Delta HVR1}$ (2b/2a), S52/JFH1$_{T2718G,T7160C,\Delta HVR1}$ (3a/2a), SA13/JFH1$_{C3405G,A3696G,\Delta HVR1}$ (5a/2a) and HK6a/JFH1$_{T1389C,A1590G,\Delta HVR1}$ (6a/2a).

HVR1 deleted JFH1-based recombinants of other subtypes (eg. b, c, etc) It is likely that deletion of HVR1 of other HCV subtype JFH1-based recombinants would result in production of viable virus and that envelope mutations mentioned herein that arose upon HVR1 deletion will prove important in the adaptation of such HCV virus constructs.

Titers

To determine the efficiency of the developed system, HCV RNA titers are determined in IU/ml (international units/ml) with Taq-Man Real-Time-PCR and infectious titers are determined with a tissue culture infectious dose 50% method. This titer indicates the dilution of the examined viral stock, at which 50% of the replicate cell cultures used in the assay become infected and is given in $TCID_{50}$/ml or by Focus Forming Unit (FFU) infectivity assays in which the number of infected foci are simply counted and used in the calculation of virus titer.

One embodiment of the present invention relates to a nucleic acid molecule of the present invention, wherein said molecule is capable of generating a HCV RNA titer of $10^4$ IU/ml or above following transfection and/or subsequent viral passage, such as a titer of at least $10^5$ IU/mL, such as a titer of at least $10^6$ IU/mL, such as a titer of at least $10^7$ IU/mL, such as a titer of at least $10^8$ IU/mL, such as a titer of at least $10^9$ IU/mL, such as a titer of at least $10^{10}$ IU/mL, such as a titer of at least $10^{11}$ IU/mL, or such as a titer of at least $10^{12}$ IU/mL.

In another embodiment, the present invention relates to a nucleic acid molecule according to the invention, wherein said molecule is capable of generating a HCV infectivity titer of at least $10^2$ $TCID_{50}$/ml or above following transfection and/or subsequent viral passage, such as a titer of at least $10^3$ TCID50/ml, such as a titer of at least $10^4$ $TCID_{50}$/ml, such as a titer of at least $10^5$ $TCID_{50}$/ml, such as a titer of at least $10^6$ $TCID_{50}$/ml, such as a titer of at least $10^7$ $TCID_{50}$/ml, such as a titer of at least $10^8$ $TCID_{50}$/ml, such as a titer of at least $10^9$ $TCID_{50}$/ml or such as a titer of at least $10^{10}$ $TCID_{50}$/ml.

In another embodiment, the present invention relates to a nucleic acid molecule according to the invention, wherein said molecule is capable of generating a HCV infectivity titer of at least $10^2$ FFUs/ml or above following transfection and/or subsequent viral passage, such as a titer of at least $10^3$ FFUs/ml, such as a titer of at least $10^4$ FFUs/ml, such as a titer of at least $10^5$ FFUs/ml, such as a titer of at least $10^6$ FFUs/ml, such as a titer of at least $10^7$ FFUs/ml, such as a titer of at least $10^8$ FFUs/ml, such as a titer of at least $10^9$ FFUs/ml or such as a titer of at least $10^{10}$ FFUs/ml.

It is of course evident to the skilled addressee that the titers described here are obtained using the assay described in this text. Any similar or equivalent titer determined by any method is thus evidently within the scope of the present invention.

Compositions

One embodiment of the present invention relates to a composition comprising a nucleic acid molecule according to the invention suspended in a suitable amount of a pharmaceutical acceptable diluent or excipient.

In another embodiment, this invention provides for compositions comprising an isolated nucleic acid, vector or cell of this invention, or an isolated nucleic acid obtained via the methods of this invention.

In one embodiment, the term "composition" refers to any such composition suitable for administration to a subject, and such compositions may comprise a pharmaceutically acceptable carrier or diluent, for any of the indications or modes of administration as described. The active materials in the compositions of this invention can be administered by any appropriate route, for example, orally, parenterally, intravenously, intradermally, subcutaneously, or topically, in liquid or solid form.

It is to be understood that any applicable drug delivery system may be used with the compositions and/or agents/vectors/cells/nucleic acids of this invention, for administration to a subject, and is to be considered as part of this invention.

The compositions of the invention can be administered as conventional HCV therapeutics. The compositions of the invention may include more than one active ingredient, which interrupts or otherwise alters groove formation, or occupancy by RNA or other cellular host factors, in one embodiment, or replicase components, in another embodiment, or zinc incorporation, in another embodiment.

The precise formulations and modes of administration of the compositions of the invention will depend on the nature of the anti-HCV agent, the condition of the subject, and the judgment of the practitioner. Design of such administration and formulation is routine optimization generally carried out without difficulty by the practitioner.

It is to be understood that any of the methods of this invention, whereby a nucleic acid, vector or cell of this invention is used, may also employ a composition comprising the same as herein described, and is to be considered as part of this invention.

"Pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

The term "excipient" refers to a diluent, adjuvant, carrier, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The term "adjuvant" refers to a compound or mixture that enhances the immune response to an antigen. An adjuvant can serve as a tissue depot that slowly releases the antigen and also as a lymphoid system activator that non-specifically enhances the immune response. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and Corynebacterium parvmm. Preferably, the adjuvant is pharmaceutically acceptable.

Cells

The nucleotides of the present invention may be used to provide a method for identifying additional cell lines that are permissive for infection with HCV, comprising contacting (e.g. transfecting) a cell line in tissue culture with an infectious amount of HCV RNA of the present invention, e.g., as produced from the plasmid clones, and detecting replication and formation and release of viral particles of HCV in cells of the cell line.

Naturally, the invention also extends to a method for identifying an animal that is permissive for infection with HCV, comprising introducing an infectious amount of the HCV RNA, e.g., as produced by the plasmids, to the animal, and detecting replication and formation and release of viral particles of HCV in the animal. By providing infectious HCV, e.g. comprising a dominant selectable marker, the invention further provides a method for selecting for HCV with further adaptive mutations that permit higher levels of HCV replication in a permissive cell line or animal comprising contacting (e.g. transfecting) a cell line in culture, or introducing into an animal, an infectious amount of the HCV RNA, and detecting progressively increasing levels of HCV RNA and infectious HCV viral particles in the cell line or the animal.

In a specific embodiment, the adaptive mutation permits modification of HCV tropism. An immediate implication of this aspect of the invention is creation of new valid cell culture and animal models for HCV infection.

The permissive cell lines or animals that are identified using the nucleic acids of the invention are very useful, inter alia, for studying the natural history of HCV infection, isolating functional components of HCV, and for sensitive, fast diagnostic applications, in addition to producing authentic HCV virus or components thereof.

Because the HCV DNA, e.g., plasmid vectors, of the invention encode HCV components, expression of such vectors in a host cell line transfected, transformed, or transduced with the HCV DNA can be effected.

For example, a baculovirus or plant expression system can be used to express HCV virus particles or components thereof. Thus, a host cell line may be selected from the group consisting of a bacterial cell, a yeast cell, a plant cell, an insect cell, and a mammalian cell.

In one embodiment, the cell is a hepatocyte, or in another embodiment, the cell is the Huh-7 hepatoma cell line or a derived cell line such as Huh7.5, Huh7.5.1 cell line.

In one embodiment, the cell, or in another embodiment, cell systems of this invention comprise primary cultures or other, also non-hepatic cell lines. "Primary cultures" refers, in one embodiment, to a culture of cells that is directly derived from cells or tissues from an individual, as well as cells derived by passage from these cells, or immortalized cells.

In one embodiment, "cell line" refers to a population of cells capable of continuous or prolonged growth and division in vitro. The term "cell lines" also includes immortalized cells. Often, cell lines are clonal populations derived from a single progenitor cell. Such cell lines are also termed "cell clones". It is further known in the art that spontaneous or induced changes can occur in karyotype during storage or transfer of such clonal populations. Therefore, cells derived from the cell clones referred to may not be precisely identical to the ancestral cells or cultures. According to the present invention, such cell clones may be capable of supporting replication of a vector, virus, viral particle, etc., of this invention, without a significant decrease in their growth properties, and are to be considered as part of this invention.

It is to be understood that any cell of any organism that is susceptible to infection by or propagation of an HCV construct, virus or viral particle of this invention is to be considered as part of this invention, and may be used in any method of this invention, such as for screening or other assays, as described herein.

Also, a method for in vitro producing a hepatitis C virus-infected cell comprising culturing the cell which produces virus particles of the present invention and infecting other cells with the produced virus particle in the culture.

Naturally, the invention extends to any cell obtainable by such methods, for example any in vitro cell line infected with HCV, wherein the HCV has a genomic RNA sequence as described herein, such as a hepatitis C virus infected cell obtainable by any of the methods described.

In one embodiment, the cell line is a hepatocyte cell line such as Huh7 or derived cell lines e.g. Huh7.5 or Huh7.5.1.

Thus in one embodiment the present invention relates to a cassette vector for cloning viral genomes inserted therein the nucleic acid of the invention and having an active promoter upstream thereof.

An embodiment is a method for producing a cell which replicates strains from the group consisting of H77/JFH1$_{T2700C,A4080T,\Delta HVR1}$ (1a/2a), J4/JFH1$_{T2996C,A4827T,\Delta HVR1}$ (1b/2a), J6/JFH 1$_{\Delta HVR1}$ (2a/2a), J8/JFH1$_{\Delta HVR1}$ (2b/2a), S52/JFH1$_{T2718G,T7160C,\Delta HVR1}$ (3a/2a), ED43/JFH1$_{A2819G,A3269T,\Delta HVR1}$ (4a/2a), SA13/JFH1$_{C3405G,A3696G,\Delta HVR1}$ (5a/2a), HK6a/JFH1$_{T1389C,A1590G,\Delta HVR1}$ (6a/2a) and QC69/JFH1$_{\Delta HVR1}$ (7a/2a) comprising introducing the RNAs of the invention into a cell.

In an embodiment this cell is Huh7.5.

An embodiment is the cell obtainable by the method for producing a cell which replicates strains from the group consisting of H77/JFH1$_{T2700C,A4080T,\Delta HVR1}$ (1a/2a), J4/JFH1$_{T2996C,A4827T,\Delta HVR1}$ (1b/2a), J6/JFH1$_{\Delta HVR1}$ (2a/2a), J8/JFH1$_{\Delta HVR1}$ (2b/2a), S52/JFH1$_{T2718G,T7160C,\Delta HVR1}$ (3a/2a), ED43/JFH1$_{A2819G,A3269T,\Delta HVR1}$ (4a/2a), SA13/JFH1$_{C3405G,A3696G,\Delta HVR1}$ (5a/2a), HK6a/JFH1$_{T1389C,A1590G,\Delta HVR1}$ (6a/2a) and QC69/JFH1$_{\Delta HVR1}$ (7a/2a) comprising introducing the RNAs of the invention into a cell.

In a further embodiment the present invention relates to a method for producing a cell, which replicates H77/JFH1$_{T2700C,A4080T,\Delta HVR1}$ (1a/2a), 14/JFH1$_{T2996C,A4827T,\Delta HVR1}$ (1b/2a), J6/JFH1$_{\Delta HVR1}$ (2a/2a), J8/JFH1$_{\Delta HVR1}$ (2b/2a), S52/JFH1$_{T2718G,T7160C,\Delta HVR1}$ (3a/2a), ED43/JFH1$_{A2819G,A3269T,\Delta HVR1}$ (4a/2a), SA13/JFH1$_{C3405G,A3696G,\Delta HVR1}$ (5a/2a), HK6a/JFH1$_{T1389C,A1590G,\Delta HVR1}$ (6a/2a) or QC69/JFH1$_{\Delta HVR1}$ (7a/2a) and produces a virus particle comprising introducing a nucleic acid molecule into a cell, wherein said nucleic acid molecule comprises at least 90% identity to that of SEQ ID NOs: 7, 8, 9, 10, 11, 12, 19 or 20.

In a further embodiment the present invention relates to a method for producing a cell, which replicates HCV H77/JFH1$_{T2700C,A4080T,\Delta HVR1}$ (1a/2a), J4/JFH1$_{T2996C,A4827T,\Delta HVR1}$ (1b/2a), J6/JFH1$_{\Delta HVR1}$ (2a/2a), J8/JFH1$_{\Delta HVR1}$ (2b/2a), S52/JFH1$_{T2718G,T7160C,\Delta HVR1}$ (3a/2a), ED43/JFH1$_{A2819G,A3269T,\Delta HVR1}$ (4a/2a), SA13/JFH1$_{C3405G,A3696G,\Delta HVR1}$ (5a/2a), HK6a/JFH1$_{T1389C,A1590G,\Delta HVR1}$ (6a/2a) or QC69/JFH1$_{\Delta HVR1}$ (7a/2a) and produces a virus particle comprising introducing an amino acid molecule into a cell, wherein said amino acid molecule comprises at least 90% identity to that of SEQ ID NOs: 1, 2, 3, 4, 5, 6, 22 or 23.

In a further embodiment the present invention relates to a method for producing a cell, which replicates H77/JFH1$_{T2700C,A4080T,\Delta HVR1}$ (1a/2a), J4/JFH1$_{T2996C,A4827T,\Delta HVR1}$ (1b/2a), J8/JFH1$_{\Delta HVR1}$ (2b/2a) or S52/JFH1$_{T2718G,T7160C,\Delta HVR1}$ (3a/2a) and produces a virus particle comprising (i) introducing a nucleic acid molecule into a cell, wherein said nucleic acid molecule comprises at least 90% identity to that of SEQ ID NOs: 7, 19, 20 or 9 which (ii) at least one adaptive mutation in the nucleic acid sequence of E1 or E2.

In a further embodiment the present invention relates to a method for producing a cell, which replicates HCV H77/JFH1$_{T2700C,A4080T,\Delta HVR1}$ (1a/2a), J4/JFH1$_{T2996C,A4827T,\Delta HVR1}$ (1b/2a), J8/JFH1$_{\Delta HVR1}$ (2b/2a) or S52/JFH1$_{T2718G,T7160C,\Delta HVR1}$ (3a/2a) and produces a virus particle comprising (i) introducing an amino acid molecule into a cell, wherein said amino acid molecule comprises at least 90% identity to that of SEQ ID NOs: 1, 22, 23 or 3 which (ii) at least one adaptive mutation in the nucleic acid sequence of E1 or E2.

In another embodiment the present invention relates to a method for producing a cell, which replicates HCV H77/JFH1$_{T2700C,A4080T,\Delta HVR1}$ (1a/2a) and produces a virus particle comprising:

(i) introducing a nucleic acid molecule into a cell, wherein said nucleic acid molecule comprises at least 90% identity to that of SEQ ID NO: 7, which (ii) at least one adaptive mutation in the nucleic acid sequence of E1 or E2 selected from the group consisting of A1122G, A1671G, A1766G and C2538T.

In another embodiment the present invention relates to a method for producing a cell, which replicates HCV H77/JFH1$_{T2700C,A4080T,\Delta HVR1}$ (1a/2a) and produces a virus particle comprising:

(i) introducing a nucleic acid molecule into a cell, wherein said nucleic acid molecule comprises at least 90% identity to that of SEQ ID NO: 7, which (ii) at least one adaptive mutation in the nucleic acid sequence of E1 or E2 selected from the group consisting of T1383G, T1421C, A1628G and T2385A.

In another embodiment the present invention relates to a method for producing a cell, which replicates HCV J4/JFH1$_{T2996C,A4827T,\Delta HVR1}$ (1b/2a) and produces a virus particle comprising:

(i) introducing a nucleic acid molecule into a cell, wherein said nucleic acid molecule comprises at least 90% identity to that of SEQ ID NO: 19, which (ii) at least one adaptive mutation in the nucleic acid sequence of E1 or E2 selected from the group consisting of A1236G, C1428T, A1643C, A2066G, G2225A and G2468C.

In another embodiment the present invention relates to a method for producing a cell, which replicates HCV J8/JFH1$_{\Delta HVR1}$ (2b/2a) and produces a virus particle comprising:

(i) introducing a nucleic acid molecule into a cell, wherein said nucleic acid molecule comprises at least 90% identity to that of SEQ ID NO: 20, which (ii) at least one adaptive mutation in the nucleic acid sequence of E1 or E2 selected from the group consisting of T1574A.

In another embodiment the present invention relates to a method for producing a cell, which replicates HCV J8/JFH1$_{\Delta HVR1}$ (2b/2a) and produces a virus particle comprising:

(i) introducing a nucleic acid molecule into a cell, wherein said nucleic acid molecule comprises at least 90% identity to that of SEQ ID NO: 20, which (ii) at least one adaptive mutation in the nucleic acid sequence of E1 or E2 selected from the group consisting of C1571G, T1572G, A1580G, A1652T and A1941C.

In another embodiment the present invention relates to a method for producing a cell, which replicates HCV S52/JFH1$_{T2718G,T7160C,\Delta HVR1}$ (3a/2a) and produces a virus particle comprising:

(i) introducing a nucleic acid molecule into a cell, wherein said nucleic acid molecule comprises at least 90% identity to that of SEQ ID NO: 9, which (ii) at least one adaptive mutation in the nucleic acid sequence of E1 or E2 selected from the group consisting of C1446T.

In another embodiment the cell is any cell expressing the genes necessary for HCV infection and replication, such as but not limited to CD81, SR-BI, Claudin-1, -4, -6 or -9 and the low-density lipoprotein receptor.

The invention further provides various methods for producing HCV virus particles, including by isolating HCV virus particles from the HCV-infected non-human animal of invention; culturing a cell line of the invention under conditions that permit HCV replication and virus particle formation; or culturing a host expression cell line transfected with HCV DNA under conditions that permit expression of HCV particle proteins; and isolating HCV particles or particle proteins from the cell culture. The present invention extends to an HCV virus particle comprising a replication-competent HCV genome RNA, or a replication-defective HCV genome RNA, corresponding to an HCV nucleic acid of the invention as well.

Virus Particles

The production of authentic virus proteins (antigens) may be used for the development and/or evaluation of diagnostics. The cell culture system according to the invention also allows the expression of HCV antigens in cell cultures. In principle these antigens can be used as the basis for diagnostic detection methods.

The production of HCV viruses and virus-like particles, in particular for the development or production of therapeutics and vaccines as well as for diagnostic purposes is an embodiment of the present invention. Especially cell culture adapted complete HCV genomes, which could be produced by using the cell culture system according to the invention, are able to replicate and form viral particles in cell culture with high efficiency. These genomes have the complete functions of HCV and in consequence they are able to produce infectious viruses.

Thus in one embodiment the present invention relates to a method for producing a hepatitis C virus particle of the present invention or parts thereof, comprising culturing a cell or an animal to allow either to produce the virus.

In another embodiment the inventions provides a hepatitis C virus particle obtainable by the method described.

Because the invention provides, inter alia, infectious HCV RNA, the invention provides a method for infecting an animal with HCV which comprises administering an infectious dose of HCV RNA, such as the HCV RNA transcribed from the plasmids described above, to the animal. Naturally, the invention provides a non-human animal infected with HCV of the invention, which non-human animal can be prepared by the foregoing methods.

A further advantage of the present invention is that, by providing a complete functional HCV genome, authentic HCV viral particles or components thereof, which may be produced with native HCV proteins or RNA in a way that is not possible in subunit expression systems, can be prepared.

In addition, since each component of HCV of the invention is functional (thus yielding the authentic HCV), any specific HCV component is an authentic component, i.e., lacking any errors that may, at least in part, affect the clones of the prior art. Indeed, a further advantage of the invention is the ability to generate HCV virus particles or virus particle proteins that are structurally identical to or closely related to natural HCV virions or proteins. Thus, in a further embodiment, the invention provides a method for propagating HCV in vitro comprising culturing a cell line contacted with an infectious amount of HCV RNA of the invention, e.g., HCV RNA translated from the plasmids described above, under conditions that permit replication of the HCV RNA.

Thus, an embodiment of the invention refers to a method for in vitro producing a hepatitis C virus-infected cell comprising culturing a cell which replicates strains from the group consisting of H77/JFH1$_{T2700C,A4080T,\Delta HVR1}$ (1a/2a), J4/JFH1$_{T2996C,A4827T,\Delta HVR1}$ (1b/2a), J6/JFH1$_{\Delta HVR1}$ (2a/2a), J8/JFH1$_{\Delta HVR1}$ (2b/2a), S52/JFH1$_{T2718G,T7160C,\Delta HVR1}$ (3a/2a), ED43/JFH1$_{A2819G,A3269T,\Delta HVR1}$ (4a/2a), SA13/JFH1$_{C3405G,A3696G,\Delta HVR1}$ (5a/2a), HK6a/JFH1$_{T1389C,A1590G,\Delta HVR1}$ (6a/2a) and QC69/JFH1$_{\Delta HVR1}$ (7a/2a) comprising introducing the RNAs of the invention into a cell, and infecting other cells with the produced virus particle in the culture.

A hepatitis C virus infected cell obtainable by the method described is an embodiment of the invention.

Further the viability of the developed viruses may be determined in vivo, either in SCID-uPA mice engrafted with human liver tissue or in chimpanzees as shown in Lindenbach et al. 2006.

In one embodiment, the method further comprises isolating infectious HCV. In another embodiment, the method further comprises freezing aliquots of said infectious HCV. According to this aspect of the invention, and in one embodiment, the HCV is infectious following thawing of said aliquots, and in another embodiment, the HCV is infectious following repeated freeze-thaw cycles of said aliquots.

Screening for anti-viral drugs and the determination of drug resistance

It can be assumed that resistance to therapy occurs due to the high mutation rate of the HCV genome. This resistance, which is very important for the clinical approval of a substance, can be detected with the cell culture system according to the invention. Cell lines, in which the HCV-RNA construct or the HCV genome or subgenome replicates and produces infectious viral particles, are incubated with increasing concentrations of the relevant substance and the replication of the viral RNA is either determined by means of an introduced reporter gene or through the qualitative or quantitative detection of the viral nucleic acids or proteins. The release of viral particles is determined by measuring HCV RNA and infectivity titers in the cell culture supernatant. Resistance is given if no, or a reduced inhibition of the replication and release of viral particles, can be observed with the normal concentration of the active substance. The nucleotide and amino acid replacements responsible for the therapy resistance can be determined by recloning the HCV-RNA (for example by the means of RT-PCR) and sequence analysis. By cloning the relevant replacement(s) into the original construct its causality for the resistance to therapy can be proven.

While the replicon systems facilitated testing of drugs interfering with replication such as NS3/4A protease and polymerase inhibitors, the variant genomes obtained in the present study may prove useful for different research topics.

The systems developed in this invention are ideal candidates for specific testing of therapeutics in general and therapeutics targeting viral entry in particular. The genomes can be valuable for testing antibodies and other drugs acting on entry level, such as fusion inhibitors.

The present inventors conducted cross-genotype neutralization studies in HCV cell culture systems recapitulating the entire viral life cycle using JFH1-based viruses with envelope sequences of all 7 major genotypes, and important subtypes 1b and 2b, which has previously not been possible. HCV E1/E2 assembled on HCV pseudo particles (HCVpp), used in previous neutralization studies could show an unphysiological confirmation, glycosylation pattern and/or lipoprotein association due to the nature of the HCVpp as well as the non-hepatic producer cell-lines used in such experiments.

In such studies the viral particles are incubated with the neutralizing substance, e.g. patient derived antibodies present in serum, prior to incubation with cells permissive and susceptible to viral infection. The neutralizing effect, i.e. the inhibitory effect on viral entry, is measured e.g. by relating the number of focus forming units (FFUs, defined as foci of adjacent infected cells) to the equivalent count in a control experiment done under same circumstances without the active inhibitor molecule.

The inventors of the present invention showed that JFH1-based viruses of the genotype 1a, 1b, 2b, 4a, 5a, 6a and 7a were efficiently neutralized by chronic phase H06 genotype 1a serum derived from reference Patient H. The results in the cell culture systems compare well to neutralization experiments using Patient H serum from year 26 (H03) carried out in HCVpp systems with envelope proteins of the same prototype isolates of all 6 HCV genotypes as used in the present application, and heterogeneity between the genotypes is thus as previously reported by Meunier et al. 2005.

In addition the present inventors found that cross-genotype neutralization extended to a chronic phase genotype 4a serum (AA), which efficiently neutralized genotype 2b, 4a, 5a, 6a and 7a. Also, the cross-genotype neutralization extended to a chronic phase genotype 5a serum (SA3), which efficiently neutralized genotype 2b, 4a, 5a, 6a and 7a. Accordingly, the JFH1-based cell culture systems which have been developed for HCV genotype 1a, 1b, 2a, 2b, 3a, 4a, 5a, 6a and 7a provide a valuable tool for efficiently screening for and identifying new candidate HCV genotype 1a, 1b, 2a, 2b, 3a, 4a, 5a, 6a and 7a inhibitors e.g. of entry e.g. in serum derived from infected patients. Accordingly this invention, allows identification and raise of cross-neutralizing antibodies, which is important for the development of active and passive immunization strategies. Furthermore the availability of cell culture grown HCV particles bearing envelope proteins of the seven major genotypes and important subtypes enables the development of inactivated whole virus vaccines and comprehensive virus neutralization studies. The development of infectious viruses without HVR1 facilitates the development of inhibitors and antibodies specifically aimed at other, less variable targets on the surface of the virus particle.

It has been demonstrated that infectious particles without HVR1 possess a uniform density around 1.1 g/ml (Example 6), unlike that seen for the wt viruses where infectious particle densities are found in a range of 1.0 to 1.1 g/ml. This difference is interesting, especially in conjunction with the neutralization data showing marked improvement in neutralization of the HVR1 deleted viruses when compared to their respective wt counterpart (Example 5). These neutralization data show complete neutralization of all HVR1 deleted viruses at high dilutions of the patient sera. In the case of wt viruses the neutralization effect is much more varied, ranging from no neutralization (AA and SA3 serum against J6/JFH$_{\Delta HVR1}$,), to neutralization reaching a plateau beyond which further neutralization seems unattainable (H06 serum against J6/JFH$_{\Delta HVR1}$ and S52/JFH1$_{T2718G,T7160C,\Delta HVR1}$), to going toward full neutralization spread out over an extended serum dilution interval (H06 serum against H77/JFH1$_{T2700C,A4080T,\Delta HVR1}$, SA13/JFH1$_{C3405G,A3696G,\Delta HVR1}$, and HK6a/JFH1$_{T1389C,A1590C,\Delta HVR1}$).

Taken together, this shows that wt viruses are found greatly associated to a low density moiety, the candidate being lipoproteins of low density, and that this association appears to have a shielding effect on, otherwise, readily available neutralization epitopes. It has also been shown that H77/JFH1$_{T2700C,A4080T,\Delta HVR1}$ displays HVR1 on its surface and that antibodies raised against this region will neutralize the virus (Example 5). It would therefore stand to reason that one would need neutralizing antibodies against both HVR1 and other epitopes to attain a complete neutralization against all types of HCV virus particles. Testing of these mixed products would depend on viruses with and without HVR1, like the ones the present inventors have generated for this invention.

One might draw into question the clinical importance of non-naturally occurring, HVR1 truncated viruses. Although this issue is a complex one there are several factors suggesting that the study of these viruses yields data of clinical importance. Firstly, H77 with HVR1 truncation has been shown to spread, albeit attenuated, in two chimpanzees (Forms et al, 2000). Secondly, chronic patient serum often contains high titers of non-HVR1 antibodies capable of neutralizing the HVR1 truncated viruses without this leading to viral clearance.

In one embodiment the present invention relates to a method for identifying neutralizing antibodies.

In another one embodiment the present invention relates to a method for identifying cross-genotype neutralizing antibodies.

In one embodiment the present invention relates to a method of raising neutralizing antibodies.

In another embodiment the present invention relates to a method of raising cross-neutralizing antibodies.

In one embodiment the present invention related to a method for screening new HCV genotype 1a, 1b, 2a, 2b, 3a, 4a, 5a, 6a and/or 7a inhibitors or neutralizing antibodies, comprising a) culturing at least one selected from the group consisting of a cell according to the present invention, a hepatitis C virus infected cell according to the present invention and a hepatitis C virus particle obtainable by the present invention together with a hepatitis C virus permissive cell, and
b) subjecting said virus or virus infected cell culture to a blood sample or derivatives thereof from a HCV genotype 1a, 1b, 2a, 2b, 3a, 4a, 5a, 6a and/or 7a infected patient
c) detecting the amount of replicating RNA and/or the virus particles.

Thus, one embodiment of the present invention relates to a method for screening an anti-hepatitis C virus substance, comprising a) culturing at least one selected from the group consisting of a cell according to the present invention, a hepatitis C virus infected cell according to the present invention and a hepatitis C virus particle obtainable by the present invention together with a hepatitis C virus permissive cell,
b) subjecting said virus or virus infected cell culture to the anti-hepatitis C virus substance, and
c) detecting the replicating RNA and/or the virus particles in the resulting culture.

In another embodiment, the inhibition of HCV replication and/or infection and/or pathogenesis includes inhibition of downstream effects of HCV. In one embodiment, downstream effects include neoplastic disease, including, in one embodiment, the development of hepatocellular carcinoma.

In one embodiment, the invention provides a method of screening for anti-HCV therapeutics, the method comprising contacting a cell with an isolated nucleic acid molecule encoding an infectious recombinant HCV genome, comprising a chimeric HCV genome and contacting the cell with a candidate molecule, independently contacting the cell with a placebo and determining the effects of the candidate molecule on HCV infection, replication, or cell-to-cell spread, versus the effects of the placebo, wherein a decrease in the level of HCV infection, replication, or cell-to-cell spread indicates the candidate molecule is an anti-HCV therapeutic.

In one embodiment, the method may be conducted be in vitro or in vivo. In one embodiment, the cells as described may be in an animal model, or a human subject, entered in a clinical trial to evaluate the efficacy of a candidate molecule. In one embodiment, the molecule is labelled for easier detection, including radio-labelled, antibody labelled for fluorescently labelled molecules, which may be detected by any means well known to one skilled in the art.

In one embodiment, the candidate molecule is an antibody.

In one embodiment, the term "antibody" refers to intact molecules as well as functional fragments thereof, such as Fab, F(ab')2, and Fv. In one embodiment, the term "Fab" refers to a fragment, which contains a monovalent antigen-binding fragment of an antibody molecule, and in one embodiment, can be produced by digestion of whole antibody with the enzyme papain to yield an intact light chain and a portion of one heavy chain, or in another embodiment can be obtained by treating whole antibody with pepsin, followed by reduction, to yield an intact light chain and a portion of the heavy chain. In one embodiment, the term "F(ab')2", refers to the fragment of the antibody that can be obtained by treating whole antibody with the enzyme pepsin without subsequent reduction, F(ab')2 is a dimer of two Fab' fragments held together by two disulfide bonds. In another embodiment, the term "Fv" refers to a genetically engineered fragment containing the variable region of the light chain and the variable region of the heavy chain expressed as two chains, and in another embodiment, the term "single chain antibody" or "SCA" refers to a genetically engineered molecule containing the variable region of the light chain and the variable region of the heavy chain, linked by a suitable polypeptide linker as a genetically fused single chain molecule.

Methods of producing these fragments are known in the art.

In another embodiment, the candidate molecule is a small molecule. In one embodiment, the phrase "small molecule" refers to, inter-alia, synthetic organic structures typical of pharmaceuticals, peptides, nucleic acids, peptide nucleic acids, carbohydrates, lipids, and others, as will be appreciated by one skilled in the art. In another embodiment, small molecules, may refer to chemically synthesized peptidomimetics of the 6-mer to 9-mer peptides of the invention.

In another embodiment, the candidate molecule is a nucleic acid. Numerous nucleic acid molecules can be envisioned for use in such applications, including antisense, siRNA, ribozymes, etc., as will be appreciated by one skilled in the art.

It is to be understood that the candidate molecule identified and/or evaluated by the methods of this invention, may be any compound, including, inter-alia, a crystal, protein, peptide or nucleic acid, and may comprise an HCV viral product or derivative thereof, of a cellular product or derivative thereof. The candidate molecule in other embodiments, may be isolated, generated synthetically, obtained via translation of sequences subjected to any mutagenesis technique, or obtained via protein evolution techniques, well known to those skilled in the art, each of which represents an embodiment of this invention, and may be used in the methods of this invention, as well.

In one embodiment, the compound identified in the screening methods as described, may be identified by computer modeling techniques, and others, as described herein. Verification of the activity of these compounds may be accomplished by the methods described herein, where, in one embodiment, the test compound demonstrably affects HCV infection, replication and/or pathogenesis in an assay, as described. In one embodiment, the assay is a cell-based assay, which, in one embodiment, makes use of primary isolates, or in another embodiment, cell lines, etc. In one embodiment, the cell is within a homogenate, or in another embodiment, a tissue slice, or in another embodiment, an organ culture. In one embodiment, the cell or tissue is hepatic in origin, or is a derivative thereof. In another embodiment, the cell is a commonly used mammalian cell line, which has been engineered to express key molecules known to be, or in another embodiment, thought to be involved in HCV infection, replication and/or pathogenesis.

In another embodiment, protein, or in another embodiment, peptide or in another embodiment, other inhibitors of the present invention cause inhibition of infection, replication, or pathogenesis of HCV in vitro or, in another embodiment, in vivo when introduced into a host cell containing the virus, and may exhibit, in another embodiment, an IC50 in the range of from about 0.0001 nM to 100 μM in an in vitro assay for at least one step in infection, replication, or pathogenesis of HCV, more preferably from about 0.0001 nM to 75 μM, more preferably from about 0.0001 nM to 50 μM, more preferably from about 0.0001 nM to 25 μM, more preferably from about 0.0001 nM to 10 μM, and even more preferably from about 0.0001 nM to 1 μM.

In another embodiment, the inhibitors of HCV infection, or in another embodiment, replication, or in another embodiment, pathogenesis, may be used, in another embodiment, in ex vivo scenarios, such as, for example, in routine treatment of blood products wherein a possibility of HCV infection exists, when serology indicates a lack of HCV infection.

In another embodiment, the anti-HCV therapeutic compounds identified via any of the methods of the present invention can be further characterized using secondary screens in cell cultures and/or susceptible animal models. In one embodiment, a small animal model may be used, such as, for example, a tree shrew Tupaia belangeri chinensis. In another embodiment, an animal model may make use of a chimpanzee. Test animals may be treated with the candidate compounds that produced the strongest inhibitory effects in any of the assays/methods of this invention. In another embodiment, the animal models provide a platform for pharmacokinetic and toxicology studies.

Vaccines

The construct according to the invention by itself can also be used for various purposes in all its embodiments. This includes the construction of hepatitis C viruses or HCV-like particles and their production in cell cultures as described.

These HCV or HCV-like particles can be used in particular as vaccine. Thus, one embodiment of the present invention relates to a hepatitis C vaccine comprising a hepatitis C virus particle according to the invention or a part thereof.

In another embodiment, the nucleic acids, vectors, viruses, or viral particles may be further engineered to express a heterologous protein, which, in another embodiment, is mammalian or a derivative thereof, which is useful in combating HCV infection or disease progression. Such proteins may comprise cytokines, growth factors, tumor suppressors, or in one embodiment, may following infection, be expressed predominantly or exclusively on an infected cell surface. According to this aspect of the invention, and in one embodiment, such molecules may include costimulatory molecules, which may serve to enhance immune response to infected cells, or preneoplastic cells, or neoplastic cells, which may have become preneoplastic or neoplastic as a result of HCV infection. In one embodiment, the heterologous sequence encoded in the nucleic acids, vectors, viruses, or viral particles of this invention may be involved in enhanced uptake of a nucleic acids, vectors, viruses, or viral particles, and may specifically target receptors thought to mediate HCV infection.

Thus, one embodiment of the invention relates to a hepatitis C vaccine comprising a hepatitis C virus particle from a cell which replicates strains from the group consisting of H77/JFH1$_{T2700C,A4080T,\Delta HVR1}$ (1a/2a), J4/JFH1$_{T2996C,A4827T,\Delta HVR1}$ (1b/2a), J6/JFH1$_{\Delta HVR1}$ (2a/2a), J8/JFH1$_{\Delta HVR1}$ (2b/2a), S52/JFH1$_{T2718G,T7160C,\Delta HVR1}$ (3a/2a), ED43/JFH1$_{A2819G,A3269T,\Delta HVR1}$ (4a/2a), SA13/JFH1$_{C3405G,A3696G,\Delta HVR1}$ (5a/2a), HK6a/JFH1$_{T1389C,A1590G,\Delta HVR1}$ (6a/2a) and QC69/JFH1$_{\Delta HVR1}$ (7a/2a) comprising introducing the RNA of the invention.

An embodiment relates to an antibody against the hepatitis C virus particle described above.

Further, the present invention relates to a method for producing a hepatitis C virus vaccine comprising using a hepatitis C virus particle according to the invention or part thereof as an antigen, and naturally any antibody against such hepatitis C virus particle.

Using the HVR1 deleted constructs one could recombinantly express HVR1 deleted E2 protein. This protein could be used for the generation of specific antibodies that might serve in passive immunization. In addition the recombinantly expressed protein could be used in vaccine development. This vaccine development would also allow for non-HVR1 specific effects and the recombinant protein lacking HVR1 does therefore offer many of the same possibilities as the HVR1 deleted HCV virus particle itself.

Use of the HVR1 Viruses for Diagnostic/Prognostic Purposes

The developed viruses could be applied as prognostic tool in infected patient and could thus contribute to individualized patient treatment. The availability of genotype specific virus with and without HVR1 may allow for the development of a prognostic assay where the antibody response of the patient was tested against the relevant genotype virus with and without HVR1 to ascertain whether the antibodies raised by the patient will have a lasting effect. This is possible due to the broadly neutralizing effect of antibodies in patient sera raised against HCV.

Kits

In a related aspect, the invention also provides a test kit for HCV comprising HCV virus components, and a diagnostic test kit for HCV comprising components derived from an HCV virus as described herein.

Furthermore the invention also provide test kits, for screening for new HCV genotype 1a, 1b, 2a, 2b, 3a, 5a, 6a and 7a inhibitors, neutralizing and cross neutralizing antibodies, comprising HCV virus components.

General

Reference to any prior art in this specification is not, and should not be taken as, an acknowledgment or any form of suggestion that this prior art forms part of the common general knowledge in any country.

All patent and non-patent references cited in the present application, are hereby incorporated by reference in their entirety.

As will be apparent, preferred features and characteristics of one aspect of the invention may be applicable to other aspects of the invention. The invention may be embodied in other specific forms without departing from the spirit or essential characteristics thereof. The foregoing embodiments are therefore to be considered in all respects illustrative rather than limiting on the invention described herein. Scope of the invention is thus indicated be the appended claims rather than by the foregoing description, and all changes that come within the meaning and range of equivalency of the claims are intended to be embraced by reference therein.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In addition, singular reference do not exclude a plurality. Thus, references to "a", "an", "first", "second" etc. do not preclude a plurality.

The invention may be embodied in other specific forms without departing from the spirit or essential characteristics thereof. The foregoing embodiments are therefore to be considered in all respects illustrative rather than limiting on the invention described herein. Scope of the invention is thus indicated be the appended claims rather than by the foregoing description, and all changes that come within the meaning and range of equivalency of the claims are intended to be embraced by reference therein.

The invention will hereinafter be described by way of the following non-limiting Figures and Examples.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

| Sequence listing | |
|---|---|
| SEQ ID NO: 1 | H77/JFH1$_{V787A, Q1247L, \Delta HVR1}$ (1a/2a) - Amino Acid Sequence |
| SEQ ID NO: 2 | J6/JFH1$_{\Delta HVR1}$ (2a/2a) - Amino Acid Sequence |
| SEQ ID NO: 3 | S52/JFH1$_{I793S, S2274P, \Delta HVR1}$ (3a/2a) - Amino Acid Sequence |
| SEQ ID NO: 4 | ED43/JFH1$_{T827A, T977S, \Delta HVR1}$ (4a/2a) - Amino Acid Sequence |
| SEQ ID NO: 5 | SA13/JFH1$_{A1022G, K1119R, \Delta HVR1}$ (5a/2a) - Amino Acid Sequence |
| SEQ ID NO: 6 | HK6a/JFH1$_{F350S, N417T, \Delta HVR1}$ (6a/2a) - Amino Acid Sequence |
| SEQ ID NO: 7 | H77/JFH1$_{T2700C, A4080T, \Delta HVR1}$ (1a/2a) - DNA |
| SEQ ID NO: 8 | J6/JFH1$_{\Delta HVR1}$ (2a/2a) - DNA |
| SEQ ID NO: 9 | S52/JFH1$_{T2718G, T7160C, \Delta HVR1}$ (3a/2a) - DNA |
| SEQ ID NO: 10 | ED43/JFH1$_{A2819G, A3269T, \Delta HVR1}$ (4a/2a) - DNA |
| SEQ ID NO: 11 | SA13/JFH1$_{C3405G, A3696G, \Delta HVR1}$ (5a/2a) - DNA |
| SEQ ID NO: 12 | HK6a/JFH1$_{T1389C, A1590G, \Delta HVR1}$ (6a/2a) - DNA |
| SEQ ID NO: 13 | H77/JFH1$_{(H261R, Q444R), V787A, Q1247L, \Delta HVR1}$ (1a/2a) - Amino Acid Sequence |
| SEQ ID NO: 14 | H77/JFH1$_{(N476D, S733F), V787A, Q1247L, \Delta HVR1}$ (1a/2a) - Amino Acid Sequence |
| SEQ ID NO: 15 | S52/JFH1$_{(A369V), I793S, S2274P, \Delta HVR1}$ (3a/2a) - Amino Acid Sequence |
| SEQ ID NO: 16 | H77/JFH1$_{(A1122G, A1671G), T2700C, A4080T, \Delta HVR1}$ (1a/2a) - DNA |
| SEQ ID NO: 17 | H77/JFH1$_{(A1766G, C2538T), T2700C, A4080T, \Delta HVR1}$ (1a/2a) - DNA |
| SEQ ID NO: 18 | S52/JFH1$_{(C1446T), T2718G, T7160C, \Delta HVR1}$ (3a/2a) - DNA |
| SEQ ID NO: 19 | J4/JFH1$_{T2996C, A4827T, \Delta HVR1}$ (1b/2a) - DNA |
| SEQ ID NO: 20 | J8/JFH1$_{\Delta HVR1}$ (2b/2a) - DNA |
| SEQ ID NO: 21 | J8/JFH1$_{(T1574A), \Delta HVR1}$ (2b/2a) - DNA |
| SEQ ID NO: 22 | J4/JFH1$_{F886L, Q1496L, \Delta HVR1}$ (1b/2a)- Amino Acid Sequence |
| SEQ ID NO: 23 | J8/JFH1$_{\Delta HVR1}$ (2b/2a) - Amino Acid Sequence |
| SEQ ID NO: 24 | J8/JFH1$_{(Y412N), \Delta HVR1}$ (2b/2a) - Amino Acid Sequence |

EXAMPLES

Materials and Methods

Culturing, Transfection and Infection of Huh7.5 Cells

Culturing of Huh7.5 The human hepatoma cell line Huh7.5 was cultured in Dulbecco's modified Eagle medium 4500 mg/L glucose GlutaMAX-I_Pyruvate (Gibco/Invitrogen Corporation, Carlsbad, Calif.) containing 10% heat-inactivated fetal bovine serum (Sigma, St. Louis, Mo.), penicillin 100 U/mL and streptomycin 100 g/mL (Gibco/Invitrogen Corporation), at 5% CO2 and 37° C. Cells were split every second to third day at a ratio of 1:2 to 1:3. One day prior to transfection or infection, 4*$10^5$ cells/well were plated into 6-well plates (NUNC). In transfections, 2.5 μg HCV RNA derived from in vitro transcription was mixed with 5 μl of Lipofectamine 2000 (Invitrogen) and incubated in 500 µl OptiMEM (Invitrogen) for 20 min. The RNA-Lipofectamine 2000 complexes were then added to the 6-well plates and left to transfect cells at 37° C., 5% $CO_2$ for 16-24 h before washing with PBS. In infections, virus supernatants were added and left to infect for 16-24 h before washing with PBS. Collected cell culture supernatants were sterile filtered with a pore size of 0.45 µm (Nalgene) and stored at −80° C. Every time cells were split, a small amount of each culture was transferred to cover slides (NUNC) for evaluation of the percentage of infected cells by HCV antigen immunostaining (see below). Positive control virus for transfections of mutated virus was always the non-mutated virus. Negative control virus for transfections was always the replication deficient J6/JFH$_{GND}$ (abbreviated: GND).

Evaluation of Infected Cell Cultures

Viral spread in cell cultures was monitored by immunostaining of cells on cover slides for HCV Core or NS5A antigen with 1:200 dilution of mouse anti-HCV core protein monoclonal antibody (B2) (Anogen, Yes Biotech Laboratories) in PBS containing 5% BSA or 1:500 dilution of mouse anti-NS5A, 9E10 in PBS containing 5% BSA, respectively, followed by a 1:500 dilution of goat anti-mouse Alexa594 conjugated (H+L) secondary antibody (Invitrogen) in PBS/Tween. Cell nuclei were counterstained with Hoechst 33342 (Invitrogen). The percentage of HCV-positive cells was evaluated by fluorescence microscopy, assigning values of 0% (no cells infected), 1%, 5%, 10%-100% (in steps of 10%) cells infected. Supernatant infectivity titers were determined as 50% tissue culture infectious dose (TCID$_{50}$)/mL or as focus forming units (FFU)/mL. In both assays, 6×103 Huh7.5 cells/well of poly-D-lysine coated 96 well plates (Nunc) were plated out the day before infection with 10-fold dilutions of virus containing supernatant. After 48 h incubation at 37° C., 5% $CO_2$, HCV infected cells were visualized by immunostaining for HCV NS5A. NS5A antigen staining was performed as previously described using primary antibody anti-NS5A, 9E10 at 1:1000 in PBS/Tween, secondary antibody ECL anti-mouse immunoglobulin (Ig)G, horseradish-peroxidase-linked whole antibody (GE Healthcare Amersham, Buckinghamshire, UK) at 1:300 in PBS/Tween, and horseradish-peroxidase substrate (DAB substrate kit, DAKO, Glostrup, Denmark). HCV infected cells were detected by light microscopy. In transfections FFU/mL calculations were based on counting FFU of wells with 5-100 FFU in three independent virus dilutions with one replicate each and in kinetic experiments calculations were based on taking average of triplicates by counting FFU of wells with 5-100 FFU. TCID$_{50}$/ml calculations were done using the standard Reed-Munch limiting dilution formula for six replicates.

Real-Time PCR (TaqMan) Quantification of HCV RNA

Supernatant HCV RNA titers were measured by a 5' UTR based Real Time RT-PCR. RNA was purified from 200 µL of heat inactivated (56° C. for 30 min) cell culture supernatant and eluted in a final volume of 50 µL using the Total Nucleic Acid Isolation Kit (Roche) in combination with the Total NA Variable Elution Volume protocol on a MagNA Pure LC Instrument (Roche). As an internal control, Phocine Distemper Virus (PDV) was added to the lysis buffer in a concentration titrated to yield a Ct of ~32 upon real-time PCR analysis. In parallel to RNA purified from cell culture supernatants a quantitative HCV standard panel covering RNA concentrations of 0 to 5×10$^6$ IU/mL in one-log increments (OptiQuant HCV Panel, AcroMetrix) was analysed. Real-time PCR analyses of HCV and PDV RNA were carried out in two separate reactions using the TaqMan EZ RT-PCR Kit (Applied Biosystems). For HCV, primers and a FAM-labelled MGB-probe were directed against the 5' UTR and were previously shown to perform equivalently against a panel of the six major HCV genotypes in a different TaqMan assay (Engle et al. 2008). For PDV, a ready-to-use primer/probe mix was used (Dr. H. G. M. Niesters, Department of Virology, Erasmus Medical Centre, Rotterdam, The Netherlands). The PCR analysis was performed on a 7500 Real-Time PCR System (Applied Biosystems) using 50° C. for 2 min, 60° C. for 30 min and 95° C. for 5 min followed by 45 cycles of 94° C. for 20 min and 62° C. for 1 min. HCV RNA titers (IU/ml) were calculated using a standard curve created from the known concentrations of the standard panel and their corresponding Ct values. The reproducible detection limit of the assay was 500 IU/ml. In order to confirm successful purification, amplification and the absence of PCR inhibitors, the Ct value of the PDV reaction was compared to the expected Ct value (based on a mean of all previous runs; n>9) using the MedLab QC freeware programme. The results of samples with an actual Ct value within ±25D of the expected Ct value were accepted.

Sequencing of Cell Culture Derived HCV RNA

HCV RNA was extracted using High Pure Viral Nucleic Acid Kit (Roche) and cDNA was generated using Superscript III (Invitrogen). RNA was degraded using RNase T and H (Ambion). Next, 1st and 2nd round PCR was carried out using BD Advantage II polymerase mix (Clontech) using specific primers (as described in the previous patent applications for H77/JFH1$_{T2700C,A4080T}$ (1a/2a), J4/JFH1$_{T2996C,A4827T}$(1b/2a), J8/JFH1 (2b/2a), S52/JFH1$_{T2718G,T7160C}$ (3a/2a), ED43/JFH1$_{A2819G,A3269T}$ (4a/2a), SA13/JFH1$_{C3405G,A3696G}$ (5a/2a), and HK6a/JFH1$_{T1389C,A1590G}$ (6a/2a)). The resulting 12 amplicons were directly sequenced using specific primers (As described in the previous patent applications for H77/JFH1$_{T2700C,A4080T}$ (1a/2a), J4/JFH1$_{T2996C,A4827T}$ (1b/2a), J8/JFH1 (2b/2a), S52/JFH1$_{T2718G,T7160C}$ (3a/2a), ED43/JFH1$_{A2819G,A3269T}$ (4a/2a), SA13/JFH1$_{C3405G,A3696G}$ (5a/2a) and HK6a/JFH1$_{T1389C,A1590G}$ (6a/2a)) and the sequence files were assembled and analyzed in Sequencher software version 4.7. All plasmids used in transfections were sequenced in the entire HCV coding sequence.

Cloning

Deletions were carried out by fusion PCR using PFU polymerase (Stratagene) or Quikchange XL kit (Invitrogen) and the generation of point mutations was done using the Quikchange XL kit (Invitrogen).

In Vitro Transcription

5 µg of plasmids were linearized using XbaI (New England Biolabs) and treated with mung bean nuclease (New England Biolabs) for 1 h to obtain the correct 3' end of the HCV genome. The DNA was then purified using Qiaquick PCR purification kit (Qiagen) and subsequently used to generate HCV coding RNA by T7 polymerase in vitro transcription (Promega) for 2 h at 37° C.

Density Gradient Centrifugation

Continuous gradients were made using Iodixanol, which has been shown to best preserve host-lipoprotein virus complexes. The gradient was generated by layering 2.5 ml each of 40%, 30%, 20% and 10% Optiprer™ (Iodixanol, Axis-Shield) diluted with PBS from a 60% stock. The step gradients were then left upright for 24 h at 4° C. for the formation of semi-continuous gradients. To reduce sample volume and to concentrate infectious virus we used amicon centrifugation filters (Millipore), obtaining virus in a volume of ~250 µl and loaded this on top of the gradient immediately prior to ultracentrifugation. This was carried out at 35000 RPM (151263×rcf) for 18 h at 4° C. using a Beckman SW-41 rotor mounted in a Beckman XL-70 ultracentrifuge. After centrifugation gradient fractions were harvested from the bottom into ~550

μl fractions and 400 μl of these were weighed to calculate the fraction densities. Fractions were infectivity and HCV RNA titrated at a 1:10 dilution as we had tested and found that up to 10% Iodixanol had no significant effect on HCV infectivity and HCV RNA titers.

Neutralization of $HCV_{cc}$ by Patient Sera 100-400×$TCID_{50}$ of viruses were incubated for 1 h at 37° C. with either two-fold dilutions of heat-inactivated (56° C. for 30 min) patient serum or four-fold dilutions of polyclonal IgGs purified from serum. Huh7.5 cells were plated at $6\times10^3$/well the day before the experiment in a poly-D-lysine-coated 96-well plate. The viruses were incubated with serum or IgG for 1 h at 37° C. and subsequently incubated with the cells for 3 h. Then cells were washed once with pre-warmed media and incubated in 200 μl of fresh medium for 48 h before NS5A staining as described for infectivity titration. All dilutions were done in triplicates and normalized to a 6 replicate virus only control. Data from neutralization experiments was presented as dose-response curves with variable slope to best fit the data and to allow for a detailed comparison between neutralization profiles across the serum dilution series.

Example 1

Deletion of HVR1 from genotype 2a virus J6/JFH does not result in significantly reduced viral infectivity and does not incur the need for adaptive mutations.

Figure 2:
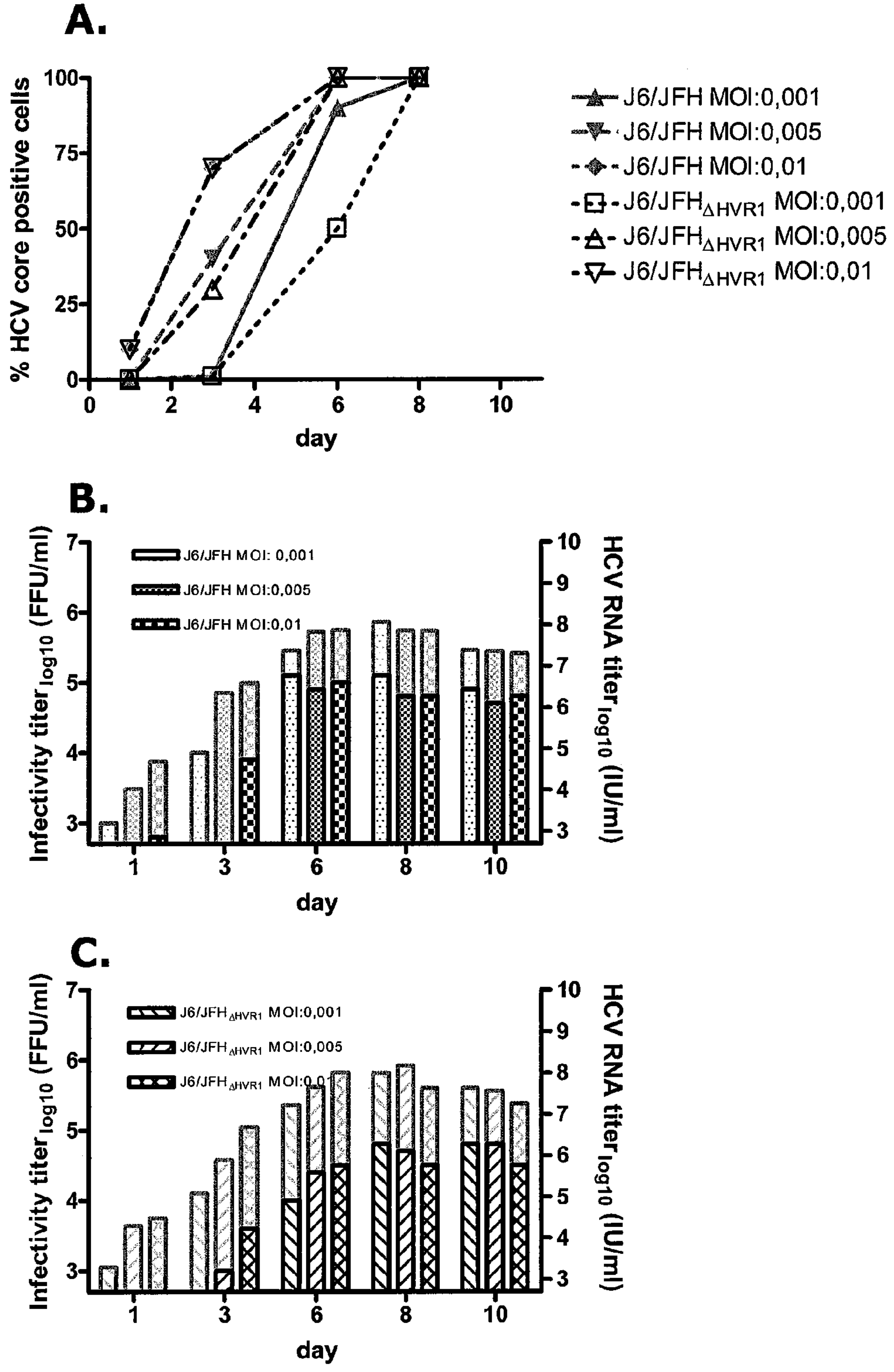
FIG. 2 shows growth kinetics of J6/JFH with and without HVR1 after inoculation with different MOI (multiplicity of infection).

The 81 N-terminal nucleotides of the HCV envelope E2 gene, coding for the 27 N-terminal amino acids of the E2 protein, were deleted from pJ6/JFH yielding the plasmid pJ6/$JFH_{\Delta HVR1}$ (SEQ ID NO: 2 and 8). After transfections of Huh7.5 cells with RNA transcripts of pJ6/JFH and pJ6/$JFH_{\Delta HVR1}$, the percentage of infected cells was estimated by immunostaining and FFU infectivity titers were measured in cell culture supernatants derived on days 3, 6 and 8 post transfection. Both viruses spread immediately upon transfection and had very similar infectivity titers as shown in FIGS. 1, A & B. J6/$JFH_{\Delta HVR1}$ supernatant from day 6 of the transfection was serially passaged to naïve Huh7.5 cells, by transfer of cell culture supernatant, derived at a time point at which virus had spread to at least 80% of cells. Direct sequence analysis of viral genomes contained in supernatant derived from first and second passage of J6/$JFH_{\Delta HVR1}$ at the peak of infection showed no mutations. Thus, J6/$JFH_{\Delta HVR1}$ was not dependent on adaptive mutations. To further investigate whether infectivity of J6/JFH was affected by deletion of HVR1, a kinetic infection experiment was set up with three different MOIs (Multiplicity of Infection, $TCID_{50}$/number of Huh7.5 cells): 0.001, 0.005 and 0.01. The spread of both viruses correlated well with the rises in infectivity and HCV RNA titers and the two viruses behaved quite similarly at all three MOIs (FIGS. 2, A, B & C). Thus, HVR1 deletion does not measurably inhibit infectivity of J6/JFH, even though peak virus infectivity titers of cell culture supernatant might be slightly delayed.

Example 2

Figure 3:
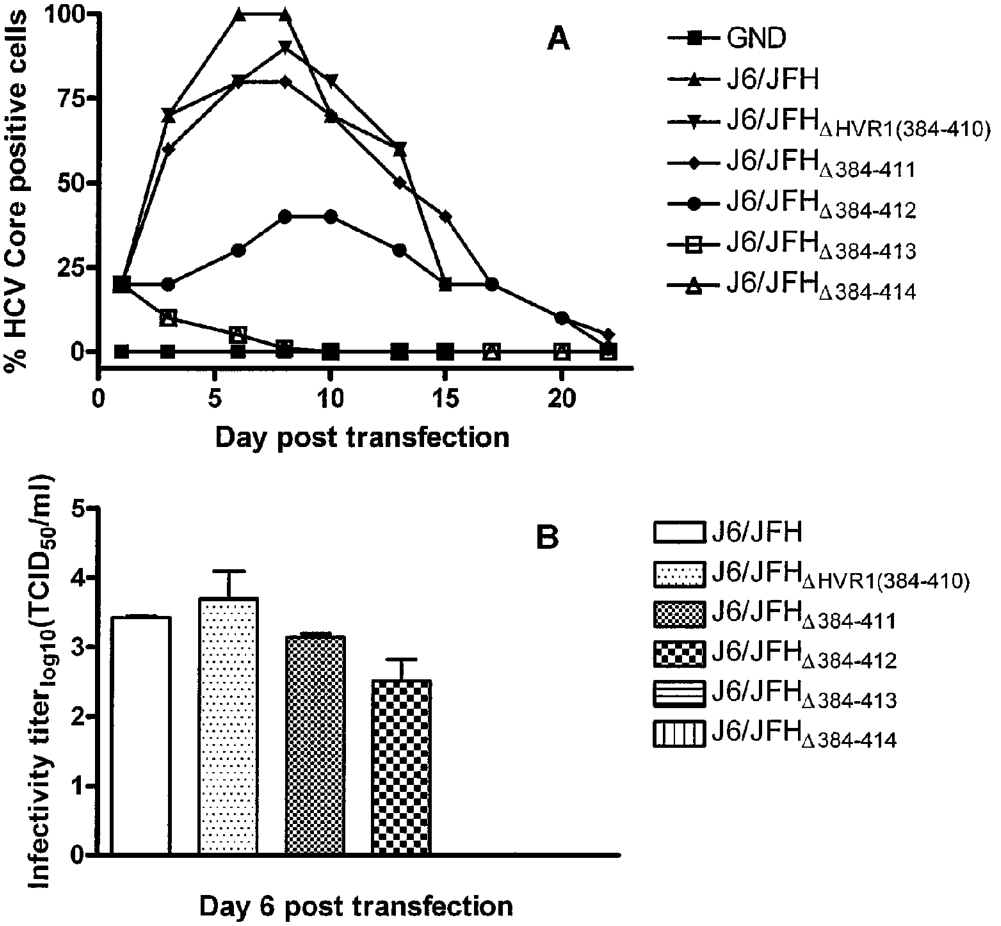
FIG. 3 shows transfection of J6/JFH$_{\Delta HVR1}$ (corresponding to deletion of aa 384-410) compared to J6/JFH$_{\Delta 384\text{-}411}$, J6/JFH$_{\Delta 384\text{-}412}$, J6/JFH$_{\Delta 384\text{-}413}$ and J6/JFH$_{\Delta 384\text{-}414}$.

Determination of the functional borders of HVR1 by deletion of additional amino acids downstream of HVR1.

pJ6/$JFH_{\Delta HVR1}$ with an additional deletion of 1 to 4 aa immediately downstream of HVR1 were generated and tested in cell culture. Supernatant from day 6 post transfection was titrated twice for infectivity ($TCID_{50}$) to ascertain viability of the generated constructs. This showed that J6/$JFH_{\Delta HVR1}$ tolerates the removal of 1 aa downstream of HVR1, is attenuated by the removal of 2 aa and is rendered non-infectious by deletions of 3 and 4 additional aa (FIGS. 3 A & B). This new data lends credence to the original classification of HVR1, which was based on sequence variability, by linking HVR1 truncation extension downstream in J6/$JFH_{\Delta HVR1}$ to reduced virus viability.

Example 3

Deletion of HVR1 across all 6 major genotypes.

H77/$JFH1_{T2700C,A4080T}$ (1a/2a)

Figure 4:
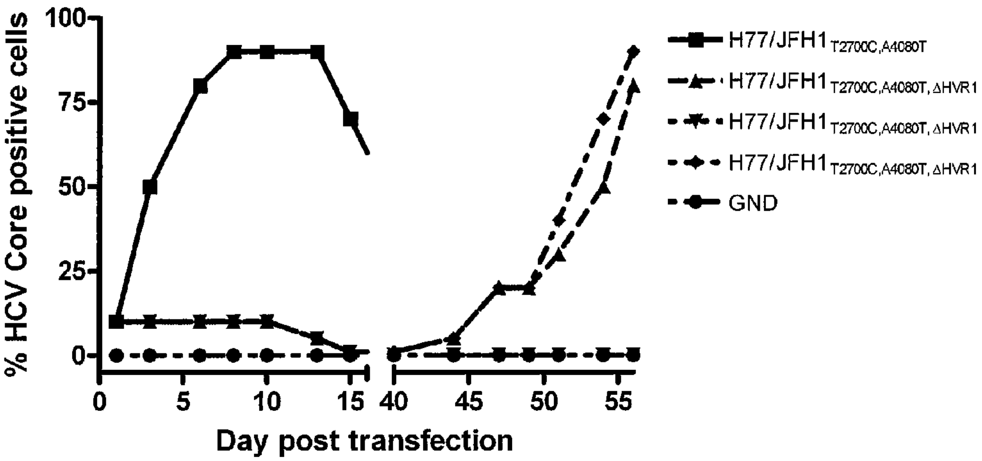
FIG. 4 shows transfection of H77/JFH1$_{T2700C,A4080T,\Delta HVR1}$.
Figure 5:
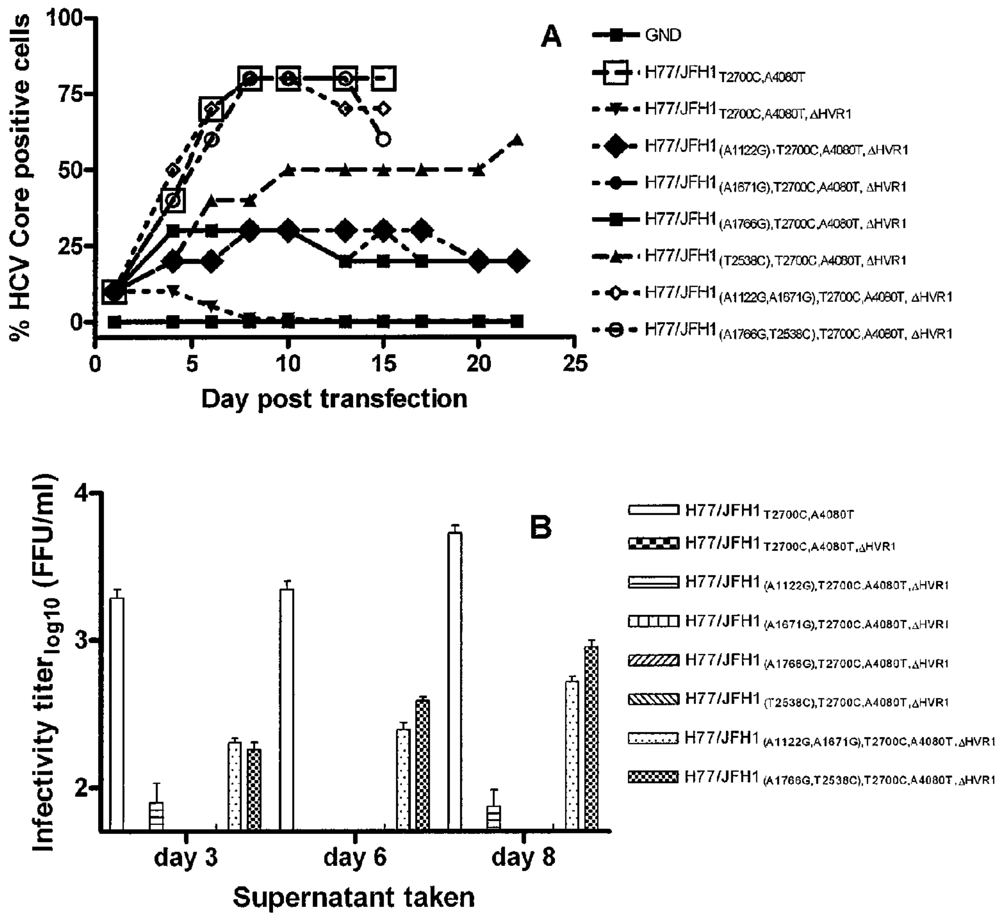
FIG. 5 shows transfection testing efficacy of adaptive mutations identified for H77/JFH1$_{T2700C,A4080T,\Delta HVR1}$.

The HVR1 region corresponding to the 27 N-terminal aa of E2 was deleted in pH77/$JFH1_{T2700C,A4080T}$, and yielding the plasmid pH77/$JFH1_{T2700C,A4080T,\Delta HVR1}$ (SEQ ID NO: 1 and 7). A transfection of H77/$JFH1_{T2700C,A4080T,\Delta HVR1}$ was set up in triplicates. H77/$JFH1_{T2700C,A4080T,\Delta HVR1}$ was highly attenuated in all three transfections with no immediate increase in the percentage of infected cells (FIG. 4), although very low infectivity was evident in $TCID_{50}$ titration of cell culture supernatant from day 3 (data not shown). However, infected cells persisted and on day 56, in two out of three transfection experiments, viral spread that eventually lead to infection of almost the entire cell culture was observed. At the peak of infection, viral genomes were extracted and sequenced as described. Interestingly, both viruses had a combination of two mutations in the envelope genes and in each set of mutations there was a mutation either in HVR2 or HVR3 (Table 1). In reverse genetic studies, H77/$JFH1_{T2700C,A4080T,\Delta HVR1}$ were tested with the identified four envelope mutations singly or in the two observed combinations. The resulting 6 virus constructs were set up in a transfection alongside the original pH77/$JFH1_{T2700C,A4080T,\Delta HVR1}$. The transfection data is shown in FIGS. 5, A & B and clearly shows that the HVR1 deleted constructs with either of the two envelope mutation combinations (H77/$JFH1_{(A1122G,A1671G),T2700C,A4080T,\Delta HVR1}$: SEQ ID NO: 13 and 16, H77/$JFH1_{(A1766G,T2538C),T2700C,A4080T,\Delta HVR1}$: SEQ ID NO: 14 and 17) spreads as quickly as the parental virus. In contrast, the single mutation constructs did not. However, from the supernatant infectivity titration it is evident, that these two viruses are still attenuated, reaching infectivity titers of $10^{2,7}$ and $10^{3,0}$ FFU/ml respectively on day 8 as compared to $10^{3,8}$ FFU/ml for H77/$JFH1_{T2700C,A4080T}$, on day 8 while viruses with single mutations had infectivity titers below $10^{2,0}$ FFU/ml on all days.

J4/$JFH1_{T1389C,A1590G}$, (1b/2a)

Figure 6:
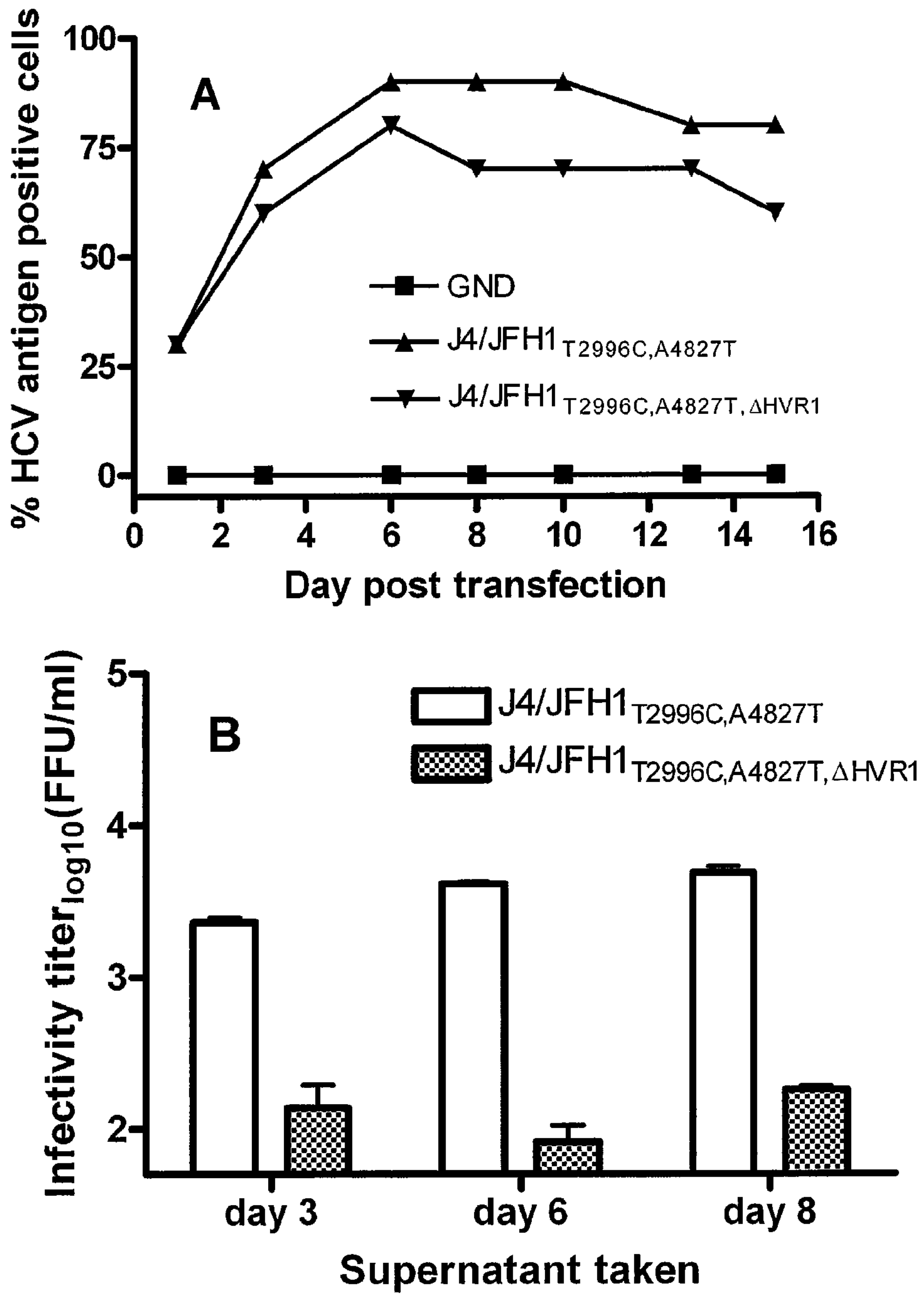
FIG. 6 shows transfection of J4/JFH1$_{T2996C,A4827T,\Delta HVR1}$ (1b/2a).

The HVR1 motif was deleted in pJ4/$JFH1_{T2996C,A4827T}$, corresponding to the 27 N-terminal aa of E2, and yielding the plasmid pJ4/$JFH1_{T2996C,A4827T,\Delta HVR1}$ (SEQ ID NO: 19 and 22). A transfection was set up with pJ4/$JFH1_{T2996C,A4827T,\Delta HVR1}$. The virus spread immediately, but only to about 60-70% of the cells and had very slow spread in viral passaging of supernatant. The virus was sequenced after spread. Transfection data is summarized in FIGS. 6, A & B and shows that the HVR1 deleted virus is about 20-fold less infectious than the parental J4/$JFH1_{T2996C,A4827T}$. Viruses identified in 1st and 2nd passage of J4/$JFH1_{T2996C,A4827T,\Delta HVR1}$ are shown in Table 2.

J8/JFH1 (2b/2a)

Figure 7:
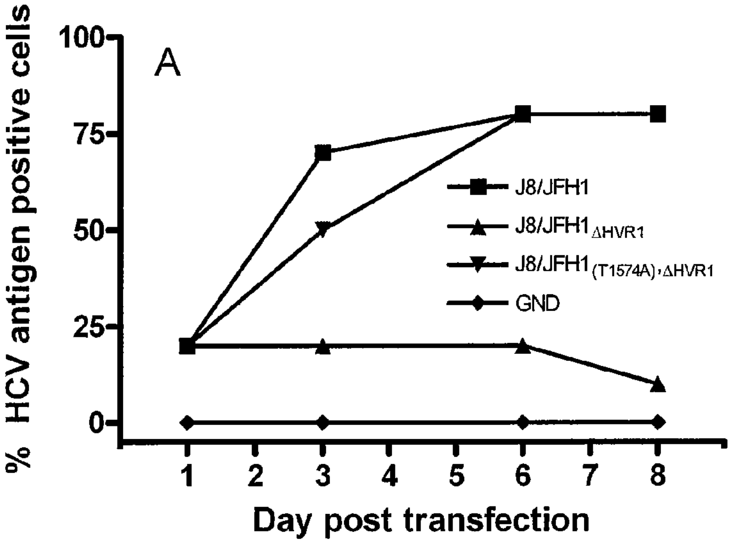
FIG. 7 shows transfection to test efficacy of adaptive mutation T1574A on J8/JFH1$_{\Delta HVR1}$ (2b/2a).
Figure 7:
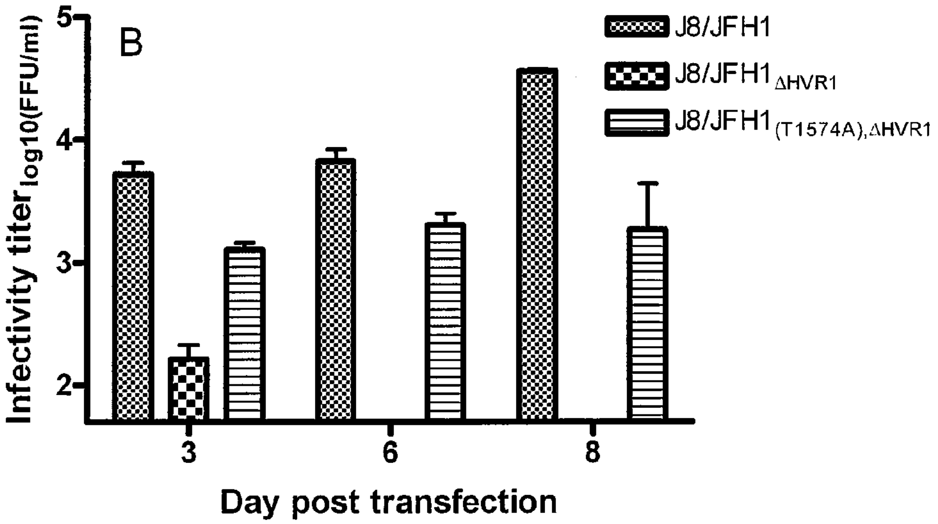

The HVR1 motif was deleted in pJ8/JFH1, corresponding to the 27 N-terminal aa of E2, and yielding the plasmid pJ8/$JFH1_{\Delta HVR1}$ (SEQ ID NO: 20 and 23). A transfection was set up with pJ8/$JFH1_{\Delta HVR1}$. The virus did not spread immediately. 1st passage viral supernatants were sequenced once they spread. The mutation T1574A was seen in two separate 1st viral passages and was introduced into J8/$JFH1_{\Delta HVR1}$ for reverse genetic studies. This was set up in a transfection alongside J8/JFH1 and J8/JFH1$_{\Delta HVR1}$ Transfection data is summarized in FIGS. 7 A and B and shows that T1574A is clearly adapting the HVR1 deleted virus, although J8/JFH1$_{(T1574A),\Delta HVR1}$ is still about 10-fold less infectious than the parental J8/JFH1 (J8/JFH1$_{(T1574A),\Delta HVR1}$ SEQ ID NO: 21 & 24). Viruses identified in 1$^{st}$ passages of J8/JFH1$_{\Delta HVR1}$ are shown in Table 3.

S52/JFH1$_{T2718G,T7160C}$, (3a/2a)

Figure 8:
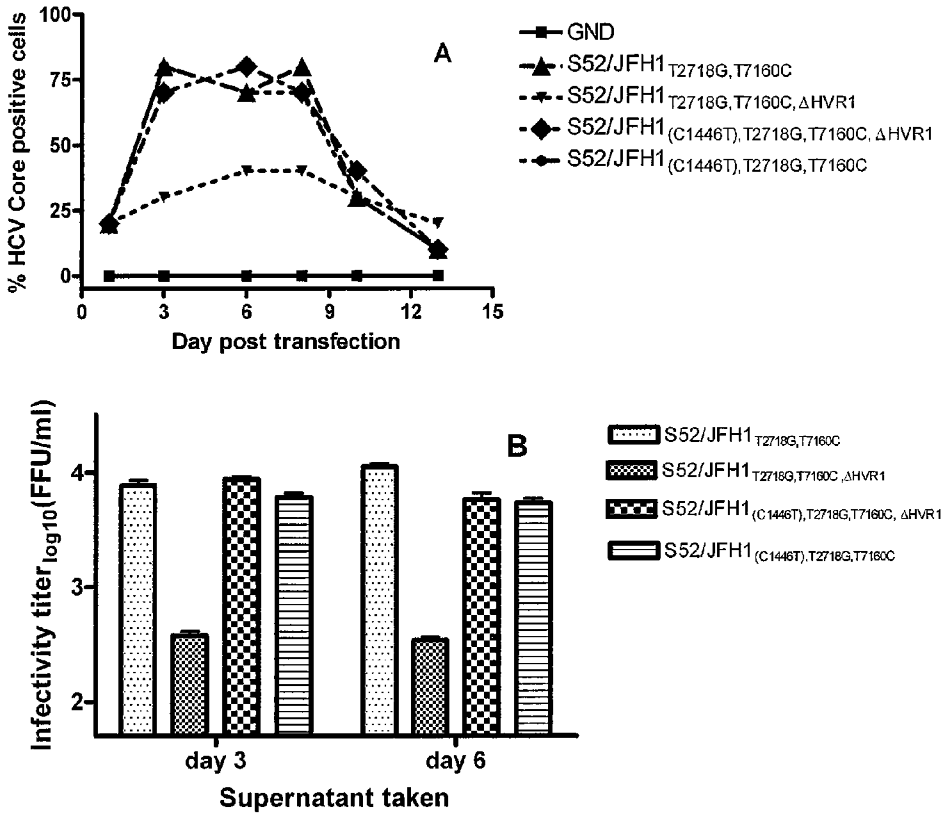
FIG. 8 shows transfection to test efficacy of adaptive mutation C1446T on S52/JFH1$_{T2718G,T7160C}$, and S52/JFH1$_{T2718G,T7160C,\Delta HVR1}$ (3a/2a).

The HVR1 motif was deleted in pS52/JFH1$_{T2718G,T7160C}$, corresponding to the 27 N-terminal aa of E2, and yielding the plasmid pS52/JFH1$_{T2718G,T7160C,\Delta HVR1}$ (SEQ ID NO: 3 and 9). In a transfection experiment, S52/JFH1$_{T2718G,T7160C,\Delta HVR1}$ spread immediately, however, delayed viral spread in a first passage as well as TCID$_{50}$ infectivity assays of both transfection and 1$^{st}$ passage (data not shown) indicated that the virus was attenuated. Growth kinetic improved upon serial passages (data not shown) and the HCV ORFs were sequenced in passages 2 and 4 once virus had spread to at least 80% infected cells. In both sequences a mutation in the transmembrane domain of E1 was identified corresponding to plasmid nucleotide change C1446T (Table 4). This mutation was introduced into both pS52/JFH 1$_{T2718G,T7160C}$ and pS52/JFH 1$_{T2718G,T7160C,\Delta HVR1}$ (pS52/JFH1$_{(C1446T),T2718G,T7160C,\Delta HVR1}$: SEQ ID NO: 15 and 18). A transfection was set up including S52/JFH1$_{(C1446T),T2718G,T7160C,\Delta HVR1}$, S52/JFH1$_{T2718G,T7160C,\Delta HVR1}$ and S52/JFH1$_{(C1446T),T2718G,T7160C}$ alongside S52/JFH1$_{T2718G,T7160C}$. Of these only pS52/JFH1$_{T2718G,T7160C,\Delta HVR1}$ did not spread immediately and the suggested lower infectivity was confirmed by infectivity titration of days 3 and 6 (FIGS. 8, A & B). This data clearly shows that the E1 mutation C1446T adapts the virus quite effectively to the HVR1 deletion, but does not boost infectivity of the parental S52/JFH1$_{T2718G,T7160C}$ virus.

ED43/JFH1$_{A2819G,A3269T}$ (4a/2a)

Figure 9:
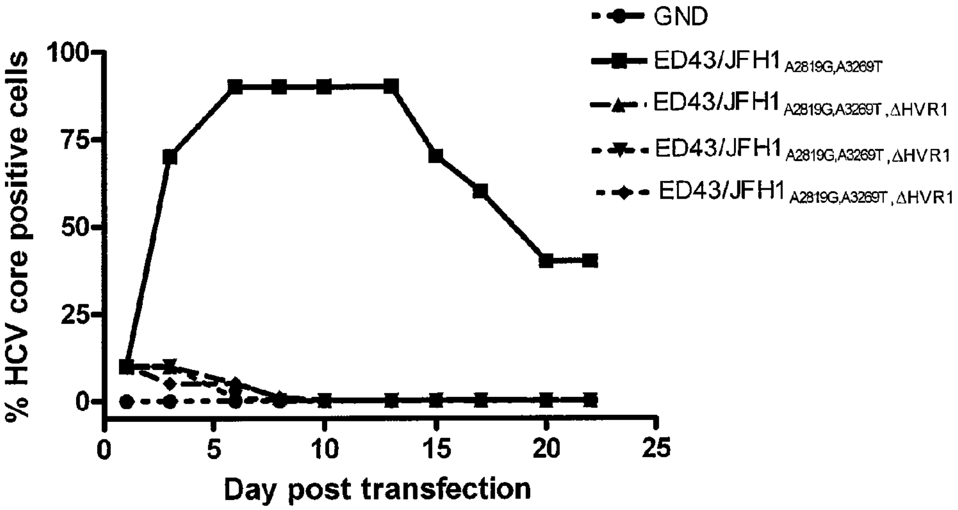
FIG. 9 shows transfection of ED43/JFH1$_{A2819G,A3269T,\Delta HVR1}$ (4a/2a).

The HVR1 motif was deleted in pED43/JFH1$_{A2819G,A3269T}$, corresponding to the 27 N-terminal aa of E2, and yielding the plasmid pED43/JFH1$_{A2819G,A3269T,\Delta HVR1}$ (SEQ ID NO: 4 and 10). A transfection was set up in triplicates. The transfection data in FIG. 9 shows that ED43/JFH1$_{A2819G,A3269T,\Delta HVR1}$ did not spread and no infectivity was detected in culture supernatants (data not shown). Transfections were followed until no infected cells could be detected in HCV specific immunostainings.

SA13/JFH1$_{C3405G,A3696G}$, (5a/2a)

Figure 10:
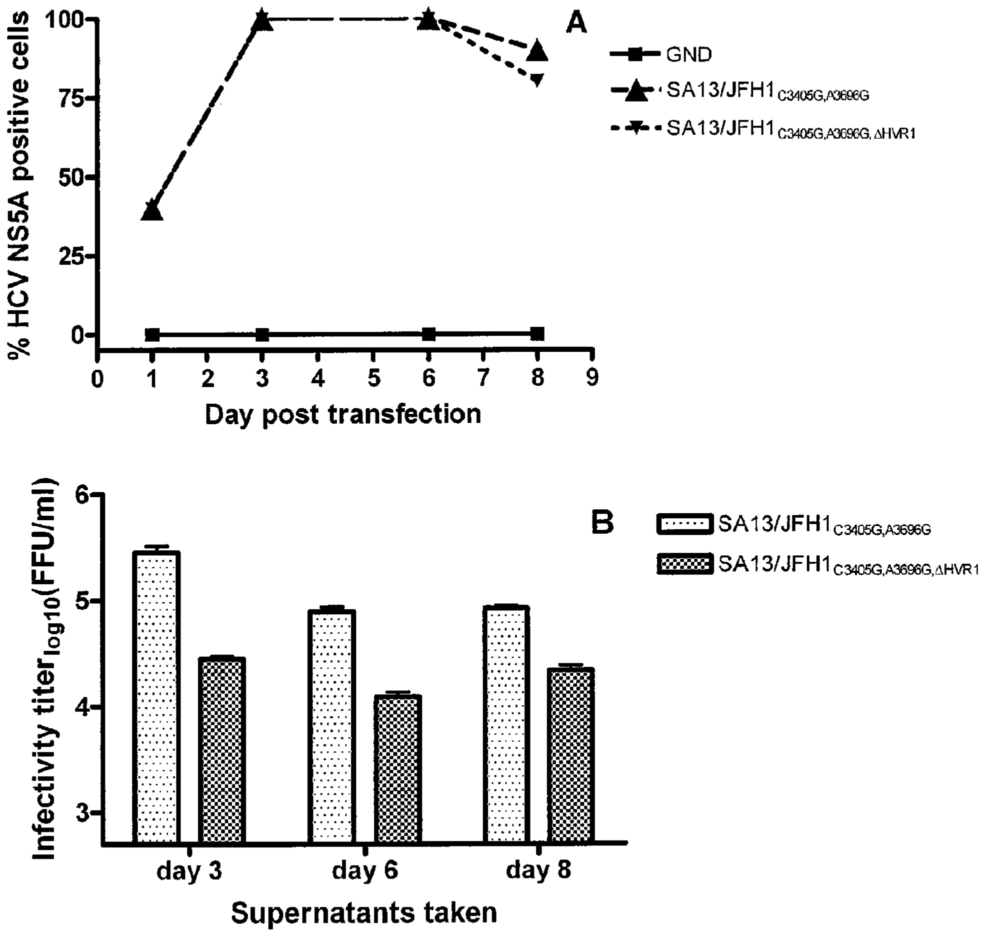
FIG. 10 shows transfection of SA13/JFH1$_{C3405G,A3696G,\Delta HVR1}$ (5a/2a).

The HVR1 motif was deleted in pSA13/JFH1$_{C3405G,A3696G}$, corresponding to the 27 N-terminal aa of E2, and yielding the plasmid pSA13/JFH1$_{C3405G,A3696G,\Delta HVR1}$ (SEQ ID NO: 5 and 11). FIGS. 10, A & B shows the transfection data with immediate virus spread of SA13/JFH1$_{C3405G,A3696G,\Delta HVR1}$ and that it was only slightly less infectious than the parental SA13/JFH1$_{C3405G,A3696G}$.

HK6a/JFH1$_{T1389C,A1590G}$, (6a/2a)

Figure 11:
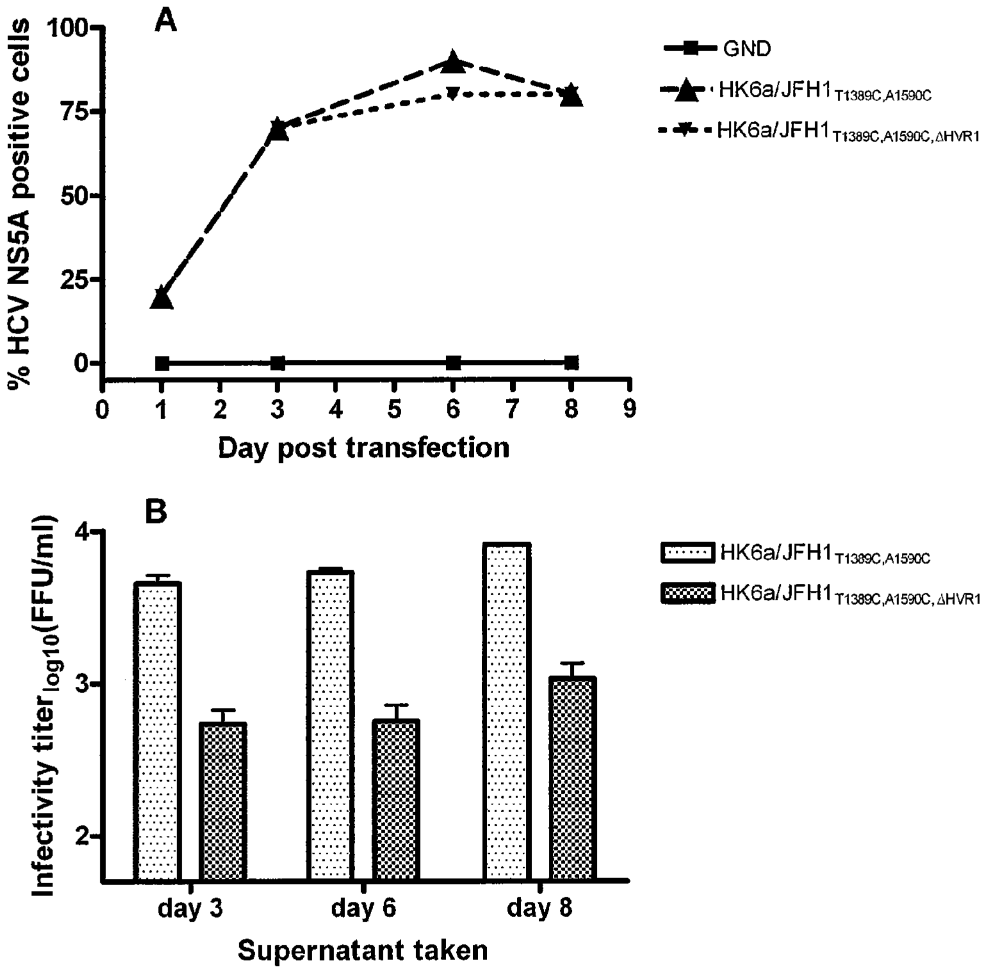
FIG. 11 shows transfection of HK6a/JFH1$_{T1389C,A1590G,\Delta HVR1}$ (6a/2a).

The HVR1 motif was deleted in pHK6a/JFH1$_{T1389C,A1590G}$, corresponding to the 26 N-terminal aa of E2, and yielding the plasmid pHK6a/JFH1$_{T1389C,A1590G,\Delta HVR1}$ (SEQ ID NO: 6 and 12). A transfection was set up with HK6a/JFH1$_{T1389C,A1590G,\Delta HVR1}$. The virus spread immediately and had acquired no additional mutations in sequence analysis of 2nd passage supernatant of cell culture having at least 80% infected cells. Transfection data is summarized in FIGS. 11, A & B and shows that the HVR1 deleted virus is about ten-fold less infectious than the parental HK6a/JFH1$_{T1389C,A1590G}$.

In Table 5 the viability of the HVR1 deleted viruses is summarized by listing required adaptive mutations when appropriate as well as infectivity titers determined on supernatants derived on the first days after transfection. These titers are used in the calculations of the relative infectivities compared to the respective parental viruses on the given day of transfection and the present inventors thereby show that the HVR1 deleted viruses are viable in a range of non-affected (J6) to complete disruption of infectivity (ED43). These differences are dependent on the isolate and possibly the subtype. Additionally, it is shown that H77/JFH1$_{T2700C,A4080T,\Delta HVR1}$ (1a/2a), J4/JFH1$_{T2996C,A4827T,\Delta HVR1}$ (1b/2a), J8/JFH1$_{\Delta HVR1}$ (2b/2a) and S52/JFH1$_{T2718G,T7160C,\Delta HVR1}$ (3a/2a) are dependent on adaptive mutations.

Accordingly, the present inventors were able to generate HVR1 motif deleted viruses of JFH1-based intra- and intergenotypic HCV recombinants H77/JFH1$_{T2700C,A4080T}$ (1a/2a), J4/JFH1$_{T2996C,A4827T}$ (1b/2a), J6/JFH (2a/2a), J8/JFH1 (2b/2a), S52/JFH1$_{T2718G,T7160C}$ (3a/2a), SA13/JFH1$_{C3405G,A3696G}$ (5a/2a) and HK6a/JFH1$_{T1389C,A1590G}$ (6a/2a). H77/JFH1$_{T2700C,A4080T,\Delta HVR1}$ (1a/2a), J4/JFH1$_{T2996C,A4827T,\Delta HVR1}$ (1b/2a), J8/JFH1$_{\Delta HVR1}$ (2b/2a) and S52/JFH1$_{T2718G,T7160C,\Delta HVR1}$ (3a/2a) required adaptive mutations in the envelope genes E1 and/or E2 to improve virus infectivity.

Example 4

21 aa Deletion N-Terminally in E2 of H77/JFH1$_{T2700C,A4080T}$ (1a/2a) and ED43/JFH1$_{A2819G,A3269T}$ (4a/2a)

Figure 12:
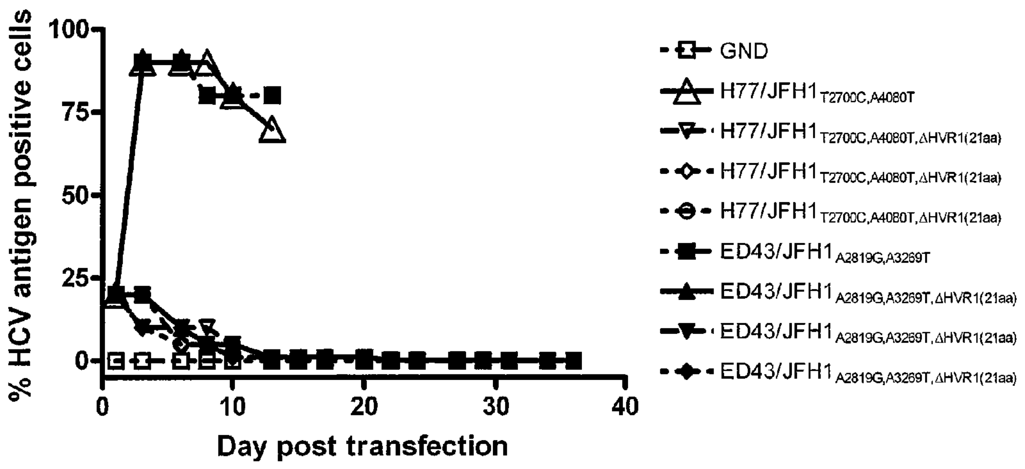
FIG. 12 shows transfection of Huh7.5 cells with E2 N-terminal deletions of only 21 aa for H77/JFH1$_{T2700C,A4080T}$ (1a/2a) and ED43/JFH1$_{A2819G,A3269T}$ (4a/2a).

To investigate if shorter HVR1 regions for H77/JFH1$_{T2700C,A4080T}$ and ED43/JFH1$_{A2819G,A3269T}$ were the reason why these constructs did not spread with a 27 aa HVR1 deletion the present inventors generated constructs in which 21 N-terminal amino acids of E2 were deleted. These were then set up in triplicate transfections (FIG. 12). Since no improvements in viral spread were observed shorter deletions did not improve the fitness of the truncated viruses.

Example 5

Neutralization of HCV by Patient Sera

Figure 13:
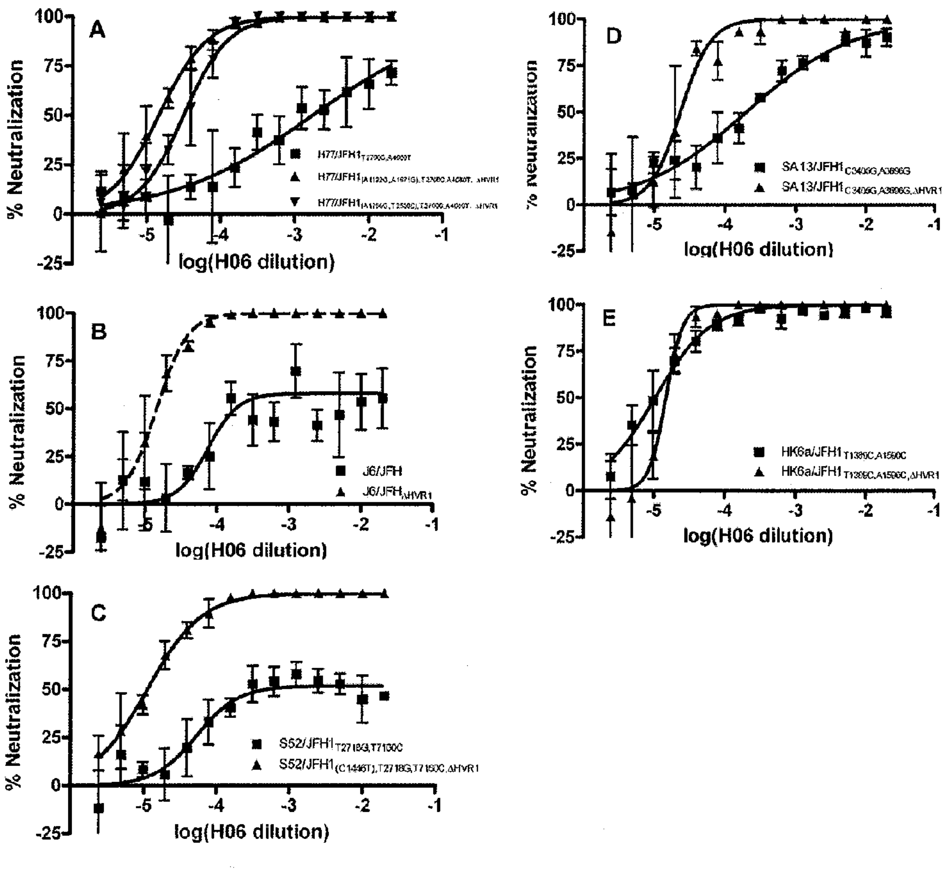
FIG. 13 shows neutralization with HCV patient serum H06 for viruses with and without HVR1.

Neutralization of HCV by patient sera shows distinct differences between genotypes and between identical viruses with and without HVR1. The present inventors investigated how neutralization of wt and HVR1 truncated viruses compared using the H06 serum. It is evident (FIG. 13, A-E) that in all direct comparisons, except for HK6a/JFH1$_{T1389C,A1590C}$ neutralization is markedly improved for the HVR1 truncated viruses. Since the amino acid sequences are identical, aside from the HVR1 truncation, the conclusion is that additional epitopes are available on the surface of the HVR1 truncated viruses, indicating that they must somehow be shielded in the wt virus particle. This is further substantiated by the much higher degree of neutralization diversity seen for the wt viruses, when compared to the complete and narrow transition from 0 to 100% neutralization at high serum dilutions for all of the HVR1 truncated viruses. The J6/JFH and S52/JFH1$_{T2718G,T7160C}$ viruses reach a plateau of neutralization suggesting at least two structurally distinct populations of viruses whereas their HVR1 truncated counterparts are both neutralized very efficiently. The H77/JFH$_{T2700C,A4080T}$, SA13/JFH1$_{C3405G,A3696G}$ and HK6a/

$JFH1_{T1389C,A1590G,\Delta HVR1}$ all show the same pattern going toward complete neutralization stretched over a large span of the serum dilution series, indicating either that multiple populations are also present for these viruses and being neutralized at different efficiencies by the serum or that the serum targeted epitopes, though available, are not as easily accessible as for the HVR1 truncated viruses.

Figure 15:
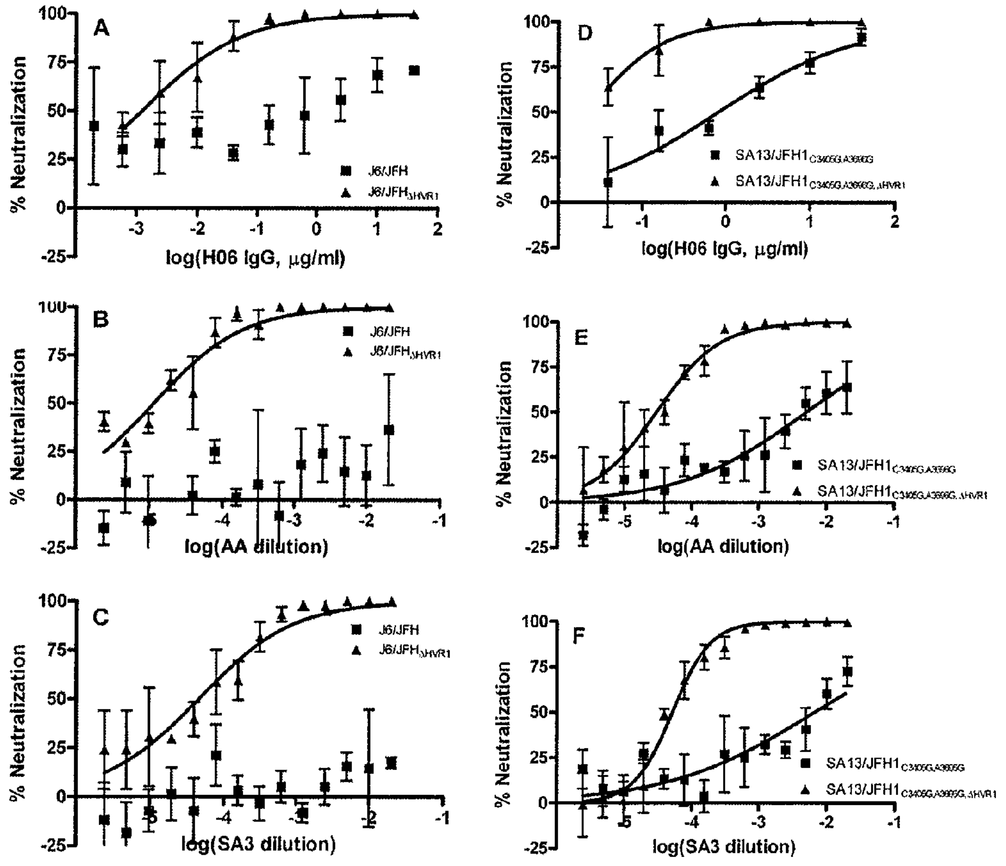
FIG. 15 shows neutralization of HVR1 truncated viruses with IgG purified from serum H06 and also by HCV patient sera AA and SA3.

To further substantiate these findings two wt viruses and their HVR1 truncated counterparts were selected, based on differences in the wt neutralization pattern. These viruses were subjected to neutralization with purified H06 IgG as well as two different sera; AA and SA3 (FIGS. 15 A-F). The trend of the H06 serum is seen again for the purified H06 IgG though it is not as clearly defined, showing that the neutralizing effects seen for full serum can be attributed to specific, neutralizing IgG antibodies present in the patient serum. Both the AA and the SA3 sera effectively block $J6/JFH_{\Delta HVR1}$, much like what was seen for H06, but the corresponding J6/JFH is not significantly neutralized even at the lowest serum dilution of 1:50.

Figure 14:
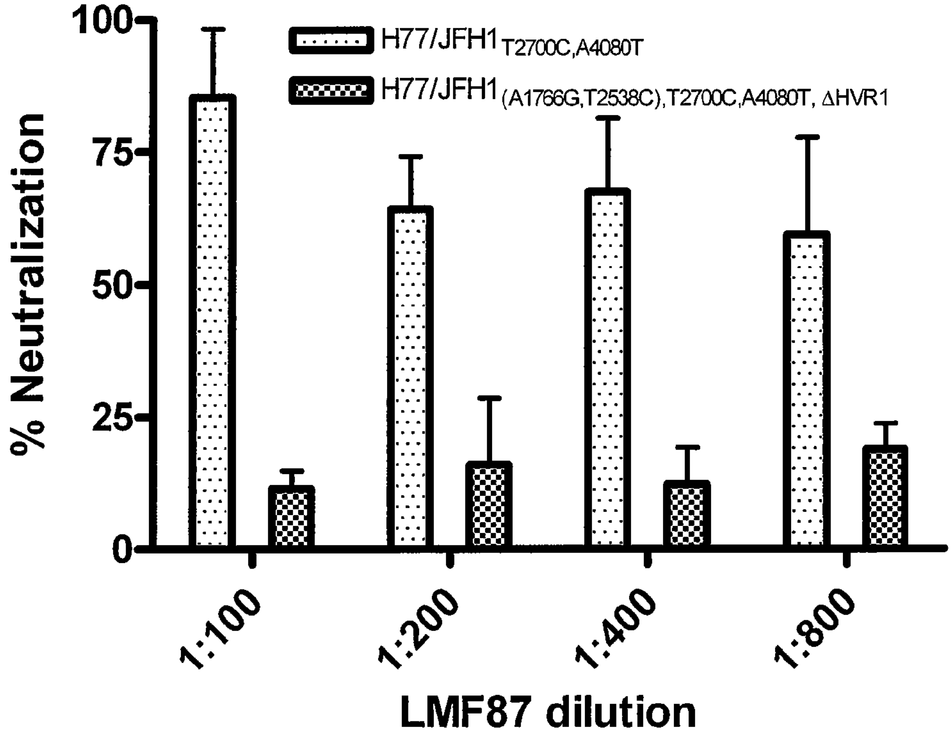
FIG. 14 shows activity of HVR1 specific hyperimmune serum against H77/JFH1$_{T2700C,A4080T}$ (1a/2a) and H77/JFH1$_{T2700C,A4080T,\Delta HVR1}$ (1a/2a).

To investigate whether HVR1 in fact contains neutralization epitopes for the wt viruses, the present inventors used the rabbit hyper-immune serum, LMF87, raised against an HVR1 peptide from H77 in a neutralizing assay against $H77/JFH1_{T2700C,A4080T}$ and $H77/JFH1_{(A1766G,T2538C),T2700C,A4080T,\Delta HVR1}$ (FIG. 14). It clearly demonstrates a significant effect against the wt virus and no significant effect against the HVR1 truncated virus, lacking the HVR1 epitopes against which the hyper-immune serum was raised. This shows that HVR1 is, indeed, displayed on the surface of the wt virus particle, despite the probable shielding of other epitopes that are available for the HVR1 truncated viruses. The neutralizing effect against HVR1 epitopes could be a purely steric one, but it might also suggest a functional role for HVR1 in the wt virus particle.

Example 6

Figure 16:
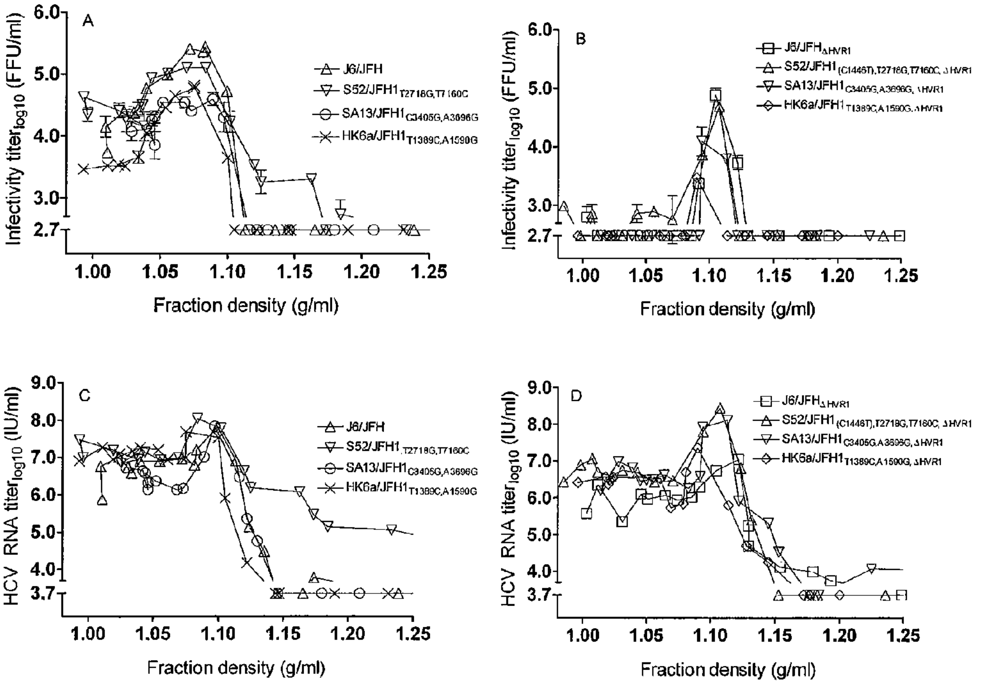
FIG. 16 shows analysis of samples following ultracentrifugation. Specifically, RNA and infectivity titers of fractions with different densities for viruses: J6/JFH (2a/2a), J6/JFH$_{\Delta HVR1}$ (2a/2a), S52/JFH1$_{T2718G,T7160C}$ (3a/2a), S52/JFH1$_{(C1446T),T2718G,T7160C,\Delta HVR1}$ (3a/2a), SA13/JFH1$_{C3405G,A3696G}$ (5a/2a), SA13/JFH1$_{C3405G,A3696G,\Delta HVR1}$ (5a/2a) and HK6a/JFH1$_{T1389C,A1590G}$ (6a/2a) and HK6a/JFH1$_{T1389C,A1590G,\Delta HVR1}$ (6a/2a).

Density of HCV RNA and infectious particles of virus with and without HVR1. To investigate the reason why HVR1 truncated viruses were continuously being neutralized more effectively than their non-truncated counterparts the present inventors ran density gradients of the viruses J6/JFH, $S52/JFH1_{T2718G,T7160C}$, $SA13/JFH1_{C3405G,A3696G}$ and $HK6a/JFH1_{T1389C,A1590G}$ against the respective HVR1 deleted counterparts and assessed infectivity titers in the different fractions (FIGS. 16 A, B, C & D). No difference is observed when comparing HCV RNA distributions of the density analysis. However, clear differences between HVR1 truncated and non-truncated viruses are seen for density of infectious virus. HVR1 deletion changed the density of infectious virus from between 1.0-1.1 g/ml to a single peak around 1.1 g/ml. This shift suggests that virus particles with a high degree of lipid association are not infectious in the absence of HVR1. The increased homogeneity of the infectious virus particles coupled with a low lipid association might well be what is reflected in the observed neutralization data.

FIGURE LEGENDS

FIG. 1

Transfection of Huh7.5 cells with J6/JFH with and without HVR1.

HCV RNA was transfected into Huh7.5 cells to test the performance of $J6/JFH_{\Delta HVR1}$ as compared to J6/JFH. A GND motif replication deficient J6/JFH virus (GND) was used as negative control. A: Percentage of infected cells was estimated by fluorescence microscopy after immunostaining for HCV proteins Core or NS5A to quantify viral spread. B: Infectivity titers were determined as FFU/mL using three independent ten-fold dilution series of each cell culture supernatant from the indicated day of the transfection experiment (cut-off: 1.7). Means are shown and Error bars are SD.

FIG. 2

Growth kinetics of J6/JFH with and without HVR1 after inoculation with different MOI.

Huh7.5 cells were infected with three different MOIs of both J6/JFH and $J6/JFH_{\Delta HVR1}$. A: Cells were immunostained for HCV proteins Core or NS5A to quantify viral spread. B: Three replicates of a ten-fold dilution series of cell culture supernatants from the indicated day of transfection was used in HCV infectivity titrations (cut-off: 2.7 logs) of J6/JFH and $J6/JFH_{\Delta HVR1}$ (black bars, left Y-axis). C: A single HCV RNA titration using TaqMan realtime PCR (cut-off: 2.7 logs, grey bars, right Y-axis).

FIG. 3

Transfection of Huh7.5 cells with J6/JFH, $J6/JFH_{\Delta HVR1}$ (Corresponding to aa deletion of 384-410), $J6/JFH_{\Delta 384-411}$, $J6/JFH_{\Delta 384-412}$, $J6/JFH_{\Delta 384-413}$ and $J6/JFH_{\Delta 384-414}$.

RNA transcripts were transfected into Huh7.5 cells to test the performance of $J6/JFH_{\Delta HVR1}$ (Corresponding to aa deletion of 384-410), $J6/JFH_{\Delta 384-411}$, $J6/JFH_{\Delta 384-412}$, $J6/JFH_{\Delta 384-413}$ and $J6/JFH_{\Delta 384-414}$ as compared to J6/JFH. A GND motif replication deficient J6/JFH virus (GND) was used as negative control. A: Cells were immunostained for HCV proteins Core or NS5A to quantify viral spread. B: Ten-fold dilution series of cell culture supernatants from day 6 of transfection was used in two separate HCV infectivity titrations by TCID50.

FIG. 4

Transfection of Huh7.5 cells with $H77/JFH1_{T2700C,A4080T}$ with and without HVR1.

HCV RNA was transfected into Huh7.5 cells to test the performance of $H77/JFH1_{T2700C,A4080T,\Delta HVR1}$ as compared to $H77/JFH1_{T2700C,A4080T}$ with a GND motif replication deficient J6/JFH virus (GND). $H77/JFH1_{T2700C,A4080T,\Delta HVR1}$ was set up in three separate transfections; transfection 1 (upward triangles), transfection 2 (downward triangles) and transfection 3 (diamonds). Cells were immunostained for HCV proteins Core or NS5A to quantify viral spread.

FIG. 5

Transfection of Huh7.5 cells testing efficacy of adaptive mutations identified for $H77/JFH1_{T2700C,A4080T,\Delta HVR1}$.

HCV RNA was transfected into Huh7.5 cells to test the performance of the mutations A1122G, A1671G, A1766G and T2538C on viability of $H77/JFH1_{T2700C,A4080T,\Delta HVR1}$ as compared to $H77/JFH1_{T2700C,A4080T}$ with a GND motif replication deficient J6/JFH virus (GND). A: Cells were immunostained for HCV proteins Core or NS5A to quantify viral spread. B: Three independent ten-fold dilution series of cell culture supernatants from the indicated day of transfection was used in HCV infectivity titrations (cut-off: 1.7 logs). Single mutation constructs showed slightly improved infectivity over $H77/JFH1_{T2700C,A4080T,\Delta HVR1}$ (trend below assay cut-off and therefore not shown by barplot). Means are shown and Error bars are SD.

FIG. 6

Transfection of Huh7.5 cells with $J4/JFH1_{T2996C,A4827T}$ with and without HVR1.

HCV RNA was transfected into Huh7.5 cells to test the performance of $J4/JFH1_{T2996C,A4827T,\Delta HVR1}$ as compared to $J4/JFH1_{T2996C,A4827T}$. A GND motif replication deficient J6/JFH virus (GND) was used as negative control. A: Percentage of infected cells was estimated by fluorescence microscopy after immunostaining for HCV proteins Core or NS5A to quantify viral spread. B: Infectivity titers were determined as FFU/mL using three independent ten-fold dilution series of each cell culture supernatant from the indicated day of the transfection experiment (cut-off: 1.7). Means are shown and Error bars are SD.

FIG. 7

Transfection of Huh7.5 cells with J8/JFH1, J8/JFH1$_{\Delta HVR1}$ and J8/JFH1$_{(T1574A),\Delta HVR1}$.

HCV RNA was transfected into Huh7.5 cells to test the performance of the putative adaptive mutation T1574A on J8/JFH$_{\Delta HVR1}$ viability as compared to J8/JFH1 and J8/JFH1$_{\Delta HVR1}$. A GND motif replication deficient J6/JFH virus (GND) was used as negative control. A: Percentage of infected cells was estimated by fluorescence microscopy after immunostaining for HCV proteins Core or NS5A to quantify viral spread. B: Infectivity titers were determined as FFU/mL using three independent ten-fold dilution series of each cell culture supernatant from the indicated day of the transfection experiment (cut-off: 1.7). Means are shown and Error bars are SD.

FIG. 8

Transfection of Huh7.5 cells to test efficacy adaptive mutation C1446T on S52/JFH1$_{T2718G,T7160C}$ and S52/JFH1$_{T2718G,T7160C,\Delta HVR1}$.

HCV RNA was transfected into Huh7.5 cells to test the performance of the effect of C1446T on S52/JFH1$_{T2718G,T7160C}$ and S52/JFH1$_{T2718G,T7160C,\Delta HVR1}$ as compared to S52/JFH1$_{T2718G,T7160C}$ with a GND motif replication deficient J6/JFH virus (GND) as negative control. A: Cells were immunostained for HCV proteins Core or NS5A to quantify viral spread. B: Three independent ten-fold dilution series of cell culture supernatants from the indicated day of transfection was used in HCV infectivity titrations (cut-off: 1.7 logs).

FIG. 9

Transfection of Huh7.5 cells with ED43/JFH1$_{A2819G,A3269T}$ with and without HVR1

HCV RNA was transfected into Huh7.5 cells to test the performance of ED43/JFH1$_{A2819G,A3269T,\Delta HVR1}$ as compared to ED43/JFH1$_{A2819G,A3269T}$ with a GND motif replication deficient J6/JFH virus (GND). ED43/JFH1$_{A2819G,A3269T,\Delta HVR1}$ was set up in three separate transfections; transfection 1 (upward triangles), transfection 2 (downward triangles) and transfection 3 (diamonds). Cells were immunostained for HCV proteins Core or NS5A to quantify viral spread.

FIG. 10

Transfection of Huh7.5 cells with SA13/JFH1$_{C3405G,A3696G}$ with and without HVR1.

HCV RNA was transfected into Huh7.5 cells to test the performance of SA13/JFH1$_{C3405G,A3696G,\Delta HVR1}$ as compared to SA13/JFH1$_{C3405G,A3696G}$. A GND motif replication deficient J6/JFH virus (GND) was used as negative control. A: Percentage of infected cells was estimated by fluorescence microscopy after immunostaining for HCV proteins Core or NS5A to quantify viral spread. B: Infectivity titers were determined as FFU/mL using three independent ten-fold dilution series of each cell culture supernatant from the indicated day of the transfection experiment (cut-off: 1.7). Means are shown and Error bars are SD.

FIG. 11

Transfection of Huh7.5 cells with HK6a/JFH1$_{T1389C,A1590G}$ with and without HVR1.

HCV RNA was transfected into Huh7.5 cells to test the performance of HK6a/JFH1$_{T1389C,A1590G,\Delta HVR1}$ as compared to HK6a/JFH1$_{T1389C,A1590G}$ with a GND motif replication deficient J6/JFH virus (GND). A: Cells were immunostained for HCV proteins Core or NS5A to quantify viral spread. B: Three independent ten-fold dilution series of cell culture supernatants from the indicated day of transfection was used in HCV infectivity titrations (cut-off: 1.7).

FIG. 12

Transfection of Huh7.5 cells with 21 aa N-terminal deletion of E2 for H77/JFH1$_{T2700C,A4080T}$ and ED43/JFH1$_{A2819G,A3269T}$.

HCV RNA was transfected into Huh7.5 cells to test the performance of the 21 aa N-terminal deletions of E2 for H77/JFH1$_{T2700C,A4080T}$ and ED43/JFH1$_{A2819G,A3269T}$ as compared to their respective parental viruses (both 21 aa constructs set up in triplicates). A GND motif replication deficient J6/JFH virus (GND) was used as negative control. Percentage of infected cells was estimated by fluorescence microscopy after immunostaining for HCV proteins Core or NS5A to quantify viral spread.

FIG. 13

Neutralization with HCV patient serum H06 of HVR1 truncated viruses is significantly more effective than that of their wt counterparts.

Huh7.5 cells were plated at 6000/well in 96 well plates and incubated ON at 37° C. The next day the indicated viruses were incubated with the patient serum for 1 h at 37° C. prior to adding the virus/serum mix to the cells in 100 μl/well in triplicates. The virus was allowed to enter the cells for 3 h prior to washing and addition of 200 μl of fresh medium. After 48 h incubation and immunostaining for HCV NS5A antigen, FFU/well was counted; % inhibition of entry was calculated by normalization to the wells with virus only.

FIG. 14

Neutralization of H77/JFH1$_{T2700C,A4080T}$ with and without HVR1 with H77 HVR1 specific rabbit hyper-immune serum, LMF87.

Huh7.5 cells were plated at 6000/well in 96 well plates and incubated ON at 37° C. The next day viruses H77/JFH1$_{T2700C,A4080T}$ and H77/JFH1$_{(A1766G,T2538C),T2700C,A4080T,\Delta HVR1}$ were incubated with the patient serum for 1 h at 37° C. prior to adding the virus/serum mix to the cells in 100 μl/well in triplicates. The virus was allowed to enter the cells for 3 h prior to washing and addition of 200 μl of fresh medium. After 48 h incubation and immunostaining for HCV NS5A antigen, FFU/well was counted; % inhibition of entry was calculated by normalization to the wells with virus only.

FIG. 15

The improved neutralization of HVR1 truncated viruses is seen for both purified IgG from H06 and two other patient sera: AA and SA3.

Huh7.5 cells were plated at 6000/well in 96 well plates and incubated ON at 37° C. The next day the indicated viruses were incubated with the purified IgG or patient serum for 1 h at 37° C. prior to addition of the virus/serum (or IgG) mix to the cells at 100 μl/well in triplicates. The virus was allowed to enter the cells for 3 h prior to washing and addition of 200 μl of fresh medium. After 48 h incubation and immunostaining for HCV NS5A antigen, FFU/well were counted; % inhibition of entry was calculated by normalization to the wells with only virus

FIG. 16

Density centrifugation of J6/JFH, S52/JFH1$_{T2718G,T7160C}$, SA13/JFH1$_{C3405G,A3696G}$ and HK6a/JFH1$_{T1389C,A1590G}$ with and without HVR1.

Four steps of iodixanol/PBS mixtures were prepared at 10, 20, 30 and 40% iodixanol. 2.5 ml of these were then layered on top of each other and left upright for 24 h at 4° C. Virus was concentrated to a volume of ~200 μl in Amicon centrifugation columns and then added to the top of the iodixanol gradient. Next the gradients were centrifuged at 150000×RCF for 18 h at 4° C. Afterwards the tube was punctured at the bottom and 18 550 μl fractions were collected. Density of each fraction was determined by weighing 400 μl from each fraction. Fractions were HCV infectivity titrated (A & B) and HCV RNA titrated (C & D).

Tables

TABLE 1

Putative adaptive mutations in the envelope genes for H77/JFH1$_{T2700C,A4080T,\Delta HVR1}$.

| HCV gene | | E1 | E1 | E1 | E2 | E2 | E2 | E2 | E2 |
|---|---|---|---|---|---|---|---|---|---|
| Nucleotide number | | | | | | | | | |
| pH77/JFH1$_{T2700C,A4080T}$ position | | 1122 | 1383 | 1421 | 1628 | 1671 | 1766 | 2385 | 2538 |
| H77 abs. ref. (AF009606) | | 1123 | 1384 | 1422 | 1629 | 1672 | 1767 | 2386 | 2539 |
| plasmid nucleotide | | A | T | T | A | A | A | T | C |
| H77/JFH1$_{T2700C,A4080T,\Delta HVR1}$ transfections | Titer$^{I}$ (day) | | | | | | | | |
| H77/JFH1$_{T2700C,A4080T,\Delta HVR1}$, Transfection 1 | 2.9 (56) | G/a | — | — | — | G/a | — | — | — |
| H77/JFH1$_{T2700C,A4080T,\Delta HVR1}$, Transfection 3 | 2.9 (56) | — | — | — | — | — | G/a | — | T |
| Mutated H77/JFH1$_{T2700C,A4080T,\Delta HVR1}$ transfections | Titer$^{I}$ (day) | | | | | | | | |
| H77/JFH1$_{T2700C,A4080T,\Delta HVR1}$ | 2.7 (55) | — | — | C | — | G/a | — | — | — |
| H77/JFH1$_{(A1122G),T2700C,A4080T,\Delta HVR1}$ | 3.2 (50) | G | — | — | G/a | G | — | A/t | — |
| H77/JFH1$_{(A1671G),T2700C,A4080T,\Delta HVR1}$ | 2.6 (31) | — | T/g | — | — | G | — | — | C/t |
| H77/JFH1$_{(A1766G),T2700C,A4080T,\Delta HVR1}$ | 3.1 (50) | — | — | — | — | G/a | G | — | C/t |
| H77/JFH1$_{(C2538T),T2700C,A4080T,\Delta HVR1}$ | 2.1 (24) | — | — | — | — | — | — | — | T |
| H77/JFH1$_{(A1122G,A1671G),T2700C,A4080T,\Delta HVR1}$ | 3.0 (15$^{II}$) | G | — | — | — | G | — | T/a | — |
| H77/JFH1$_{(A1766G,C2538T),T2700C,A4080T,\Delta HVR1}$ | 3.2 (15$^{II}$) | — | — | — | — | — | G | — | T |
| Amino Acid number | | | | | | | | | |
| pH77/JFH1$_{T2700C,A4080T}$ position | | 261 | 348 | 361 | 430 | 444 | 476 | 682 | 733 |
| H77 abs. ref. (AF009606) | | 261 | 348 | 361 | 430 | 444 | 476 | 682 | 733 |
| Change | | H→R | I→S | Y→H | N→D | Q→R | N→D | L→Q | S→F |

$^{I}$Titer is the mean log10 of three independent FFU infectivity titrations.

$^{II}$Virus transfection was passaged on day 10 and FFU titration was carried out on 1st passage virus on day 15.

Shaded cells are mutations that were present in the construct upon transfection.

TABLE 2

Putative adaptive mutations in the envelope genes for J4/JFH1$_{T2996C,\ A4827T,\ \Delta HVR1}$.

| HCV gene | | E1 | E1 | E2 | E2 | E2 | E2 |
|---|---|---|---|---|---|---|---|
| Nucleotide number | | | | | | | |
| pJ4/JFH1$_{T2996C,\ A4827T}$ position | | 1236 | 1428 | 1643 | 2066 | 2225 | 2468 |
| H77 abs. ref. (AF009606) | | 1237 | 1429 | 1644 | 2067 | 2226 | 2469 |
| plasmid nucleotide | | A | C | A | A | G | G |
| J4/JFH1$_{T2996C,\ A4827T,\ \Delta HVR1}$, 1st transfection | Titer$^{I}$ (day) | | | | | | |
| 1st passage | below detection$^{II}$ (84) | — | T | C | — | — | C |
| 2nd passage | 4.1 (22) | G/a | T | C | G/a | A/g | C |
| Amino Acid number | | | | | | | |
| pJ4/JFH1$_{T2996C,\ A4827T}$ position | | 299 | 363 | 435 | 576 | 629 | 710 |
| H77 abs. ref. (AF009606) | | 299 | 363 | 435 | 576 | 629 | 710 |
| Change | | E-G | S-F | T-P | N-D | V-I | V-L |

$^{I}$Titer is expressed as the mean log10 of three independent FFU infectivity titrations.

$^{II}$The low titer at this timepoint is likely caused by a prolonged infection of the cells of about 10-20%

TABLE 3

Putative adaptive mutations in the envelope genes for J8/JFH1$_{\Delta HVR1}$.

| HCV gene | | E2 | E2 | E2 | E2 | E2 | E2 |
|---|---|---|---|---|---|---|---|
| Nucleotide number | | | | | | | |
| pJ8/JFH1 position | | 1571 | 1572 | 1574 | 1580 | 1652 | 1941 |
| H77 abs. ref. (AF009606) | | 1572 | 1573 | 1575 | 1581 | 1653 | 1936 |
| plasmid nucleotide | | C | T | T | A | A | A |
| J8/JFH1$_{\Delta HVR1}$, 1st transfection | Titer[I] (day) | | | | | | |
| J8/JFH1$_{\Delta HVR1}$, Transfection 1 | 3.5 (24[II]) | — | — | A | — | — | A/c |
| J8/JFH1$_{\Delta HVR1}$, Transfection 2 | 4.4 (15[II]) | G/C | G/T | — | A/g | T/A | — |
| J8/JFH1$_{\Delta HVR1}$, Transfection 3 | 3.3 (15[II]) | — | — | A | — | — | — |
| J8/JFH1$_{\Delta HVR1}$, 1st transfection | Titer[I] (day) | | | | | | |

TABLE 4

Putative adaptive mutations in the envelope genes for S52/JFH1$_{T2718G,T7160C,\Delta HVR1}$.

| Gene region | | TM |
|---|---|---|
| Nucleotide number | | |
| pS52/JFH1$_{T2718G,T7160C}$ position | | 1446 |
| H77 abs. ref. (AF009606) | | 1447 |
| plasmid nucleotide | | C |
| S52/JFH1$_{T2718G,T7160C,\Delta HVR1}$, 1st transfection | day | |
| 1st passage | 2.6 (6) | — |
| 2nd passage | 2.7 (13) | T/c |
| 4th passage | 3.9 (6) | T |
| S52/JFH1$_{T2718G,T7160C,\Delta HVR1}$, 2nd transfection | day | |
| 3rd passage | 3.8 (10) | T |
| Amino Acid number | | |
| pS52/JFH1$_{T2718G,T7160C}$ position | | 369 |
| H77 abs. ref. (AF009606) | | 369 |
| Change | | A-V |

TABLE 5

HVR1 deleted HCV recombinants and viral kinetics in transfection as compared to respective parental virus.

| | Viable* | HVR1 adaptive mutations (HCV gene affected) | Infectivity (FFU/ml)log10 | | | Infectivity relative to parental virusŧ | | |
|---|---|---|---|---|---|---|---|---|
| | | | Day of transfection | | | Day of transfection | | |
| | | | 3 | 6 | 8 | 3 | 6 | 8 |
| H77/JFH1$_{T2700C, A4080T, \Delta HVR1}$ Ŧ | (Y) | A1122G (E1), A1671G (E2) | 2.3 | 2.4 | 2.7 | 10% | 13% | 10% |
| H77/JFH1$_{T2700C, A4080T, \Delta HVR1}$ ¥ | (Y) | A1766G (E2), C2538T (E2) | 2.3 | 2.6 | 3.0 | 10% | 20% | 20% |
| J4/JFH1$_{T2996C, A4827T, \Delta HVR1}$ | (Y) | — | 2.1 | 1.9 | 2.3 | 5% | 2% | 4% |
| J6/JFH$_{\Delta HVR1}$ | Y | — | 4.8 | 5.1 | 4.0 | 50% | 79% | 25% |
| J8/JFH1$_{\Delta HVR1}$ | (Y) | T1574A (E2) | 3.1 | 3.3 | 3.4 | 24% | 30% | 7% |
| S52/JFH1$_{T2718G, T7160C, \Delta HVR1}$ | (Y) | C1446T (E1) | 3.9 | 3.8 | — | 100% | 63% | — |
| ED43/JFH1$_{A2819G, A3269T}$ | N | — | — | — | — | ~0% | ~0% | ~0% |
| SA13/JFH1$_{C3405G, A3696G, \Delta HVR1}$ | Y | — | 4.5 | 4.1 | 4.3 | 13% | 16% | 25% |
| HK6a/JFH1$_{T1389C, A1590G, \Delta HVR1}$ | Y | — | 2.7 | 2.8 | 3.0 | 10% | 13% | 13% |

*Viability of HVR1 deleted construct without any adaptive mutations. Y: Spreads immediately and does not acquire adaptive mutations in 1st passage. (Y): Virus is infectious, but acquires adaptive mutations. N: Virus is non-infectious.

Ŧ Transfection 1 of H77/JFH1$_{T2700C, A4080T, \Delta HVR1}$ construct.

¥ Transfection 3 of H77/JFH1$_{T2700C, A4080T, \Delta HVR1}$ construct.

ŧcalculated as infectivity of HVR1 deleted virus on given day of transfection divided by infectivity of parental virus on given day of transfection.

TABLE 3-continued

Putative adaptive mutations in the envelope genes for J8/JFH1$_{\Delta HVR1}$.

| | | | | | | | |
|---|---|---|---|---|---|---|---|
| J8/JFH1$_{\Delta HVR1, T1574A}$ | 1.8 (16) | — | — | A | — | — | — |
| Amino Acid number | | | | | | | |
| pJ8/JFH1 position | | 411 | 411 | 412 | 414 | 438 | 534 |
| H77 abs. ref. (AF009606) | | 411 | 411 | 412 | 414 | 438 | 532 |
| Change | | L-V | L-R | Y-N | I-V | M-L | N-T |

[I]Titer is expressed as the mean log10 of three independent FFU infectivity titrations.

[II]All viruses were sequenced in a first passage of the transfection at the indicated day.

[III]Gray cells signify that the mutation was present in the construct upon transfection.

REFERENCES

Altschul S F, Lipman D J. Protein database searches for multiple alignments. Proc Natl Acad Sci USA 1990 July; 87(14):5509-5513.

Cerino, A., Bissolati, M., Cividini, A., Nicosia, A., Esumi, M., Hayashi, N., Mizuno, K., Slobbe, R., Oudshoorn, P., Silini, E. et al. (1997) J. Med. Virol. 51, 1-5.

Forms, X., Thimme, R., Govindarajan, S., Emerson, S. U., Purcell, R. H., Chisari, F. V., & Bukh, J. (2000) Proc. Natl. Acad. Sci. U.S.A 97, 13318-13323.

Gottwein, J. M., Scheel, T. K., Hoegh, A. M., Lademann, J. B., Eugen-Olsen, J., Lisby, G., & Bukh, J. (2007) Gastroenterology 133, 1614-1626.

Kato, T., T. Date, M. Miyamoto, A. Furusaka, K. Tokushige, M. Mizokami, and T. Wakita. 2003. Efficient replication of the genotype 2a hepatitis C virus subgenomic replicon. Gastroenterology 125:1808-1817.

Kato, T., A. Furusaka, M. Miyamoto, T. Date, K. Yasui, J. Hiramoto, K. Nagayama, T. Tanaka, and T. Wakita. 2001.

Sequence analysis of hepatitis C virus isolated from a fulminant hepatitis patient. J Med Virol 64:334-339.

Lindenbach, B. D., M. J. Evans, A. J. Syder, B. Wolk, T. L. Tellinghuisen, C. C. Liu, T. Maruyama, R. O. Hynes, D. R. Burton, J. A. McKeating, and C. M. Rice. 2005. Complete replication of hepatitis C virus in cell culture. Science 309:623-626.

Lindenbach B D, Meuleman P, Ploss A, Vanwolleghem T, Syder A J, McKeating J A, Lanford R E, Feinstone S M, Major M E, Leroux-Roels G, Rice CM. Cell culture-grown hepatitis C virus is infectious in vivo and can be recultured in vitro. Proc Natl Acad Sci USA. 2006 Mar. 7; 103(10): 3805-9. Epub 2006 Feb. 16.

Manzin, A., Solforosi, L., Debiaggi, M., Zara, F., Tanzi, E., Romano, L., Zanetti, A. R., & Clementi, M. (2000) J. Virol. 74, 4327-4334.

Mondelli, M. U., Cerino, A., Segagni, L., Meola, A., Cividini, A., Silini, E., & Nicosia, A. (2001) Antiviral Res. 52, 153-159.

Ray, S. C., Wang, Y. M., Laeyendecker, O., Ticehurst, J. R., Villano, S. A., & Thomas, D. L. (1999) J. Virol. 73, 2938-2946.

Scarselli, E., Ansuini, H., Cerino, R., Roccasecca, R. M., Acali, S., Filocamo, G., Traboni, C., Nicosia, A., Cortese, R., & Vitelli, A. (2002) EMBO J. 21, 5017-5025.

Steinmann, E., Penin, F., Kallis, S., Patel, A. H., Bartenschlager, R., & Pietschmann, T. (2007) PLoS. Pathog. 3, e103.

Scheel, T. K., Gottwein, J. M., Jensen, T. B., Prentoe, J. C., Hoegh, A. M., Alter, H. J., Eugen-Olsen, J., & Bukh, J. (2008) Proc. Natl. Acad. Sci. U.S.A 105, 997-1002.

Wakita, T., T. Pietschmann, T. Kato, T. Date, M. Miyamoto, Z. Zhao, K. Murthy, A. Habermann, H. G. Krausslich, M. Mizokami, R. Bartenschlager, and T. J. Liang. 2005. Production of infectious hepatitis C virus in tissue culture from a cloned viral genome. Nat Med 11:791-796.

Zhong, J., P. Gastaminza, G. Cheng, S. Kapadia, T. Kato, D. R. Burton, S. F. Wieland, S. L. Uprichard, T. Wakita, and F. V. Chisari. 2005. Robust hepatitis C virus infection in vitro. Proc Natl Acad Sci USA 102:9294-9299.

The invention claimed is:

1. A recombinant nucleic acid comprising an infectious inter-genotypic Hepatitis C Virus (HCV) genome encoding the structural genes, Core, E1, E2, the p7 gene, and the NS2 gene of genotype 1a, wherein the E1 and/or E2 gene(s) comprise adaptive mutations corresponding to amino acid replacements H261R and Q444R with reference to SEQ ID NO: 1 or corresponding to amino acid replacements N476D and S733F with reference to SEQ ID NO:1 that improve infectivity of the HCV genome, and the non-structural genes NS3, NS4A, NS4B, NS5A and NS5B from the human hepatitis C virus genotype 2a strain JFH1, and wherein 26 or 27 N-terminal amino acids of the encoded E2 gene that comprise the Hypervariable Region 1 (HVR1) of E2 are deleted.

2. The nucleic acid molecule according to claim 1, wherein the inter-genotypic Hepatitis C Virus (HCV) genome comprises a nucleic acid sequence with a sequence identity of at least 99% to that of SEQ ID NO: 7.

3. An isolated cell comprising the recombinant nucleic acid of claim 1.

4. A recombinant Hepatitis C Virus particle comprising the nucleic acid of claim 1.

5. The recombinant nucleic acid of claim 1, wherein said adaptive mutations correspond to an H261R and Q444R amino acid replacement with reference to SEQ ID NO:1.

6. The nucleic acid molecule according to claim 5, wherein the inter-genotypic Hepatitis C Virus (HCV) genome encodes the amino acid sequence of SEQ ID NO:13.

* * * * *

SEQUENCE LISTING

```
<160> NUMBER OF SEQ ID NOS: 24

<210> SEQ ID NO 1
<211> LENGTH: 3002
<212> TYPE: PRT
<213> ORGANISM: Hepatitis C virus

<400> SEQUENCE: 1

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
```

-continued

```
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Leu Phe Ala Gly Val Asp Ala Ile
    370                 375                 380

Gln Leu Ile Asn Thr Asn Gly Ser Trp His Ile Asn Ser Thr Ala Leu
385                 390                 395                 400

Asn Cys Asn Glu Ser Leu Asn Thr Gly Trp Leu Ala Gly Leu Phe Tyr
                405                 410                 415

Gln His Lys Phe Asn Ser Ser Gly Cys Pro Glu Arg Leu Ala Ser Cys
            420                 425                 430

Arg Arg Leu Thr Asp Phe Ala Gln Gly Trp Gly Pro Ile Ser Tyr Ala
        435                 440                 445

Asn Gly Ser Gly Leu Asp Glu Arg Pro Tyr Cys Trp His Tyr Pro Pro
    450                 455                 460

Arg Pro Cys Gly Ile Val Pro Ala Lys Ser Val Cys Gly Pro Val Tyr
465                 470                 475                 480

Cys Phe Thr Pro Ser Pro Val Val Val Gly Thr Thr Asp Arg Ser Gly
                485                 490                 495

Ala Pro Thr Tyr Ser Trp Gly Ala Asn Asp Thr Asp Val Phe Val Leu
            500                 505                 510

Asn Asn Thr Arg Pro Pro Leu Gly Asn Trp Phe Gly Cys Thr Trp Met
        515                 520                 525

Asn Ser Thr Gly Phe Thr Lys Val Cys Gly Ala Pro Pro Cys Val Ile
    530                 535                 540

Gly Gly Val Gly Asn Asn Thr Leu Leu Cys Pro Thr Asp Cys Phe Arg
545                 550                 555                 560

Lys His Pro Glu Ala Thr Tyr Ser Arg Cys Gly Ser Gly Pro Trp Ile
                565                 570                 575

Thr Pro Arg Cys Met Val Asp Tyr Pro Tyr Arg Leu Trp His Tyr Pro
            580                 585                 590

Cys Thr Ile Asn Tyr Thr Ile Phe Lys Val Arg Met Tyr Val Gly Gly
        595                 600                 605

Val Glu His Arg Leu Glu Ala Ala Cys Asn Trp Thr Arg Gly Glu Arg
    610                 615                 620

Cys Asp Leu Glu Asp Arg Asp Arg Ser Glu Leu Ser Pro Leu Leu Leu
625                 630                 635                 640

Ser Thr Thr Gln Trp Gln Val Leu Pro Cys Ser Phe Thr Thr Leu Pro
                645                 650                 655
```

```
Ala Leu Ser Thr Gly Leu Ile His Leu His Gln Asn Ile Val Asp Val
            660                 665                 670

Gln Tyr Leu Tyr Gly Val Gly Ser Ser Ile Ala Ser Trp Ala Ile Lys
        675                 680                 685

Trp Glu Tyr Val Val Leu Leu Phe Leu Leu Leu Ala Asp Ala Arg Val
    690                 695                 700

Cys Ser Cys Leu Trp Met Met Leu Leu Ile Ser Gln Ala Glu Ala Ala
705                 710                 715                 720

Leu Glu Asn Leu Val Ile Leu Asn Ala Ala Ser Leu Ala Gly Thr His
                725                 730                 735

Gly Leu Val Ser Phe Leu Val Phe Phe Cys Phe Ala Trp Tyr Leu Lys
            740                 745                 750

Gly Arg Trp Val Pro Gly Ala Ala Tyr Ala Leu Tyr Gly Met Trp Pro
        755                 760                 765

Leu Leu Leu Leu Leu Leu Ala Leu Pro Gln Arg Ala Tyr Ala Leu Asp
    770                 775                 780

Thr Glu Val Ala Ala Ser Cys Gly Gly Val Val Leu Val Gly Leu Met
785                 790                 795                 800

Ala Leu Thr Leu Ser Pro Tyr Tyr Lys Arg Tyr Ile Ser Trp Cys Met
                805                 810                 815

Trp Trp Leu Gln Tyr Phe Leu Thr Arg Val Glu Ala Gln Leu His Val
            820                 825                 830

Trp Val Pro Pro Leu Asn Val Arg Gly Gly Arg Asp Ala Val Ile Leu
        835                 840                 845

Leu Met Cys Val Val His Pro Thr Leu Val Phe Asp Ile Thr Lys Leu
    850                 855                 860

Leu Leu Ala Ile Phe Gly Pro Leu Trp Ile Leu Gln Ala Ser Leu Leu
865                 870                 875                 880

Lys Val Pro Tyr Phe Val Arg Val Gln Gly Leu Leu Arg Ile Cys Ala
                885                 890                 895

Leu Ala Arg Lys Ile Ala Gly Gly His Tyr Val Gln Met Ala Ile Ile
            900                 905                 910

Lys Leu Gly Ala Leu Thr Gly Thr Tyr Val Tyr Asn His Leu Thr Pro
        915                 920                 925

Leu Arg Asp Trp Ala His Asn Gly Leu Arg Asp Leu Ala Val Ala Val
    930                 935                 940

Glu Pro Val Val Phe Ser Arg Met Glu Thr Lys Leu Ile Thr Trp Gly
945                 950                 955                 960

Ala Asp Thr Ala Ala Cys Gly Asp Ile Ile Asn Gly Leu Pro Val Ser
                965                 970                 975

Ala Arg Arg Gly Gln Glu Ile Leu Leu Gly Pro Ala Asp Gly Met Val
            980                 985                 990

Ser Lys Gly Trp Arg Leu Leu Ala  Pro Ile Thr Ala Tyr  Ala Gln Gln
        995                 1000                1005

Thr Arg  Gly Leu Leu Gly Ala  Ile Val Val Ser Met  Thr Gly Arg
    1010                1015                1020

Asp Arg  Thr Glu Gln Ala Gly  Glu Val Gln Ile Leu  Ser Thr Val
    1025                1030                1035

Ser Gln  Ser Phe Leu Gly Thr  Thr Ile Ser Gly Val  Leu Trp Thr
    1040                1045                1050

Val Tyr  His Gly Ala Gly Asn  Lys Thr Leu Ala Gly  Leu Arg Gly
    1055                1060                1065
```

-continued

```
Pro Val  Thr Gln Met Tyr Ser  Ser Ala Glu Gly Asp  Leu Val Gly
    1070                 1075                 1080

Trp Pro  Ser Pro Pro Gly Thr  Lys Ser Leu Glu Pro  Cys Lys Cys
    1085                 1090                 1095

Gly Ala  Val Asp Leu Tyr Leu  Val Thr Arg Asn Ala  Asp Val Ile
    1100                 1105                 1110

Pro Ala  Arg Arg Arg Gly Asp  Lys Arg Gly Ala Leu  Leu Ser Pro
    1115                 1120                 1125

Arg Pro  Ile Ser Thr Leu Lys  Gly Ser Ser Gly Gly  Pro Val Leu
    1130                 1135                 1140

Cys Pro  Arg Gly His Val Val  Gly Leu Phe Arg Ala  Ala Val Cys
    1145                 1150                 1155

Ser Arg  Gly Val Ala Lys Ser  Ile Asp Phe Ile Pro  Val Glu Thr
    1160                 1165                 1170

Leu Asp  Val Val Thr Arg Ser  Pro Thr Phe Ser Asp  Asn Ser Thr
    1175                 1180                 1185

Pro Pro  Ala Val Pro Gln Thr  Tyr Gln Val Gly Tyr  Leu His Ala
    1190                 1195                 1200

Pro Thr  Gly Ser Gly Lys Ser  Thr Lys Val Pro Val  Ala Tyr Ala
    1205                 1210                 1215

Ala Leu  Gly Tyr Lys Val Leu  Val Leu Asn Pro Ser  Val Ala Ala
    1220                 1225                 1230

Thr Leu  Gly Phe Gly Ala Tyr  Leu Ser Lys Ala His  Gly Ile Asn
    1235                 1240                 1245

Pro Asn  Ile Arg Thr Gly Val  Arg Thr Val Met Thr  Gly Glu Ala
    1250                 1255                 1260

Ile Thr  Tyr Ser Thr Tyr Gly  Lys Phe Leu Ala Asp  Gly Gly Cys
    1265                 1270                 1275

Ala Ser  Gly Ala Tyr Asp Ile  Ile Ile Cys Asp Glu  Cys His Ala
    1280                 1285                 1290

Val Asp  Ala Thr Ser Ile Leu  Gly Ile Gly Thr Val  Leu Asp Gln
    1295                 1300                 1305

Ala Glu  Thr Ala Gly Val Arg  Leu Thr Val Leu Ala  Thr Ala Thr
    1310                 1315                 1320

Pro Pro  Gly Ser Val Thr Thr  Pro His Pro Asp Ile  Glu Glu Val
    1325                 1330                 1335

Gly Leu  Gly Arg Glu Gly Glu  Ile Pro Phe Tyr Gly  Arg Ala Ile
    1340                 1345                 1350

Pro Leu  Ser Cys Ile Lys Gly  Gly Arg His Leu Ile  Phe Cys His
    1355                 1360                 1365

Ser Lys  Lys Lys Cys Asp Glu  Leu Ala Ala Ala Leu  Arg Gly Met
    1370                 1375                 1380

Gly Leu  Asn Ala Val Ala Tyr  Tyr Arg Gly Leu Asp  Val Ser Ile
    1385                 1390                 1395

Ile Pro  Ala Gln Gly Asp Val  Val Val Val Ala Thr  Asp Ala Leu
    1400                 1405                 1410

Met Thr  Gly Tyr Thr Gly Asp  Phe Asp Ser Val Ile  Asp Cys Asn
    1415                 1420                 1425

Val Ala  Val Thr Gln Ala Val  Asp Phe Ser Leu Asp  Pro Thr Phe
    1430                 1435                 1440

Thr Ile  Thr Thr Gln Thr Val  Pro Gln Asp Ala Val  Ser Arg Ser
    1445                 1450                 1455

Gln Arg  Arg Gly Arg Thr Gly  Arg Gly Arg Gln Gly  Thr Tyr Arg
```

-continued

```
    1460                1465                1470

Tyr Val  Ser Thr Gly Glu Arg  Ala Ser Gly Met Phe  Asp Ser Val
    1475                1480                1485

Val Leu  Cys Glu Cys Tyr Asp  Ala Gly Ala Ala Trp  Tyr Asp Leu
    1490                1495                1500

Thr Pro  Ala Glu Thr Thr Val  Arg Leu Arg Ala Tyr  Phe Asn Thr
    1505                1510                1515

Pro Gly  Leu Pro Val Cys Gln  Asp His Leu Glu Phe  Trp Glu Ala
    1520                1525                1530

Val Phe  Thr Gly Leu Thr His  Ile Asp Ala His Phe  Leu Ser Gln
    1535                1540                1545

Thr Lys  Gln Ala Gly Glu Asn  Phe Ala Tyr Leu Val  Ala Tyr Gln
    1550                1555                1560

Ala Thr  Val Cys Ala Arg Ala  Lys Ala Pro Pro Pro  Ser Trp Asp
    1565                1570                1575

Ala Met  Trp Lys Cys Leu Ala  Arg Leu Lys Pro Thr  Leu Ala Gly
    1580                1585                1590

Pro Thr  Pro Leu Leu Tyr Arg  Leu Gly Pro Ile Thr  Asn Glu Val
    1595                1600                1605

Thr Leu  Thr His Pro Gly Thr  Lys Tyr Ile Ala Thr  Cys Met Gln
    1610                1615                1620

Ala Asp  Leu Glu Val Met Thr  Ser Thr Trp Val Leu  Ala Gly Gly
    1625                1630                1635

Val Leu  Ala Ala Val Ala Ala  Tyr Cys Leu Ala Thr  Gly Cys Val
    1640                1645                1650

Ser Ile  Ile Gly Arg Leu His  Val Asn Gln Arg Val  Val Val Ala
    1655                1660                1665

Pro Asp  Lys Glu Val Leu Tyr  Glu Ala Phe Asp Glu  Met Glu Glu
    1670                1675                1680

Cys Ala  Ser Arg Ala Ala Leu  Ile Glu Glu Gly Gln  Arg Ile Ala
    1685                1690                1695

Glu Met  Leu Lys Ser Lys Ile  Gln Gly Leu Leu Gln  Gln Ala Ser
    1700                1705                1710

Lys Gln  Ala Gln Asp Ile Gln  Pro Ala Met Gln Ala  Ser Trp Pro
    1715                1720                1725

Lys Val  Glu Gln Phe Trp Ala  Arg His Met Trp Asn  Phe Ile Ser
    1730                1735                1740

Gly Ile  Gln Tyr Leu Ala Gly  Leu Ser Thr Leu Pro  Gly Asn Pro
    1745                1750                1755

Ala Val  Ala Ser Met Met Ala  Phe Ser Ala Ala Leu  Thr Ser Pro
    1760                1765                1770

Leu Ser  Thr Ser Thr Thr Ile  Leu Leu Asn Ile Met  Gly Gly Trp
    1775                1780                1785

Leu Ala  Ser Gln Ile Ala Pro  Pro Ala Gly Ala Thr  Gly Phe Val
    1790                1795                1800

Val Ser  Gly Leu Val Gly Ala  Ala Val Gly Ser Ile  Gly Leu Gly
    1805                1810                1815

Lys Val  Leu Val Asp Ile Leu  Ala Gly Tyr Gly Ala  Gly Ile Ser
    1820                1825                1830

Gly Ala  Leu Val Ala Phe Lys  Ile Met Ser Gly Glu  Lys Pro Ser
    1835                1840                1845

Met Glu  Asp Val Ile Asn Leu  Leu Pro Gly Ile Leu  Ser Pro Gly
    1850                1855                1860
```

```
Ala Leu Val Val Gly Val Ile Cys Ala Ala Ile Leu Arg Arg His
    1865                1870                1875

Val Gly Pro Gly Glu Gly Ala Val Gln Trp Met Asn Arg Leu Ile
    1880                1885                1890

Ala Phe Ala Ser Arg Gly Asn His Val Ala Pro Thr His Tyr Val
    1895                1900                1905

Thr Glu Ser Asp Ala Ser Gln Arg Val Thr Gln Leu Leu Gly Ser
    1910                1915                1920

Leu Thr Ile Thr Ser Leu Leu Arg Arg Leu His Asn Trp Ile Thr
    1925                1930                1935

Glu Asp Cys Pro Ile Pro Cys Ser Gly Ser Trp Leu Arg Asp Val
    1940                1945                1950

Trp Asp Trp Val Cys Thr Ile Leu Thr Asp Phe Lys Asn Trp Leu
    1955                1960                1965

Thr Ser Lys Leu Phe Pro Lys Leu Pro Gly Leu Pro Phe Ile Ser
    1970                1975                1980

Cys Gln Lys Gly Tyr Lys Gly Val Trp Ala Gly Thr Gly Ile Met
    1985                1990                1995

Thr Thr Arg Cys Pro Cys Gly Ala Asn Ile Ser Gly Asn Val Arg
    2000                2005                2010

Leu Gly Ser Met Arg Ile Thr Gly Pro Lys Thr Cys Met Asn Thr
    2015                2020                2025

Trp Gln Gly Thr Phe Pro Ile Asn Cys Tyr Thr Glu Gly Gln Cys
    2030                2035                2040

Ala Pro Lys Pro Pro Thr Asn Tyr Lys Thr Ala Ile Trp Arg Val
    2045                2050                2055

Ala Ala Ser Glu Tyr Ala Glu Val Thr Gln His Gly Ser Tyr Ser
    2060                2065                2070

Tyr Val Thr Gly Leu Thr Thr Asp Asn Leu Lys Ile Pro Cys Gln
    2075                2080                2085

Leu Pro Ser Pro Glu Phe Phe Ser Trp Val Asp Gly Val Gln Ile
    2090                2095                2100

His Arg Phe Ala Pro Thr Pro Lys Pro Phe Phe Arg Asp Glu Val
    2105                2110                2115

Ser Phe Cys Val Gly Leu Asn Ser Tyr Ala Val Gly Ser Gln Leu
    2120                2125                2130

Pro Cys Glu Pro Glu Pro Asp Ala Asp Val Leu Arg Ser Met Leu
    2135                2140                2145

Thr Asp Pro Pro His Ile Thr Ala Glu Thr Ala Ala Arg Arg Leu
    2150                2155                2160

Ala Arg Gly Ser Pro Pro Ser Glu Ala Ser Ser Ser Val Ser Gln
    2165                2170                2175

Leu Ser Ala Pro Ser Leu Arg Ala Thr Cys Thr Thr His Ser Asn
    2180                2185                2190

Thr Tyr Asp Val Asp Met Val Asp Ala Asn Leu Leu Met Glu Gly
    2195                2200                2205

Gly Val Ala Gln Thr Glu Pro Glu Ser Arg Val Pro Val Leu Asp
    2210                2215                2220

Phe Leu Glu Pro Met Ala Glu Glu Glu Ser Asp Leu Glu Pro Ser
    2225                2230                2235

Ile Pro Ser Glu Cys Met Leu Pro Arg Ser Gly Phe Pro Arg Ala
    2240                2245                2250
```

-continued

```
Leu Pro  Ala Trp Ala Arg Pro  Asp Tyr Asn Pro Pro  Leu Val Glu
    2255                 2260                 2265

Ser Trp  Arg Arg Pro Asp Tyr  Gln Pro Pro Thr Val  Ala Gly Cys
    2270                 2275                 2280

Ala Leu  Pro Pro Pro Lys Lys  Ala Pro Thr Pro Pro  Pro Arg Arg
    2285                 2290                 2295

Arg Arg  Thr Val Gly Leu Ser  Glu Ser Thr Ile Ser  Glu Ala Leu
    2300                 2305                 2310

Gln Gln  Leu Ala Ile Lys Thr  Phe Gly Gln Pro Pro  Ser Ser Gly
    2315                 2320                 2325

Asp Ala  Gly Ser Ser Thr Gly  Ala Gly Ala Ala Glu  Ser Gly Gly
    2330                 2335                 2340

Pro Thr  Ser Pro Gly Glu Pro  Ala Pro Ser Glu Thr  Gly Ser Ala
    2345                 2350                 2355

Ser Ser  Met Pro Pro Leu Glu  Gly Glu Pro Gly Asp  Pro Asp Leu
    2360                 2365                 2370

Glu Ser  Asp Gln Val Glu Leu  Gln Pro Pro Pro Gln  Gly Gly Gly
    2375                 2380                 2385

Val Ala  Pro Gly Ser Gly Ser  Gly Ser Trp Ser Thr  Cys Ser Glu
    2390                 2395                 2400

Glu Asp  Asp Thr Thr Val Cys  Cys Ser Met Ser Tyr  Ser Trp Thr
    2405                 2410                 2415

Gly Ala  Leu Ile Thr Pro Cys  Ser Pro Glu Glu Glu  Lys Leu Pro
    2420                 2425                 2430

Ile Asn  Pro Leu Ser Asn Ser  Leu Leu Arg Tyr His  Asn Lys Val
    2435                 2440                 2445

Tyr Cys  Thr Thr Ser Lys Ser  Ala Ser Gln Arg Ala  Lys Lys Val
    2450                 2455                 2460

Thr Phe  Asp Arg Thr Gln Val  Leu Asp Ala His Tyr  Asp Ser Val
    2465                 2470                 2475

Leu Lys  Asp Ile Lys Leu Ala  Ala Ser Lys Val Ser  Ala Arg Leu
    2480                 2485                 2490

Leu Thr  Leu Glu Glu Ala Cys  Gln Leu Thr Pro Pro  His Ser Ala
    2495                 2500                 2505

Arg Ser  Lys Tyr Gly Phe Gly  Ala Lys Glu Val Arg  Ser Leu Ser
    2510                 2515                 2520

Gly Arg  Ala Val Asn His Ile  Lys Ser Val Trp Lys  Asp Leu Leu
    2525                 2530                 2535

Glu Asp  Pro Gln Thr Pro Ile  Pro Thr Thr Ile Met  Ala Lys Asn
    2540                 2545                 2550

Glu Val  Phe Cys Val Asp Pro  Ala Lys Gly Gly Lys  Lys Pro Ala
    2555                 2560                 2565

Arg Leu  Ile Val Tyr Pro Asp  Leu Gly Val Arg Val  Cys Glu Lys
    2570                 2575                 2580

Met Ala  Leu Tyr Asp Ile Thr  Gln Lys Leu Pro Gln  Ala Val Met
    2585                 2590                 2595

Gly Ala  Ser Tyr Gly Phe Gln  Tyr Ser Pro Ala Gln  Arg Val Glu
    2600                 2605                 2610

Tyr Leu  Leu Lys Ala Trp Ala  Glu Lys Lys Asp Pro  Met Gly Phe
    2615                 2620                 2625

Ser Tyr  Asp Thr Arg Cys Phe  Asp Ser Thr Val Thr  Glu Arg Asp
    2630                 2635                 2640

Ile Arg  Thr Glu Glu Ser Ile  Tyr Gln Ala Cys Ser  Leu Pro Glu
```

```
    2645                2650                2655

Glu Ala  Arg Thr Ala Ile His  Ser Leu Thr Glu Arg  Leu Tyr Val
    2660                2665                2670

Gly Gly  Pro Met Phe Asn Ser  Lys Gly Gln Thr Cys  Gly Tyr Arg
    2675                2680                2685

Arg Cys  Arg Ala Ser Gly Val  Leu Thr Thr Ser Met  Gly Asn Thr
    2690                2695                2700

Ile Thr  Cys Tyr Val Lys Ala  Leu Ala Ala Cys Lys  Ala Ala Gly
    2705                2710                2715

Ile Val  Ala Pro Thr Met Leu  Val Cys Gly Asp Asp  Leu Val Val
    2720                2725                2730

Ile Ser  Glu Ser Gln Gly Thr  Glu Glu Asp Glu Arg  Asn Leu Arg
    2735                2740                2745

Ala Phe  Thr Glu Ala Met Thr  Arg Tyr Ser Ala Pro  Pro Gly Asp
    2750                2755                2760

Pro Pro  Arg Pro Glu Tyr Asp  Leu Glu Leu Ile Thr  Ser Cys Ser
    2765                2770                2775

Ser Asn  Val Ser Val Ala Leu  Gly Pro Arg Gly Arg  Arg Arg Tyr
    2780                2785                2790

Tyr Leu  Thr Arg Asp Pro Thr  Thr Pro Leu Ala Arg  Ala Ala Trp
    2795                2800                2805

Glu Thr  Val Arg His Ser Pro  Ile Asn Ser Trp Leu  Gly Asn Ile
    2810                2815                2820

Ile Gln  Tyr Ala Pro Thr Ile  Trp Val Arg Met Val  Leu Met Thr
    2825                2830                2835

His Phe  Phe Ser Ile Leu Met  Val Gln Asp Thr Leu  Asp Gln Asn
    2840                2845                2850

Leu Asn  Phe Glu Met Tyr Gly  Ser Val Tyr Ser Val  Asn Pro Leu
    2855                2860                2865

Asp Leu  Pro Ala Ile Ile Glu  Arg Leu His Gly Leu  Asp Ala Phe
    2870                2875                2880

Ser Met  His Thr Tyr Ser His  His Glu Leu Thr Arg  Val Ala Ser
    2885                2890                2895

Ala Leu  Arg Lys Leu Gly Ala  Pro Pro Leu Arg Val  Trp Lys Ser
    2900                2905                2910

Arg Ala  Arg Ala Val Arg Ala  Ser Leu Ile Ser Arg  Gly Gly Lys
    2915                2920                2925

Ala Ala  Val Cys Gly Arg Tyr  Leu Phe Asn Trp Ala  Val Lys Thr
    2930                2935                2940

Lys Leu  Lys Leu Thr Pro Leu  Pro Glu Ala Arg Leu  Leu Asp Leu
    2945                2950                2955

Ser Ser  Trp Phe Thr Val Gly  Ala Gly Gly Gly Asp  Ile Phe His
    2960                2965                2970

Ser Val  Ser Arg Ala Arg Pro  Arg Ser Leu Leu Phe  Gly Leu Leu
    2975                2980                2985

Leu Leu  Phe Val Gly Val Gly  Leu Phe Leu Leu Pro  Ala Arg
    2990                2995                3000


<210> SEQ ID NO 2
<211> LENGTH: 3006
<212> TYPE: PRT
<213> ORGANISM: Hepatitis C virus

<400> SEQUENCE: 2
```

-continued

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
    130                 135                 140

Gly Gly Val Ala Arg Ala Leu Ala His Gly Val Arg Val Leu Glu Asp
145                 150                 155                 160

Gly Val Asn Phe Ala Thr Gly Asn Leu Pro Gly Cys Ser Phe Ser Ile
                165                 170                 175

Phe Leu Leu Ala Leu Leu Ser Cys Ile Thr Thr Pro Val Ser Ala Ala
            180                 185                 190

Glu Val Lys Asn Ile Ser Thr Gly Tyr Met Val Thr Asn Asp Cys Thr
        195                 200                 205

Asn Asp Ser Ile Thr Trp Gln Leu Gln Ala Ala Val Leu His Val Pro
    210                 215                 220

Gly Cys Val Pro Cys Glu Lys Val Gly Asn Ala Ser Gln Cys Trp Ile
225                 230                 235                 240

Pro Val Ser Pro Asn Val Ala Val Gln Arg Pro Gly Ala Leu Thr Gln
                245                 250                 255

Gly Leu Arg Thr His Ile Asp Met Val Val Met Ser Ala Thr Leu Cys
            260                 265                 270

Ser Ala Leu Tyr Val Gly Asp Leu Cys Gly Gly Val Met Leu Ala Ala
        275                 280                 285

Gln Met Phe Ile Val Ser Pro Gln His His Trp Phe Val Gln Asp Cys
    290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Ala Met Arg Val Pro Glu Val Ile Ile Asp Ile Ile Ser Gly Ala His
            340                 345                 350

Trp Gly Val Met Phe Gly Leu Ala Tyr Phe Ser Met Gln Gly Ala Trp
        355                 360                 365

Ala Lys Val Val Val Ile Leu Leu Leu Ala Ala Gly Val Asp Ala Ile
    370                 375                 380

Gln Leu Val Asn Thr Asn Gly Ser Trp His Ile Asn Arg Thr Ala Leu
385                 390                 395                 400

Asn Cys Asn Asp Ser Leu His Thr Gly Phe Ile Ala Ser Leu Phe Tyr
                405                 410                 415

Thr His Ser Phe Asn Ser Ser Gly Cys Pro Glu Arg Met Ser Ala Cys
```

-continued

```
            420                 425                 430

Arg Ser Ile Glu Ala Phe Arg Val Gly Trp Gly Ala Leu Gln Tyr Glu
        435                 440                 445

Asp Asn Val Thr Asn Pro Glu Asp Met Arg Pro Tyr Cys Trp His Tyr
    450                 455                 460

Pro Pro Arg Gln Cys Gly Val Val Ser Ala Lys Thr Val Cys Gly Pro
465                 470                 475                 480

Val Tyr Cys Phe Thr Pro Ser Pro Val Val Val Gly Thr Thr Asp Arg
                485                 490                 495

Leu Gly Ala Pro Thr Tyr Thr Trp Gly Glu Asn Glu Thr Asp Val Phe
            500                 505                 510

Leu Leu Asn Ser Thr Arg Pro Pro Leu Gly Ser Trp Phe Gly Cys Thr
        515                 520                 525

Trp Met Asn Ser Ser Gly Tyr Thr Lys Thr Cys Gly Ala Pro Pro Cys
    530                 535                 540

Arg Thr Arg Ala Asp Phe Asn Ala Ser Thr Asp Leu Leu Cys Pro Thr
545                 550                 555                 560

Asp Cys Phe Arg Lys His Pro Asp Thr Thr Tyr Leu Lys Cys Gly Ser
                565                 570                 575

Gly Pro Trp Leu Thr Pro Arg Cys Leu Ile Asp Tyr Pro Tyr Arg Leu
            580                 585                 590

Trp His Tyr Pro Cys Thr Val Asn Tyr Thr Ile Phe Lys Ile Arg Met
        595                 600                 605

Tyr Val Gly Gly Val Glu His Arg Leu Thr Ala Ala Cys Asn Phe Thr
    610                 615                 620

Arg Gly Asp Arg Cys Asn Leu Glu Asp Arg Asp Arg Ser Gln Leu Ser
625                 630                 635                 640

Pro Leu Leu His Ser Thr Thr Glu Trp Ala Ile Leu Pro Cys Ser Tyr
                645                 650                 655

Ser Asp Leu Pro Ala Leu Ser Thr Gly Leu Leu His Leu His Gln Asn
            660                 665                 670

Ile Val Asp Val Gln Phe Met Tyr Gly Leu Ser Pro Ala Leu Thr Lys
        675                 680                 685

Tyr Ile Val Arg Trp Glu Trp Val Ile Leu Leu Phe Leu Leu Leu Ala
    690                 695                 700

Asp Ala Arg Val Cys Ala Cys Leu Trp Met Leu Ile Leu Leu Gly Gln
705                 710                 715                 720

Ala Glu Ala Ala Leu Glu Lys Leu Val Ile Leu His Ala Ala Ser Ala
                725                 730                 735

Ala Ser Cys Asn Gly Phe Leu Tyr Phe Val Ile Phe Phe Val Ala Ala
            740                 745                 750

Trp Tyr Ile Lys Gly Arg Val Val Pro Leu Ala Thr Tyr Ser Leu Thr
        755                 760                 765

Gly Leu Trp Ser Phe Ser Leu Leu Leu Leu Ala Leu Pro Gln Gln Ala
    770                 775                 780

Tyr Ala Tyr Asp Ala Ser Val His Gly Gln Ile Gly Ala Ala Leu Leu
785                 790                 795                 800

Val Met Ile Thr Leu Phe Thr Leu Thr Pro Gly Tyr Lys Thr Leu Leu
                805                 810                 815

Ser Arg Phe Leu Trp Trp Leu Cys Tyr Leu Leu Thr Leu Gly Glu Ala
            820                 825                 830

Met Val Gln Glu Trp Ala Pro Pro Met Gln Val Arg Gly Gly Arg Asp
        835                 840                 845
```

-continued

```
Gly Ile Ile Trp Ala Val Ala Ile Phe Tyr Pro Gly Val Val Phe Asp
    850                 855                 860

Ile Thr Lys Trp Leu Leu Ala Val Leu Gly Pro Ala Tyr Leu Leu Lys
865                 870                 875                 880

Gly Ala Leu Thr Arg Val Pro Tyr Phe Val Arg Ala His Ala Leu Leu
                885                 890                 895

Arg Met Cys Thr Met Ala Arg His Leu Ala Gly Gly Arg Tyr Val Gln
            900                 905                 910

Met Ala Leu Leu Ala Leu Gly Arg Trp Thr Gly Thr Tyr Ile Tyr Asp
        915                 920                 925

His Leu Thr Pro Met Ser Asp Trp Ala Ala Ser Gly Leu Arg Asp Leu
    930                 935                 940

Ala Val Ala Val Glu Pro Ile Ile Phe Ser Pro Met Glu Lys Lys Val
945                 950                 955                 960

Ile Val Trp Gly Ala Glu Thr Ala Ala Cys Gly Asp Ile Leu His Gly
                965                 970                 975

Leu Pro Val Ser Ala Arg Leu Gly Arg Glu Val Leu Leu Gly Pro Ala
            980                 985                 990

Asp Gly Tyr Thr Ser Lys Gly Trp  Ser Leu Leu Ala Pro  Ile Thr Ala
        995                 1000                1005

Tyr Ala  Gln Gln Thr Arg Gly  Leu Leu Gly Ala Ile  Val Val Ser
    1010                 1015                 1020

Met Thr  Gly Arg Asp Arg Thr  Glu Gln Ala Gly Glu  Val Gln Ile
    1025                 1030                 1035

Leu Ser  Thr Val Ser Gln Ser  Phe Leu Gly Thr Thr  Ile Ser Gly
    1040                 1045                 1050

Val Leu  Trp Thr Val Tyr His  Gly Ala Gly Asn Lys  Thr Leu Ala
    1055                 1060                 1065

Gly Leu  Arg Gly Pro Val Thr  Gln Met Tyr Ser Ser  Ala Glu Gly
    1070                 1075                 1080

Asp Leu  Val Gly Trp Pro Ser  Pro Pro Gly Thr Lys  Ser Leu Glu
    1085                 1090                 1095

Pro Cys  Lys Cys Gly Ala Val  Asp Leu Tyr Leu Val  Thr Arg Asn
    1100                 1105                 1110

Ala Asp  Val Ile Pro Ala Arg  Arg Arg Gly Asp Lys  Arg Gly Ala
    1115                 1120                 1125

Leu Leu  Ser Pro Arg Pro Ile  Ser Thr Leu Lys Gly  Ser Ser Gly
    1130                 1135                 1140

Gly Pro  Val Leu Cys Pro Arg  Gly His Val Val Gly  Leu Phe Arg
    1145                 1150                 1155

Ala Ala  Val Cys Ser Arg Gly  Val Ala Lys Ser Ile  Asp Phe Ile
    1160                 1165                 1170

Pro Val  Glu Thr Leu Asp Val  Val Thr Arg Ser Pro  Thr Phe Ser
    1175                 1180                 1185

Asp Asn  Ser Thr Pro Pro Ala  Val Pro Gln Thr Tyr  Gln Val Gly
    1190                 1195                 1200

Tyr Leu  His Ala Pro Thr Gly  Ser Gly Lys Ser Thr  Lys Val Pro
    1205                 1210                 1215

Val Ala  Tyr Ala Ala Gln Gly  Tyr Lys Val Leu Val  Leu Asn Pro
    1220                 1225                 1230

Ser Val  Ala Ala Thr Leu Gly  Phe Gly Ala Tyr Leu  Ser Lys Ala
    1235                 1240                 1245
```

-continued

```
His Gly  Ile Asn Pro Asn Ile  Arg Thr Gly Val Arg  Thr Val Met
    1250                 1255                 1260

Thr Gly  Glu Ala Ile Thr Tyr  Ser Thr Tyr Gly Lys  Phe Leu Ala
    1265                 1270                 1275

Asp Gly  Gly Cys Ala Ser Gly  Ala Tyr Asp Ile Ile  Ile Cys Asp
    1280                 1285                 1290

Glu Cys  His Ala Val Asp Ala  Thr Ser Ile Leu Gly  Ile Gly Thr
    1295                 1300                 1305

Val Leu  Asp Gln Ala Glu Thr  Ala Gly Val Arg Leu  Thr Val Leu
    1310                 1315                 1320

Ala Thr  Ala Thr Pro Pro Gly  Ser Val Thr Thr Pro  His Pro Asp
    1325                 1330                 1335

Ile Glu  Glu Val Gly Leu Gly  Arg Glu Gly Glu Ile  Pro Phe Tyr
    1340                 1345                 1350

Gly Arg  Ala Ile Pro Leu Ser  Cys Ile Lys Gly Gly  Arg His Leu
    1355                 1360                 1365

Ile Phe  Cys His Ser Lys Lys  Lys Cys Asp Glu Leu  Ala Ala Ala
    1370                 1375                 1380

Leu Arg  Gly Met Gly Leu Asn  Ala Val Ala Tyr Tyr  Arg Gly Leu
    1385                 1390                 1395

Asp Val  Ser Ile Ile Pro Ala  Gln Gly Asp Val Val  Val Val Ala
    1400                 1405                 1410

Thr Asp  Ala Leu Met Thr Gly  Tyr Thr Gly Asp Phe  Asp Ser Val
    1415                 1420                 1425

Ile Asp  Cys Asn Val Ala Val  Thr Gln Ala Val Asp  Phe Ser Leu
    1430                 1435                 1440

Asp Pro  Thr Phe Thr Ile Thr  Thr Gln Thr Val Pro  Gln Asp Ala
    1445                 1450                 1455

Val Ser  Arg Ser Gln Arg Arg  Gly Arg Thr Gly Arg  Gly Arg Gln
    1460                 1465                 1470

Gly Thr  Tyr Arg Tyr Val Ser  Thr Gly Glu Arg Ala  Ser Gly Met
    1475                 1480                 1485

Phe Asp  Ser Val Val Leu Cys  Glu Cys Tyr Asp Ala  Gly Ala Ala
    1490                 1495                 1500

Trp Tyr  Asp Leu Thr Pro Ala  Glu Thr Thr Val Arg  Leu Arg Ala
    1505                 1510                 1515

Tyr Phe  Asn Thr Pro Gly Leu  Pro Val Cys Gln Asp  His Leu Glu
    1520                 1525                 1530

Phe Trp  Glu Ala Val Phe Thr  Gly Leu Thr His Ile  Asp Ala His
    1535                 1540                 1545

Phe Leu  Ser Gln Thr Lys Gln  Ala Gly Glu Asn Phe  Ala Tyr Leu
    1550                 1555                 1560

Val Ala  Tyr Gln Ala Thr Val  Cys Ala Arg Ala Lys  Ala Pro Pro
    1565                 1570                 1575

Pro Ser  Trp Asp Ala Met Trp  Lys Cys Leu Ala Arg  Leu Lys Pro
    1580                 1585                 1590

Thr Leu  Ala Gly Pro Thr Pro  Leu Leu Tyr Arg Leu  Gly Pro Ile
    1595                 1600                 1605

Thr Asn  Glu Val Thr Leu Thr  His Pro Gly Thr Lys  Tyr Ile Ala
    1610                 1615                 1620

Thr Cys  Met Gln Ala Asp Leu  Glu Val Met Thr Ser  Thr Trp Val
    1625                 1630                 1635

Leu Ala  Gly Gly Val Leu Ala  Ala Val Ala Ala Tyr  Cys Leu Ala
```

```
    1640                1645                1650

Thr Gly  Cys Val Ser Ile Ile  Gly Arg Leu His Val  Asn Gln Arg
    1655                1660                1665

Val Val  Val Ala Pro Asp Lys  Glu Val Leu Tyr Glu  Ala Phe Asp
    1670                1675                1680

Glu Met  Glu Glu Cys Ala Ser  Arg Ala Ala Leu Ile  Glu Glu Gly
    1685                1690                1695

Gln Arg  Ile Ala Glu Met Leu  Lys Ser Lys Ile Gln  Gly Leu Leu
    1700                1705                1710

Gln Gln  Ala Ser Lys Gln Ala  Gln Asp Ile Gln Pro  Ala Met Gln
    1715                1720                1725

Ala Ser  Trp Pro Lys Val Glu  Gln Phe Trp Ala Arg  His Met Trp
    1730                1735                1740

Asn Phe  Ile Ser Gly Ile Gln  Tyr Leu Ala Gly Leu  Ser Thr Leu
    1745                1750                1755

Pro Gly  Asn Pro Ala Val Ala  Ser Met Met Ala Phe  Ser Ala Ala
    1760                1765                1770

Leu Thr  Ser Pro Leu Ser Thr  Ser Thr Thr Ile Leu  Leu Asn Ile
    1775                1780                1785

Met Gly  Gly Trp Leu Ala Ser  Gln Ile Ala Pro Pro  Ala Gly Ala
    1790                1795                1800

Thr Gly  Phe Val Val Ser Gly  Leu Val Gly Ala Ala  Val Gly Ser
    1805                1810                1815

Ile Gly  Leu Gly Lys Val Leu  Val Asp Ile Leu Ala  Gly Tyr Gly
    1820                1825                1830

Ala Gly  Ile Ser Gly Ala Leu  Val Ala Phe Lys Ile  Met Ser Gly
    1835                1840                1845

Glu Lys  Pro Ser Met Glu Asp  Val Ile Asn Leu Leu  Pro Gly Ile
    1850                1855                1860

Leu Ser  Pro Gly Ala Leu Val  Val Gly Val Ile Cys  Ala Ala Ile
    1865                1870                1875

Leu Arg  Arg His Val Gly Pro  Gly Glu Gly Ala Val  Gln Trp Met
    1880                1885                1890

Asn Arg  Leu Ile Ala Phe Ala  Ser Arg Gly Asn His  Val Ala Pro
    1895                1900                1905

Thr His  Tyr Val Thr Glu Ser  Asp Ala Ser Gln Arg  Val Thr Gln
    1910                1915                1920

Leu Leu  Gly Ser Leu Thr Ile  Thr Ser Leu Leu Arg  Arg Leu His
    1925                1930                1935

Asn Trp  Ile Thr Glu Asp Cys  Pro Ile Pro Cys Ser  Gly Ser Trp
    1940                1945                1950

Leu Arg  Asp Val Trp Asp Trp  Val Cys Thr Ile Leu  Thr Asp Phe
    1955                1960                1965

Lys Asn  Trp Leu Thr Ser Lys  Leu Phe Pro Lys Leu  Pro Gly Leu
    1970                1975                1980

Pro Phe  Ile Ser Cys Gln Lys  Gly Tyr Lys Gly Val  Trp Ala Gly
    1985                1990                1995

Thr Gly  Ile Met Thr Thr Arg  Cys Pro Cys Gly Ala  Asn Ile Ser
    2000                2005                2010

Gly Asn  Val Arg Leu Gly Ser  Met Arg Ile Thr Gly  Pro Lys Thr
    2015                2020                2025

Cys Met  Asn Thr Trp Gln Gly  Thr Phe Pro Ile Asn  Cys Tyr Thr
    2030                2035                2040
```

```
Glu Gly  Gln Cys Ala Pro Lys  Pro Pro Thr Asn Tyr  Lys Thr Ala
    2045                 2050                 2055

Ile Trp  Arg Val Ala Ala Ser  Glu Tyr Ala Glu Val  Thr Gln His
    2060                 2065                 2070

Gly Ser  Tyr Ser Tyr Val Thr  Gly Leu Thr Thr Asp  Asn Leu Lys
    2075                 2080                 2085

Ile Pro  Cys Gln Leu Pro Ser  Pro Glu Phe Phe Ser  Trp Val Asp
    2090                 2095                 2100

Gly Val  Gln Ile His Arg Phe  Ala Pro Thr Pro Lys  Pro Phe Phe
    2105                 2110                 2115

Arg Asp  Glu Val Ser Phe Cys  Val Gly Leu Asn Ser  Tyr Ala Val
    2120                 2125                 2130

Gly Ser  Gln Leu Pro Cys Glu  Pro Glu Pro Asp Ala  Asp Val Leu
    2135                 2140                 2145

Arg Ser  Met Leu Thr Asp Pro  Pro His Ile Thr Ala  Glu Thr Ala
    2150                 2155                 2160

Ala Arg  Arg Leu Ala Arg Gly  Ser Pro Pro Ser Glu  Ala Ser Ser
    2165                 2170                 2175

Ser Val  Ser Gln Leu Ser Ala  Pro Ser Leu Arg Ala  Thr Cys Thr
    2180                 2185                 2190

Thr His  Ser Asn Thr Tyr Asp  Val Asp Met Val Asp  Ala Asn Leu
    2195                 2200                 2205

Leu Met  Glu Gly Gly Val Ala  Gln Thr Glu Pro Glu  Ser Arg Val
    2210                 2215                 2220

Pro Val  Leu Asp Phe Leu Glu  Pro Met Ala Glu Glu  Glu Ser Asp
    2225                 2230                 2235

Leu Glu  Pro Ser Ile Pro Ser  Glu Cys Met Leu Pro  Arg Ser Gly
    2240                 2245                 2250

Phe Pro  Arg Ala Leu Pro Ala  Trp Ala Arg Pro Asp  Tyr Asn Pro
    2255                 2260                 2265

Pro Leu  Val Glu Ser Trp Arg  Arg Pro Asp Tyr Gln  Pro Pro Thr
    2270                 2275                 2280

Val Ala  Gly Cys Ala Leu Pro  Pro Pro Lys Lys Ala  Pro Thr Pro
    2285                 2290                 2295

Pro Pro  Arg Arg Arg Arg Thr  Val Gly Leu Ser Glu  Ser Thr Ile
    2300                 2305                 2310

Ser Glu  Ala Leu Gln Gln Leu  Ala Ile Lys Thr Phe  Gly Gln Pro
    2315                 2320                 2325

Pro Ser  Ser Gly Asp Ala Gly  Ser Ser Thr Gly Ala  Gly Ala Ala
    2330                 2335                 2340

Glu Ser  Gly Gly Pro Thr Ser  Pro Gly Glu Pro Ala  Pro Ser Glu
    2345                 2350                 2355

Thr Gly  Ser Ala Ser Ser Met  Pro Pro Leu Glu Gly  Glu Pro Gly
    2360                 2365                 2370

Asp Pro  Asp Leu Glu Ser Asp  Gln Val Glu Leu Gln  Pro Pro Pro
    2375                 2380                 2385

Gln Gly  Gly Gly Val Ala Pro  Gly Ser Gly Ser Gly  Ser Trp Ser
    2390                 2395                 2400

Thr Cys  Ser Glu Glu Asp Asp  Thr Thr Val Cys Cys  Ser Met Ser
    2405                 2410                 2415

Tyr Ser  Trp Thr Gly Ala Leu  Ile Thr Pro Cys Ser  Pro Glu Glu
    2420                 2425                 2430
```

```
Glu Lys  Leu Pro Ile Asn Pro  Leu Ser Asn Ser Leu  Leu Arg Tyr
    2435                 2440                 2445

His Asn  Lys Val Tyr Cys Thr  Thr Ser Lys Ser Ala  Ser Gln Arg
    2450                 2455                 2460

Ala Lys  Lys Val Thr Phe Asp  Arg Thr Gln Val Leu  Asp Ala His
    2465                 2470                 2475

Tyr Asp  Ser Val Leu Lys Asp  Ile Lys Leu Ala Ala  Ser Lys Val
    2480                 2485                 2490

Ser Ala  Arg Leu Leu Thr Leu  Glu Glu Ala Cys Gln  Leu Thr Pro
    2495                 2500                 2505

Pro His  Ser Ala Arg Ser Lys  Tyr Gly Phe Gly Ala  Lys Glu Val
    2510                 2515                 2520

Arg Ser  Leu Ser Gly Arg Ala  Val Asn His Ile Lys  Ser Val Trp
    2525                 2530                 2535

Lys Asp  Leu Leu Glu Asp Pro  Gln Thr Pro Ile Pro  Thr Thr Ile
    2540                 2545                 2550

Met Ala  Lys Asn Glu Val Phe  Cys Val Asp Pro Ala  Lys Gly Gly
    2555                 2560                 2565

Lys Lys  Pro Ala Arg Leu Ile  Val Tyr Pro Asp Leu  Gly Val Arg
    2570                 2575                 2580

Val Cys  Glu Lys Met Ala Leu  Tyr Asp Ile Thr Gln  Lys Leu Pro
    2585                 2590                 2595

Gln Ala  Val Met Gly Ala Ser  Tyr Gly Phe Gln Tyr  Ser Pro Ala
    2600                 2605                 2610

Gln Arg  Val Glu Tyr Leu Leu  Lys Ala Trp Ala Glu  Lys Lys Asp
    2615                 2620                 2625

Pro Met  Gly Phe Ser Tyr Asp  Thr Arg Cys Phe Asp  Ser Thr Val
    2630                 2635                 2640

Thr Glu  Arg Asp Ile Arg Thr  Glu Glu Ser Ile Tyr  Gln Ala Cys
    2645                 2650                 2655

Ser Leu  Pro Glu Glu Ala Arg  Thr Ala Ile His Ser  Leu Thr Glu
    2660                 2665                 2670

Arg Leu  Tyr Val Gly Gly Pro  Met Phe Asn Ser Lys  Gly Gln Thr
    2675                 2680                 2685

Cys Gly  Tyr Arg Arg Cys Arg  Ala Ser Gly Val Leu  Thr Thr Ser
    2690                 2695                 2700

Met Gly  Asn Thr Ile Thr Cys  Tyr Val Lys Ala Leu  Ala Ala Cys
    2705                 2710                 2715

Lys Ala  Ala Gly Ile Val Ala  Pro Thr Met Leu Val  Cys Gly Asp
    2720                 2725                 2730

Asp Leu  Val Val Ile Ser Glu  Ser Gln Gly Thr Glu  Glu Asp Glu
    2735                 2740                 2745

Arg Asn  Leu Arg Ala Phe Thr  Glu Ala Met Thr Arg  Tyr Ser Ala
    2750                 2755                 2760

Pro Pro  Gly Asp Pro Pro Arg  Pro Glu Tyr Asp Leu  Glu Leu Ile
    2765                 2770                 2775

Thr Ser  Cys Ser Ser Asn Val  Ser Val Ala Leu Gly  Pro Arg Gly
    2780                 2785                 2790

Arg Arg  Arg Tyr Tyr Leu Thr  Arg Asp Pro Thr Thr  Pro Leu Ala
    2795                 2800                 2805

Arg Ala  Ala Trp Glu Thr Val  Arg His Ser Pro Ile  Asn Ser Trp
    2810                 2815                 2820

Leu Gly  Asn Ile Ile Gln Tyr  Ala Pro Thr Ile Trp  Val Arg Met
```

```
    2825                2830                2835

Val Leu  Met Thr His Phe Phe  Ser Ile Leu Met Val  Gln Asp Thr
    2840                2845                2850

Leu Asp  Gln Asn Leu Asn Phe  Glu Met Tyr Gly Ser  Val Tyr Ser
    2855                2860                2865

Val Asn  Pro Leu Asp Leu Pro  Ala Ile Ile Glu Arg  Leu His Gly
    2870                2875                2880

Leu Asp  Ala Phe Ser Met His  Thr Tyr Ser His His  Glu Leu Thr
    2885                2890                2895

Arg Val  Ala Ser Ala Leu Arg  Lys Leu Gly Ala Pro  Pro Leu Arg
    2900                2905                2910

Val Trp  Lys Ser Arg Ala Arg  Ala Val Arg Ala Ser  Leu Ile Ser
    2915                2920                2925

Arg Gly  Gly Lys Ala Ala Val  Cys Gly Arg Tyr Leu  Phe Asn Trp
    2930                2935                2940

Ala Val  Lys Thr Lys Leu Lys  Leu Thr Pro Leu Pro  Glu Ala Arg
    2945                2950                2955

Leu Leu  Asp Leu Ser Ser Trp  Phe Thr Val Gly Ala  Gly Gly Gly
    2960                2965                2970

Asp Ile  Phe His Ser Val Ser  Arg Ala Arg Pro Arg  Ser Leu Leu
    2975                2980                2985

Phe Gly  Leu Leu Leu Leu Phe  Val Gly Val Gly Leu  Phe Leu Leu
    2990                2995                3000

Pro Ala  Arg
    3005


<210> SEQ ID NO 3
<211> LENGTH: 3008
<212> TYPE: PRT
<213> ORGANISM: Hepatitis C virus

<400> SEQUENCE: 3

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175
```

-continued

```
Phe Leu Leu Ala Leu Phe Ser Cys Leu Val His Pro Ala Ala Ser Leu
            180                 185                 190

Glu Trp Arg Asn Thr Ser Gly Leu Tyr Val Leu Thr Asn Asp Cys Ser
        195                 200                 205

Asn Ser Ser Ile Val Tyr Glu Ala Asp Asp Val Ile Leu His Thr Pro
    210                 215                 220

Gly Cys Val Pro Cys Val Gln Asp Asp Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Leu Cys
            260                 265                 270

Ser Ala Leu Tyr Val Gly Asp Met Cys Gly Ala Val Phe Leu Val Gly
        275                 280                 285

Gln Ala Phe Thr Phe Arg Pro Arg Arg His Gln Thr Val Gln Thr Cys
    290                 295                 300

Asn Cys Ser Leu Tyr Pro Gly His Val Ser Gly His Arg Met Ala Trp
305                 310                 315                 320

Asp Met Met Met Asn Trp Ser Pro Ala Val Gly Met Val Val Ala His
                325                 330                 335

Ile Leu Arg Leu Pro Gln Thr Leu Phe Asp Ile Leu Ala Gly Ala His
            340                 345                 350

Trp Gly Ile Leu Ala Gly Leu Ala Tyr Tyr Ser Met Gln Gly Asn Trp
        355                 360                 365

Ala Lys Val Ala Ile Val Met Ile Met Phe Ser Gly Val Asp Ala Leu
    370                 375                 380

Gln Leu Val Asn Thr Asn Gly Ser Trp His Ile Asn Ser Thr Ala Leu
385                 390                 395                 400

Asn Cys Asn Glu Ser Ile Asn Thr Gly Phe Ile Ala Gly Leu Phe Tyr
                405                 410                 415

Tyr His Lys Phe Asn Ser Thr Gly Cys Pro Gln Arg Leu Ser Ser Cys
            420                 425                 430

Lys Pro Ile Ile Ser Phe Arg Gln Gly Trp Gly Pro Leu Thr Asp Ala
        435                 440                 445

Asn Ile Thr Gly Pro Ser Asp Asp Arg Pro Tyr Cys Trp His Tyr Ala
    450                 455                 460

Pro Arg Pro Cys Ser Val Val Pro Ala Ser Ser Val Cys Gly Pro Val
465                 470                 475                 480

Tyr Cys Phe Thr Pro Ser Pro Val Val Val Gly Thr Thr Asp Ile Lys
                485                 490                 495

Gly Lys Pro Thr Tyr Asn Trp Gly Glu Asn Glu Thr Asp Val Phe Leu
            500                 505                 510

Leu Glu Ser Leu Arg Pro Pro Ser Gly Arg Trp Phe Gly Cys Ala Trp
        515                 520                 525

Met Asn Ser Thr Gly Phe Leu Lys Thr Cys Gly Ala Pro Pro Cys Asn
    530                 535                 540

Ile Tyr Gly Gly Glu Gly Asp Pro Glu Asn Glu Thr Asp Leu Phe Cys
545                 550                 555                 560

Pro Thr Asp Cys Phe Arg Lys His Pro Glu Ala Thr Tyr Ser Arg Cys
                565                 570                 575

Gly Ala Gly Pro Trp Leu Thr Pro Arg Cys Met Val Asp Tyr Pro Tyr
            580                 585                 590

Arg Leu Trp His Tyr Pro Cys Thr Val Asn Phe Thr Leu Phe Lys Val
```

```
        595                 600                 605

Arg Met Phe Val Gly Gly Phe Glu His Arg Phe Thr Ala Ala Cys Asn
    610                 615                 620

Trp Thr Arg Gly Glu Arg Cys Asn Ile Glu Asp Arg Asp Arg Ser Glu
625                 630                 635                 640

Gln His Pro Leu Leu His Ser Thr Thr Glu Leu Ala Ile Leu Pro Cys
                645                 650                 655

Ser Phe Thr Pro Met Pro Ala Leu Ser Thr Gly Leu Ile His Leu His
            660                 665                 670

Gln Asn Ile Val Asp Val Gln Tyr Leu Tyr Gly Val Gly Ser Asp Met
        675                 680                 685

Val Gly Trp Ala Leu Lys Trp Glu Phe Val Ile Leu Val Phe Leu Leu
    690                 695                 700

Leu Ala Asp Ala Arg Val Cys Val Ala Leu Trp Leu Met Leu Met Val
705                 710                 715                 720

Ser Gln Ala Glu Ala Ala Leu Glu Asn Leu Val Thr Leu Asn Ala Val
                725                 730                 735

Ala Ala Ala Gly Thr His Gly Ile Gly Trp Tyr Leu Val Ala Phe Cys
            740                 745                 750

Ala Ala Trp Tyr Val Arg Gly Lys Leu Val Pro Leu Thr Ser Tyr Gly
        755                 760                 765

Leu Thr Gly Leu Trp Ser Leu Ala Leu Leu Val Leu Leu Leu Pro Gln
    770                 775                 780

Arg Ala Tyr Ala Trp Ser Gly Glu Asp Ser Ala Thr Leu Gly Ala Gly
785                 790                 795                 800

Val Leu Ala Leu Phe Gly Phe Phe Thr Leu Ser Pro Trp Tyr Lys His
                805                 810                 815

Trp Ile Gly Arg Leu Met Trp Trp Asn Gln Tyr Thr Ile Cys Arg Cys
            820                 825                 830

Glu Ala Ala Leu Gln Val Trp Val Pro Pro Leu Leu Ala Arg Gly Ser
        835                 840                 845

Arg Asp Gly Val Ile Leu Leu Thr Ser Leu Leu Tyr Pro Ser Leu Ile
    850                 855                 860

Phe Asp Ile Thr Lys Leu Leu Ile Ala Val Ile Gly Pro Leu Tyr Leu
865                 870                 875                 880

Ile Gln Ala Ala Ile Thr Thr Thr Pro Tyr Phe Val Arg Ala His Val
                885                 890                 895

Leu Val Arg Leu Cys Met Leu Val Arg Ser Val Met Gly Gly Lys Tyr
            900                 905                 910

Phe Gln Met Ala Ile Leu Ser Ile Gly Arg Trp Phe Asn Thr Tyr Leu
        915                 920                 925

Tyr Asp His Leu Ala Pro Met Gln His Trp Ala Ala Ala Gly Leu Lys
    930                 935                 940

Asp Leu Ala Val Ala Thr Glu Pro Val Ile Phe Ser Pro Met Glu Ile
945                 950                 955                 960

Lys Val Ile Thr Trp Gly Ala Asp Thr Ala Ala Cys Gly Asp Ile Leu
                965                 970                 975

Cys Gly Leu Pro Val Ser Ala Arg Leu Gly Arg Glu Val Leu Leu Gly
            980                 985                 990

Pro Ala Asp Asp Tyr Arg Glu Met  Gly Trp Arg Leu Leu  Ala Pro Ile
        995                 1000                 1005

Thr Ala  Tyr Ala Gln Gln Thr  Arg Gly Leu Leu Gly  Ala Ile Val
    1010                 1015                 1020
```

-continued

```
Val Ser  Met Thr Gly Arg Asp  Arg Thr Glu Gln Ala  Gly Glu Val
    1025                 1030                 1035

Gln Ile  Leu Ser Thr Val Ser  Gln Ser Phe Leu Gly  Thr Thr Ile
    1040                 1045                 1050

Ser Gly  Val Leu Trp Thr Val  Tyr His Gly Ala Gly  Asn Lys Thr
    1055                 1060                 1065

Leu Ala  Gly Leu Arg Gly Pro  Val Thr Gln Met Tyr  Ser Ser Ala
    1070                 1075                 1080

Glu Gly  Asp Leu Val Gly Trp  Pro Ser Pro Pro Gly  Thr Lys Ser
    1085                 1090                 1095

Leu Glu  Pro Cys Lys Cys Gly  Ala Val Asp Leu Tyr  Leu Val Thr
    1100                 1105                 1110

Arg Asn  Ala Asp Val Ile Pro  Ala Arg Arg Arg Gly  Asp Lys Arg
    1115                 1120                 1125

Gly Ala  Leu Leu Ser Pro Arg  Pro Ile Ser Thr Leu  Lys Gly Ser
    1130                 1135                 1140

Ser Gly  Gly Pro Val Leu Cys  Pro Arg Gly His Val  Val Gly Leu
    1145                 1150                 1155

Phe Arg  Ala Ala Val Cys Ser  Arg Gly Val Ala Lys  Ser Ile Asp
    1160                 1165                 1170

Phe Ile  Pro Val Glu Thr Leu  Asp Val Val Thr Arg  Ser Pro Thr
    1175                 1180                 1185

Phe Ser  Asp Asn Ser Thr Pro  Pro Ala Val Pro Gln  Thr Tyr Gln
    1190                 1195                 1200

Val Gly  Tyr Leu His Ala Pro  Thr Gly Ser Gly Lys  Ser Thr Lys
    1205                 1210                 1215

Val Pro  Val Ala Tyr Ala Ala  Gln Gly Tyr Lys Val  Leu Val Leu
    1220                 1225                 1230

Asn Pro  Ser Val Ala Ala Thr  Leu Gly Phe Gly Ala  Tyr Leu Ser
    1235                 1240                 1245

Lys Ala  His Gly Ile Asn Pro  Asn Ile Arg Thr Gly  Val Arg Thr
    1250                 1255                 1260

Val Met  Thr Gly Glu Ala Ile  Thr Tyr Ser Thr Tyr  Gly Lys Phe
    1265                 1270                 1275

Leu Ala  Asp Gly Gly Cys Ala  Ser Gly Ala Tyr Asp  Ile Ile Ile
    1280                 1285                 1290

Cys Asp  Glu Cys His Ala Val  Asp Ala Thr Ser Ile  Leu Gly Ile
    1295                 1300                 1305

Gly Thr  Val Leu Asp Gln Ala  Glu Thr Ala Gly Val  Arg Leu Thr
    1310                 1315                 1320

Val Leu  Ala Thr Ala Thr Pro  Pro Gly Ser Val Thr  Thr Pro His
    1325                 1330                 1335

Pro Asp  Ile Glu Glu Val Gly  Leu Gly Arg Glu Gly  Glu Ile Pro
    1340                 1345                 1350

Phe Tyr  Gly Arg Ala Ile Pro  Leu Ser Cys Ile Lys  Gly Gly Arg
    1355                 1360                 1365

His Leu  Ile Phe Cys His Ser  Lys Lys Lys Cys Asp  Glu Leu Ala
    1370                 1375                 1380

Ala Ala  Leu Arg Gly Met Gly  Leu Asn Ala Val Ala  Tyr Tyr Arg
    1385                 1390                 1395

Gly Leu  Asp Val Ser Ile Ile  Pro Ala Gln Gly Asp  Val Val Val
    1400                 1405                 1410
```

-continued

Val Ala Thr Asp Ala Leu Met Thr Gly Tyr Thr Gly Asp Phe Asp
1415 1420 1425

Ser Val Ile Asp Cys Asn Val Ala Val Thr Gln Ala Val Asp Phe
1430 1435 1440

Ser Leu Asp Pro Thr Phe Thr Ile Thr Thr Gln Thr Val Pro Gln
1445 1450 1455

Asp Ala Val Ser Arg Ser Gln Arg Arg Gly Arg Thr Gly Arg Gly
1460 1465 1470

Arg Gln Gly Thr Tyr Arg Tyr Val Ser Thr Gly Glu Arg Ala Ser
1475 1480 1485

Gly Met Phe Asp Ser Val Val Leu Cys Glu Cys Tyr Asp Ala Gly
1490 1495 1500

Ala Ala Trp Tyr Asp Leu Thr Pro Ala Glu Thr Thr Val Arg Leu
1505 1510 1515

Arg Ala Tyr Phe Asn Thr Pro Gly Leu Pro Val Cys Gln Asp His
1520 1525 1530

Leu Glu Phe Trp Glu Ala Val Phe Thr Gly Leu Thr His Ile Asp
1535 1540 1545

Ala His Phe Leu Ser Gln Thr Lys Gln Ala Gly Glu Asn Phe Ala
1550 1555 1560

Tyr Leu Val Ala Tyr Gln Ala Thr Val Cys Ala Arg Ala Lys Ala
1565 1570 1575

Pro Pro Pro Ser Trp Asp Ala Met Trp Lys Cys Leu Ala Arg Leu
1580 1585 1590

Lys Pro Thr Leu Ala Gly Pro Thr Pro Leu Leu Tyr Arg Leu Gly
1595 1600 1605

Pro Ile Thr Asn Glu Val Thr Leu Thr His Pro Gly Thr Lys Tyr
1610 1615 1620

Ile Ala Thr Cys Met Gln Ala Asp Leu Glu Val Met Thr Ser Thr
1625 1630 1635

Trp Val Leu Ala Gly Gly Val Leu Ala Ala Val Ala Ala Tyr Cys
1640 1645 1650

Leu Ala Thr Gly Cys Val Ser Ile Ile Gly Arg Leu His Val Asn
1655 1660 1665

Gln Arg Val Val Val Ala Pro Asp Lys Glu Val Leu Tyr Glu Ala
1670 1675 1680

Phe Asp Glu Met Glu Glu Cys Ala Ser Arg Ala Ala Leu Ile Glu
1685 1690 1695

Glu Gly Gln Arg Ile Ala Glu Met Leu Lys Ser Lys Ile Gln Gly
1700 1705 1710

Leu Leu Gln Gln Ala Ser Lys Gln Ala Gln Asp Ile Gln Pro Ala
1715 1720 1725

Met Gln Ala Ser Trp Pro Lys Val Glu Gln Phe Trp Ala Arg His
1730 1735 1740

Met Trp Asn Phe Ile Ser Gly Ile Gln Tyr Leu Ala Gly Leu Ser
1745 1750 1755

Thr Leu Pro Gly Asn Pro Ala Val Ala Ser Met Met Ala Phe Ser
1760 1765 1770

Ala Ala Leu Thr Ser Pro Leu Ser Thr Ser Thr Thr Ile Leu Leu
1775 1780 1785

Asn Ile Met Gly Gly Trp Leu Ala Ser Gln Ile Ala Pro Pro Ala
1790 1795 1800

Gly Ala Thr Gly Phe Val Val Ser Gly Leu Val Gly Ala Ala Val

```
    1805                 1810                 1815

Gly Ser  Ile Gly Leu Gly Lys  Val Leu Val Asp Ile  Leu Ala Gly
    1820                 1825                 1830

Tyr Gly  Ala Gly Ile Ser Gly  Ala Leu Val Ala Phe  Lys Ile Met
    1835                 1840                 1845

Ser Gly  Glu Lys Pro Ser Met  Glu Asp Val Ile Asn  Leu Leu Pro
    1850                 1855                 1860

Gly Ile  Leu Ser Pro Gly Ala  Leu Val Val Gly Val  Ile Cys Ala
    1865                 1870                 1875

Ala Ile  Leu Arg Arg His Val  Gly Pro Gly Glu Gly  Ala Val Gln
    1880                 1885                 1890

Trp Met  Asn Arg Leu Ile Ala  Phe Ala Ser Arg Gly  Asn His Val
    1895                 1900                 1905

Ala Pro  Thr His Tyr Val Thr  Glu Ser Asp Ala Ser  Gln Arg Val
    1910                 1915                 1920

Thr Gln  Leu Leu Gly Ser Leu  Thr Ile Thr Ser Leu  Leu Arg Arg
    1925                 1930                 1935

Leu His  Asn Trp Ile Thr Glu  Asp Cys Pro Ile Pro  Cys Ser Gly
    1940                 1945                 1950

Ser Trp  Leu Arg Asp Val Trp  Asp Trp Val Cys Thr  Ile Leu Thr
    1955                 1960                 1965

Asp Phe  Lys Asn Trp Leu Thr  Ser Lys Leu Phe Pro  Lys Leu Pro
    1970                 1975                 1980

Gly Leu  Pro Phe Ile Ser Cys  Gln Lys Gly Tyr Lys  Gly Val Trp
    1985                 1990                 1995

Ala Gly  Thr Gly Ile Met Thr  Thr Arg Cys Pro Cys  Gly Ala Asn
    2000                 2005                 2010

Ile Ser  Gly Asn Val Arg Leu  Gly Ser Met Arg Ile  Thr Gly Pro
    2015                 2020                 2025

Lys Thr  Cys Met Asn Thr Trp  Gln Gly Thr Phe Pro  Ile Asn Cys
    2030                 2035                 2040

Tyr Thr  Glu Gly Gln Cys Ala  Pro Lys Pro Pro Thr  Asn Tyr Lys
    2045                 2050                 2055

Thr Ala  Ile Trp Arg Val Ala  Ala Ser Glu Tyr Ala  Glu Val Thr
    2060                 2065                 2070

Gln His  Gly Ser Tyr Ser Tyr  Val Thr Gly Leu Thr  Thr Asp Asn
    2075                 2080                 2085

Leu Lys  Ile Pro Cys Gln Leu  Pro Ser Pro Glu Phe  Phe Ser Trp
    2090                 2095                 2100

Val Asp  Gly Val Gln Ile His  Arg Phe Ala Pro Thr  Pro Lys Pro
    2105                 2110                 2115

Phe Phe  Arg Asp Glu Val Ser  Phe Cys Val Gly Leu  Asn Ser Tyr
    2120                 2125                 2130

Ala Val  Gly Ser Gln Leu Pro  Cys Glu Pro Glu Pro  Asp Ala Asp
    2135                 2140                 2145

Val Leu  Arg Ser Met Leu Thr  Asp Pro Pro His Ile  Thr Ala Glu
    2150                 2155                 2160

Thr Ala  Ala Arg Arg Leu Ala  Arg Gly Ser Pro Pro  Ser Glu Ala
    2165                 2170                 2175

Ser Ser  Ser Val Ser Gln Leu  Ser Ala Pro Ser Leu  Arg Ala Thr
    2180                 2185                 2190

Cys Thr  Thr His Ser Asn Thr  Tyr Asp Val Asp Met  Val Asp Ala
    2195                 2200                 2205
```

-continued

```
Asn Leu  Leu Met Glu Gly Gly  Val Ala Gln Thr Glu  Pro Glu Ser
    2210                 2215                 2220

Arg Val  Pro Val Leu Asp Phe  Leu Glu Pro Met Ala  Glu Glu Glu
    2225                 2230                 2235

Ser Asp  Leu Glu Pro Ser Ile  Pro Pro Glu Cys Met  Leu Pro Arg
    2240                 2245                 2250

Ser Gly  Phe Pro Arg Ala Leu  Pro Ala Trp Ala Arg  Pro Asp Tyr
    2255                 2260                 2265

Asn Pro  Pro Leu Val Glu Ser  Trp Arg Arg Pro Asp  Tyr Gln Pro
    2270                 2275                 2280

Pro Thr  Val Ala Gly Cys Ala  Leu Pro Pro Pro Lys  Lys Ala Pro
    2285                 2290                 2295

Thr Pro  Pro Pro Arg Arg Arg  Arg Thr Val Gly Leu  Ser Glu Ser
    2300                 2305                 2310

Thr Ile  Ser Glu Ala Leu Gln  Gln Leu Ala Ile Lys  Thr Phe Gly
    2315                 2320                 2325

Gln Pro  Pro Ser Ser Gly Asp  Ala Gly Ser Ser Thr  Gly Ala Gly
    2330                 2335                 2340

Ala Ala  Glu Ser Gly Gly Pro  Thr Ser Pro Gly Glu  Pro Ala Pro
    2345                 2350                 2355

Ser Glu  Thr Gly Ser Ala Ser  Ser Met Pro Pro Leu  Glu Gly Glu
    2360                 2365                 2370

Pro Gly  Asp Pro Asp Leu Glu  Ser Asp Gln Val Glu  Leu Gln Pro
    2375                 2380                 2385

Pro Pro  Gln Gly Gly Gly Val  Ala Pro Gly Ser Gly  Ser Gly Ser
    2390                 2395                 2400

Trp Ser  Thr Cys Ser Glu Glu  Asp Asp Thr Thr Val  Cys Cys Ser
    2405                 2410                 2415

Met Ser  Tyr Ser Trp Thr Gly  Ala Leu Ile Thr Pro  Cys Ser Pro
    2420                 2425                 2430

Glu Glu  Glu Lys Leu Pro Ile  Asn Pro Leu Ser Asn  Ser Leu Leu
    2435                 2440                 2445

Arg Tyr  His Asn Lys Val Tyr  Cys Thr Thr Ser Lys  Ser Ala Ser
    2450                 2455                 2460

Gln Arg  Ala Lys Lys Val Thr  Phe Asp Arg Thr Gln  Val Leu Asp
    2465                 2470                 2475

Ala His  Tyr Asp Ser Val Leu  Lys Asp Ile Lys Leu  Ala Ala Ser
    2480                 2485                 2490

Lys Val  Ser Ala Arg Leu Leu  Thr Leu Glu Glu Ala  Cys Gln Leu
    2495                 2500                 2505

Thr Pro  Pro His Ser Ala Arg  Ser Lys Tyr Gly Phe  Gly Ala Lys
    2510                 2515                 2520

Glu Val  Arg Ser Leu Ser Gly  Arg Ala Val Asn His  Ile Lys Ser
    2525                 2530                 2535

Val Trp  Lys Asp Leu Leu Glu  Asp Pro Gln Thr Pro  Ile Pro Thr
    2540                 2545                 2550

Thr Ile  Met Ala Lys Asn Glu  Val Phe Cys Val Asp  Pro Ala Lys
    2555                 2560                 2565

Gly Gly  Lys Lys Pro Ala Arg  Leu Ile Val Tyr Pro  Asp Leu Gly
    2570                 2575                 2580

Val Arg  Val Cys Glu Lys Met  Ala Leu Tyr Asp Ile  Thr Gln Lys
    2585                 2590                 2595
```

-continued

```
Leu Pro  Gln Ala Val Met Gly  Ala Ser Tyr Gly Phe  Gln Tyr Ser
    2600                 2605                 2610

Pro Ala  Gln Arg Val Glu Tyr  Leu Leu Lys Ala Trp  Ala Glu Lys
    2615                 2620                 2625

Lys Asp  Pro Met Gly Phe Ser  Tyr Asp Thr Arg Cys  Phe Asp Ser
    2630                 2635                 2640

Thr Val  Thr Glu Arg Asp Ile  Arg Thr Glu Glu Ser  Ile Tyr Gln
    2645                 2650                 2655

Ala Cys  Ser Leu Pro Glu Glu  Ala Arg Thr Ala Ile  His Ser Leu
    2660                 2665                 2670

Thr Glu  Arg Leu Tyr Val Gly  Gly Pro Met Phe Asn  Ser Lys Gly
    2675                 2680                 2685

Gln Thr  Cys Gly Tyr Arg Arg  Cys Arg Ala Ser Gly  Val Leu Thr
    2690                 2695                 2700

Thr Ser  Met Gly Asn Thr Ile  Thr Cys Tyr Val Lys  Ala Leu Ala
    2705                 2710                 2715

Ala Cys  Lys Ala Ala Gly Ile  Val Ala Pro Thr Met  Leu Val Cys
    2720                 2725                 2730

Gly Asp  Asp Leu Val Val Ile  Ser Glu Ser Gln Gly  Thr Glu Glu
    2735                 2740                 2745

Asp Glu  Arg Asn Leu Arg Ala  Phe Thr Glu Ala Met  Thr Arg Tyr
    2750                 2755                 2760

Ser Ala  Pro Pro Gly Asp Pro  Pro Arg Pro Glu Tyr  Asp Leu Glu
    2765                 2770                 2775

Leu Ile  Thr Ser Cys Ser Ser  Asn Val Ser Val Ala  Leu Gly Pro
    2780                 2785                 2790

Arg Gly  Arg Arg Arg Tyr Tyr  Leu Thr Arg Asp Pro  Thr Thr Pro
    2795                 2800                 2805

Leu Ala  Arg Ala Ala Trp Glu  Thr Val Arg His Ser  Pro Ile Asn
    2810                 2815                 2820

Ser Trp  Leu Gly Asn Ile Ile  Gln Tyr Ala Pro Thr  Ile Trp Val
    2825                 2830                 2835

Arg Met  Val Leu Met Thr His  Phe Phe Ser Ile Leu  Met Val Gln
    2840                 2845                 2850

Asp Thr  Leu Asp Gln Asn Leu  Asn Phe Glu Met Tyr  Gly Ser Val
    2855                 2860                 2865

Tyr Ser  Val Asn Pro Leu Asp  Leu Pro Ala Ile Ile  Glu Arg Leu
    2870                 2875                 2880

His Gly  Leu Asp Ala Phe Ser  Met His Thr Tyr Ser  His His Glu
    2885                 2890                 2895

Leu Thr  Arg Val Ala Ser Ala  Leu Arg Lys Leu Gly  Ala Pro Pro
    2900                 2905                 2910

Leu Arg  Val Trp Lys Ser Arg  Ala Arg Ala Val Arg  Ala Ser Leu
    2915                 2920                 2925

Ile Ser  Arg Gly Gly Lys Ala  Ala Val Cys Gly Arg  Tyr Leu Phe
    2930                 2935                 2940

Asn Trp  Ala Val Lys Thr Lys  Leu Lys Leu Thr Pro  Leu Pro Glu
    2945                 2950                 2955

Ala Arg  Leu Leu Asp Leu Ser  Ser Trp Phe Thr Val  Gly Ala Gly
    2960                 2965                 2970

Gly Gly  Asp Ile Phe His Ser  Val Ser Arg Ala Arg  Pro Arg Ser
    2975                 2980                 2985

Leu Leu  Phe Gly Leu Leu Leu  Leu Phe Val Gly Val  Gly Leu Phe
```

2990 2995 3000

Leu Leu Pro Ala Arg
3005

<210> SEQ ID NO 4
<211> LENGTH: 3002
<212> TYPE: PRT
<213> ORGANISM: Hepatitis C virus

<400> SEQUENCE: 4

Met Ser Thr Asn Pro Lys Pro Gln Arg Lys Thr Lys Arg Asn Thr Asn
1 5 10 15

Arg Arg Pro Met Asp Val Lys Phe Pro Gly Gly Gly Gln Ile Val Gly
20 25 30

Gly Val Tyr Leu Leu Pro Arg Arg Gly Pro Arg Leu Gly Val Arg Ala
35 40 45

Thr Arg Lys Thr Ser Glu Arg Ser Gln Pro Arg Gly Arg Arg Gln Pro
50 55 60

Ile Pro Lys Ala Arg Arg Pro Glu Gly Arg Ser Trp Ala Gln Pro Gly
65 70 75 80

Tyr Pro Trp Pro Leu Tyr Gly Asn Glu Gly Cys Gly Trp Ala Gly Trp
85 90 95

Leu Leu Ser Pro Arg Gly Ser Arg Pro Ser Trp Gly Pro Asn Asp Pro
100 105 110

Arg Arg Arg Ser Arg Asn Leu Gly Lys Val Ile Asp Thr Leu Thr Cys
115 120 125

Gly Phe Ala Asp Leu Met Gly Tyr Ile Pro Leu Val Gly Ala Pro Val
130 135 140

Gly Gly Val Ala Arg Ala Leu Ala His Gly Val Arg Ala Leu Glu Asp
145 150 155 160

Gly Ile Asn Tyr Ala Thr Gly Asn Leu Pro Gly Cys Ser Phe Ser Ile
165 170 175

Phe Leu Leu Ala Leu Leu Ser Cys Leu Thr Val Pro Ala Ser Ala Val
180 185 190

Asn Tyr Arg Asn Val Ser Gly Ile Tyr His Val Thr Asn Asp Cys Pro
195 200 205

Asn Ser Ser Ile Val Tyr Glu Ala Asp His His Ile Leu His Leu Pro
210 215 220

Gly Cys Val Pro Cys Val Arg Glu Gly Asn Gln Ser Arg Cys Trp Val
225 230 235 240

Ala Leu Thr Pro Thr Val Ala Ala Pro Tyr Ile Gly Ala Pro Leu Glu
245 250 255

Ser Leu Arg Ser His Val Asp Leu Met Val Gly Ala Ala Thr Val Cys
260 265 270

Ser Gly Leu Tyr Ile Gly Asp Leu Cys Gly Gly Leu Phe Leu Val Gly
275 280 285

Gln Met Phe Ser Phe Arg Pro Arg Arg His Trp Thr Thr Gln Asp Cys
290 295 300

Asn Cys Ser Ile Tyr Thr Gly His Ile Thr Gly His Arg Met Ala Trp
305 310 315 320

Asp Met Met Met Asn Trp Ser Pro Thr Thr Thr Leu Val Leu Ala Gln
325 330 335

Val Met Arg Ile Pro Thr Thr Leu Val Asp Leu Leu Ser Gly Gly His
340 345 350

-continued

```
Trp Gly Val Leu Val Gly Val Ala Tyr Phe Ser Met Gln Ala Asn Trp
        355                 360                 365

Ala Lys Val Ile Leu Val Leu Phe Leu Phe Ala Gly Val Asp Ala Leu
    370                 375                 380

Gln Leu Ile Asn Ser Asn Gly Ser Trp His Ile Asn Arg Thr Ala Leu
385                 390                 395                 400

Asn Cys Asn Asp Ser Leu Asn Thr Gly Phe Leu Ala Ser Leu Phe Tyr
                405                 410                 415

Thr His Lys Phe Asn Ser Ser Gly Cys Ser Glu Arg Leu Ala Cys Cys
            420                 425                 430

Lys Ser Leu Asp Ser Tyr Gly Gln Gly Trp Gly Pro Leu Gly Val Ala
        435                 440                 445

Asn Ile Ser Gly Ser Ser Asp Asp Arg Pro Tyr Cys Trp His Tyr Ala
    450                 455                 460

Pro Arg Pro Cys Gly Ile Val Pro Ala Ser Ser Val Cys Gly Pro Val
465                 470                 475                 480

Tyr Cys Phe Thr Pro Ser Pro Val Val Val Gly Thr Thr Asp His Val
                485                 490                 495

Gly Val Pro Thr Tyr Thr Trp Gly Glu Asn Glu Thr Asp Val Phe Leu
            500                 505                 510

Leu Asn Ser Thr Arg Pro Pro His Gly Ala Trp Phe Gly Cys Val Trp
        515                 520                 525

Met Asn Ser Thr Gly Phe Thr Lys Thr Cys Gly Ala Pro Pro Cys Glu
    530                 535                 540

Val Asn Thr Asn Asn Gly Thr Trp His Cys Pro Thr Asp Cys Phe Arg
545                 550                 555                 560

Lys His Pro Glu Thr Thr Tyr Ala Lys Cys Gly Ser Gly Pro Trp Ile
                565                 570                 575

Thr Pro Arg Cys Leu Ile Asp Tyr Pro Tyr Arg Leu Trp His Phe Pro
            580                 585                 590

Cys Thr Ala Asn Phe Ser Val Phe Asn Ile Arg Thr Phe Val Gly Gly
        595                 600                 605

Ile Glu His Arg Met Gln Ala Ala Cys Asn Trp Thr Arg Gly Glu Val
    610                 615                 620

Cys Gly Leu Glu His Arg Asp Arg Val Glu Leu Ser Pro Leu Leu Leu
625                 630                 635                 640

Thr Thr Thr Ala Trp Gln Ile Leu Pro Cys Ser Phe Thr Thr Leu Pro
                645                 650                 655

Ala Leu Ser Thr Gly Leu Ile His Leu His Gln Asn Ile Val Asp Val
            660                 665                 670

Gln Tyr Leu Tyr Gly Val Gly Ser Ala Val Val Ser Trp Ala Leu Lys
        675                 680                 685

Trp Glu Tyr Val Val Leu Ala Phe Leu Leu Leu Ala Asp Ala Arg Val
    690                 695                 700

Ser Ala Cys Leu Trp Met Met Phe Met Val Ser Gln Val Glu Ala Ala
705                 710                 715                 720

Leu Ser Asn Leu Ile Asn Ile Asn Ala Ala Ser Ala Ala Gly Ala Gln
                725                 730                 735

Gly Phe Trp Tyr Ala Ile Leu Phe Ile Cys Ile Val Trp His Val Lys
            740                 745                 750

Gly Arg Phe Pro Ala Ala Ala Ala Tyr Ala Ala Cys Gly Leu Trp Pro
        755                 760                 765

Leu Phe Leu Leu Leu Leu Met Leu Pro Glu Arg Ala Tyr Ala Tyr Asp
```

-continued

```
    770                 775                 780

Gln Glu Val Ala Gly Ser Leu Gly Gly Ala Ile Val Val Met Leu Ala
785                 790                 795                 800

Ile Leu Thr Leu Ser Pro His Tyr Lys Leu Trp Leu Ala Arg Gly Leu
                805                 810                 815

Trp Trp Ile Gln Tyr Phe Ile Ala Arg Thr Glu Ala Val Leu His Val
            820                 825                 830

Tyr Ile Pro Ser Phe Asn Val Arg Gly Pro Arg Asp Ser Val Ile Val
        835                 840                 845

Leu Ala Val Leu Val Cys Pro His Leu Val Phe Asp Ile Thr Lys Tyr
    850                 855                 860

Leu Leu Ala Ile Leu Gly Pro Leu His Ile Leu Gln Ala Ser Leu Leu
865                 870                 875                 880

Arg Ile Pro Tyr Phe Val Arg Ala Gln Ala Leu Val Lys Ile Cys Ser
                885                 890                 895

Leu Leu Arg Gly Val Val Tyr Gly Lys Tyr Phe Gln Met Val Val Leu
            900                 905                 910

Lys Ala Gly Ala Leu Thr Gly Thr Tyr Ile Tyr Asp His Leu Thr Pro
        915                 920                 925

Met Ser Asp Trp Ala Ala Thr Gly Leu Arg Asp Leu Ala Val Ala Leu
    930                 935                 940

Glu Pro Val Val Phe Ser Pro Met Glu Lys Lys Val Ile Val Trp Gly
945                 950                 955                 960

Ala Asp Thr Ala Ala Cys Gly Asp Ile Ile Arg Gly Leu Pro Val Ser
                965                 970                 975

Ala Arg Leu Gly Asn Glu Ile Leu Leu Gly Pro Ala Asp Thr Glu Thr
            980                 985                 990

Ser Lys Gly Trp Arg Leu Leu Ala  Pro Ile Thr Ala Tyr  Ala Gln Gln
        995                 1000                1005

Thr Arg  Gly Leu Leu Gly Ala  Ile Val Val Ser Met  Thr Gly Arg
    1010                 1015                 1020

Asp Arg  Thr Glu Gln Ala Gly  Glu Val Gln Ile Leu  Ser Thr Val
    1025                 1030                 1035

Ser Gln  Ser Phe Leu Gly Thr  Thr Ile Ser Gly Val  Leu Trp Thr
    1040                 1045                 1050

Val Tyr  His Gly Ala Gly Asn  Lys Thr Leu Ala Gly  Leu Arg Gly
    1055                 1060                 1065

Pro Val  Thr Gln Met Tyr Ser  Ser Ala Glu Gly Asp  Leu Val Gly
    1070                 1075                 1080

Trp Pro  Ser Pro Pro Gly Thr  Lys Ser Leu Glu Pro  Cys Lys Cys
    1085                 1090                 1095

Gly Ala  Val Asp Leu Tyr Leu  Val Thr Arg Asn Ala  Asp Val Ile
    1100                 1105                 1110

Pro Ala  Arg Arg Arg Gly Asp  Lys Arg Gly Ala Leu  Leu Ser Pro
    1115                 1120                 1125

Arg Pro  Ile Ser Thr Leu Lys  Gly Ser Ser Gly Gly  Pro Val Leu
    1130                 1135                 1140

Cys Pro  Arg Gly His Val Val  Gly Leu Phe Arg Ala  Ala Val Cys
    1145                 1150                 1155

Ser Arg  Gly Val Ala Lys Ser  Ile Asp Phe Ile Pro  Val Glu Thr
    1160                 1165                 1170

Leu Asp  Val Val Thr Arg Ser  Pro Thr Phe Ser Asp  Asn Ser Thr
    1175                 1180                 1185
```

-continued

```
Pro Pro  Ala Val Pro Gln Thr  Tyr Gln Val Gly Tyr  Leu His Ala
    1190                 1195                 1200

Pro Thr  Gly Ser Gly Lys Ser  Thr Lys Val Pro Val  Ala Tyr Ala
    1205                 1210                 1215

Ala Gln  Gly Tyr Lys Val Leu  Val Leu Asn Pro Ser  Val Ala Ala
    1220                 1225                 1230

Thr Leu  Gly Phe Gly Ala Tyr  Leu Ser Lys Ala His  Gly Ile Asn
    1235                 1240                 1245

Pro Asn  Ile Arg Thr Gly Val  Arg Thr Val Met Thr  Gly Glu Ala
    1250                 1255                 1260

Ile Thr  Tyr Ser Thr Tyr Gly  Lys Phe Leu Ala Asp  Gly Gly Cys
    1265                 1270                 1275

Ala Ser  Gly Ala Tyr Asp Ile  Ile Ile Cys Asp Glu  Cys His Ala
    1280                 1285                 1290

Val Asp  Ala Thr Ser Ile Leu  Gly Ile Gly Thr Val  Leu Asp Gln
    1295                 1300                 1305

Ala Glu  Thr Ala Gly Val Arg  Leu Thr Val Leu Ala  Thr Ala Thr
    1310                 1315                 1320

Pro Pro  Gly Ser Val Thr Thr  Pro His Pro Asp Ile  Glu Glu Val
    1325                 1330                 1335

Gly Leu  Gly Arg Glu Gly Glu  Ile Pro Phe Tyr Gly  Arg Ala Ile
    1340                 1345                 1350

Pro Leu  Ser Cys Ile Lys Gly  Gly Arg His Leu Ile  Phe Cys His
    1355                 1360                 1365

Ser Lys  Lys Lys Cys Asp Glu  Leu Ala Ala Ala Leu  Arg Gly Met
    1370                 1375                 1380

Gly Leu  Asn Ala Val Ala Tyr  Tyr Arg Gly Leu Asp  Val Ser Ile
    1385                 1390                 1395

Ile Pro  Ala Gln Gly Asp Val  Val Val Val Ala Thr  Asp Ala Leu
    1400                 1405                 1410

Met Thr  Gly Tyr Thr Gly Asp  Phe Asp Ser Val Ile  Asp Cys Asn
    1415                 1420                 1425

Val Ala  Val Thr Gln Ala Val  Asp Phe Ser Leu Asp  Pro Thr Phe
    1430                 1435                 1440

Thr Ile  Thr Thr Gln Thr Val  Pro Gln Asp Ala Val  Ser Arg Ser
    1445                 1450                 1455

Gln Arg  Arg Gly Arg Thr Gly  Arg Gly Arg Gln Gly  Thr Tyr Arg
    1460                 1465                 1470

Tyr Val  Ser Thr Gly Glu Arg  Ala Ser Gly Met Phe  Asp Ser Val
    1475                 1480                 1485

Val Leu  Cys Glu Cys Tyr Asp  Ala Gly Ala Ala Trp  Tyr Asp Leu
    1490                 1495                 1500

Thr Pro  Ala Glu Thr Thr Val  Arg Leu Arg Ala Tyr  Phe Asn Thr
    1505                 1510                 1515

Pro Gly  Leu Pro Val Cys Gln  Asp His Leu Glu Phe  Trp Glu Ala
    1520                 1525                 1530

Val Phe  Thr Gly Leu Thr His  Ile Asp Ala His Phe  Leu Ser Gln
    1535                 1540                 1545

Thr Lys  Gln Ala Gly Glu Asn  Phe Ala Tyr Leu Val  Ala Tyr Gln
    1550                 1555                 1560

Ala Thr  Val Cys Ala Arg Ala  Lys Ala Pro Pro Pro  Ser Trp Asp
    1565                 1570                 1575
```

Ala Met Trp Lys Cys Leu Ala Arg Leu Lys Pro Thr Leu Ala Gly
1580 1585 1590

Pro Thr Pro Leu Leu Tyr Arg Leu Gly Pro Ile Thr Asn Glu Val
1595 1600 1605

Thr Leu Thr His Pro Gly Thr Lys Tyr Ile Ala Thr Cys Met Gln
1610 1615 1620

Ala Asp Leu Glu Val Met Thr Ser Thr Trp Val Leu Ala Gly Gly
1625 1630 1635

Val Leu Ala Ala Val Ala Ala Tyr Cys Leu Ala Thr Gly Cys Val
1640 1645 1650

Ser Ile Ile Gly Arg Leu His Val Asn Gln Arg Val Val Val Ala
1655 1660 1665

Pro Asp Lys Glu Val Leu Tyr Glu Ala Phe Asp Glu Met Glu Glu
1670 1675 1680

Cys Ala Ser Arg Ala Ala Leu Ile Glu Glu Gly Gln Arg Ile Ala
1685 1690 1695

Glu Met Leu Lys Ser Lys Ile Gln Gly Leu Leu Gln Gln Ala Ser
1700 1705 1710

Lys Gln Ala Gln Asp Ile Gln Pro Ala Met Gln Ala Ser Trp Pro
1715 1720 1725

Lys Val Glu Gln Phe Trp Ala Arg His Met Trp Asn Phe Ile Ser
1730 1735 1740

Gly Ile Gln Tyr Leu Ala Gly Leu Ser Thr Leu Pro Gly Asn Pro
1745 1750 1755

Ala Val Ala Ser Met Met Ala Phe Ser Ala Ala Leu Thr Ser Pro
1760 1765 1770

Leu Ser Thr Ser Thr Thr Ile Leu Leu Asn Ile Met Gly Gly Trp
1775 1780 1785

Leu Ala Ser Gln Ile Ala Pro Pro Ala Gly Ala Thr Gly Phe Val
1790 1795 1800

Val Ser Gly Leu Val Gly Ala Ala Val Gly Ser Ile Gly Leu Gly
1805 1810 1815

Lys Val Leu Val Asp Ile Leu Ala Gly Tyr Gly Ala Gly Ile Ser
1820 1825 1830

Gly Ala Leu Val Ala Phe Lys Ile Met Ser Gly Glu Lys Pro Ser
1835 1840 1845

Met Glu Asp Val Ile Asn Leu Leu Pro Gly Ile Leu Ser Pro Gly
1850 1855 1860

Ala Leu Val Val Gly Val Ile Cys Ala Ala Ile Leu Arg Arg His
1865 1870 1875

Val Gly Pro Gly Glu Gly Ala Val Gln Trp Met Asn Arg Leu Ile
1880 1885 1890

Ala Phe Ala Ser Arg Gly Asn His Val Ala Pro Thr His Tyr Val
1895 1900 1905

Thr Glu Ser Asp Ala Ser Gln Arg Val Thr Gln Leu Leu Gly Ser
1910 1915 1920

Leu Thr Ile Thr Ser Leu Leu Arg Arg Leu His Asn Trp Ile Thr
1925 1930 1935

Glu Asp Cys Pro Ile Pro Cys Ser Gly Ser Trp Leu Arg Asp Val
1940 1945 1950

Trp Asp Trp Val Cys Thr Ile Leu Thr Asp Phe Lys Asn Trp Leu
1955 1960 1965

Thr Ser Lys Leu Phe Pro Lys Leu Pro Gly Leu Pro Phe Ile Ser

```
    1970                 1975                 1980

Cys Gln  Lys Gly Tyr Lys Gly  Val Trp Ala Gly Thr  Gly Ile Met
    1985                 1990                 1995

Thr Thr  Arg Cys Pro Cys Gly  Ala Asn Ile Ser Gly  Asn Val Arg
    2000                 2005                 2010

Leu Gly  Ser Met Arg Ile Thr  Gly Pro Lys Thr Cys  Met Asn Thr
    2015                 2020                 2025

Trp Gln  Gly Thr Phe Pro Ile  Asn Cys Tyr Thr Glu  Gly Gln Cys
    2030                 2035                 2040

Ala Pro  Lys Pro Pro Thr Asn  Tyr Lys Thr Ala Ile  Trp Arg Val
    2045                 2050                 2055

Ala Ala  Ser Glu Tyr Ala Glu  Val Thr Gln His Gly  Ser Tyr Ser
    2060                 2065                 2070

Tyr Val  Thr Gly Leu Thr Thr  Asp Asn Leu Lys Ile  Pro Cys Gln
    2075                 2080                 2085

Leu Pro  Ser Pro Glu Phe Phe  Ser Trp Val Asp Gly  Val Gln Ile
    2090                 2095                 2100

His Arg  Phe Ala Pro Thr Pro  Lys Pro Phe Phe Arg  Asp Glu Val
    2105                 2110                 2115

Ser Phe  Cys Val Gly Leu Asn  Ser Tyr Ala Val Gly  Ser Gln Leu
    2120                 2125                 2130

Pro Cys  Glu Pro Glu Pro Asp  Ala Asp Val Leu Arg  Ser Met Leu
    2135                 2140                 2145

Thr Asp  Pro Pro His Ile Thr  Ala Glu Thr Ala Ala  Arg Arg Leu
    2150                 2155                 2160

Ala Arg  Gly Ser Pro Pro Ser  Glu Ala Ser Ser Ser  Val Ser Gln
    2165                 2170                 2175

Leu Ser  Ala Pro Ser Leu Arg  Ala Thr Cys Thr Thr  His Ser Asn
    2180                 2185                 2190

Thr Tyr  Asp Val Asp Met Val  Asp Ala Asn Leu Leu  Met Glu Gly
    2195                 2200                 2205

Gly Val  Ala Gln Thr Glu Pro  Glu Ser Arg Val Pro  Val Leu Asp
    2210                 2215                 2220

Phe Leu  Glu Pro Met Ala Glu  Glu Glu Ser Asp Leu  Glu Pro Ser
    2225                 2230                 2235

Ile Pro  Ser Glu Cys Met Leu  Pro Arg Ser Gly Phe  Pro Arg Ala
    2240                 2245                 2250

Leu Pro  Ala Trp Ala Arg Pro  Asp Tyr Asn Pro Pro  Leu Val Glu
    2255                 2260                 2265

Ser Trp  Arg Arg Pro Asp Tyr  Gln Pro Pro Thr Val  Ala Gly Cys
    2270                 2275                 2280

Ala Leu  Pro Pro Pro Lys Lys  Ala Pro Thr Pro Pro  Pro Arg Arg
    2285                 2290                 2295

Arg Arg  Thr Val Gly Leu Ser  Glu Ser Thr Ile Ser  Glu Ala Leu
    2300                 2305                 2310

Gln Gln  Leu Ala Ile Lys Thr  Phe Gly Gln Pro Pro  Ser Ser Gly
    2315                 2320                 2325

Asp Ala  Gly Ser Ser Thr Gly  Ala Gly Ala Ala Glu  Ser Gly Gly
    2330                 2335                 2340

Pro Thr  Ser Pro Gly Glu Pro  Ala Pro Ser Glu Thr  Gly Ser Ala
    2345                 2350                 2355

Ser Ser  Met Pro Pro Leu Glu  Gly Glu Pro Gly Asp  Pro Asp Leu
    2360                 2365                 2370
```

```
Glu Ser  Asp Gln Val Glu Leu  Gln Pro Pro Pro Gln  Gly Gly Gly
    2375                 2380                 2385

Val Ala  Pro Gly Ser Gly Ser  Gly Ser Trp Ser Thr  Cys Ser Glu
    2390                 2395                 2400

Glu Asp  Asp Thr Thr Val Cys  Cys Ser Met Ser Tyr  Ser Trp Thr
    2405                 2410                 2415

Gly Ala  Leu Ile Thr Pro Cys  Ser Pro Glu Glu Glu  Lys Leu Pro
    2420                 2425                 2430

Ile Asn  Pro Leu Ser Asn Ser  Leu Leu Arg Tyr His  Asn Lys Val
    2435                 2440                 2445

Tyr Cys  Thr Thr Ser Lys Ser  Ala Ser Gln Arg Ala  Lys Lys Val
    2450                 2455                 2460

Thr Phe  Asp Arg Thr Gln Val  Leu Asp Ala His Tyr  Asp Ser Val
    2465                 2470                 2475

Leu Lys  Asp Ile Lys Leu Ala  Ala Ser Lys Val Ser  Ala Arg Leu
    2480                 2485                 2490

Leu Thr  Leu Glu Glu Ala Cys  Gln Leu Thr Pro Pro  His Ser Ala
    2495                 2500                 2505

Arg Ser  Lys Tyr Gly Phe Gly  Ala Lys Glu Val Arg  Ser Leu Ser
    2510                 2515                 2520

Gly Arg  Ala Val Asn His Ile  Lys Ser Val Trp Lys  Asp Leu Leu
    2525                 2530                 2535

Glu Asp  Pro Gln Thr Pro Ile  Pro Thr Thr Ile Met  Ala Lys Asn
    2540                 2545                 2550

Glu Val  Phe Cys Val Asp Pro  Ala Lys Gly Gly Lys  Lys Pro Ala
    2555                 2560                 2565

Arg Leu  Ile Val Tyr Pro Asp  Leu Gly Val Arg Val  Cys Glu Lys
    2570                 2575                 2580

Met Ala  Leu Tyr Asp Ile Thr  Gln Lys Leu Pro Gln  Ala Val Met
    2585                 2590                 2595

Gly Ala  Ser Tyr Gly Phe Gln  Tyr Ser Pro Ala Gln  Arg Val Glu
    2600                 2605                 2610

Tyr Leu  Leu Lys Ala Trp Ala  Glu Lys Lys Asp Pro  Met Gly Phe
    2615                 2620                 2625

Ser Tyr  Asp Thr Arg Cys Phe  Asp Ser Thr Val Thr  Glu Arg Asp
    2630                 2635                 2640

Ile Arg  Thr Glu Glu Ser Ile  Tyr Gln Ala Cys Ser  Leu Pro Glu
    2645                 2650                 2655

Glu Ala  Arg Thr Ala Ile His  Ser Leu Thr Glu Arg  Leu Tyr Val
    2660                 2665                 2670

Gly Gly  Pro Met Phe Asn Ser  Lys Gly Gln Thr Cys  Gly Tyr Arg
    2675                 2680                 2685

Arg Cys  Arg Ala Ser Gly Val  Leu Thr Thr Ser Met  Gly Asn Thr
    2690                 2695                 2700

Ile Thr  Cys Tyr Val Lys Ala  Leu Ala Ala Cys Lys  Ala Ala Gly
    2705                 2710                 2715

Ile Val  Ala Pro Thr Met Leu  Val Cys Gly Asp Asp  Leu Val Val
    2720                 2725                 2730

Ile Ser  Glu Ser Gln Gly Thr  Glu Glu Asp Glu Arg  Asn Leu Arg
    2735                 2740                 2745

Ala Phe  Thr Glu Ala Met Thr  Arg Tyr Ser Ala Pro  Pro Gly Asp
    2750                 2755                 2760
```

```
Pro Pro  Arg Pro Glu Tyr Asp  Leu Glu Leu Ile Thr  Ser Cys Ser
    2765                 2770                 2775

Ser Asn  Val Ser Val Ala Leu  Gly Pro Arg Gly Arg  Arg Arg Tyr
    2780                 2785                 2790

Tyr Leu  Thr Arg Asp Pro Thr  Thr Pro Leu Ala Arg  Ala Ala Trp
    2795                 2800                 2805

Glu Thr  Val Arg His Ser Pro  Ile Asn Ser Trp Leu  Gly Asn Ile
    2810                 2815                 2820

Ile Gln  Tyr Ala Pro Thr Ile  Trp Val Arg Met Val  Leu Met Thr
    2825                 2830                 2835

His Phe  Phe Ser Ile Leu Met  Val Gln Asp Thr Leu  Asp Gln Asn
    2840                 2845                 2850

Leu Asn  Phe Glu Met Tyr Gly  Ser Val Tyr Ser Val  Asn Pro Leu
    2855                 2860                 2865

Asp Leu  Pro Ala Ile Ile Glu  Arg Leu His Gly Leu  Asp Ala Phe
    2870                 2875                 2880

Ser Met  His Thr Tyr Ser His  His Glu Leu Thr Arg  Val Ala Ser
    2885                 2890                 2895

Ala Leu  Arg Lys Leu Gly Ala  Pro Pro Leu Arg Val  Trp Lys Ser
    2900                 2905                 2910

Arg Ala  Arg Ala Val Arg Ala  Ser Leu Ile Ser Arg  Gly Gly Lys
    2915                 2920                 2925

Ala Ala  Val Cys Gly Arg Tyr  Leu Phe Asn Trp Ala  Val Lys Thr
    2930                 2935                 2940

Lys Leu  Lys Leu Thr Pro Leu  Pro Glu Ala Arg Leu  Leu Asp Leu
    2945                 2950                 2955

Ser Ser  Trp Phe Thr Val Gly  Ala Gly Gly Gly Asp  Ile Phe His
    2960                 2965                 2970

Ser Val  Ser Arg Ala Arg Pro  Arg Ser Leu Leu Phe  Gly Leu Leu
    2975                 2980                 2985

Leu Leu  Phe Val Gly Val Gly  Leu Phe Leu Leu Pro  Ala Arg
    2990                 2995                 3000


<210> SEQ ID NO 5
<211> LENGTH: 3003
<212> TYPE: PRT
<213> ORGANISM: Hepatitis C virus

<400> SEQUENCE: 5

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125
```

```
Gly Phe Ala Asp Leu Met Gly Tyr Ile Pro Leu Val Gly Gly Pro Val
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Ile Leu Ala Leu Leu Ser Cys Leu Thr Val Pro Thr Ser Ala Val
            180                 185                 190

Pro Tyr Arg Asn Ala Ser Gly Val Tyr His Val Thr Asn Asp Cys Pro
        195                 200                 205

Asn Ser Ser Ile Val Tyr Glu Ala Glu Asp Leu Ile Leu His Ala Pro
    210                 215                 220

Gly Cys Val Pro Cys Val Arg Gln Gly Asn Val Ser Arg Cys Trp Val
225                 230                 235                 240

Gln Ile Thr Pro Thr Leu Ser Ala Pro Ser Leu Gly Ala Val Thr Ala
                245                 250                 255

Pro Leu Arg Arg Ala Val Asp Tyr Leu Ala Gly Gly Ala Ala Leu Cys
            260                 265                 270

Ser Ala Leu Tyr Val Gly Asp Ala Cys Gly Ala Val Phe Leu Val Gly
        275                 280                 285

Gln Met Phe Thr Tyr Ser Pro Arg Arg His Asn Val Val Gln Asp Cys
    290                 295                 300

Asn Cys Ser Ile Tyr Ser Gly His Ile Thr Gly His Arg Met Ala Trp
305                 310                 315                 320

Asp Met Met Met Asn Trp Ser Pro Thr Thr Ala Leu Val Met Ala Gln
                325                 330                 335

Leu Leu Arg Ile Pro Gln Val Val Ile Asp Ile Ile Ala Gly Ala His
            340                 345                 350

Trp Gly Val Leu Phe Ala Ala Ala Tyr Tyr Ala Ser Ala Ala Asn Trp
        355                 360                 365

Ala Lys Val Val Leu Val Leu Phe Leu Phe Ala Gly Val Asp Ala Leu
    370                 375                 380

Gln Leu Ile Asn Thr Asn Gly Ser Trp His Ile Asn Arg Thr Ala Leu
385                 390                 395                 400

Asn Cys Asn Asp Ser Leu Gln Thr Gly Phe Val Ala Gly Leu Leu Tyr
                405                 410                 415

Tyr His Lys Phe Asn Ser Thr Gly Cys Pro Gln Arg Met Ala Ser Cys
            420                 425                 430

Arg Pro Leu Ala Ala Phe Asp Gln Gly Trp Gly Thr Ile Ser Tyr Ala
        435                 440                 445

Ala Val Ser Gly Pro Ser Asp Asp Lys Pro Tyr Cys Trp His Tyr Pro
    450                 455                 460

Pro Arg Pro Cys Gly Ile Val Pro Ala Arg Gly Val Cys Gly Pro Val
465                 470                 475                 480

Tyr Cys Phe Thr Pro Ser Pro Val Val Val Gly Thr Thr Asp Arg Lys
                485                 490                 495

Gly Asn Pro Thr Tyr Ser Trp Gly Glu Asn Glu Thr Asp Ile Phe Leu
            500                 505                 510

Leu Asn Asn Thr Arg Pro Pro Thr Gly Asn Trp Phe Gly Cys Thr Trp
        515                 520                 525

Met Asn Ser Thr Gly Phe Val Lys Thr Cys Gly Ala Pro Pro Cys Asn
    530                 535                 540
```

-continued

```
Leu Gly Pro Thr Gly Asn Asn Ser Leu Lys Cys Pro Thr Asp Cys Phe
545                 550                 555                 560

Arg Lys His Pro Asp Ala Thr Tyr Thr Lys Cys Gly Ser Gly Pro Trp
                565                 570                 575

Leu Thr Pro Arg Cys Leu Val His Tyr Pro Tyr Arg Leu Trp His Tyr
            580                 585                 590

Pro Cys Thr Leu Asn Tyr Thr Ile Phe Lys Val Arg Met Tyr Ile Gly
        595                 600                 605

Gly Leu Glu His Arg Leu Glu Val Ala Cys Asn Trp Thr Arg Gly Glu
    610                 615                 620

Arg Cys Asp Leu Glu Asp Arg Asp Arg Ala Glu Leu Ser Pro Leu Leu
625                 630                 635                 640

His Thr Thr Thr Gln Trp Ala Ile Leu Pro Cys Ser Phe Thr Pro Thr
                645                 650                 655

Pro Ala Leu Ser Thr Gly Leu Ile His Leu His Gln Asn Ile Val Asp
            660                 665                 670

Thr Gln Tyr Leu Tyr Gly Leu Ser Ser Ser Ile Val Ser Trp Ala Val
        675                 680                 685

Lys Trp Glu Tyr Ile Val Leu Ala Phe Leu Leu Leu Ala Asp Ala Arg
    690                 695                 700

Ile Cys Thr Cys Leu Trp Ile Met Leu Leu Val Cys Gln Ala Glu Ala
705                 710                 715                 720

Ala Leu Glu Asn Val Ile Val Leu Asn Ala Ala Ala Ala Ala Gly Thr
                725                 730                 735

His Gly Phe Phe Trp Gly Leu Leu Val Ile Cys Phe Ala Trp His Phe
            740                 745                 750

Lys Gly Arg Leu Val Pro Gly Ala Thr Tyr Leu Cys Leu Gly Ile Trp
        755                 760                 765

Pro Leu Leu Leu Leu Leu Phe Leu Leu Pro Gln Arg Ala Leu Ala Leu
    770                 775                 780

Asp Ser Ser Asp Gly Gly Thr Val Gly Cys Leu Val Leu Thr Ile Leu
785                 790                 795                 800

Thr Ile Phe Thr Leu Thr Pro Gly Tyr Lys Lys Met Val Val Leu Val
                805                 810                 815

Ile Trp Trp Leu Gln Tyr Phe Ile Ala Arg Val Glu Ala Phe Ile His
            820                 825                 830

Val Trp Val Pro Pro Leu Gln Val Arg Gly Gly Arg Asp Ala Ile Ile
        835                 840                 845

Met Leu Thr Cys Leu Phe His Pro Ala Leu Gly Phe Glu Val Thr Lys
    850                 855                 860

Ile Leu Leu Gly Ile Leu Gly Pro Leu Tyr Leu Leu Gln Tyr Ser Leu
865                 870                 875                 880

Ile Lys Leu Pro Tyr Phe Ile Arg Ala Arg Ala Leu Leu Arg Ala Cys
                885                 890                 895

Leu Leu Ala Lys His Leu Ala Cys Gly Arg Tyr Val Gln Ala Ala Leu
            900                 905                 910

Leu His Leu Gly Arg Leu Thr Gly Thr Tyr Ile Tyr Asp His Leu Ala
        915                 920                 925

Pro Met Lys Asp Trp Ala Ala Ser Gly Leu Arg Asp Leu Ala Val Ala
    930                 935                 940

Thr Glu Pro Ile Ile Phe Ser Pro Met Glu Thr Lys Val Ile Thr Trp
945                 950                 955                 960

Gly Ala Asp Thr Ala Ala Cys Gly Asp Ile Leu Ala Gly Leu Pro Val
```

-continued

```
            965                 970                 975

Ser Ala Arg Arg Gly His Glu Ile Phe Leu Gly Pro Ala Asp Asp Ile
        980                 985                 990

Arg Glu Gly Gly Trp Arg Leu Leu  Ala Pro Ile Thr Ala  Tyr Ala Gln
        995                 1000                1005

Gln Thr  Arg Gly Leu Leu Gly  Ala Ile Val Val Ser  Met Thr Gly
    1010                 1015                 1020

Arg Asp  Arg Thr Glu Gln Ala  Gly Glu Val Gln Ile  Leu Ser Thr
    1025                 1030                 1035

Val Ser  Gln Ser Phe Leu Gly  Thr Thr Ile Ser Gly  Val Leu Trp
    1040                 1045                 1050

Thr Val  Tyr His Gly Ala Gly  Asn Lys Thr Leu Ala  Gly Leu Arg
    1055                 1060                 1065

Gly Pro  Val Thr Gln Met Tyr  Ser Ser Ala Glu Gly  Asp Leu Val
    1070                 1075                 1080

Gly Trp  Pro Ser Pro Pro Gly  Thr Arg Ser Leu Glu  Pro Cys Lys
    1085                 1090                 1095

Cys Gly  Ala Val Asp Leu Tyr  Leu Val Thr Arg Asn  Ala Asp Val
    1100                 1105                 1110

Ile Pro  Ala Arg Arg Arg Gly  Asp Lys Arg Gly Ala  Leu Leu Ser
    1115                 1120                 1125

Pro Arg  Pro Ile Ser Thr Leu  Lys Gly Ser Ser Gly  Gly Pro Val
    1130                 1135                 1140

Leu Cys  Pro Arg Gly His Val  Val Gly Leu Phe Arg  Ala Ala Val
    1145                 1150                 1155

Cys Ser  Arg Gly Val Ala Lys  Ser Ile Asp Phe Ile  Pro Val Glu
    1160                 1165                 1170

Thr Leu  Asp Val Val Thr Arg  Ser Pro Thr Phe Ser  Asp Asn Ser
    1175                 1180                 1185

Thr Pro  Pro Ala Val Pro Gln  Thr Tyr Gln Val Gly  Tyr Leu His
    1190                 1195                 1200

Ala Pro  Thr Gly Ser Gly Lys  Ser Thr Lys Val Pro  Val Ala Tyr
    1205                 1210                 1215

Ala Ala  Gln Gly Tyr Lys Val  Leu Val Leu Asn Pro  Ser Val Ala
    1220                 1225                 1230

Ala Thr  Leu Gly Phe Gly Ala  Tyr Leu Ser Lys Ala  His Gly Ile
    1235                 1240                 1245

Asn Pro  Asn Ile Arg Thr Gly  Val Arg Thr Val Met  Thr Gly Glu
    1250                 1255                 1260

Ala Ile  Thr Tyr Ser Thr Tyr  Gly Lys Phe Leu Ala  Asp Gly Gly
    1265                 1270                 1275

Cys Ala  Ser Gly Ala Tyr Asp  Ile Ile Ile Cys Asp  Glu Cys His
    1280                 1285                 1290

Ala Val  Asp Ala Thr Ser Ile  Leu Gly Ile Gly Thr  Val Leu Asp
    1295                 1300                 1305

Gln Ala  Glu Thr Ala Gly Val  Arg Leu Thr Val Leu  Ala Thr Ala
    1310                 1315                 1320

Thr Pro  Pro Gly Ser Val Thr  Thr Pro His Pro Asp  Ile Glu Glu
    1325                 1330                 1335

Val Gly  Leu Gly Arg Glu Gly  Glu Ile Pro Phe Tyr  Gly Arg Ala
    1340                 1345                 1350

Ile Pro  Leu Ser Cys Ile Lys  Gly Gly Arg His Leu  Ile Phe Cys
    1355                 1360                 1365
```

His Ser Lys Lys Lys Cys Asp Glu Leu Ala Ala Ala Leu Arg Gly
1370 1375 1380

Met Gly Leu Asn Ala Val Ala Tyr Tyr Arg Gly Leu Asp Val Ser
1385 1390 1395

Ile Ile Pro Ala Gln Gly Asp Val Val Val Val Ala Thr Asp Ala
1400 1405 1410

Leu Met Thr Gly Tyr Thr Gly Asp Phe Asp Ser Val Ile Asp Cys
1415 1420 1425

Asn Val Ala Val Thr Gln Ala Val Asp Phe Ser Leu Asp Pro Thr
1430 1435 1440

Phe Thr Ile Thr Thr Gln Thr Val Pro Gln Asp Ala Val Ser Arg
1445 1450 1455

Ser Gln Arg Arg Gly Arg Thr Gly Arg Gly Arg Gln Gly Thr Tyr
1460 1465 1470

Arg Tyr Val Ser Thr Gly Glu Arg Ala Ser Gly Met Phe Asp Ser
1475 1480 1485

Val Val Leu Cys Glu Cys Tyr Asp Ala Gly Ala Ala Trp Tyr Asp
1490 1495 1500

Leu Thr Pro Ala Glu Thr Thr Val Arg Leu Arg Ala Tyr Phe Asn
1505 1510 1515

Thr Pro Gly Leu Pro Val Cys Gln Asp His Leu Glu Phe Trp Glu
1520 1525 1530

Ala Val Phe Thr Gly Leu Thr His Ile Asp Ala His Phe Leu Ser
1535 1540 1545

Gln Thr Lys Gln Ala Gly Glu Asn Phe Ala Tyr Leu Val Ala Tyr
1550 1555 1560

Gln Ala Thr Val Cys Ala Arg Ala Lys Ala Pro Pro Pro Ser Trp
1565 1570 1575

Asp Ala Met Trp Lys Cys Leu Ala Arg Leu Lys Pro Thr Leu Ala
1580 1585 1590

Gly Pro Thr Pro Leu Leu Tyr Arg Leu Gly Pro Ile Thr Asn Glu
1595 1600 1605

Val Thr Leu Thr His Pro Gly Thr Lys Tyr Ile Ala Thr Cys Met
1610 1615 1620

Gln Ala Asp Leu Glu Val Met Thr Ser Thr Trp Val Leu Ala Gly
1625 1630 1635

Gly Val Leu Ala Ala Val Ala Ala Tyr Cys Leu Ala Thr Gly Cys
1640 1645 1650

Val Ser Ile Ile Gly Arg Leu His Val Asn Gln Arg Val Val Val
1655 1660 1665

Ala Pro Asp Lys Glu Val Leu Tyr Glu Ala Phe Asp Glu Met Glu
1670 1675 1680

Glu Cys Ala Ser Arg Ala Ala Leu Ile Glu Glu Gly Gln Arg Ile
1685 1690 1695

Ala Glu Met Leu Lys Ser Lys Ile Gln Gly Leu Leu Gln Gln Ala
1700 1705 1710

Ser Lys Gln Ala Gln Asp Ile Gln Pro Ala Met Gln Ala Ser Trp
1715 1720 1725

Pro Lys Val Glu Gln Phe Trp Ala Arg His Met Trp Asn Phe Ile
1730 1735 1740

Ser Gly Ile Gln Tyr Leu Ala Gly Leu Ser Thr Leu Pro Gly Asn
1745 1750 1755

-continued

```
Pro Ala  Val Ala Ser Met Met  Ala Phe Ser Ala Ala  Leu Thr Ser
    1760                 1765                 1770

Pro Leu  Ser Thr Ser Thr Thr  Ile Leu Leu Asn Ile  Met Gly Gly
    1775                 1780                 1785

Trp Leu  Ala Ser Gln Ile Ala  Pro Pro Ala Gly Ala  Thr Gly Phe
    1790                 1795                 1800

Val Val  Ser Gly Leu Val Gly  Ala Ala Val Gly Ser  Ile Gly Leu
    1805                 1810                 1815

Gly Lys  Val Leu Val Asp Ile  Leu Ala Gly Tyr Gly  Ala Gly Ile
    1820                 1825                 1830

Ser Gly  Ala Leu Val Ala Phe  Lys Ile Met Ser Gly  Glu Lys Pro
    1835                 1840                 1845

Ser Met  Glu Asp Val Ile Asn  Leu Leu Pro Gly Ile  Leu Ser Pro
    1850                 1855                 1860

Gly Ala  Leu Val Val Gly Val  Ile Cys Ala Ala Ile  Leu Arg Arg
    1865                 1870                 1875

His Val  Gly Pro Gly Glu Gly  Ala Val Gln Trp Met  Asn Arg Leu
    1880                 1885                 1890

Ile Ala  Phe Ala Ser Arg Gly  Asn His Val Ala Pro  Thr His Tyr
    1895                 1900                 1905

Val Thr  Glu Ser Asp Ala Ser  Gln Arg Val Thr Gln  Leu Leu Gly
    1910                 1915                 1920

Ser Leu  Thr Ile Thr Ser Leu  Leu Arg Arg Leu His  Asn Trp Ile
    1925                 1930                 1935

Thr Glu  Asp Cys Pro Ile Pro  Cys Ser Gly Ser Trp  Leu Arg Asp
    1940                 1945                 1950

Val Trp  Asp Trp Val Cys Thr  Ile Leu Thr Asp Phe  Lys Asn Trp
    1955                 1960                 1965

Leu Thr  Ser Lys Leu Phe Pro  Lys Leu Pro Gly Leu  Pro Phe Ile
    1970                 1975                 1980

Ser Cys  Gln Lys Gly Tyr Lys  Gly Val Trp Ala Gly  Thr Gly Ile
    1985                 1990                 1995

Met Thr  Thr Arg Cys Pro Cys  Gly Ala Asn Ile Ser  Gly Asn Val
    2000                 2005                 2010

Arg Leu  Gly Ser Met Arg Ile  Thr Gly Pro Lys Thr  Cys Met Asn
    2015                 2020                 2025

Thr Trp  Gln Gly Thr Phe Pro  Ile Asn Cys Tyr Thr  Glu Gly Gln
    2030                 2035                 2040

Cys Ala  Pro Lys Pro Pro Thr  Asn Tyr Lys Thr Ala  Ile Trp Arg
    2045                 2050                 2055

Val Ala  Ala Ser Glu Tyr Ala  Glu Val Thr Gln His  Gly Ser Tyr
    2060                 2065                 2070

Ser Tyr  Val Thr Gly Leu Thr  Thr Asp Asn Leu Lys  Ile Pro Cys
    2075                 2080                 2085

Gln Leu  Pro Ser Pro Glu Phe  Phe Ser Trp Val Asp  Gly Val Gln
    2090                 2095                 2100

Ile His  Arg Phe Ala Pro Thr  Pro Lys Pro Phe Phe  Arg Asp Glu
    2105                 2110                 2115

Val Ser  Phe Cys Val Gly Leu  Asn Ser Tyr Ala Val  Gly Ser Gln
    2120                 2125                 2130

Leu Pro  Cys Glu Pro Glu Pro  Asp Ala Asp Val Leu  Arg Ser Met
    2135                 2140                 2145

Leu Thr  Asp Pro Pro His Ile  Thr Ala Glu Thr Ala  Ala Arg Arg
```

```
    2150                2155                2160

Leu Ala  Arg Gly Ser Pro Pro  Ser Glu Ala Ser Ser  Ser Val Ser
    2165                2170                2175

Gln Leu  Ser Ala Pro Ser Leu  Arg Ala Thr Cys Thr  Thr His Ser
    2180                2185                2190

Asn Thr  Tyr Asp Val Asp Met  Val Asp Ala Asn Leu  Leu Met Glu
    2195                2200                2205

Gly Gly  Val Ala Gln Thr Glu  Pro Glu Ser Arg Val  Pro Val Leu
    2210                2215                2220

Asp Phe  Leu Glu Pro Met Ala  Glu Glu Glu Ser Asp  Leu Glu Pro
    2225                2230                2235

Ser Ile  Pro Ser Glu Cys Met  Leu Pro Arg Ser Gly  Phe Pro Arg
    2240                2245                2250

Ala Leu  Pro Ala Trp Ala Arg  Pro Asp Tyr Asn Pro  Pro Leu Val
    2255                2260                2265

Glu Ser  Trp Arg Arg Pro Asp  Tyr Gln Pro Pro Thr  Val Ala Gly
    2270                2275                2280

Cys Ala  Leu Pro Pro Pro Lys  Lys Ala Pro Thr Pro  Pro Pro Arg
    2285                2290                2295

Arg Arg  Arg Thr Val Gly Leu  Ser Glu Ser Thr Ile  Ser Glu Ala
    2300                2305                2310

Leu Gln  Gln Leu Ala Ile Lys  Thr Phe Gly Gln Pro  Pro Ser Ser
    2315                2320                2325

Gly Asp  Ala Gly Ser Ser Thr  Gly Ala Gly Ala Ala  Glu Ser Gly
    2330                2335                2340

Gly Pro  Thr Ser Pro Gly Glu  Pro Ala Pro Ser Glu  Thr Gly Ser
    2345                2350                2355

Ala Ser  Ser Met Pro Pro Leu  Glu Gly Glu Pro Gly  Asp Pro Asp
    2360                2365                2370

Leu Glu  Ser Asp Gln Val Glu  Leu Gln Pro Pro Pro  Gln Gly Gly
    2375                2380                2385

Gly Val  Ala Pro Gly Ser Gly  Ser Gly Ser Trp Ser  Thr Cys Ser
    2390                2395                2400

Glu Glu  Asp Asp Thr Thr Val  Cys Cys Ser Met Ser  Tyr Ser Trp
    2405                2410                2415

Thr Gly  Ala Leu Ile Thr Pro  Cys Ser Pro Glu Glu  Glu Lys Leu
    2420                2425                2430

Pro Ile  Asn Pro Leu Ser Asn  Ser Leu Leu Arg Tyr  His Asn Lys
    2435                2440                2445

Val Tyr  Cys Thr Thr Ser Lys  Ser Ala Ser Gln Arg  Ala Lys Lys
    2450                2455                2460

Val Thr  Phe Asp Arg Thr Gln  Val Leu Asp Ala His  Tyr Asp Ser
    2465                2470                2475

Val Leu  Lys Asp Ile Lys Leu  Ala Ala Ser Lys Val  Ser Ala Arg
    2480                2485                2490

Leu Leu  Thr Leu Glu Glu Ala  Cys Gln Leu Thr Pro  Pro His Ser
    2495                2500                2505

Ala Arg  Ser Lys Tyr Gly Phe  Gly Ala Lys Glu Val  Arg Ser Leu
    2510                2515                2520

Ser Gly  Arg Ala Val Asn His  Ile Lys Ser Val Trp  Lys Asp Leu
    2525                2530                2535

Leu Glu  Asp Pro Gln Thr Pro  Ile Pro Thr Thr Ile  Met Ala Lys
    2540                2545                2550
```

```
Asn Glu Val Phe Cys Val Asp Pro Ala Lys Gly Gly Lys Lys Pro
    2555                2560                2565

Ala Arg Leu Ile Val Tyr Pro Asp Leu Gly Val Arg Val Cys Glu
    2570                2575                2580

Lys Met Ala Leu Tyr Asp Ile Thr Gln Lys Leu Pro Gln Ala Val
    2585                2590                2595

Met Gly Ala Ser Tyr Gly Phe Gln Tyr Ser Pro Ala Gln Arg Val
    2600                2605                2610

Glu Tyr Leu Leu Lys Ala Trp Ala Glu Lys Lys Asp Pro Met Gly
    2615                2620                2625

Phe Ser Tyr Asp Thr Arg Cys Phe Asp Ser Thr Val Thr Glu Arg
    2630                2635                2640

Asp Ile Arg Thr Glu Glu Ser Ile Tyr Gln Ala Cys Ser Leu Pro
    2645                2650                2655

Glu Glu Ala Arg Thr Ala Ile His Ser Leu Thr Glu Arg Leu Tyr
    2660                2665                2670

Val Gly Gly Pro Met Phe Asn Ser Lys Gly Gln Thr Cys Gly Tyr
    2675                2680                2685

Arg Arg Cys Arg Ala Ser Gly Val Leu Thr Thr Ser Met Gly Asn
    2690                2695                2700

Thr Ile Thr Cys Tyr Val Lys Ala Leu Ala Ala Cys Lys Ala Ala
    2705                2710                2715

Gly Ile Val Ala Pro Thr Met Leu Val Cys Gly Asp Asp Leu Val
    2720                2725                2730

Val Ile Ser Glu Ser Gln Gly Thr Glu Glu Asp Glu Arg Asn Leu
    2735                2740                2745

Arg Ala Phe Thr Glu Ala Met Thr Arg Tyr Ser Ala Pro Pro Gly
    2750                2755                2760

Asp Pro Pro Arg Pro Glu Tyr Asp Leu Glu Leu Ile Thr Ser Cys
    2765                2770                2775

Ser Ser Asn Val Ser Val Ala Leu Gly Pro Arg Gly Arg Arg Arg
    2780                2785                2790

Tyr Tyr Leu Thr Arg Asp Pro Thr Thr Pro Leu Ala Arg Ala Ala
    2795                2800                2805

Trp Glu Thr Val Arg His Ser Pro Ile Asn Ser Trp Leu Gly Asn
    2810                2815                2820

Ile Ile Gln Tyr Ala Pro Thr Ile Trp Val Arg Met Val Leu Met
    2825                2830                2835

Thr His Phe Phe Ser Ile Leu Met Val Gln Asp Thr Leu Asp Gln
    2840                2845                2850

Asn Leu Asn Phe Glu Met Tyr Gly Ser Val Tyr Ser Val Asn Pro
    2855                2860                2865

Leu Asp Leu Pro Ala Ile Ile Glu Arg Leu His Gly Leu Asp Ala
    2870                2875                2880

Phe Ser Met His Thr Tyr Ser His His Glu Leu Thr Arg Val Ala
    2885                2890                2895

Ser Ala Leu Arg Lys Leu Gly Ala Pro Pro Leu Arg Val Trp Lys
    2900                2905                2910

Ser Arg Ala Arg Ala Val Arg Ala Ser Leu Ile Ser Arg Gly Gly
    2915                2920                2925

Lys Ala Ala Val Cys Gly Arg Tyr Leu Phe Asn Trp Ala Val Lys
    2930                2935                2940
```

```
Thr Lys  Leu Lys Leu Thr Pro  Leu Pro Glu Ala Arg  Leu Leu Asp
    2945                2950                2955

Leu Ser  Ser Trp Phe Thr Val  Gly Ala Gly Gly Gly  Asp Ile Phe
    2960                2965                2970

His Ser  Val Ser Arg Ala Arg  Pro Arg Ser Leu Leu  Phe Gly Leu
    2975                2980                2985

Leu Leu  Leu Phe Val Gly Val  Gly Leu Phe Leu Leu  Pro Ala Arg
    2990                2995                3000


<210> SEQ ID NO 6
<211> LENGTH: 3009
<212> TYPE: PRT
<213> ORGANISM: Hepatitis C virus

<400> SEQUENCE: 6

Met Ser Thr Leu Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Gln Gly Arg His Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro His Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Val Val Gly Ala Pro Leu
    130                 135                 140

Gly Gly Val Ala Ala Ala Leu Ala His Gly Val Arg Ala Ile Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser Ala Leu
            180                 185                 190

Thr Tyr Gly Asn Ser Ser Gly Leu Tyr His Leu Thr Asn Asp Cys Pro
        195                 200                 205

Asn Ser Ser Ile Val Leu Glu Ala Asp Ala Met Ile Leu His Leu Pro
    210                 215                 220

Gly Cys Leu Pro Cys Val Arg Val Asn Asn Asn Gln Ser Ile Cys Trp
225                 230                 235                 240

His Ala Val Ser Pro Thr Leu Ala Ile Pro Asn Ala Ser Thr Pro Ala
                245                 250                 255

Thr Gly Phe Arg Arg His Val Asp Leu Leu Ala Gly Ala Ala Val Val
            260                 265                 270

Cys Ser Ser Leu Tyr Ile Gly Asp Leu Cys Gly Ser Leu Phe Leu Ala
        275                 280                 285

Gly Gln Leu Phe Thr Phe Gln Pro Arg Arg His Trp Thr Val Gln Asp
    290                 295                 300

Cys Asn Cys Ser Ile Tyr Thr Gly His Val Thr Gly His Arg Met Ala
305                 310                 315                 320
```

-continued

```
Trp Asp Met Met Met Asn Trp Ser Pro Thr Thr Thr Leu Val Leu Ser
                325                 330                 335

Ser Ile Leu Arg Val Pro Glu Ile Cys Ala Ser Val Ile Ser Gly Gly
            340                 345                 350

His Trp Gly Ile Leu Leu Ala Val Ala Tyr Phe Gly Met Ala Gly Asn
        355                 360                 365

Trp Leu Lys Val Leu Ala Val Leu Phe Leu Phe Ala Gly Val Glu Ala
    370                 375                 380

Leu Gln Leu Ile Asn Thr Thr Gly Ser Trp His Ile Asn Arg Thr Ala
385                 390                 395                 400

Leu Asn Cys Asn Asp Ser Leu Gln Thr Gly Phe Ile Thr Ser Leu Phe
                405                 410                 415

Tyr Ala Lys Asn Val Asn Ser Ser Gly Cys Pro Glu Arg Met Ala Ala
            420                 425                 430

Cys Lys Pro Leu Ala Asp Phe Arg Gln Gly Trp Gly Gln Ile Thr Tyr
        435                 440                 445

Lys Val Asn Ile Ser Gly Pro Ser Asp Asp Arg Pro Tyr Cys Trp His
    450                 455                 460

Tyr Ala Pro Arg Pro Cys Asp Val Val Ser Ala Arg Thr Val Cys Gly
465                 470                 475                 480

Pro Val Tyr Cys Phe Thr Pro Ser Pro Val Val Val Gly Thr Thr Asp
                485                 490                 495

Lys Leu Gly Ile Pro Thr Tyr Asn Trp Gly Glu Asn Glu Thr Asp Val
            500                 505                 510

Phe Met Leu Glu Ser Leu Arg Pro Pro Thr Gly Gly Trp Phe Gly Cys
        515                 520                 525

Thr Trp Met Asn Ser Thr Gly Phe Thr Lys Thr Cys Gly Ala Pro Pro
    530                 535                 540

Cys Gln Ile Val Pro Gly Asp Tyr Asn Ser Ser Ala Asn Glu Leu Leu
545                 550                 555                 560

Cys Pro Thr Asp Cys Phe Arg Lys His Pro Glu Ala Thr Tyr Gln Arg
                565                 570                 575

Cys Gly Ser Gly Pro Trp Ile Thr Pro Arg Cys Leu Val Asp Tyr Pro
            580                 585                 590

Tyr Arg Leu Trp His Tyr Pro Cys Thr Val Asn Phe Thr Leu His Lys
        595                 600                 605

Val Arg Met Phe Val Gly Gly Ile Glu His Arg Phe Asp Ala Ala Cys
    610                 615                 620

Asn Trp Thr Arg Gly Glu Arg Cys Asp Leu His Asp Arg Asp Arg Ile
625                 630                 635                 640

Glu Met Ser Pro Leu Leu Phe Ser Thr Thr Gln Leu Ala Ile Leu Pro
                645                 650                 655

Cys Ser Phe Ser Thr Met Pro Ala Leu Ser Thr Gly Leu Ile His Leu
            660                 665                 670

His Gln Asn Ile Val Asp Val Gln Tyr Leu Tyr Gly Val Ser Ser Ser
        675                 680                 685

Val Thr Ser Trp Val Val Lys Trp Glu Tyr Ile Val Leu Val Phe Leu
    690                 695                 700

Val Leu Ala Asp Ala Arg Ile Cys Thr Cys Leu Trp Leu Met Leu Leu
705                 710                 715                 720

Ile Thr Asn Val Glu Ala Ala Val Glu Arg Leu Val Val Leu Asn Ala
                725                 730                 735
```

```
Ala Ser Ala Ala Gly Thr Ala Gly Trp Trp Trp Ala Val Leu Phe Leu
            740                 745                 750

Cys Cys Ala Trp Tyr Val Lys Gly Arg Leu Val Pro Ala Cys Thr Tyr
        755                 760                 765

Met Ala Leu Gly Met Trp Pro Leu Leu Leu Thr Ile Leu Ala Leu Pro
    770                 775                 780

Arg Arg Ala Tyr Ala Met Asp Asn Glu Gln Ala Ala Ser Leu Gly Ala
785                 790                 795                 800

Val Gly Leu Leu Val Leu Thr Ile Phe Thr Ile Thr Pro Met Tyr Lys
                805                 810                 815

Lys Leu Leu Thr Cys Ser Ile Trp Trp Asn Gln Tyr Phe Leu Ala Arg
            820                 825                 830

Ala Glu Ala Met Ile His Glu Trp Val Pro Asp Leu Arg Val Arg Gly
        835                 840                 845

Gly Arg Asp Ser Ile Ile Leu Leu Thr Cys Leu Leu His Pro Gln Leu
    850                 855                 860

Gly Phe Glu Val Thr Lys Ile Leu Leu Ala Ile Leu Ala Pro Leu Tyr
865                 870                 875                 880

Ile Leu Gln Tyr Ser Leu Leu Lys Val Pro Tyr Phe Val Arg Ala His
                885                 890                 895

Val Leu Leu Arg Ala Cys Leu Leu Val Arg Arg Leu Ala Gly Gly Lys
            900                 905                 910

Tyr Val Gln Ala Cys Leu Leu Arg Leu Gly Ala Trp Thr Gly Thr Phe
        915                 920                 925

Val Tyr Asp His Leu Ala Pro Leu Ser Asp Trp Ala Ser Asp Gly Leu
    930                 935                 940

Arg Asp Leu Ala Val Ala Ile Glu Pro Val Ile Phe Ser Pro Met Glu
945                 950                 955                 960

Lys Lys Ile Ile Thr Trp Gly Ala Asp Thr Ala Ala Cys Gly Asp Ile
                965                 970                 975

Leu Ser Gly Leu Pro Val Ser Ala Arg Leu Gly Asn Leu Val Leu Leu
            980                 985                 990

Gly Pro Ala Asp Asp Met Gln Arg  Gly Gly Trp Lys Leu  Leu Ala Pro
        995                 1000                1005

Ile Thr  Ala Tyr Ala Gln Gln  Thr Arg Gly Leu Leu  Gly Ala Ile
    1010                 1015                 1020

Val Val  Ser Met Thr Gly Arg  Asp Arg Thr Glu Gln  Ala Gly Glu
    1025                 1030                 1035

Val Gln  Ile Leu Ser Thr Val  Ser Gln Ser Phe Leu  Gly Thr Thr
    1040                 1045                 1050

Ile Ser  Gly Val Leu Trp Thr  Val Tyr His Gly Ala  Gly Asn Lys
    1055                 1060                 1065

Thr Leu  Ala Gly Leu Arg Gly  Pro Val Thr Gln Met  Tyr Ser Ser
    1070                 1075                 1080

Ala Glu  Gly Asp Leu Val Gly  Trp Pro Ser Pro Pro  Gly Thr Lys
    1085                 1090                 1095

Ser Leu  Glu Pro Cys Lys Cys  Gly Ala Val Asp Leu  Tyr Leu Val
    1100                 1105                 1110

Thr Arg  Asn Ala Asp Val Ile  Pro Ala Arg Arg Arg  Gly Asp Lys
    1115                 1120                 1125

Arg Gly  Ala Leu Leu Ser Pro  Arg Pro Ile Ser Thr  Leu Lys Gly
    1130                 1135                 1140

Ser Ser  Gly Gly Pro Val Leu  Cys Pro Arg Gly His  Val Val Gly
```

-continued

```
    1145                1150                1155

Leu Phe  Arg Ala Ala Val Cys  Ser Arg Gly Val Ala  Lys Ser Ile
    1160                1165                1170

Asp Phe  Ile Pro Val Glu Thr  Leu Asp Val Val Thr  Arg Ser Pro
    1175                1180                1185

Thr Phe  Ser Asp Asn Ser Thr  Pro Pro Ala Val Pro  Gln Thr Tyr
    1190                1195                1200

Gln Val  Gly Tyr Leu His Ala  Pro Thr Gly Ser Gly  Lys Ser Thr
    1205                1210                1215

Lys Val  Pro Val Ala Tyr Ala  Ala Gln Gly Tyr Lys  Val Leu Val
    1220                1225                1230

Leu Asn  Pro Ser Val Ala Ala  Thr Leu Gly Phe Gly  Ala Tyr Leu
    1235                1240                1245

Ser Lys  Ala His Gly Ile Asn  Pro Asn Ile Arg Thr  Gly Val Arg
    1250                1255                1260

Thr Val  Met Thr Gly Glu Ala  Ile Thr Tyr Ser Thr  Tyr Gly Lys
    1265                1270                1275

Phe Leu  Ala Asp Gly Gly Cys  Ala Ser Gly Ala Tyr  Asp Ile Ile
    1280                1285                1290

Ile Cys  Asp Glu Cys His Ala  Val Asp Ala Thr Ser  Ile Leu Gly
    1295                1300                1305

Ile Gly  Thr Val Leu Asp Gln  Ala Glu Thr Ala Gly  Val Arg Leu
    1310                1315                1320

Thr Val  Leu Ala Thr Ala Thr  Pro Pro Gly Ser Val  Thr Thr Pro
    1325                1330                1335

His Pro  Asp Ile Glu Glu Val  Gly Leu Gly Arg Glu  Gly Glu Ile
    1340                1345                1350

Pro Phe  Tyr Gly Arg Ala Ile  Pro Leu Ser Cys Ile  Lys Gly Gly
    1355                1360                1365

Arg His  Leu Ile Phe Cys His  Ser Lys Lys Lys Cys  Asp Glu Leu
    1370                1375                1380

Ala Ala  Ala Leu Arg Gly Met  Gly Leu Asn Ala Val  Ala Tyr Tyr
    1385                1390                1395

Arg Gly  Leu Asp Val Ser Ile  Ile Pro Ala Gln Gly  Asp Val Val
    1400                1405                1410

Val Val  Ala Thr Asp Ala Leu  Met Thr Gly Tyr Thr  Gly Asp Phe
    1415                1420                1425

Asp Ser  Val Ile Asp Cys Asn  Val Ala Val Thr Gln  Ala Val Asp
    1430                1435                1440

Phe Ser  Leu Asp Pro Thr Phe  Thr Ile Thr Thr Gln  Thr Val Pro
    1445                1450                1455

Gln Asp  Ala Val Ser Arg Ser  Gln Arg Arg Gly Arg  Thr Gly Arg
    1460                1465                1470

Gly Arg  Gln Gly Thr Tyr Arg  Tyr Val Ser Thr Gly  Glu Arg Ala
    1475                1480                1485

Ser Gly  Met Phe Asp Ser Val  Val Leu Cys Glu Cys  Tyr Asp Ala
    1490                1495                1500

Gly Ala  Ala Trp Tyr Asp Leu  Thr Pro Ala Glu Thr  Thr Val Arg
    1505                1510                1515

Leu Arg  Ala Tyr Phe Asn Thr  Pro Gly Leu Pro Val  Cys Gln Asp
    1520                1525                1530

His Leu  Glu Phe Trp Glu Ala  Val Phe Thr Gly Leu  Thr His Ile
    1535                1540                1545
```

```
Asp Ala His Phe Leu Ser Gln Thr Lys Gln Ala Gly Glu Asn Phe
    1550                1555                1560

Ala Tyr Leu Val Ala Tyr Gln Ala Thr Val Cys Ala Arg Ala Lys
    1565                1570                1575

Ala Pro Pro Pro Ser Trp Asp Ala Met Trp Lys Cys Leu Ala Arg
    1580                1585                1590

Leu Lys Pro Thr Leu Ala Gly Pro Thr Pro Leu Leu Tyr Arg Leu
    1595                1600                1605

Gly Pro Ile Thr Asn Glu Val Thr Leu Thr His Pro Gly Thr Lys
    1610                1615                1620

Tyr Ile Ala Thr Cys Met Gln Ala Asp Leu Glu Val Met Thr Ser
    1625                1630                1635

Thr Trp Val Leu Ala Gly Gly Val Leu Ala Ala Val Ala Ala Tyr
    1640                1645                1650

Cys Leu Ala Thr Gly Cys Val Ser Ile Ile Gly Arg Leu His Val
    1655                1660                1665

Asn Gln Arg Val Val Val Ala Pro Asp Lys Glu Val Leu Tyr Glu
    1670                1675                1680

Ala Phe Asp Glu Met Glu Glu Cys Ala Ser Arg Ala Ala Leu Ile
    1685                1690                1695

Glu Glu Gly Gln Arg Ile Ala Glu Met Leu Lys Ser Lys Ile Gln
    1700                1705                1710

Gly Leu Leu Gln Gln Ala Ser Lys Gln Ala Gln Asp Ile Gln Pro
    1715                1720                1725

Ala Met Gln Ala Ser Trp Pro Lys Val Glu Gln Phe Trp Ala Arg
    1730                1735                1740

His Met Trp Asn Phe Ile Ser Gly Ile Gln Tyr Leu Ala Gly Leu
    1745                1750                1755

Ser Thr Leu Pro Gly Asn Pro Ala Val Ala Ser Met Met Ala Phe
    1760                1765                1770

Ser Ala Ala Leu Thr Ser Pro Leu Ser Thr Ser Thr Thr Ile Leu
    1775                1780                1785

Leu Asn Ile Met Gly Gly Trp Leu Ala Ser Gln Ile Ala Pro Pro
    1790                1795                1800

Ala Gly Ala Thr Gly Phe Val Val Ser Gly Leu Val Gly Ala Ala
    1805                1810                1815

Val Gly Ser Ile Gly Leu Gly Lys Val Leu Val Asp Ile Leu Ala
    1820                1825                1830

Gly Tyr Gly Ala Gly Ile Ser Gly Ala Leu Val Ala Phe Lys Ile
    1835                1840                1845

Met Ser Gly Glu Lys Pro Ser Met Glu Asp Val Ile Asn Leu Leu
    1850                1855                1860

Pro Gly Ile Leu Ser Pro Gly Ala Leu Val Val Gly Val Ile Cys
    1865                1870                1875

Ala Ala Ile Leu Arg Arg His Val Gly Pro Gly Glu Gly Ala Val
    1880                1885                1890

Gln Trp Met Asn Arg Leu Ile Ala Phe Ala Ser Arg Gly Asn His
    1895                1900                1905

Val Ala Pro Thr His Tyr Val Thr Glu Ser Asp Ala Ser Gln Arg
    1910                1915                1920

Val Thr Gln Leu Leu Gly Ser Leu Thr Ile Thr Ser Leu Leu Arg
    1925                1930                1935
```

```
Arg Leu  His Asn Trp Ile Thr  Glu Asp Cys Pro Ile  Pro Cys Ser
    1940                 1945                 1950

Gly Ser  Trp Leu Arg Asp Val  Trp Asp Trp Val Cys  Thr Ile Leu
    1955                 1960                 1965

Thr Asp  Phe Lys Asn Trp Leu  Thr Ser Lys Leu Phe  Pro Lys Leu
    1970                 1975                 1980

Pro Gly  Leu Pro Phe Ile Ser  Cys Gln Lys Gly Tyr  Lys Gly Val
    1985                 1990                 1995

Trp Ala  Gly Thr Gly Ile Met  Thr Thr Arg Cys Pro  Cys Gly Ala
    2000                 2005                 2010

Asn Ile  Ser Gly Asn Val Arg  Leu Gly Ser Met Arg  Ile Thr Gly
    2015                 2020                 2025

Pro Lys  Thr Cys Met Asn Thr  Trp Gln Gly Thr Phe  Pro Ile Asn
    2030                 2035                 2040

Cys Tyr  Thr Glu Gly Gln Cys  Ala Pro Lys Pro Pro  Thr Asn Tyr
    2045                 2050                 2055

Lys Thr  Ala Ile Trp Arg Val  Ala Ala Ser Glu Tyr  Ala Glu Val
    2060                 2065                 2070

Thr Gln  His Gly Ser Tyr Ser  Tyr Val Thr Gly Leu  Thr Thr Asp
    2075                 2080                 2085

Asn Leu  Lys Ile Pro Cys Gln  Leu Pro Ser Pro Glu  Phe Phe Ser
    2090                 2095                 2100

Trp Val  Asp Gly Val Gln Ile  His Arg Phe Ala Pro  Thr Pro Lys
    2105                 2110                 2115

Pro Phe  Phe Arg Asp Glu Val  Ser Phe Cys Val Gly  Leu Asn Ser
    2120                 2125                 2130

Tyr Ala  Val Gly Ser Gln Leu  Pro Cys Glu Pro Glu  Pro Asp Ala
    2135                 2140                 2145

Asp Val  Leu Arg Ser Met Leu  Thr Asp Pro Pro His  Ile Thr Ala
    2150                 2155                 2160

Glu Thr  Ala Ala Arg Arg Leu  Ala Arg Gly Ser Pro  Pro Ser Glu
    2165                 2170                 2175

Ala Ser  Ser Ser Val Ser Gln  Leu Ser Ala Pro Ser  Leu Arg Ala
    2180                 2185                 2190

Thr Cys  Thr Thr His Ser Asn  Thr Tyr Asp Val Asp  Met Val Asp
    2195                 2200                 2205

Ala Asn  Leu Leu Met Glu Gly  Gly Val Ala Gln Thr  Glu Pro Glu
    2210                 2215                 2220

Ser Arg  Val Pro Val Leu Asp  Phe Leu Glu Pro Met  Ala Glu Glu
    2225                 2230                 2235

Glu Ser  Asp Leu Glu Pro Ser  Ile Pro Ser Glu Cys  Met Leu Pro
    2240                 2245                 2250

Arg Ser  Gly Phe Pro Arg Ala  Leu Pro Ala Trp Ala  Arg Pro Asp
    2255                 2260                 2265

Tyr Asn  Pro Pro Leu Val Glu  Ser Trp Arg Arg Pro  Asp Tyr Gln
    2270                 2275                 2280

Pro Pro  Thr Val Ala Gly Cys  Ala Leu Pro Pro Pro  Lys Lys Ala
    2285                 2290                 2295

Pro Thr  Pro Pro Pro Arg Arg  Arg Arg Thr Val Gly  Leu Ser Glu
    2300                 2305                 2310

Ser Thr  Ile Ser Glu Ala Leu  Gln Gln Leu Ala Ile  Lys Thr Phe
    2315                 2320                 2325

Gly Gln  Pro Pro Ser Ser Gly  Asp Ala Gly Ser Ser  Thr Gly Ala
```

2330 2335 2340

Gly Ala Ala Glu Ser Gly Gly Pro Thr Ser Pro Gly Glu Pro Ala
2345 2350 2355

Pro Ser Glu Thr Gly Ser Ala Ser Ser Met Pro Pro Leu Glu Gly
2360 2365 2370

Glu Pro Gly Asp Pro Asp Leu Glu Ser Asp Gln Val Glu Leu Gln
2375 2380 2385

Pro Pro Pro Gln Gly Gly Gly Val Ala Pro Gly Ser Gly Ser Gly
2390 2395 2400

Ser Trp Ser Thr Cys Ser Glu Glu Asp Asp Thr Thr Val Cys Cys
2405 2410 2415

Ser Met Ser Tyr Ser Trp Thr Gly Ala Leu Ile Thr Pro Cys Ser
2420 2425 2430

Pro Glu Glu Glu Lys Leu Pro Ile Asn Pro Leu Ser Asn Ser Leu
2435 2440 2445

Leu Arg Tyr His Asn Lys Val Tyr Cys Thr Thr Ser Lys Ser Ala
2450 2455 2460

Ser Gln Arg Ala Lys Lys Val Thr Phe Asp Arg Thr Gln Val Leu
2465 2470 2475

Asp Ala His Tyr Asp Ser Val Leu Lys Asp Ile Lys Leu Ala Ala
2480 2485 2490

Ser Lys Val Ser Ala Arg Leu Leu Thr Leu Glu Glu Ala Cys Gln
2495 2500 2505

Leu Thr Pro Pro His Ser Ala Arg Ser Lys Tyr Gly Phe Gly Ala
2510 2515 2520

Lys Glu Val Arg Ser Leu Ser Gly Arg Ala Val Asn His Ile Lys
2525 2530 2535

Ser Val Trp Lys Asp Leu Leu Glu Asp Pro Gln Thr Pro Ile Pro
2540 2545 2550

Thr Thr Ile Met Ala Lys Asn Glu Val Phe Cys Val Asp Pro Ala
2555 2560 2565

Lys Gly Gly Lys Lys Pro Ala Arg Leu Ile Val Tyr Pro Asp Leu
2570 2575 2580

Gly Val Arg Val Cys Glu Lys Met Ala Leu Tyr Asp Ile Thr Gln
2585 2590 2595

Lys Leu Pro Gln Ala Val Met Gly Ala Ser Tyr Gly Phe Gln Tyr
2600 2605 2610

Ser Pro Ala Gln Arg Val Glu Tyr Leu Leu Lys Ala Trp Ala Glu
2615 2620 2625

Lys Lys Asp Pro Met Gly Phe Ser Tyr Asp Thr Arg Cys Phe Asp
2630 2635 2640

Ser Thr Val Thr Glu Arg Asp Ile Arg Thr Glu Glu Ser Ile Tyr
2645 2650 2655

Gln Ala Cys Ser Leu Pro Glu Glu Ala Arg Thr Ala Ile His Ser
2660 2665 2670

Leu Thr Glu Arg Leu Tyr Val Gly Gly Pro Met Phe Asn Ser Lys
2675 2680 2685

Gly Gln Thr Cys Gly Tyr Arg Arg Cys Arg Ala Ser Gly Val Leu
2690 2695 2700

Thr Thr Ser Met Gly Asn Thr Ile Thr Cys Tyr Val Lys Ala Leu
2705 2710 2715

Ala Ala Cys Lys Ala Ala Gly Ile Val Ala Pro Thr Met Leu Val
2720 2725 2730

Cys Gly Asp Asp Leu Val Val Ile Ser Glu Ser Gln Gly Thr Glu
2735 2740 2745

Glu Asp Glu Arg Asn Leu Arg Ala Phe Thr Glu Ala Met Thr Arg
2750 2755 2760

Tyr Ser Ala Pro Pro Gly Asp Pro Pro Arg Pro Glu Tyr Asp Leu
2765 2770 2775

Glu Leu Ile Thr Ser Cys Ser Ser Asn Val Ser Val Ala Leu Gly
2780 2785 2790

Pro Arg Gly Arg Arg Arg Tyr Tyr Leu Thr Arg Asp Pro Thr Thr
2795 2800 2805

Pro Leu Ala Arg Ala Ala Trp Glu Thr Val Arg His Ser Pro Ile
2810 2815 2820

Asn Ser Trp Leu Gly Asn Ile Ile Gln Tyr Ala Pro Thr Ile Trp
2825 2830 2835

Val Arg Met Val Leu Met Thr His Phe Phe Ser Ile Leu Met Val
2840 2845 2850

Gln Asp Thr Leu Asp Gln Asn Leu Asn Phe Glu Met Tyr Gly Ser
2855 2860 2865

Val Tyr Ser Val Asn Pro Leu Asp Leu Pro Ala Ile Ile Glu Arg
2870 2875 2880

Leu His Gly Leu Asp Ala Phe Ser Met His Thr Tyr Ser His His
2885 2890 2895

Glu Leu Thr Arg Val Ala Ser Ala Leu Arg Lys Leu Gly Ala Pro
2900 2905 2910

Pro Leu Arg Val Trp Lys Ser Arg Ala Arg Ala Val Arg Ala Ser
2915 2920 2925

Leu Ile Ser Arg Gly Gly Lys Ala Ala Val Cys Gly Arg Tyr Leu
2930 2935 2940

Phe Asn Trp Ala Val Lys Thr Lys Leu Lys Leu Thr Pro Leu Pro
2945 2950 2955

Glu Ala Arg Leu Leu Asp Leu Ser Ser Trp Phe Thr Val Gly Ala
2960 2965 2970

Gly Gly Gly Asp Ile Phe His Ser Val Ser Arg Ala Arg Pro Arg
2975 2980 2985

Ser Leu Leu Phe Gly Leu Leu Leu Leu Phe Val Gly Val Gly Leu
2990 2995 3000

Phe Leu Leu Pro Ala Arg
3005

<210> SEQ ID NO 7
<211> LENGTH: 9585
<212> TYPE: DNA
<213> ORGANISM: Hepatitis C virus

<400> SEQUENCE: 7
acctgcccct aataggggcg acactccgcc atgaatcact cccctgtgag gaactactgt 60
cttcacgcag aaagcgccta gccatggcgt tagtatgagt gtcgtacagc ctccaggccc 120
ccccctcccg ggagagccat agtggtctgc ggaaccggtg agtacaccgg aattgccggg 180
aagactgggt cctttcttgg ataaacccac tctatgcccg gccatttggg cgtgcccccg 240
caagactgct agccgagtag cgttgggttg cgaaaggcct tgtggtactg cctgataggg 300
cgcttgcgag tgccccggga ggtctcgtag accgtgcacc atgagcacga atcctaaacc 360
tcaaagaaaa accaaacgta acaccaaccg tcgcccacag gacgtcaagt tcccgggtgg 420

-continued

```
cggtcagatc gttggtggag tttacttgtt gccgcgcagg ggccctagat tgggtgtgcg    480
cgcgacgagg aagacttccg agcggtcgca acctcgaggt agacgtcagc ctatccccaa    540
ggcacgtcgg cccgagggca ggacctgggc tcagcccggg tacccttggc ccctctatgg    600
caatgagggt tgcgggtggg cgggatggct cctgtctccc cgtggctctc ggcctagctg    660
gggccccaca gacccccggc gtaggtcgcg caatttgggt aaggtcatcg atacccttac    720
gtgcggcttc gccgacctca tggggtacat accgctcgtc ggcgcccctc ttggaggcgc    780
tgccagggcc ctggcgcatg gcgtccgggt tctggaagac ggcgtgaact atgcaacagg    840
gaaccttcct ggttgctctt tctctatctt ccttctggcc ctgctctctt gcctgactgt    900
gcccgcttca gcctaccaag tgcgcaattc ctcggggctt taccatgtca ccaatgattg    960
ccctaactcg agtattgtgt acgaggcggc cgatgccatc ctgcacactc cggggtgtgt   1020
cccttgcgtt cgcgagggta acgcctcgag gtgttgggtg gcggtgaccc ccacggtggc   1080
caccagggac ggcaaactcc ccacaacgca gcttcgacgt catatcgatc tgcttgtcgg   1140
gagcgccacc ctctgctcgg ccctctacgt gggggacctg tgcgggtctg tctttcttgt   1200
tggtcaactg tttaccttct ctcccaggcg ccactggacg acgcaagact gcaattgttc   1260
tatctatccc ggccatataa cgggtcatcg catggcatgg gatatgatga tgaactggtc   1320
ccctacggca gcgttggtgg tagctcagct gctccggatc ccacaagcca tcatggacat   1380
gatcgctggt gctcactggg gagtcctggc gggcatagcg tatttctcca tggtggggaa   1440
ctgggcgaag gtcctggtag tgctgctgct atttgccggc gtcgacgcga tccaactgat   1500
caacaccaac ggcagttggc acatcaatag cacggccttg aattgcaatg aaagccttaa   1560
caccggctgg ttagcagggc tcttctatca acacaaattc aactcttcag gctgtcctga   1620
gaggttggcc agctgccgac gccttaccga ttttgcccag ggctggggtc ctatcagtta   1680
tgccaacgga agcggcctcg acgaacgccc ctactgctgg cactaccctc caagaccttg   1740
tggcattgtg cccgcaaaga gcgtgtgtgg cccggtatat tgcttcactc ccagccccgt   1800
ggtggtggga acgaccgaca ggtcgggcgc gcctacctac agctggggtg caaatgatac   1860
ggatgtcttc gtccttaaca acaccaggcc accgctgggc aattggttcg gttgtacctg   1920
gatgaactca actggattca ccaaagtgtg cggagcgccc ccttgtgtca tcggaggggt   1980
gggcaacaac accttgctct gccccactga ttgcttccgc aaacatccgg aagccacata   2040
ctctcggtgc ggctccggtc cctggattac acccaggtgc atggtcgact acccgtatag   2100
gctttggcac tatccttgta ccatcaatta caccatattc aaagtcagga tgtacgtggg   2160
aggggtcgag cacaggctgg aagcggcctg caactggacg cggggcgaac gctgtgatct   2220
ggaagacagg gacaggtccg agctcagccc gttgctgctg tccaccacac agtggcaggt   2280
ccttccgtgt tctttcacga ccctgccagc cttgtccacc ggcctcatcc acctccacca   2340
gaacattgtg gacgtgcagt acttgtacgg ggtagggtca agcatcgcgt cctgggccat   2400
taagtgggag tacgtcgttc tcctgttcct tctgcttgca gacgcgcgcg tctgctcctg   2460
cttgtggatg atgttactca tatcccaagc ggaggcggct ttggagaacc tcgtaatact   2520
caatgcagca tccctggccg ggacgcacgg tcttgtgtcc ttcctcgtgt tcttctgctt   2580
tgcgtggtat ctgaagggta ggtgggtgcc cggagcggcc tacgccctct acgggatgtg   2640
gcctctcctc ctgctcctgc tggcgttgcc tcagcgggca tacgcactgg acacggaggt   2700
ggccgcgtcg tgtggcggcg ttgttcttgt cgggttaatg gcgctgactc tgtcgccata   2760
```

-continued ttacaagcgc tatatcagct ggtgcatgtg gtggcttcag tattttctga ccagagtaga 2820
agcgcaactg cacgtgtggg ttcccccccct caacgtccgg ggggggcgcg atgccgtcat 2880
cttactcatg tgtgtagtac acccgaccct ggtatttgac atcaccaaac tactcctggc 2940
catcttcgga cccctttgga ttcttcaagc cagtttgctt aaagtcccct acttcgtgcg 3000
cgttcaaggc cttctccgga tctgcgcgct agcgcggaag atagccggag gtcattacgt 3060
gcaaatggcc atcatcaagt taggggcgct tactggcacc tatgtgtata accatctcac 3120
ccctcttcga gactgggcgc acaacggcct gcgagatctg gccgtggctg tggaaccagt 3180
cgtcttctcc cgaatggaga ccaagctcat cacgtggggg gcagataccg ccgcgtgcgg 3240
tgacatcatc aacggcttgc ccgtctctgc ccgtaggggc caggagatac tgcttgggcc 3300
agccgacgga atggtctcca aggggtggag gttgctggct cccatcactg cttatgccca 3360
gcaaacacga ggcctcctgg gcgccatagt ggtgagtatg acggggcgtg acaggacaga 3420
acaggccggg gaagtccaaa tcctgtccac agtctctcag tccttcctcg gaacaaccat 3480
ctcgggggtt ttgtggactg tttaccacgg agctggcaac aagactctag ccggcttacg 3540
gggtccggtc acgcagatgt actcgagtgc tgagggggac ttggtaggct ggcccagccc 3600
ccctgggacc aagtctttgg agccgtgcaa gtgtggagcc gtcgacctat atctggtcac 3660
gcggaacgct gatgtcatcc cggctcggag acgcggggac aagcggggag cattgctctc 3720
cccgagaccc atttcgacct tgaaggggtc ctcgggggggg ccggtgctct gccctagggg 3780
ccacgtcgtt gggctcttcc gagcagctgt gtgctctcgg ggcgtggcca aatccatcga 3840
tttcatcccc gttgagacac tcgacgttgt tacaaggtct cccactttca gtgacaacag 3900
cacgccaccg gctgtgcccc agacctatca ggtcgggtac ttgcatgctc caactggcag 3960
tggaaagagc accaaggtcc ctgtcgcgta tgccgccctg ggtacaaag tactagtgct 4020 taacccctcg gtagctgcca ccctggggtt tggggcgtac ctatccaagg cacatggcat 4080
caatcccaac attaggactg gagtcaggac cgtgatgacc ggggaggcca tcacgtactc 4140
cacatatggc aaatttctcg ccgatggggg ctgcgctagc ggcgcctatg acatcatcat 4200
atgcgatgaa tgccacgctg tggatgctac ctccattctc ggcatcggaa cggtccttga 4260
tcaagcagag acagccgggg tcagactaac tgtgctggct acggccacac cccccgggtc 4320
agtgacaacc ccccatcccg atatagaaga ggtaggcctc gggcgggagg gtgagatccc 4380
cttctatggg agggcgattc ccctatcctg catcaaggga gggagacacc tgattttctg 4440
ccactcaaag aaaaagtgtg acgagctcgc ggcggccctt cggggcatgg gcttgaatgc 4500
cgtggcatac tatagagggt tggacgtctc cataatacca gctcagggag atgtggtggt 4560
cgtcgccacc gacgccctca tgacggggta cactggagac tttgactccg tgatcgactg 4620
caatgtagcg gtcacccaag ctgtcgactt cagcctggac cccaccttca ctataaccac 4680
acagactgtc ccacaagacg ctgtctcacg cagtcagcgc cgcgggcgca caggtagagg 4740
aagacagggc acttataggt atgtttccac tggtgaacga gcctcaggaa tgtttgacag 4800
tgtagtgctt tgtgagtgct acgacgcagg ggctgcgtgg tacgatctca caccagcgga 4860
gaccaccgtc aggcttagag cgtatttcaa cacgcccggc ctacccgtgt gtcaagacca 4920
tcttgaattt tgggaggcag ttttcaccgg cctcacacac atagacgccc acttcctctc 4980
ccaaacaaag caagcggggg agaacttcgc gtacctagta gcctaccaag ctacggtgtg 5040
cgccagagcc aaggcccctc ccccgtcctg ggacgccatg tggaagtgcc tggcccgact 5100
caagcctacg cttgcgggcc ccacacctct cctgtaccgt ttgggcccta ttaccaatga 5160
ggtcaccctc acacaccctg ggacgaagta catcgccaca tgcatgcaag ctgaccttga 5220
ggtcatgacc agcacgtggg tcctagctgg aggagtcctg gcagccgtcg ccgcatattg 5280
cctggcgact ggatgcgttt ccatcatcgg ccgcttgcac gtcaaccagc gagtcgtcgt 5340
tgcgccggat aaggaggtcc tgtatgaggc ttttgatgag atggaggaat gcgcctctag 5400
ggcggctctc atcgaagagg ggcagcggat agccgagatg ttgaagtcca agatccaagg 5460
cttgctgcag caggcctcta agcaggccca ggacatacaa cccgctatgc aggcttcatg 5520
gcccaaagtg gaacaatttt gggccagaca catgtggaac ttcattagcg gcatccaata 5580
cctcgcagga ttgtcaacac tgccagggaa ccccgcggtg gcttccatga tggcattcag 5640
tgccgccctc accagtccgt tgtcgaccag taccaccatc cttctcaaca tcatgggagg 5700
ctggttagcg tcccagatcg caccacccgc gggggccacc ggctttgtcg tcagtggcct 5760
ggtgggggct gccgtgggca gcataggcct gggtaaggtg ctggtggaca tcctggcagg 5820
atatggtgcg ggcatttcgg gggccctcgt cgcattcaag atcatgtctg gcgagaagcc 5880
ctctatggaa gatgtcatca atctactgcc tgggatcctg tctccgggag ccctggtggt 5940
gggggtcatc tgcgcggcca ttctgcgccg ccacgtggga ccgggggagg gcgcggtcca 6000
atggatgaac aggcttattg cctttgcttc cagaggaaac cacgtcgccc ctactcacta 6060
cgtgacggag tcggatgcgt cgcagcgtgt gacccaacta cttggctctc ttactataac 6120
cagcctactc agaagactcc acaattggat aactgaggac tgccccatcc catgctccgg 6180
atcctggctc cgcgacgtgt gggactgggt ttgcaccatc ttgacagact tcaaaaattg 6240
gctgacctct aaattgttcc ccaagctgcc cggcctcccc ttcatctctt gtcaaaaggg 6300
gtacaagggt gtgtgggccg gcactggcat catgaccacg cgctgccctt gcggcgccaa 6360
catctctggc aatgtccgcc tggctctat gaggatcaca gggcctaaaa cctgcatgaa 6420
cacctggcag ggaccttc ctatcaattg ctacacggag ggccagtgcg cgccgaaacc 6480
ccccacgaac tacaagaccg ccatctggag ggtggcggcc tcggagtacg cggaggtgac 6540
gcagcatggg tcgtactcct atgtaacagg actgaccact gacaatctga aaattccttg 6600
ccaactacct tctccagagt ttttctcctg ggtggacggt gtgcagatcc ataggtttgc 6660
acccacacca aagccgtttt tccgggatga ggtctcgttc tgcgttgggc ttaattccta 6720
tgctgtcggg tcccagcttc cctgtgaacc tgagcccgac gcagacgtat tgaggtccat 6780
gctaacagat ccgccccaca tcacggcgga gactgcggcg cggcgcttgg cacggggatc 6840
acctccatct gaggcgagct cctcagtgag ccagctatca gcaccgtcgc tgcgggccac 6900
ctgcaccacc cacagcaaca cctatgacgt ggacatggtc gatgccaacc tgctcatgga 6960
gggcggtgtg gctcagacag agcctgagtc cagggtgccc gttctggact ttctcgagcc 7020
aatggccgag gaagagagcg accttgagcc ctcaatacca tcggagtgca tgctccccag 7080
gagcgggttt ccacgggcct taccggcttg ggcacggcct gactacaacc cgccgctcgt 7140
ggaatcgtgg aggaggccag attaccaacc gcccaccgtt gctggttgtg ctctcccccc 7200
ccccaagaag gccccgacgc ctccccaag gagacgccgg acagtgggtc tgagcgagag 7260
caccatatca gaagccctcc agcaactggc catcaagacc tttggccagc ccccctcgag 7320
cggtgatgca ggctcgtcca cgggggcggg cgccgccgaa tccggcggtc cgacgtcccc 7380
tggtgagccg gccccctcag agacaggttc cgcctcctct atgccccccc tcgaggggga 7440
gcctggagat ccggacctgg agtctgatca ggtagagctt caacctcccc cccagggggg 7500

-continued gggggtagct cccggttcgg gctcggggtc ttggtctact tgctccgagg aggacgatac 7560
caccgtgtgc tgctccatgt catactcctg gaccggggct ctaataactc cctgtagccc 7620
cgaagaggaa aagttgccaa tcaacccttt gagtaactcg ctgttgcgat accataacaa 7680
ggtgtactgt acaacatcaa agagcgcctc acagagggct aaaaaggtaa cttttgacag 7740
gacgcaagtg ctcgacgccc attatgactc agtcttaaag gacatcaagc tagcggcttc 7800
caaggtcagc gcaaggctcc tcaccttgga ggaggcgtgc cagttgactc caccccattc 7860
tgcaagatcc aagtatggat tcggggccaa ggaggtccgc agcttgtccg ggagggccgt 7920
taaccacatc aagtccgtgt ggaaggacct cctggaagac ccacaaacac caattcccac 7980
aaccatcatg gccaaaaatg aggtgttctg cgtggacccc gccaaggggg gtaagaaacc 8040
agctcgcctc atcgtttacc ctgacctcgg cgtccgggtc tgcgagaaaa tggccctcta 8100
tgacattaca caaaagcttc ctcaggcggt aatgggagct tcctatggct tccagtactc 8160
ccctgcccaa cgggtggagt atctcttgaa agcatgggcg gaaaagaagg accccatggg 8220
tttttcgtat gatacccgat gcttcgactc aaccgtcact gagagagaca tcaggaccga 8280
ggagtccata taccaggcct gctccctgcc cgaggaggcc cgcactgcca tacactcgct 8340
gactgagaga ctttacgtag gagggcccat gttcaacagc aagggtcaaa cctgcggtta 8400
cagacgttgc cgcgccagcg gggtgctaac cactagcatg ggtaacacca tcacatgcta 8460
tgtgaaagcc ctagcggcct gcaaggctgc ggggatagtt gcgcccacaa tgctggtatg 8520
cggcgatgac ctagtagtca tctcagaaag ccaggggact gaggaggacg agcggaacct 8580
gagagccttc acggaggcca tgaccaggta ctctgcccct cctggtgatc cccccagacc 8640
ggaatatgac ctggagctaa taacatcctg ttcctcaaat gtgtctgtgg cgttgggccc 8700
gcggggccgc cgcagatact acctgaccag agacccaacc actccactcg cccgggctgc 8760
ctgggaaaca gttagacact cccctatcaa ttcatggctg ggaaacatca tccagtatgc 8820
tccaaccata tgggttcgca tggtcctaat gacacacttc ttctccattc tcatggtcca 8880
agacaccctg gaccagaacc tcaactttga gatgtatgga tcagtatact ccgtgaatcc 8940
tttggacctt ccagccataa ttgagaggtt acacgggctt gacgcctttt ctatgcacac 9000
atactctcac cacgaactga cgcgggtggc ttcagccctc agaaaacttg ggcgccacc 9060 cctcagggtg tggaagagtc gggctcgcgc agtcagggcg tccctcatct cccgtggagg 9120
gaaagcggcc gtttgcggcc gatatctctt caattgggcg gtgaagacca agctcaaact 9180
cactccattg ccggaggcgc gcctactgga cttatccagt tggttcaccg tcggcgccgg 9240
cgggggcgac atttttcaca gcgtgtcgcg cgcccgaccc cgctcattac tcttcggcct 9300
actcctactt ttcgtagggg taggcctctt cctactcccc gctcggtaga gcggcacaca 9360
ctaggtacac tccatagcta actgttcctt tttttttttt tttttttttt tttttttttt 9420
tttttttttt tctttttttt ttttttccct ctttcttccc ttctcatctt attctacttt 9480
ctttcttggt ggctccatct tagccctagt cacggctagc tgtgaaaggt ccgtgagccg 9540
catgactgca gagagtgccg taactggtct ctctgcagat catgt 9585

<210> SEQ ID NO 8
<211> LENGTH: 9597
<212> TYPE: DNA
<213> ORGANISM: Hepatitis C virus

<400> SEQUENCE: 8
acctgcccct aataggggcg acactccgcc atgaatcact cccctgtgag gaactactgt 60

```
cttcacgcag aaagcgccta gccatggcgt tagtatgagt gtcgtacagc ctccaggccc    120
ccccctcccg ggagagccat agtggtctgc ggaaccggtg agtacaccgg aattgccggg    180
aagactgggt cctttcttgg ataaacccac tctatgcccg gccatttggg cgtgcccccg    240
caagactgct agccgagtag cgttgggttg cgaaaggcct tgtggtactg cctgataggg    300
tgcttgcgag tgccccggga ggtctcgtag accgtgcacc atgagcacaa atcctaaacc    360
tcaaagaaaa accaaaagaa acaccaaccg tcgcccacaa gacgttaagt ttccgggcgg    420
cggccagatc gttggcggag tatacttgtt gccgcgcagg ggccccaggt tgggtgtgcg    480
cgcgacaagg aagacttcgg agcggtccca gccacgtgga aggcgccagc ccatccctaa    540
agatcggcgc tccactggca aatcctgggg aaaaccagga tacccctggc ccctatacgg    600
gaatgaggga ctcggctggg caggatggct cctgtccccc cgaggttccc gtccctcttg    660
gggccccaat gacccccggc ataggtcgcg caacgtgggt aaggtcatcg ataccctaac    720
gtgcggcttt gccgacctca tggggtacat ccctgtcgtg ggcgccccgc tcggcggcgt    780
cgccagagct ctcgcgcatg gcgtgagagt cctggaggac ggggttaatt ttgcaacagg    840
gaacttaccc ggttgctcct ttctatcttt cttgctggcc ctgctgtcct gcatcaccac    900
cccggtctcc gctgccgaag tgaagaacat cagtaccggc tacatggtga ctaacgactg    960
caccaatgac agcattacct ggcagctcca ggctgctgtc ctccacgtcc ccgggtgcgt   1020
cccgtgcgag aaagtgggga atgcatctca gtgctggata ccggtctcac cgaatgtggc   1080
cgtgcagcgg cccggcgccc tcacgcaggg cttgcggacg cacatcgaca tggttgtgat   1140
gtccgccacg ctctgctctg ccctctacgt gggggacctc tgcggtgggg tgatgctcgc   1200
agcccaaatg ttcattgtct cgccgcagca ccactggttt gtccaagact gcaattgctc   1260
catctaccct ggtaccatca ctggacaccg catggcatgg gacatgatga tgaactggtc   1320
gcccacggct accatgatct tggcgtacgc gatgcgtgtc cccgaggtca ttatagacat   1380
cattagcggg gctcattggg gcgtcatgtt cggcttggcc tacttctcta tgcagggagc   1440
gtgggcgaaa gtcgttgtca tccttctgtt ggccgccggg gtggacgcga tccagctcgt   1500
taacaccaat ggcagctggc acatcaaccg caccgccctg aactgcaatg actccttgca   1560
caccggcttt atcgcgtctc tgttctacac ccacagcttc aactcgtcag gatgtcccga   1620
acgcatgtcc gcctgccgca gtatcgaggc cttccgggtg ggatggggcg ccttgcaata   1680
tgaggataat gtcaccaatc cagaggatat gagaccctat tgctggcact acccaccaag   1740
gcagtgtggc gtggtctccg cgaagactgt gtgtggccca gtgtactgtt tcacccccag   1800
cccagtggta gtgggcacga ccgacaggct tggagcgccc acttacacgt ggggggagaa   1860
tgagacagat gtcttcctat tgaacagcac tcgaccaccg ctggggtcat ggttcggctg   1920
cacgtggatg aactcttctg gctacaccaa gacttgcggc gcaccaccct gccgtactag   1980
agctgacttc aacgccagca cggacctgtt gtgccccacg gactgtttta ggaagcatcc   2040
tgataccact tacctcaaat gcggctctgg gccctggctc acgccaaggt gcctgatcga   2100
ctacccctac aggctctggc attacccctg cacagttaac tataccatct tcaaaataag   2160
gatgtatgtg ggaggggttg agcacaggct cacggctgca tgcaatttca ctcgtgggga   2220
tcgttgcaac ttggaggaca gagacagaag tcaactgtct cctttgttgc actccaccac   2280
ggaatgggcc attttacctt gctcttactc ggacctgccc gccttgtcga ctggtcttct   2340
ccacctccac caaaacatcg tggacgtaca attcatgtat ggcctatcac ctgccctcac   2400
```

aaaatacatc gtccgatggg agtgggtaat actcttattc ctgctcttag cggacgccag 2460
ggtttgcgcc tgcttatgga tgctcatctt gttgggccag gccgaagcag cactagagaa 2520
gctggtcatc ttgcacgctg cgagcgcagc tagctgcaat ggcttcctat attttgtcat 2580
ctttttcgtg gctgcttggt acatcaaggg tcgggtagtc cccttagcta cctattccct 2640
cactggcctg tggtccttta gcctactgct cctagcattg ccccaacagg cttatgctta 2700
tgacgcatct gtgcatggcc agataggagc ggctctgctg gtaatgatca ctctctttac 2760
tctcaccccc gggtataaga cccttctcag ccggtttttg tggtggttgt gctatcttct 2820
gaccctgggg gaagctatgg tccaggagtg ggcaccacct atgcaggtgc gcggtggccg 2880
tgatggcatc atatgggccg tcgccatatt ctacccaggt gtggtgtttg acataaccaa 2940
gtggctcttg gcggtgcttg ggcctgctta cctcctaaaa ggtgctttga cgcgcgtgcc 3000
gtacttcgtc agggctcacg ctctactgag gatgtgcacc atggcaaggc atctcgcggg 3060
gggcaggtac gtccagatgg cgctactagc ccttggcagg tggactggca cttacatcta 3120
tgaccacctc acccctatgt cggattgggc tgctagtggc ctgcgggacc tggcggtcgc 3180
cgttgagcct atcatcttca gtccgatgga gaagaaagtc attgtctggg gagcggagac 3240
agctgcttgt ggggacattt tacacggact tcccgtgtcc gcccgacttg gtcgggaggt 3300
cctccttggc ccagctgatg gctatacctc caaggggtgg agtcttctcg ctcccatcac 3360
tgcttatgcc cagcaaacac gaggcctcct gggcgccata gtggtgagta tgacggggcg 3420
tgacaggaca gaacaggccg gggaagtcca aatcctgtcc acagtctctc agtccttcct 3480
cggaacaacc atctcggggg ttttgtggac tgtttaccac ggagctggca acaagactct 3540
agccggctta cggggtccgg tcacgcagat gtactcgagt gctgaggggg acttggtagg 3600
ctggcccagc ccccctggga ccaagtcttt ggagccgtgc aagtgtggag ccgtcgacct 3660
atatctggtc acgcggaacg ctgatgtcat cccggctcgg agacgcgggg acaagcgggg 3720
agcattgctc tccccgagac ccatttcgac cttgaagggg tcctcggggg ggccggtgct 3780
ctgccctagg ggccacgtcg ttgggctctt ccgagcagct gtgtgctctc ggggcgtggc 3840
caaatccatc gatttcatcc ccgttgagac actcgacgtt gttacaaggt ctcccacttt 3900
cagtgacaac agcacgccac cggctgtgcc ccagacctat caggtcgggt acttgcatgc 3960
tccaactggc agtggaaaga gcaccaaggt ccctgtcgcg tatgccgccc aggggtacaa 4020
agtactagtg cttaacccct cggtagctgc caccctgggg tttggggcgt acctatccaa 4080
ggcacatggc atcaatccca acattaggac tggagtcagg accgtgatga ccggggaggc 4140
catcacgtac tccacatatg gcaaatttct cgccgatggg ggctgcgcta gcggcgccta 4200
tgacatcatc atatgcgatg aatgccacgc tgtggatgct acctccattc tcggcatcgg 4260
aacggtcctt gatcaagcag agacagccgg ggtcagacta actgtgctgg ctacggccac 4320
accccccggg tcagtgacaa ccccccatcc cgatatagaa gaggtaggcc tcgggcggga 4380
gggtgagatc cccttctatg ggagggcgat tcccctatcc tgcatcaagg gagggagaca 4440
cctgattttc tgccactcaa agaaaaagtg tgacgagctc gcggcggccc ttcggggcat 4500
gggcttgaat gccgtggcat actatagagg gttggacgtc tccataatac cagctcaggg 4560
agatgtggtg gtcgtcgcca ccgacgccct catgacgggg tacactggag actttgactc 4620
cgtgatcgac tgcaatgtag cggtcaccca agctgtcgac ttcagcctgg accccacctt 4680
cactataacc acacagactg tcccacaaga cgctgtctca cgcagtcagc gccgcgggcg 4740
cacaggtaga ggaagacagg gcacttatag gtatgtttcc actggtgaac gagcctcagg 4800

-continued aatgtttgac agtgtagtgc tttgtgagtg ctacgacgca ggggctgcgt ggtacgatct 4860
cacaccagcg gagaccaccg tcaggcttag agcgtatttc aacacgcccg gcctacccgt 4920
gtgtcaagac catcttgaat tttgggaggc agttttcacc ggcctcacac acatagacgc 4980
ccacttcctc tcccaaacaa agcaagcggg ggagaacttc gcgtacctag tagcctacca 5040
agctacggtg tgcgccagag ccaaggcccc tcccccgtcc tgggacgcca tgtggaagtg 5100
cctggcccga ctcaagccta cgcttgcggg ccccacacct ctcctgtacc gtttgggccc 5160
tattaccaat gaggtcaccc tcacacaccc tgggacgaag tacatcgcca catgcatgca 5220
agctgacctt gaggtcatga ccagcacgtg ggtcctagct ggaggagtcc tggcagccgt 5280
cgccgcatat tgcctggcga ctggatgcgt ttccatcatc ggccgcttgc acgtcaacca 5340
gcgagtcgtc gttgcgccgg ataaggaggt cctgtatgag gcttttgatg agatggagga 5400
atgcgcctct agggcggctc tcatcgaaga ggggcagcgg atagccgaga tgttgaagtc 5460
caagatccaa ggcttgctgc agcaggcctc taagcaggcc caggacatac aacccgctat 5520
gcaggcttca tggcccaaag tggaacaatt ttgggccaga cacatgtgga acttcattag 5580
cggcatccaa tacctcgcag gattgtcaac actgccaggg aaccccgcgg tggcttccat 5640
gatggcattc agtgccgccc tcaccagtcc gttgtcgacc agtaccacca tccttctcaa 5700
catcatggga ggctggttag cgtcccagat cgcaccaccc gcgggggcca ccggctttgt 5760
cgtcagtggc ctggtggggg ctgccgtggg cagcataggc ctgggtaagg tgctggtgga 5820
catcctggca ggatatggtg cgggcatttc gggggccctc gtcgcattca agatcatgtc 5880
tggcgagaag ccctctatgg aagatgtcat caatctactg cctgggatcc tgtctccggg 5940
agccctggtg gtgggggtca tctgcgcggc cattctgcgc cgccacgtgg gaccgggga 6000
gggcgcggtc caatggatga acaggcttat tgcctttgct tccagaggaa accacgtcgc 6060
ccctactcac tacgtgacgg agtcggatgc gtcgcagcgt gtgacccaac tacttggctc 6120
tcttactata accagcctac tcagaagact ccacaattgg ataactgagg actgccccat 6180
cccatgctcc ggatcctggc tccgcgacgt gtgggactgg gtttgcacca tcttgacaga 6240
cttcaaaaat tggctgacct ctaaattgtt ccccaagctg cccggcctcc ccttcatctc 6300
ttgtcaaaag ggtacaagg gtgtgtgggc cggcactggc atcatgacca cgcgctgccc 6360
ttgcggcgcc aacatctctg gcaatgtccg cctgggctct atgaggatca cagggcctaa 6420
aacctgcatg aacacctggc aggggacctt tcctatcaat tgctacacgg agggccagtg 6480
cgcgccgaaa ccccccacga actacaagac cgccatctgg agggtggcgg cctcggagta 6540
cgcggaggtg acgcagcatg ggtcgtactc ctatgtaaca ggactgacca ctgacaatct 6600
gaaaattcct tgccaactac cttctccaga gtttttctcc tgggtggacg gtgtgcagat 6660
ccataggttt gcacccacac caaagccgtt tttccgggat gaggtctcgt tctgcgttgg 6720
gcttaattcc tatgctgtcg ggtcccagct tccctgtgaa cctgagcccg acgcagacgt 6780
attgaggtcc atgctaacag atccgcccca catcacggcg gagactgcgg cgcggcgctt 6840
ggcacgggga tcacctccat ctgaggcgag ctcctcagtg agccagctat cagcaccgtc 6900
gctgcgggcc acctgcacca cccacagcaa cacctatgac gtggacatgg tcgatgccaa 6960
cctgctcatg gagggcggtg tggctcagac agagcctgag tccagggtgc ccgttctgga 7020
ctttctcgag ccaatggccg aggaagagag cgaccttgag ccctcaatac catcggagtg 7080
catgctcccc aggagcgggt ttccacgggc cttaccggct tgggcacggc ctgactacaa 7140

```
cccgccgctc gtggaatcgt ggaggaggcc agattaccaa ccgcccaccg ttgctggttg   7200
tgctctcccc ccccccaaga aggccccgac gcctccccca aggagacgcc ggacagtggg   7260
tctgagcgag agcaccatat cagaagccct ccagcaactg gccatcaaga cctttggcca   7320
gccccccctcg agcggtgatg caggctcgtc cacgggggcg ggcgccgccg aatccggcgg   7380
tccgacgtcc cctggtgagc cggcccccctc agagacaggt tccgcctcct ctatgccccc   7440
cctcgagggg gagcctggag atccggacct ggagtctgat caggtagagc ttcaacctcc   7500
cccccagggg gggggggtag ctcccggttc gggctcgggg tcttggtcta cttgctccga   7560
ggaggacgat accaccgtgt gctgctccat gtcatactcc tggaccgggg ctctaataac   7620
tccctgtagc cccgaagagg aaaagttgcc aatcaaccct ttgagtaact cgctgttgcg   7680
ataccataac aaggtgtact gtacaacatc aaagagcgcc tcacagaggg ctaaaaaggt   7740
aacttttgac aggacgcaag tgctcgacgc ccattatgac tcagtcttaa aggacatcaa   7800
gctagcggct tccaaggtca gcgcaaggct cctcaccttg gaggaggcgt gccagttgac   7860
tccaccccat tctgcaagat ccaagtatgg attcggggcc aaggaggtcc gcagcttgtc   7920
cgggagggcc gttaaccaca tcaagtccgt gtggaaggac ctcctggaag acccacaaac   7980
accaattccc acaaccatca tggccaaaaa tgaggtgttc tgcgtggacc ccgccaaggg   8040
gggtaagaaa ccagctcgcc tcatcgttta ccctgacctc ggcgtccggg tctgcgagaa   8100
aatggccctc tatgacatta cacaaaagct tcctcaggcg gtaatgggag cttcctatgg   8160
cttccagtac tcccctgccc aacgggtgga gtatctcttg aaagcatggg cggaaaagaa   8220
ggaccccatg ggtttttcgt atgatacccg atgcttcgac tcaaccgtca ctgagagaga   8280
catcaggacc gaggagtcca tataccaggc ctgctccctg cccgaggagg cccgcactgc   8340
catacactcg ctgactgaga gactttacgt aggagggccc atgttcaaca gcaagggtca   8400
aacctgcggt tacagacgtt gccgcgccag cggggtgcta accactagca tgggtaacac   8460
catcacatgc tatgtgaaag ccctagcggc ctgcaaggct gcggggatag ttgcgcccac   8520
aatgctggta tgcggcgatg acctagtagt catctcagaa agccagggga ctgaggagga   8580
cgagcggaac ctgagagcct tcacggaggc catgaccagg tactctgccc ctcctggtga   8640
tccccccaga ccggaatatg acctggagct aataacatcc tgttcctcaa atgtgtctgt   8700
ggcgttgggc ccgcggggcc gccgcagata ctacctgacc agagacccaa ccactccact   8760
cgcccgggct gcctgggaaa cagttagaca ctcccctatc aattcatggc tgggaaacat   8820
catccagtat gctccaacca tatgggttcg catggtccta atgacacact tcttctccat   8880
tctcatggtc caagacaccc tggaccagaa cctcaacttt gagatgtatg gatcagtata   8940
ctccgtgaat cctttggacc ttccagccat aattgagagg ttacacgggc ttgacgcctt   9000
ttctatgcac acatactctc accacgaact gacgcgggtg gcttcagccc tcagaaaact   9060
tggggcgcca cccctcaggg tgtggaagag tcgggctcgc gcagtcaggg cgtccctcat   9120
ctcccgtgga gggaaagcgg ccgtttgcgg ccgatatctc ttcaattggg cggtgaagac   9180
caagctcaaa ctcactccat tgccggaggc gcgcctactg gacttatcca gttggttcac   9240
cgtcggcgcc ggcgggggcg acatttttca cagcgtgtcg cgcgcccgac cccgctcatt   9300
actcttcggc ctactcctac ttttcgtagg ggtaggcctc ttcctactcc ccgctcggta   9360
gagcggcaca cactaggtac actccatagc taactgttcc tttttttttt tttttttttt   9420
tttttttttt tttttttttt tttcttttt ttttttttcc ctctttcttc ccttctcatc   9480
ttattctact ttctttcttg gtggctccat cttagcccta gtcacggcta gctgtgaaag   9540
```

gtccgtgagc cgcatgactg cagagagtgc cgtaactggt ctctctgcag atcatgt 9597

<210> SEQ ID NO 9
<211> LENGTH: 9603
<212> TYPE: DNA
<213> ORGANISM: Hepatitis C virus

<400> SEQUENCE: 9
acctgcccct aatagggggcg acactccgcc atgaatcact cccctgtgag gaactactgt 60
cttcacgcag aaagcgccta gccatggcgt tagtatgagt gtcgtacagc ctccaggccc 120
ccccctcccg ggagagccat agtggtctgc ggaaccggtg agtacaccgg aattgccggg 180
aagactgggt cctttcttgg ataaacccac tctatgcccg gccatttggg cgtgcccccg 240
caagactgct agccgagtag cgttgggttg cgaaaggcct tgtggtactg cctgataggg 300
tgcttgcgag tgccccggga ggtctcgtag accgtgcacc atgagcacac ttcctaaacc 360
tcaaagaaaa accaaaagaa acaccatccg tcgcccacag gacgttaagt tcccgggtgg 420
cggacagatc gttggtggag tatacgtgtt gccgcgcagg ggcccacgat tgggtgtgcg 480
cgcgacgcgt aaaacttctg aacggtcaca gcctcgcgga cgacgacagc ctatccccaa 540
ggcgcgtcgg agcgaaggcc ggtcctgggc tcagcccggg taccettggc ccctctatgg 600 taatgagggc tgcgggtggg cagggtggct cctgtccccg cgcggctccc gtccatcttg 660
gggcccaaac gaccccccggc ggaggtcccg caatttgggt aaagtcatcg ataccettac 720 gtgcggattc gccgacctca tggggtacat cccgctcgtc ggcgctcccg taggaggcgt 780
cgcaagagcc ctcgcgcatg gcgtgagggc ccttgaagac gggataaatt ttgcaacagg 840
gaacttgccc ggttgctcct tttctatctt ccttcttgct ctgttctcct gcttagttca 900
tcctgcagct agtcttgagt ggcggaatac gtctggcctc tatgtcctta ccaacgactg 960
ttccaatagc agtattgtgt atgaggccga tgacgtcatt ctgcacacac ccggctgtgt 1020
accttgtgtt caggacgaca atacatccac gtgctggacc ccagtgacac ctacggtggc 1080
agtcaggtac gtcggagcaa ccaccgcttc gatacgcagt catgtggacc tattagtggg 1140
cgcggccacg ctgtgctctg cgctctatgt gggtgatatg tgtggggccg tctttctcgt 1200
gggacaagcc ttcacgttca gacctcgtcg ccatcaaacg gtccagacct gtaactgctc 1260
gctgtaccca ggccatgttt caggacatcg aatggcttgg gatatgatga tgaattggtc 1320
ccccgctgtg ggtatggtgg tggcgcacat cctgcgattg ccccagacct tgtttgacat 1380
actggccggg gcccattggg gcatcttggc gggcctagcc tattattcta tgcagggcaa 1440
ctgggccaag gtcgctattg tcatgattat gttttcaggg gtcgatgctc tgcaattggt 1500
caacaccaat ggctcgtggc acatcaacag tactgccctg aactgcaatg agtccataaa 1560
caccgggttc atagctgggt tgttttatta ccataagttc aactctactg gatgtcctca 1620
aaggcttagc agctgcaagc ccatcatttc cttcaggcag ggtggggcc ccttgacaga 1680 tgctaacatc accggtcctt ctgatgatag accgtattgc tggcactacg cacctagacc 1740
ttgtagtgtt gtcccggcat caagtgtctg cggccctgtg tactgcttca caccatcgcc 1800
agtggtcgta ggcactactg atatcaaagg caagccgacc tacaactggg gtgagaatga 1860
gacagatgtg ttcctgctgg agtccctgcg gcctcccagt ggccggtggt ttggatgcgc 1920
gtggatgaac tccacggggt tcctcaagac gtgtggagct ccccccttgta acatctatgg 1980 gggtgagggg gatcccgaaa atgagacaga cctcttctgc ccccaccgact gcttcaggaa 2040

-continued

```
acatcctgag gccacataca gccggtgtgg tgcggggccc tggttgacac ctcgctgcat   2100
ggtcgactat ccataccggc tttggcatta cccatgtaca gtcaatttca cattgttcaa   2160
ggtgaggatg tttgtgggcg gatttgaaca ccggtttacc gccgcttgta actggaccag   2220
gggggagcgc tgcaatatcg aggatcgtga tcgcagcgag caacatccgc tgctgcattc   2280
aacaactgag cttgctatac tgccttgctc tttcacgccc atgcctgcat tgtcaacagg   2340
tctaatacac ctccaccaaa atatcgtgga tgtccaatac ctttatggtg ttggatctga   2400
catggtggga tgggcgctga aatgggagtt cgtcatcctc gttttcctcc tcctggcaga   2460
cgcacgcgtg tgcgttgccc tttggctgat gctgatggta tcacaagcag aagcagcctt   2520
ggagaacctt gtcacgctga acgccgtcgc tgctgctggg acacatggta ttggttggta   2580
cctggtagcc ttttgcgcgg cgtggtacgt gcggggtaaa cttgtcccgc tgacgagcta   2640
cggcctgacg ggtctttggt ccctagcatt gcttgtcctc ttgctccccc aacgggcgta   2700
tgcttggtcg ggtgaagaca gcgctactct cggcgctggg gtcttggccc tcttcggctt   2760
ctttacctta tcaccctggt acaagcattg gatcggccgc ctcatgtggt ggaaccagta   2820
cactatatgt agatgcgagg ccgcccttca agtgtgggtc cccccottac ttgcacgcgg   2880
gagtagggac ggtgtcatcc tgctaacaag cttgctttat ccatccttaa tttttgacat   2940
cactaagctg ctgatagcag taataggccc attatactta atacaggctg ccatcactac   3000
cacccctac tttgtgcgcg cacatgtact ggtccgcctt tgcatgctcg tgcgctccgt   3060
gatgggggga aagtacttcc agatggccat actgagcatt ggcagatggt tcaacaccta   3120
cctatatgac cacctagcgc caatgcaaca ttgggccgca gctggcctca aagacctagc   3180
agtggccact gaacctgtaa tatttagtcc catggaaatt aaggtcatca cctggggcgc   3240
ggacacagcg gcttgcggag atattctttg cgggctgccg gtctccgcgc gattaggccg   3300
tgaggtattg ttgggacctg ctgatgatta tcgggaaatg ggttggcgtc tgttggctcc   3360
catcactgct tatgcccagc aaacacgagg cctcctgggc gccatagtgg tgagtatgac   3420
ggggcgtgac aggacagaac aggccgggga agtccaaatc ctgtccacag tctctcagtc   3480
cttcctcgga acaaccatct cgggggtttt gtggactgtt taccacggag ctggcaacaa   3540
gactctagcc ggcttacggg gtccggtcac gcagatgtac tcgagtgctg agggggactt   3600
ggtaggctgg cccagccccc ctgggaccaa gtctttggag ccgtgcaagt gtggagccgt   3660
cgacctatat ctggtcacgc ggaacgctga tgtcatcccg gctcggagac gcggggacaa   3720
gcggggagca ttgctctccc cgagacccat ttcgaccttg aaggggtcct cggggggggcc   3780
ggtgctctgc cctaggggcc acgtcgttgg gctcttccga gcagctgtgt gctctcgggg   3840
cgtggccaaa tccatcgatt tcatccccgt tgagacactc gacgttgtta caaggtctcc   3900
cactttcagt gacaacagca cgccaccggc tgtgccccag acctatcagg tcgggtactt   3960
gcatgctcca actggcagtg gaaagagcac caaggtccct gtcgcgtatg ccgcccaggg   4020
gtacaaagta ctagtgctta acccctcggt agctgccacc ctggggtttg ggcgtacct   4080
atccaaggca catggcatca atcccaacat taggactgga gtcaggaccg tgatgaccgg   4140
ggaggccatc acgtactcca catatggcaa atttctcgcc gatgggggct gcgctagcgg   4200
cgcctatgac atcatcatat gcgatgaatg ccacgctgtg gatgctacct ccattctcgg   4260
catcggaacg gtccttgatc aagcagagac agccggggtc agactaactg tgctggctac   4320
ggccacaccc cccgggtcag tgacaacccc ccatcccgat atagaagagg taggcctcgg   4380
gcgggagggt gagatcccct tctatgggag ggcgattccc ctatcctgca tcaagggagg   4440
```

-continued

```
gagacacctg attttctgcc actcaaagaa aaagtgtgac gagctcgcgg cggcccttcg   4500
gggcatgggc ttgaatgccg tggcatacta tagagggttg gacgtctcca taataccagc   4560
tcagggagat gtggtggtcg tcgccaccga cgccctcatg acggggtaca ctggagactt   4620
tgactccgtg atcgactgca atgtagcggt cacccaagct gtcgacttca gcctggaccc   4680
caccttcact ataaccacac agactgtccc acaagacgct gtctcacgca gtcagcgccg   4740
cgggcgcaca ggtagaggaa gacagggcac ttataggtat gtttccactg gtgaacgagc   4800
ctcaggaatg tttgacagtg tagtgctttg tgagtgctac gacgcagggg ctgcgtggta   4860
cgatctcaca ccagcggaga ccaccgtcag gcttagagcg tatttcaaca cgcccggcct   4920
acccgtgtgt caagaccatc ttgaattttg ggaggcagtt ttcaccggcc tcacacacat   4980
agacgcccac ttcctctccc aaacaaagca agcgggggag aacttcgcgt acctagtagc   5040
ctaccaagct acggtgtgcg ccagagccaa ggcccctccc ccgtcctggg acgccatgtg   5100
gaagtgcctg gcccgactca agcctacgct tgcgggcccc acacctctcc tgtaccgttt   5160
gggccctatt accaatgagg tcaccctcac acaccctggg acgaagtaca tcgccacatg   5220
catgcaagct gaccttgagg tcatgaccag cacgtgggtc ctagctggag gagtcctggc   5280
agccgtcgcc gcatattgcc tggcgactgg atgcgtttcc atcatcggcc gcttgcacgt   5340
caaccagcga gtcgtcgttg cgccggataa ggaggtcctg tatgaggctt ttgatgagat   5400
ggaggaatgc gcctctaggg cggctctcat cgaagagggg cagcggatag ccgagatgtt   5460
gaagtccaag atccaaggct tgctgcagca ggcctctaag caggcccagg acatacaacc   5520
cgctatgcag gcttcatggc ccaaagtgga acaattttgg gccagacaca tgtggaactt   5580
cattagcggc atccaatacc tcgcaggatt gtcaacactg ccagggaacc ccgcggtggc   5640
ttccatgatg gcattcagtg ccgccctcac cagtccgttg tcgaccagta ccaccatcct   5700
tctcaacatc atgggaggct ggttagcgtc ccagatcgca ccacccgcgg gggccaccgg   5760
ctttgtcgtc agtggcctgg tgggggctgc cgtgggcagc ataggcctgg gtaaggtgct   5820
ggtggacatc ctggcaggat atggtgcggg catttcgggg gccctcgtcg cattcaagat   5880
catgtctggc gagaagccct ctatggaaga tgtcatcaat ctactgcctg ggatcctgtc   5940
tccgggagcc ctggtggtgg gggtcatctg cgcggccatt ctgcgccgcc acgtgggacc   6000
gggggagggc gcggtccaat ggatgaacag gcttattgcc tttgcttcca gaggaaacca   6060
cgtcgcccct actcactacg tgacggagtc ggatgcgtcg cagcgtgtga cccaactact   6120
tggctctctt actataacca gcctactcag aagactccac aattggataa ctgaggactg   6180
ccccatccca tgctccggat cctggctccg cgacgtgtgg gactgggttt gcaccatctt   6240
gacagacttc aaaaattggc tgacctctaa attgttcccc aagctgcccg gcctcccctt   6300
catctcttgt caaaaggggt acaagggtgt gtgggccggc actggcatca tgaccacgcg   6360
ctgcccttgc ggcgccaaca tctctggcaa tgtccgcctg ggctctatga ggatcacagg   6420
gcctaaaacc tgcatgaaca cctggcaggg gacctttcct atcaattgct acacggaggg   6480
ccagtgcgcg ccgaaacccc ccacgaacta caagaccgcc atctggaggg tggcggcctc   6540
ggagtacgcg gaggtgacgc agcatgggtc gtactcctat gtaacaggac tgaccactga   6600
caatctgaaa attccttgcc aactaccttc tccagagttt ttctcctggg tggacggtgt   6660
gcagatccat aggtttgcac ccacaccaaa gccgtttttc cgggatgagg tctcgttctg   6720
cgttgggctt aattcctatg ctgtcgggtc ccagcttccc tgtgaacctg agcccgacgc   6780
```

-continued agacgtattg aggtccatgc taacagatcc gccccacatc acggcggaga ctgcggcgcg 6840
gcgcttggca cggggatcac ctccatctga ggcgagctcc tcagtgagcc agctatcagc 6900
accgtcgctg cgggccacct gcaccaccca cagcaacacc tatgacgtgg acatggtcga 6960
tgccaacctg ctcatggagg gcggtgtggc tcagacagag cctgagtcca gggtgcccgt 7020
tctggacttt ctcgagccaa tggccgagga agagagcgac cttgagccct caataccacc 7080
ggagtgcatg ctccccagga gcgggtttcc acgggcctta ccggcttggg cacggcctga 7140
ctacaacccg ccgctcgtgg aatcgtggag gaggccagat taccaaccgc ccaccgttgc 7200
tggttgtgct ctcccccccc ccaagaaggc cccgacgcct cccccaagga gacgccggac 7260
agtgggtctg agcgagagca ccatatcaga agccctccag caactggcca tcaagacctt 7320
tggccagccc ccctcgagcg gtgatgcagg ctcgtccacg gggcgggcg ccgccgaatc 7380 cggcggtccg acgtcccctg gtgagccggc cccctcagag acaggttccg cctcctctat 7440 gcccccccctc gagggggagc ctggagatcc ggacctggag tctgatcagg tagagcttca 7500
acctcccccc caggggggggg gggtagctcc cggttcgggc tcggggtctt ggtctacttg 7560
ctccgaggag gacgatacca ccgtgtgctg ctccatgtca tactcctgga ccggggctct 7620
aataactccc tgtagccccg aagaggaaaa gttgccaatc aaccctttga gtaactcgct 7680
gttgcgatac cataacaagg tgtactgtac aacatcaaag agcgcctcac agagggctaa 7740
aaaggtaact tttgacagga cgcaagtgct cgacgcccat tatgactcag tcttaaagga 7800
catcaagcta gcggcttcca aggtcagcgc aaggctcctc accttggagg aggcgtgcca 7860
gttgactcca ccccattctg caagatccaa gtatggattc ggggccaagg aggtccgcag 7920
cttgtccggg agggccgtta accacatcaa gtccgtgtgg aaggacctcc tggaagaccc 7980
acaaacacca attcccacaa ccatcatggc caaaaatgag gtgttctgcg tggaccccgc 8040 caagggggggt aagaaaccag ctcgcctcat cgtttaccct gacctcggcg tccgggtctg 8100
cgagaaaatg gccctctatg acattacaca aaagcttcct caggcggtaa tgggagcttc 8160
ctatggcttc cagtactccc ctgcccaacg ggtggagtat ctcttgaaag catgggcgga 8220
aaagaaggac cccatgggtt tttcgtatga tacccgatgc ttcgactcaa ccgtcactga 8280
gagagacatc aggaccgagg agtccatata ccaggcctgc tccctgcccg aggaggcccg 8340
cactgccata cactcgctga ctgagagact ttacgtagga gggcccatgt tcaacagcaa 8400
gggtcaaacc tgcggttaca gacgttgccg cgccagcggg gtgctaacca ctagcatggg 8460
taacaccatc acatgctatg tgaaagccct agcggcctgc aaggctgcgg ggatagttgc 8520
gcccacaatg ctggtatgcg gcgatgacct agtagtcatc tcagaaagcc aggggactga 8580
ggaggacgag cggaacctga gagccttcac ggaggccatg accaggtact ctgcccctcc 8640
tggtgatccc cccagaccgg aatatgacct ggagctaata acatcctgtt cctcaaatgt 8700
gtctgtggcg ttgggcccgc ggggccgccg cagatactac ctgaccagag acccaaccac 8760
tccactcgcc cgggctgcct gggaaacagt tagacactcc cctatcaatt catggctggg 8820
aaacatcatc cagtatgctc caaccatatg ggttcgcatg gtcctaatga cacacttctt 8880
ctccattctc atggtccaag acaccctgga ccagaacctc aactttgaga tgtatggatc 8940
agtatactcc gtgaatcctt tggaccttcc agccataatt gagaggttac acgggcttga 9000
cgccttttct atgcacacat actctcacca cgaactgacg cgggtggctt cagccctcag 9060
aaaacttggg gcgccacccc tcagggtgtg gaagagtcgg gctcgcgcag tcagggcgtc 9120
cctcatctcc cgtggaggga aagcggccgt ttgcggccga tatctcttca attgggcggt 9180
gaagaccaag ctcaaactca ctccattgcc ggaggcgcgc ctactggact tatccagttg 9240
gttcaccgtc ggcgccggcg ggggcgacat ttttcacagc gtgtcgcgcg cccgaccccg 9300
ctcattactc ttcggcctac tcctactttt cgtaggggta ggcctcttcc tactccccgc 9360
tcggtagagc ggcacacact aggtacactc catagctaac tgttcctttt tttttttttt 9420
tttttttttt tttttttttt tttttttttc tttttttttt ttttccctct ttcttccctt 9480
ctcatcttat tctactttct ttcttggtgg ctccatctta gccctagtca cggctagctg 9540
tgaaaggtcc gtgagccgca tgactgcaga gagtgccgta actggtctct ctgcagatca 9600
tgt 9603

<210> SEQ ID NO 10
<211> LENGTH: 9585
<212> TYPE: DNA
<213> ORGANISM: Hepatitis C virus

<400> SEQUENCE: 10
acctgcccct aatagggggcg acactccgcc atgaatcact cccctgtgag gaactactgt 60
cttcacgcag aaagcgccta gccatggcgt tagtatgagt gtcgtacagc ctccaggccc 120
ccccctcccg ggagagccat agtggtctgc ggaaccggtg agtacaccgg aattgccggg 180
aagactgggt cctttcttgg ataaacccac tctatgcccg gccatttggg cgtgcccccg 240
caagactgct agccgagtag cgttgggttg cgaaaggcct tgtggtactg cctgataggg 300
cgcttgcgag tgccccggga ggtctcgtag accgtgcacc atgagcacga atcctaaacc 360
tcaaagaaaa accaaacgta acaccaaccg ccgcccaatg gacgttaagt tcccgggtgg 420
tggccagatc gttggcggag tttacttgtt gccgcgcagg ggccccagat tgggtgtgcg 480
cgcgactcgg aagacttcgg agcggtcgca acctcgtgga agacgccaac ctatccccaa 540
ggcgcgtcga cccgagggaa ggtcctgggc acaaccagga tatccatggc ctctttacgg 600
taatgagggt tgtgggtggg caggatggct cttgtccccc cgtggctctc gaccgtcttg 660
gggcccaaat gatccccggc ggaggtcccg caatttgggt aaggtcatcg ataccctaac 720
ctgcggcttc gccgacctca tgggatacat cccgctcgta ggcgcccccg tgggtggcgt 780
cgccagggcc ctggcacatg gtgtcagggc tttggaggac gggatcaatt atgcaacagg 840
gaatctcccc ggttgctcct tttctatctt cctcttggca cttctttcgt gcctgactgt 900
ccccgcttcg gccgttaact atcgcaatgt ctcgggcatc taccatgtca ccaatgactg 960
cccgaattca agcatagtgt atgaggccga ccatcacatc ttgcaccttc caggttgcgt 1020
gccctgcgtg agagagggga atcagtcacg ctgctgggtg gcccttactc ctaccgtcgc 1080
agcgccatac atcggcgcac cgcttgagtc cttacggagt catgtggatt tgatggtggg 1140
ggccgccact gtttgctcgg gtctttacat cggggacctg tgtggcggct tgttcctagt 1200
tggccagatg ttttcattcc gaccacggcg ccactggacc acccaggatt gcaattgttc 1260
catctacaca gggcacatta caggccacag aatggcctgg gacatgatga tgaactggag 1320
tccaacaacc accttagttc tcgcccaggt catgaggatc ccaaccactc tggtagactt 1380
actctctgga ggccactggg gtgtcctcgt gggagtggcc tatttcagca tgcaggccaa 1440
ttgggccaaa gtcatcttgg tcctattcct ctttgcaggg gttgatgcct tacagctcat 1500
caacagcaat gggagctggc atataaatag gactgccctt aactgcaatg acagcttaaa 1560
cactgggttc ttggctagct tgttctacac ccacaagttt aacagctcag ggtgttccga 1620

-continued acggctcgcg tgctgcaaga gccttgacag ctacggccaa ggctggggcc cactcggggt 1680
cgctaacatc agcggctcgt ctgatgacag gccttattgc tggcactacg cgcctcggcc 1740
gtgcgggatt gtgccagcat ccagtgtgtg tggccccgtg tattgtttca ctcccagccc 1800
tgtcgtggtc ggtactactg atcacgtcgg ggtccctact tacacctggg gggagaatga 1860
gactgatgtc ttccttttga actcgaccag accgccgcat ggtgcgtggt ttggatgcgt 1920
gtggatgaac agtaccgggt tcaccaaaac ctgtggcgcc cctccatgcg aggttaacac 1980
caataatggg acctggcact gccccaccga ttgcttcagg aagcatccgg agactaccta 2040
cgccaagtgc ggatcagggc cttggatcac accgcgctgc ctgattgatt acccgtaccg 2100
gctgtggcat ttcccgtgca ccgccaactt ctccgtcttt aacatcagga catttgtcgg 2160
cggtatagag catcggatgc aagcggcatg caactggacc aggggggaag tctgtggctt 2220
ggagcacagg gatcgcgtag agctatcacc cctgctcctt accactacag cgtggcagat 2280
cctcccctgc tctttcacca ctttacctgc cctctccacc ggcttgatcc acctccacca 2340
aaatatcgtg gacgtccagt acctctatgg tgttgggtct gcagtggtat cttgggccct 2400
taagtgggaa tatgtggtgc tcgcgttcct gcttctcgcg gacgcgagag tctctgcctg 2460
cctatggatg atgtttatgg taagtcaagt tgaggcggct ctgtccaacc tgattaacat 2520
caatgctgct tcagccgctg gtgcccaagg cttctggtac gccatcctct tcatctgcat 2580
tgtctggcat gtcaagggcc ggttcccagc tgctgctgcc tacgcagcct gcgggctgtg 2640
gcccctgttt ctcctgcttc tgatgctgcc tgagagggct tatgcatacg accaggaagt 2700
ggcagggtcc cttggcggcg ccatcgttgt catgctggcc attctgacac tgtctccgca 2760
ctacaagtta tggctggcta ggggattgtg gtggatccaa tattttatag ctaggaccga 2820
ggctgtgctg catgtctata ttccatcctt caacgtgcgc gggcctcgcg actcagtgat 2880
tgttcttgca gtcctggtct gtccacacct agtatttgac atcacaaaat atcttctggc 2940
catcttaggg cccctccaca tactccaggc ctcgctccta cgcatccctt actttgtgag 3000
ggcacaagcg ctggttaaga tctgcagctt gttgcgtggg gtagtttatg gcaagtactt 3060
ccaaatggtc gtgcttaaag caggggccct gactggtact tacatctatg accaccttac 3120
tcccatgtca gattgggccg ctacgggcct ccgcgatttg gcggtggccc tagagccagt 3180
tgtgttctcg cccatggaga agaaagtcat cgtctggggc gctgacaccg ctgcgtgcgg 3240
agacatcata aggggattac ctgtttcggc caggttgggc aatgaaatct tgctcggacc 3300
agccgataca gaaacatcaa aggggtggag actccttgct cccatcactg cttatgccca 3360
gcaaacacga ggcctcctgg gcgccatagt ggtgagtatg acggggcgtg acaggacaga 3420
acaggccggg gaagtccaaa tcctgtccac agtctctcag tccttcctcg gaacaaccat 3480
ctcggggggtt ttgtggactg tttaccacgg agctggcaac aagactctag ccggcttacg 3540
ggtccggtc acgcagatgt actcgagtgc tgagggggac ttggtaggct ggcccagccc 3600
ccctgggacc aagtctttgg agccgtgcaa gtgtggagcc gtcgacctat atctggtcac 3660
gcggaacgct gatgtcatcc cggctcggag acgcggggac aagcggggag cattgctctc 3720
cccgagaccc atttcgacct tgaaggggtc ctcggggggg ccggtgctct gccctagggg 3780
ccacgtcgtt gggctcttcc gagcagctgt gtgctctcgg ggcgtggcca aatccatcga 3840
tttcatcccc gttgagacac tcgacgttgt tacaaggtct cccactttca gtgacaacag 3900
cacgccaccg gctgtgcccc agacctatca ggtcgggtac ttgcatgctc caactggcag 3960
tggaaagagc accaaggtcc ctgtcgcgta tgccgcccag ggtacaaag tactagtgct 4020 taacccctcg gtagctgcca ccctggggtt tggggcgtac ctatccaagg cacatggcat 4080
caatcccaac attaggactg gagtcaggac cgtgatgacc ggggaggcca tcacgtactc 4140
cacatatggc aaatttctcg ccgatggggg ctgcgctagc ggcgcctatg acatcatcat 4200
atgcgatgaa tgccacgctg tggatgctac ctccattctc ggcatcggaa cggtccttga 4260
tcaagcagag acagccgggg tcagactaac tgtgctggct acggccacac cccccgggtc 4320
agtgacaacc ccccatcccg atatagaaga ggtaggcctc gggcgggagg gtgagatccc 4380
cttctatggg agggcgattc ccctatcctg catcaaggga gggagacacc tgattttctg 4440
ccactcaaag aaaaagtgtg acgagctcgc ggcggccctt cggggcatgg gcttgaatgc 4500
cgtggcatac tatagagggt tggacgtctc cataatacca gctcagggag atgtggtggt 4560
cgtcgccacc gacgccctca tgacggggta cactggagac tttgactccg tgatcgactg 4620
caatgtagcg gtcacccaag ctgtcgactt cagcctggac cccaccttca ctataaccac 4680
acagactgtc ccacaagacg ctgtctcacg cagtcagcgc cgcgggcgca caggtagagg 4740
aagacagggc acttataggt atgtttccac tggtgaacga gcctcaggaa tgtttgacag 4800
tgtagtgctt tgtgagtgct acgacgcagg ggctgcgtgg tacgatctca caccagcgga 4860
gaccaccgtc aggcttagag cgtatttcaa cacgcccggc ctacccgtgt gtcaagacca 4920
tcttgaattt tgggaggcag ttttcaccgg cctcacacac atagacgccc acttcctctc 4980
ccaaacaaag caagcggggg agaacttcgc gtacctagta gcctaccaag ctacggtgtg 5040
cgccagagcc aaggcccctc ccccgtcctg ggacgccatg tggaagtgcc tggcccgact 5100
caagcctacg cttgcgggcc ccacacctct cctgtaccgt ttgggcccta ttaccaatga 5160
ggtcaccctc acacaccctg ggacgaagta catcgccaca tgcatgcaag ctgaccttga 5220
ggtcatgacc agcacgtggg tcctagctgg aggagtcctg gcagccgtcg ccgcatattg 5280
cctggcgact ggatgcgttt ccatcatcgg ccgcttgcac gtcaaccagc gagtcgtcgt 5340
tgcgccggat aaggaggtcc tgtatgaggc ttttgatgag atggaggaat gcgcctctag 5400
ggcggctctc atcgaagagg ggcagcggat agccgagatg ttgaagtcca agatccaagg 5460
cttgctgcag caggcctcta agcaggccca ggacatacaa cccgctatgc aggcttcatg 5520
gcccaaagtg gaacaatttt gggccagaca catgtggaac ttcattagcg gcatccaata 5580
cctcgcagga ttgtcaacac tgccagggaa ccccgcggtg gcttccatga tggcattcag 5640
tgccgccctc accagtccgt tgtcgaccag taccaccatc cttctcaaca tcatgggagg 5700
ctggttagcg tcccagatcg caccacccgc gggggccacc ggctttgtcg tcagtggcct 5760
ggtgggggct gccgtgggca gcataggcct gggtaaggtg ctggtggaca tcctggcagg 5820
atatggtgcg ggcatttcgg gggccctcgt cgcattcaag atcatgtctg gcgagaagcc 5880
ctctatggaa gatgtcatca atctactgcc tgggatcctg tctccgggag ccctggtggt 5940
gggggtcatc tgcgcggcca ttctgcgccg ccacgtggga ccgggggagg gcgcggtcca 6000
atggatgaac aggcttattg cctttgcttc cagaggaaac cacgtcgccc ctactcacta 6060
cgtgacggag tcggatgcgt cgcagcgtgt gacccaacta cttggctctc ttactataac 6120
cagcctactc agaagactcc acaattggat aactgaggac tgccccatcc catgctccgg 6180
atcctggctc cgcgacgtgt gggactgggt ttgcaccatc ttgacagact tcaaaaattg 6240
gctgacctct aaattgttcc ccaagctgcc cggcctcccc ttcatctctt gtcaaaaggg 6300
gtacaagggt gtgtgggccg gcactggcat catgaccacg cgctgccctt gcggcgccaa 6360

-continued

```
catctctggc aatgtccgcc tgggctctat gaggatcaca gggcctaaaa cctgcatgaa   6420
cacctggcag ggcacctttc ctatcaattg ctacacggag ggccagtgcg cgccgaaacc   6480
ccccacgaac tacaagaccg ccatctggag ggtggcggcc tcggagtacg cggaggtgac   6540
gcagcatggg tcgtactcct atgtaacagg actgaccact gacaatctga aaattccttg   6600
ccaactacct tctccagagt ttttctcctg ggtggacggt gtgcagatcc ataggtttgc   6660
acccacacca aagccgtttt tccgggatga ggtctcgttc tgcgttgggc ttaattccta   6720
tgctgtcggg tcccagcttc cctgtgaacc tgagcccgac gcagacgtat tgaggtccat   6780
gctaacagat ccgccccaca tcacggcgga gactgcggcg cggcgcttgg cacggggatc   6840
acctccatct gaggcgagct cctcagtgag ccagctatca gcaccgtcgc tgcgggccac   6900
ctgcaccacc cacagcaaca cctatgacgt ggacatggtc gatgccaacc tgctcatgga   6960
gggcggtgtg gctcagacag agcctgagtc cagggtgccc gttctggact ttctcgagcc   7020
aatggccgag gaagagagcg accttgagcc ctcaatacca tcggagtgca tgctccccag   7080
gagcgggttt ccacgggcct taccggcttg ggcacggcct gactacaacc cgccgctcgt   7140
ggaatcgtgg aggaggccag attaccaacc gcccaccgtt gctggttgtg ctctcccccc   7200
ccccaagaag gccccgacgc ctcccccaag gagacgccgg acagtgggtc tgagcgagag   7260
caccatatca gaagccctcc agcaactggc catcaagacc tttggccagc ccccctcgag   7320
cggtgatgca ggctcgtcca cgggggcggg cgccgccgaa tccggcggtc cgacgtcccc   7380
tggtgagccg gccccctcag agacaggttc cgcctcctct atgccccccc tcgaggggga   7440
gcctggagat ccggacctgg agtctgatca ggtagagctt caacctcccc cccagggggg   7500
gggggtagct cccggttcgg gctcggggtc ttggtctact tgctccgagg aggacgatac   7560
caccgtgtgc tgctccatgt catactcctg gaccggggct ctaataactc cctgtagccc   7620
cgaagaggaa aagttgccaa tcaacccttt gagtaactcg ctgttgcgat accataacaa   7680
ggtgtactgt acaacatcaa agagcgcctc acagagggct aaaaaggtaa cttttgacag   7740
gacgcaagtg ctcgacgccc attatgactc agtcttaaag gacatcaagc tagcggcttc   7800
caaggtcagc gcaaggctcc tcaccttgga ggaggcgtgc cagttgactc caccccattc   7860
tgcaagatcc aagtatggat tcggggccaa ggaggtccgc agcttgtccg ggagggccgt   7920
taaccacatc aagtccgtgt ggaaggacct cctggaagac ccacaaacac caattcccac   7980
aaccatcatg gccaaaaatg aggtgttctg cgtggacccc gccaaggggg gtaagaaacc   8040
agctcgcctc atcgtttacc ctgacctcgg cgtccgggtc tgcgagaaaa tggccctcta   8100
tgacattaca caaaagcttc ctcaggcggt aatgggagct tcctatggct tccagtactc   8160
ccctgcccaa cgggtggagt atctcttgaa agcatgggcg gaaaagaagg accccatggg   8220
tttttcgtat gatacccgat gcttcgactc aaccgtcact gagagagaca tcaggaccga   8280
ggagtccata taccaggcct gctccctgcc cgaggaggcc cgcactgcca tacactcgct   8340
gactgagaga ctttacgtag gagggcccat gttcaacagc aagggtcaaa cctgcggtta   8400
cagacgttgc cgcgccagcg gggtgctaac cactagcatg ggtaacacca tcacatgcta   8460
tgtgaaagcc ctagcggcct gcaaggctgc ggggatagtt gcgcccacaa tgctggtatg   8520
cggcgatgac ctagtagtca tctcagaaag ccaggggact gaggaggacg agcggaacct   8580
gagagccttc acggaggcca tgaccaggta ctctgcccct cctggtgatc cccccagacc   8640
ggaatatgac ctggagctaa taacatcctg ttcctcaaat gtgtctgtgg cgttgggccc   8700
gcggggccgc cgcagatact acctgaccag agacccaacc actccactcg cccgggctgc   8760
```

ctgggaaaca gttagacact cccctatcaa ttcatggctg ggaaacatca tccagtatgc 8820
tccaaccata tgggttcgca tggtcctaat gacacacttc ttctccattc tcatggtcca 8880
agacaccctg gaccagaacc tcaactttga gatgtatgga tcagtatact ccgtgaatcc 8940
tttggacctt ccagccataa ttgagaggtt acacgggctt gacgcctttt ctatgcacac 9000
atactctcac cacgaactga cgcgggtggc ttcagccctc agaaaacttg ggcgccacc 9060 cctcagggtg tggaagagtc gggctcgcgc agtcagggcg tccctcatct cccgtggagg 9120
gaaagcggcc gtttgcggcc gatatctctt caattgggcg gtgaagacca agctcaaact 9180
cactccattg ccggaggcgc gcctactgga cttatccagt tggttcaccg tcggcgccgg 9240
cgggggcgac atttttcaca gcgtgtcgcg cgcccgaccc cgctcattac tcttcggcct 9300
actcctactt ttcgtagggg taggcctctt cctactcccc gctcggtaga gcggcacaca 9360
ctaggtacac tccatagcta actgttcctt tttttttttt tttttttttt tttttttttt 9420
tttttttttt tcttttttttt ttttttccct ctttcttccc ttctcatctt attctacttt 9480
ctttcttggt ggctccatct tagccctagt cacggctagc tgtgaaaggt ccgtgagccg 9540
catgactgca gagagtgccg taactggtct ctctgcagat catgt 9585

<210> SEQ ID NO 11
<211> LENGTH: 9588
<212> TYPE: DNA
<213> ORGANISM: Hepatitis C virus

<400> SEQUENCE: 11
acctgcccct aataggggcg acactccgcc atgaatcact cccctgtgag gaactactgt 60
cttcacgcag aaagcgccta gccatggcgt tagtatgagt gtcgtacagc ctccaggccc 120
ccccctcccg ggagagccat agtggtctgc ggaaccggtg agtacaccgg aattgccggg 180
aagactgggt cctttcttgg ataaacccac tctatgcccg gccatttggg cgtgcccccg 240
caagactgct agccgagtag cgttgggttg cgaaaggcct tgtggtactg cctgataggg 300
cgcttgcgag tgccccggga ggtctcgtag accgtgcacc atgagcacga atcctaaacc 360
tcaaagaaaa accaaaagaa acaccaaccg ccgcccacag gacgtcaagt tcccgggcgg 420
tggtcagatc gttggtggag tttacttgtt gccgcgcagg ggccctaggt tgggtgtgcg 480
cgcaactcgg aagacttcag aacggtcgca accccgtgga cggcgtcagc ctatccccaa 540
ggcgcgccag cccacgggcc ggtcctgggg tcaacccggg tacccttggc ccctttatgc 600
caatgagggc ctcgggtggg cagggtggtt gctctccccc cgaggctctc ggcctaattg 660
gggccccaat gacccccggc ggaaatcgcg caacttgggt aaggtcatcg ataccctgac 720
gtgcggattc gccgacctca tggggtacat cccgctcgta ggcggccccg ttgggggcgt 780
cgcaagggct ctcgcacacg gtgtgagggt ccttgaggac ggggtaaact atgcaacagg 840
gaatttaccc ggttgctctt tctctatctt tatccttgca cttctttcat gcctgactgt 900
cccgacctct gccgttccct accgaaatgc ctctggggtt tatcatgtca ccaatgattg 960
cccaaactct tctatcgtct atgaggctga agacctgatc ttacacgcac ctggttgcgt 1020
gccctgtgtt aggcagggta atgtcagtag gtgctgggtc cagatcaccc ccacactgtc 1080
agccccgagc ctcggagcgg tcacggctcc tcttcggagg gccgttgact acttagcggg 1140
gggggctgcc ctttgctccg cgttatacgt cggagacgcg tgcggggcag tgtttttggt 1200
aggtcaaatg ttcacctata gccctcgccg gcataatgtt gtgcaggact gcaactgttc 1260

-continued

```
catttacagt ggccacatca ccggccaccg gatggcatgg gacatgatga tgaattggtc   1320
acctacaaca gctttggtga tggcccagtt gttacggatt ccccaggtgg tcattgacat   1380
cattgccggg gcccactggg ggtcttgtt cgccgccgca tactacgcgt cggcggctaa   1440
ctgggccaag gttgtgctgg tcctgtttct gtttgcgggg gtcgatgcct tgcagctcat   1500
aaataccaac gggagctggc acatcaacag aactgccctt aactgtaatg acagcctcca   1560
gactgggttt gtagccggcc tcctgtatta tcacaagttc aactccactg ggtgtccgca   1620
gcggatggct agctgtaggc ccctcgccgc attcgaccag ggctggggaa ctatcagcta   1680
tgccgccgtg tcgggcccca gtgatgacaa gccctattgc tggcactacc ccccacgccc   1740
gtgcggaata gtgccagcgc gaggtgtctg cggtccggtc tattgtttta cacctagccc   1800
ggtggtcgtc ggcaccacag accgcaaggg gaatcccact tacagttggg gcgaaaatga   1860
gactgacatc tttctcttga acaacacgag gcccccctact ggcaactggt ttggctgcac   1920
ctggatgaat tccacagggt ttgtcaagac ttgcggggct ccaccctgca acttagggcc   1980
tacaggcaac aatagcctta agtgtcctac tgattgcttc cgcaagcacc cagacgccac   2040
ctacaccaag tgtgggtcag gaccctggct cactccccgg tgtctggtgc attaccctta   2100
ccggttgtgg cattacccgt gcaccctaaa ttacaccatc ttcaaggtgc gcatgtacat   2160
tgggggcctc gagcacaggc tcgaggtggc atgcaactgg acccgtggtg agcggtgtga   2220
tcttgaagac agggataggg ccgagctgag cccgctccta cataccacca cgcagtgggc   2280
catattgccg tgctctttca cacccacacc cgctcttagc actggtctca tacacttaca   2340
tcaaaatata gtagacaccc agtatcttta cggtctgagc tccagcatcg tctcgtgggc   2400
cgttaagtgg gagtacatag tgctggcctt cttattactt gctgatgccc gtatttgtac   2460
ttgcctatgg atcatgctcc tggtttgtca ggccgaagcg gccctggaga acgtcattgt   2520
cctaaacgcg gctgcggctg cggggactca tgggtttttc tggggcctgc tcgtcatctg   2580
cttcgcctgg cacttcaagg gcaggttggt ccctggggcc acctaccttt gcttgggcat   2640
ttggccatta ctcttactcc ttttcctcct gccccaaagg gctctagccc tggactcaag   2700
cgatggcggg actgtgggtt gtcttgtgtt aaccatcctt acaatcttca cactcacccc   2760
cgggtacaag aagatggtag tgttggtcat atggtggctt cagtatttca tagcccgggt   2820
agaggccttt atccatgtgt gggtgccccc gttgcaggtt aggggtggtc gtgatgctat   2880
tatcatgctc acatgccttt tccatcctgc cctggggttt gaggtcacga aaatcctcct   2940
cgggatacta ggtcctttgt acctgctgca gtactcgctc atcaagctgc cttatttcat   3000
cagggcgcgc gccctgctga gggcgtgcct gctagcgaag cacttggcct gtggcaggta   3060
cgtgcaggcg gccttgctcc accttggtag gctgaccgga acgtacattt atgaccacct   3120
tgcccccatg aaggattggg cagcgtccgg gctgcgcgac ttagcagtgg ccacggagcc   3180
catcatattc tcccctatgg agacgaaggt catcacgtgg ggggctgaca cggccgcatg   3240
tggggacata cttgccggcc ttcctgtatc agctaggcga ggccatgaaa tcttcctggg   3300
gccagccgat gacatcagag agggggggctg gcgacttctc gctcccatca ctgcttatgc   3360
ccagcaaaca cgaggcctcc tgggcgccat agtggtgagt atgacggggc gtgacaggac   3420
agaacaggcc ggggaagtcc aaatcctgtc cacagtctct cagtccttcc tcggaacaac   3480
catctcgggg gttttgtgga ctgtttacca cggagctggc aacaagactc tagccggctt   3540
acggggtccg gtcacgcaga tgtactcgag tgctgagggg gacttggtag gctggcccag   3600
ccccccctggg accaggtctt tggagccgtg caagtgtgga gccgtcgacc tatatctggt   3660
```

-continued

```
cacgcggaac gctgatgtca tcccggctcg gagacgcggg gacaagcggg gagcattgct   3720
ctccccgaga cccatttcga ccttgaaggg gtcctcgggg gggccggtgc tctgccctag   3780
gggccacgtc gttgggctct tccgagcagc tgtgtgctct cggggcgtgg ccaaatccat   3840
cgatttcatc cccgttgaga cactcgacgt tgttacaagg tctcccactt tcagtgacaa   3900
cagcacgcca ccggctgtgc cccagaccta tcaggtcggg tacttgcatg ctccaactgg   3960
cagtggaaag agcaccaagg tccctgtcgc gtatgccgcc caggggtaca aagtactagt   4020
gcttaacccc tcggtagctg ccaccctggg gtttggggcg tacctatcca aggcacatgg   4080
catcaatccc aacattagga ctggagtcag gaccgtgatg accggggagg ccatcacgta   4140
ctccacatat ggcaaatttc tcgccgatgg gggctgcgct agcggcgcct atgacatcat   4200
catatgcgat gaatgccacg ctgtggatgc tacctccatt ctcggcatcg gaacggtcct   4260
tgatcaagca gagacagccg gggtcagact aactgtgctg gctacggcca caccccccgg   4320
gtcagtgaca accccccatc ccgatataga agaggtaggc ctcgggcggg agggtgagat   4380
ccccttctat gggagggcga ttcccctatc ctgcatcaag ggagggagac acctgatttt   4440
ctgccactca aagaaaaagt gtgacgagct cgcggcggcc cttcggggca tgggcttgaa   4500
tgccgtggca tactatagag ggttggacgt ctccataata ccagctcagg gagatgtggt   4560
ggtcgtcgcc accgacgccc tcatgacggg gtacactgga gactttgact ccgtgatcga   4620
ctgcaatgta gcggtcaccc aagctgtcga cttcagcctg gaccccacct tcactataac   4680
cacacagact gtcccacaag acgctgtctc acgcagtcag cgccgcgggc gcacaggtag   4740
aggaagacag ggcacttata ggtatgtttc cactggtgaa cgagcctcag gaatgtttga   4800
cagtgtagtg ctttgtgagt gctacgacgc aggggctgcg tggtacgatc tcacaccagc   4860
ggagaccacc gtcaggctta gagcgtattt caacacgccc ggcctacccg tgtgtcaaga   4920
ccatcttgaa ttttgggagg cagttttcac cggcctcaca cacatagacg cccacttcct   4980
ctcccaaaca aagcaagcgg gggagaactt cgcgtaccta gtagcctacc aagctacggt   5040
gtgcgccaga gccaaggccc ctcccccgtc ctgggacgcc atgtggaagt gcctggcccg   5100
actcaagcct acgcttgcgg gccccacacc tctcctgtac cgtttgggcc ctattaccaa   5160
tgaggtcacc ctcacacacc ctgggacgaa gtacatcgcc acatgcatgc aagctgacct   5220
tgaggtcatg accagcacgt gggtcctagc tggaggagtc ctggcagccg tcgccgcata   5280
ttgcctggcg actggatgcg tttccatcat cggccgcttg cacgtcaacc agcgagtcgt   5340
cgttgcgccg gataaggagg tcctgtatga ggcttttgat gagatggagg aatgcgcctc   5400
tagggcggct ctcatcgaag aggggcagcg gatagccgag atgttgaagt ccaagatcca   5460
aggcttgctg cagcaggcct ctaagcaggc ccaggacata caacccgcta tgcaggcttc   5520
atggcccaaa gtggaacaat tttgggccag acacatgtgg aacttcatta gcggcatcca   5580
atacctcgca ggattgtcaa cactgccagg gaaccccgcg gtggcttcca tgatggcatt   5640
cagtgccgcc ctcaccagtc cgttgtcgac cagtaccacc atccttctca acatcatggg   5700
aggctggtta gcgtcccaga tcgcaccacc cgcgggggcc accggctttg tcgtcagtgg   5760
cctggtgggg gctgccgtgg gcagcatagg cctgggtaag gtgctggtgg acatcctggc   5820
aggatatggt gcgggcattt cgggggccct cgtcgcattc aagatcatgt ctggcgagaa   5880
gccctctatg gaagatgtca tcaatctact gcctgggatc ctgtctccgg gagccctggt   5940
ggtgggggtc atctgcgcgg ccattctgcg ccgccacgtg ggaccggggg agggcgcggt   6000
```

-continued

```
ccaatggatg aacaggctta ttgcctttgc ttccagagga aaccacgtcg cccctactca   6060
ctacgtgacg gagtcggatg cgtcgcagcg tgtgacccaa ctacttggct ctcttactat   6120
aaccagccta ctcagaagac tccacaattg gataactgag gactgcccca tcccatgctc   6180
cggatcctgg ctccgcgacg tgtgggactg ggtttgcacc atcttgacag acttcaaaaa   6240
ttggctgacc tctaaattgt tccccaagct gcccggcctc cccttcatct cttgtcaaaa   6300
ggggtacaag ggtgtgtggg ccggcactgg catcatgacc acgcgctgcc cttgcggcgc   6360
caacatctct ggcaatgtcc gcctgggctc tatgaggatc acagggccta aaacctgcat   6420
gaacacctgg caggggacct ttcctatcaa ttgctacacg gagggccagt gcgcgccgaa   6480
accccccacg aactacaaga ccgccatctg gagggtggcg gcctcggagt acgcggaggt   6540
gacgcagcat gggtcgtact cctatgtaac aggactgacc actgacaatc tgaaaattcc   6600
ttgccaacta ccttctccag agtttttctc ctgggtggac ggtgtgcaga tccataggtt   6660
tgcacccaca ccaaagccgt tttccggga tgaggtctcg ttctgcgttg ggcttaattc   6720
ctatgctgtc gggtcccagc ttccctgtga acctgagccc gacgcagacg tattgaggtc   6780
catgctaaca gatccgcccc acatcacggc ggagactgcg gcgcggcgct tggcacgggg   6840
atcacctcca tctgaggcga gctcctcagt gagccagcta tcagcaccgt cgctgcgggc   6900
cacctgcacc acccacagca acacctatga cgtggacatg gtcgatgcca acctgctcat   6960
ggagggcggt gtggctcaga cagagcctga gtccagggtg cccgttctgg actttctcga   7020
gccaatggcc gaggaagaga gcgaccttga gccctcaata ccatcggagt gcatgctccc   7080
caggagcggg tttccacggg ccttaccggc ttgggcacgg cctgactaca acccgccgct   7140
cgtggaatcg tggaggaggc cagattacca accgcccacc gttgctggtt gtgctctccc   7200
ccccccaag aaggccccga cgcctccccc aaggagacgc cggacagtgg gtctgagcga   7260
gagcaccata tcagaagccc tccagcaact ggccatcaag acctttggcc agcccccctc   7320
gagcggtgat gcaggctcgt ccacgggggc gggcgccgcc gaatccggcg gtccgacgtc   7380
ccctggtgag ccggccccct cagagacagg ttccgcctcc tctatgcccc ccctcgaggg   7440
ggagcctgga gatccggacc tggagtctga tcaggtagag cttcaacctc ccccccaggg   7500
gggggggta gctcccggtt cgggctcggg gtcttggtct acttgctccg aggaggacga   7560
taccaccgtg tgctgctcca tgtcatactc ctggaccggg gctctaataa ctccctgtag   7620
ccccgaagag gaaaagttgc caatcaaccc tttgagtaac tcgctgttgc gataccataa   7680
caaggtgtac tgtacaacat caaagagcgc ctcacagagg gctaaaaagg taacttttga   7740
caggacgcaa gtgctcgacg cccattatga ctcagtctta aaggacatca agctagcggc   7800
ttccaaggtc agcgcaaggc tcctcacctt ggaggaggcg tgccagttga ctccacccca   7860
ttctgcaaga tccaagtatg gattcggggc caaggaggtc cgcagcttgt ccgggagggc   7920
cgttaaccac atcaagtccg tgtggaagga cctcctggaa gacccacaaa caccaattcc   7980
cacaaccatc atggccaaaa atgaggtgtt ctgcgtggac cccgccaagg ggggtaagaa   8040
accagctcgc ctcatcgttt accctgacct cggcgtccgg gtctgcgaga aaatggccct   8100
ctatgacatt acacaaaagc ttcctcaggc ggtaatggga gcttcctatg gcttccagta   8160
ctcccctgcc caacgggtgg agtatctctt gaaagcatgg gcggaaaaga aggaccccat   8220
gggtttttcg tatgataccc gatgcttcga ctcaaccgtc actgagagag acatcaggac   8280
cgaggagtcc atataccagg cctgctccct gcccgaggag gcccgcactg ccatacactc   8340
gctgactgag agactttacg taggagggcc catgttcaac agcaagggtc aaacctgcgg   8400
```

ttacagacgt tgccgcgcca gcggggtgct aaccactagc atgggtaaca ccatcacatg 8460
ctatgtgaaa gccctagcgg cctgcaaggc tgcggggata gttgcgccca caatgctggt 8520
atgcggcgat gacctagtag tcatctcaga aagccagggg actgaggagg acgagcggaa 8580
cctgagagcc ttcacggagg ccatgaccag gtactctgcc cctcctggtg atccccccag 8640
accggaatat gacctggagc taataacatc ctgttcctca aatgtgtctg tggcgttggg 8700
cccgcggggc cgccgcagat actacctgac cagagaccca accactccac tcgcccgggc 8760
tgcctgggaa acagttagac actcccctat caattcatgg ctgggaaaca tcatccagta 8820
tgctccaacc atatgggttc gcatggtcct aatgacacac ttcttctcca ttctcatggt 8880
ccaagacacc ctggaccaga acctcaactt tgagatgtat ggatcagtat actccgtgaa 8940
tcctttggac cttccagcca taattgagag gttacacggg cttgacgcct tttctatgca 9000
cacatactct caccacgaac tgacgcgggt ggcttcagcc ctcagaaaac ttggggcgcc 9060
acccctcagg gtgtggaaga gtcgggctcg cgcagtcagg gcgtccctca tctcccgtgg 9120
agggaaagcg gccgtttgcg gccgatatct cttcaattgg gcggtgaaga ccaagctcaa 9180
actcactcca ttgccggagg cgcgcctact ggacttatcc agttggttca ccgtcggcgc 9240
cggcgggggc gacatttttc acagcgtgtc gcgcgcccga ccccgctcat tactcttcgg 9300
cctactccta cttttcgtag ggtaggcct cttcctactc cccgctcggt agagcggcac 9360
acactaggta cactccatag ctaactgttc cttttttttt ttttttttt ttttttttt 9420 ttttttttt ttttctttt ttttttttc cctctttctt cccttctcat cttattctac 9480
tttctttctt ggtggctcca tcttagccct agtcacggct agctgtgaaa ggtccgtgag 9540
ccgcatgact gcagagagtg ccgtaactgg tctctctgca gatcatgt 9588

<210> SEQ ID NO 12
<211> LENGTH: 9606
<212> TYPE: DNA
<213> ORGANISM: Hepatitis C virus

<400> SEQUENCE: 12
acctgcccct aataggggcg acactccgcc atgaatcact cccctgtgag gaactactgt 60
cttcacgcag aaagcgccta gccatggcgt tagtatgagt gtcgtacagc ctccaggccc 120
ccccctcccg ggagagccat agtggtctgc ggaaccggtg agtacaccgg aattgccggg 180
aagactgggt cctttcttgg ataaacccac tctatgcccg gccatttggg cgtgcccccg 240
caagactgct agccgagtag cgttgggttg cgaaaggcct tgtggtactg cctgataggg 300
tgcttgcgag tgccccggga ggtctcgtag accgtgcacc atgagcacac ttccaaaacc 360
ccaaagaaaa accaaaagaa acaccaaccg tcgcccaatg gacgtcaagt tcccgggtgg 420
cggtcagatc gttggcggag tttacttgtt gccgcgcagg ggcccccggt tgggtgtgcg 480
cgcgacgagg aagacttccg agcgatccca gcccagaggc aggcgccaac ctataccaaa 540
ggcgcgccag ccccagggca ggcactgggc tcagcccgga tatccttggc ccctttatgg 600
gaacgagggc tgtgggtggg caggttggct cctgtccccc cgcggctccc ggccacactg 660
gggccccaac gacccccggc gtcgatcccg gaatttgggt aaggtcatcg ataccctaac 720
gtgtgggttc gccgatctca tggggtacat tcccgtcgtg ggcgcgcctt tgggcggcgt 780
cgcggctgca ctcgcacatg gtgtgagggc aatcgaggac gggatcaatt atgcaacagg 840
gaatcttccc ggttgctctt tctctatctt cctcttggca ctactctcgt gcctcacaac 900

-continued

```
gccagcgtcg gctcttacct acggtaactc cagtgggcta taccatctta caaatgattg    960
ccccaactcc agcatcgtgc tggaggcgga tgccatgatc ttgcatttgc ctggatgctt   1020
gccttgtgtg agggtcaata acaaccagtc catctgttgg catgctgtgt cccccaccct   1080
agccatacca aatgcttcca cacctgcaac gggattccgt aggcatgtgg accttcttgc   1140
gggcgccgca gtggtttgct catccctgta catcggggat ctgtgcggct ccctcttttt   1200
ggcagggcaa ctatttacct ttcagccccg ccgtcactgg actgtgcaag actgcaactg   1260
ctccatttat acaggccacg tcaccggcca caggatggct tgggacatga tgatgaattg   1320
gtcacccaca accactctgg tcctatctag tatcttgagg gtacctgaga tctgtgcgag   1380
tgtgatatct ggtggccatt gggggatact actagccgtt gcctactttg gtatggctgg   1440
caactggcta aaagttctgg ctgtcctgtt cttatttgca ggggttgaag cactacaact   1500
catcaacacc actggcagct ggcatataaa caggactgct ctgaactgca atgattccct   1560
ccagacgggg ttcataacgt cactctttta tgccaagaac gtcaactcct cgggctgccc   1620
agagcggatg gctgcgtgta agcccctcgc ggacttccgg caggggtggg gccaaataac   1680
ctacaaagtc aacatctcgg gcccctccga cgaccgtccc tactgttggc attacgctcc   1740
caggccatgt gacgtggtgt cggcccgcac ggtgtgcggc cccgtttact gcttcacgcc   1800
cagccctgtc gtagtaggaa ccactgacaa gctgggcatt cccacataca actgggggga   1860
gaatgagacg gatgtgttca tgttggaaag ccttcggcct cctactggag gatggtttgg   1920
gtgcacgtgg atgaactcta cgggctttac caagacctgt ggtgccccgc catgtcagat   1980
agtcccggga gattacaata gctctgccaa tgagcttttg tgccccaccg actgcttccg   2040
taaacatccg gaagctacat atcagcggtg tggatcggga ccctggatca cacctaggtg   2100
tctggtggat taccccctaca ggctgtggca ctacccctgt actgtcaact tcaccttgca   2160
taaagtcagg atgttcgtgg gaggcattga gcatcggttt gacgccgcat gtaactggac   2220
cagaggcgag cggtgtgatc tacatgacag agacaggatt gaaatgagcc cgctgctttt   2280
ctcaactacg cagcttgcca tacttccctg ttcattttcc accatgccgg ccttgtcaac   2340
cggcctcatc cacctgcatc agaacatagt ggacgtgcag tacctctacg gagtctcctc   2400
gagcgttacc tcgtgggtgg tgaagtggga gtacattgtt ctggtgttcc tggttctggc   2460
agatgctcgg atttgtacat gtctctggtt aatgctgctc ataaccaacg ttgaagcagc   2520
agtggaaagg cttgtcgtcc tcaatgcggc tagcgccgcc ggcaccgccg gctggtggtg   2580
ggcggtgctc ttcctgtgct gtgcttggta cgtgaaaggc cgccttgtgc ctgcgtgtac   2640
ctacatggca ctgggaatgt ggccgttgct cctgacaatc ttggccctgc ctcgccgagc   2700
atacgctatg gacaatgagc aagcggcatc cctcggagct gttggtctct tggtgctcac   2760
catctttacc atcaccccca tgtacaagaa gctgttgacc tgctccattt ggtggaatca   2820
gtatttcctc gcccgagctg aggccatgat acacgagtgg gtgcccgacc tacgggttag   2880
gggcggtagg gactccatca tcttacttac ctgcttgtta catccacagc tggggtttga   2940
ggtcaccaaa attctactag ccatcctggc ccctctatac atcctgcagt acagtttgct   3000
caaggtgcct tactttgtgc gcgcccacgt actcctgcgt gcttgcctgc ttgttcgtag   3060
gctagcaggg ggtaagtacg tgcaggcgtg ccttctgagg ttgggcgctt ggactggcac   3120
ctttgtctat gaccatctcg cccctctctc tgactgggct agcgacggac tgcgcgattt   3180
ggcagtcgca atcgagccgg tcattttctc tcccatggag aagaaaatca ttacctgggg   3240
tgcggatacc gccgcgtgtg gtgacatctt gagtggcctc ccggtgtcag cgaggttggg   3300
```

gaatttggtg ctactgggac ccgcggacga tatgcagcgc gggggttgga agcttttggc 3360
tcccatcact gcttatgccc agcaaacacg aggcctcctg ggcgccatag tggtgagtat 3420
gacggggcgt gacaggacag aacaggccgg ggaagtccaa atcctgtcca cagtctctca 3480
gtccttcctc ggaacaacca tctcgggggt tttgtggact gtttaccacg gagctggcaa 3540
caagactcta gccggcttac ggggtccggt cacgcagatg tactcgagtg ctgaggggga 3600
cttggtaggc tggcccagcc cccctgggac caagtctttg gagccgtgca agtgtggagc 3660
cgtcgaccta tatctggtca cgcggaacgc tgatgtcatc ccggctcgga gacgcgggga 3720
caagcgggga gcattgctct ccccgagacc catttcgacc ttgaaggggt cctcgggggg 3780
gccggtgctc tgccctaggg gccacgtcgt tgggctcttc cgagcagctg tgtgctctcg 3840
gggcgtggcc aaatccatcg atttcatccc cgttgagaca ctcgacgttg ttacaaggtc 3900
tcccactttc agtgacaaca gcacgccacc ggctgtgccc cagacctatc aggtcgggta 3960
cttgcatgct ccaactggca gtggaaagag caccaaggtc cctgtcgcgt atgccgccca 4020
ggggtacaaa gtactagtgc ttaacccctc ggtagctgcc accctggggt ttggggcgta 4080
cctatccaag gcacatggca tcaatcccaa cattaggact ggagtcagga ccgtgatgac 4140
cggggaggcc atcacgtact ccacatatgg caaatttctc gccgatgggg gctgcgctag 4200
cggcgcctat gacatcatca tatgcgatga atgccacgct gtggatgcta cctccattct 4260
cggcatcgga acggtccttg atcaagcaga gacagccggg gtcagactaa ctgtgctggc 4320
tacggccaca ccccccgggt cagtgacaac cccccatccc gatatagaag aggtaggcct 4380
cgggcgggag ggtgagatcc ccttctatgg gagggcgatt cccctatcct gcatcaaggg 4440
agggagacac ctgattttct gccactcaaa gaaaaagtgt gacgagctcg cggcggccct 4500
tcggggcatg ggcttgaatg ccgtggcata ctatagaggg ttggacgtct ccataatacc 4560
agctcaggga gatgtggtgg tcgtcgccac cgacgccctc atgacggggt acactggaga 4620
ctttgactcc gtgatcgact gcaatgtagc ggtcacccaa gctgtcgact tcagcctgga 4680
ccccaccttc actataacca cacagactgt cccacaagac gctgtctcac gcagtcagcg 4740
ccgcgggcgc acaggtagag gaagacaggg cacttatagg tatgtttcca ctggtgaacg 4800
agcctcagga atgtttgaca gtgtagtgct ttgtgagtgc tacgacgcag gggctgcgtg 4860
gtacgatctc acaccagcgg agaccaccgt caggcttaga gcgtatttca acacgcccgg 4920
cctacccgtg tgtcaagacc atcttgaatt ttgggaggca gttttcaccg gcctcacaca 4980
catagacgcc cacttcctct cccaaacaaa gcaagcgggg gagaacttcg cgtacctagt 5040
agcctaccaa gctacggtgt gcgccagagc caaggcccct cccccgtcct gggacgccat 5100
gtggaagtgc ctggcccgac tcaagcctac gcttgcgggc ccccacacctc tcctgtaccg 5160
tttgggccct attaccaatg aggtcaccct cacacaccct gggacgaagt acatcgccac 5220
atgcatgcaa gctgaccttg aggtcatgac cagcacgtgg gtcctagctg gaggagtcct 5280
ggcagccgtc gccgcatatt gcctggcgac tggatgcgtt tccatcatcg gccgcttgca 5340
cgtcaaccag cgagtcgtcg ttgcgccgga taaggaggtc ctgtatgagg cttttgatga 5400
gatggaggaa tgcgcctcta gggcggctct catcgaagag gggcagcgga tagccgagat 5460
gttgaagtcc aagatccaag gcttgctgca gcaggcctct aagcaggccc aggacataca 5520
acccgctatg caggcttcat ggcccaaagt ggaacaattt tgggccagac acatgtggaa 5580
cttcattagc ggcatccaat acctcgcagg attgtcaaca ctgccaggga accccgcggt 5640

-continued

```
ggcttccatg atggcattca gtgccgccct caccagtccg ttgtcgacca gtaccaccat   5700
ccttctcaac atcatgggag gctggttagc gtcccagatc gcaccacccg cgggggccac   5760
cggctttgtc gtcagtggcc tggtgggggc tgccgtgggc agcataggcc tgggtaaggt   5820
gctggtggac atcctggcag gatatggtgc gggcatttcg gggcccctcg tcgcattcaa   5880
gatcatgtct ggcgagaagc cctctatgga agatgtcatc aatctactgc ctgggatcct   5940
gtctccggga gccctggtgg tgggggtcat ctgcgcggcc attctgcgcc gccacgtggg   6000
accgggggag ggcgcggtcc aatggatgaa caggcttatt gcctttgctt ccagaggaaa   6060
ccacgtcgcc cctactcact acgtgacgga gtcggatgcg tcgcagcgtg tgacccaact   6120
acttggctct cttactataa ccagcctact cagaagactc cacaattgga taactgagga   6180
ctgccccatc ccatgctccg gatcctggct ccgcgacgtg tgggactggg tttgcaccat   6240
cttgacagac ttcaaaaatt ggctgacctc taaattgttc cccaagctgc ccggcctccc   6300
cttcatctct tgtcaaaagg ggtacaaggg tgtgtgggcc ggcactggca tcatgaccac   6360
gcgctgccct tgcggcgcca acatctctgg caatgtccgc ctgggctcta tgaggatcac   6420
agggcctaaa acctgcatga acacctggca ggggaccttt cctatcaatt gctacacgga   6480
gggccagtgc gcgccgaaac cccccacgaa ctacaagacc gccatctgga gggtggcggc   6540
ctcggagtac gcggaggtga cgcagcatgg gtcgtactcc tatgtaacag gactgaccac   6600
tgacaatctg aaaattcctt gccaactacc ttctccagag tttttctcct gggtggacgg   6660
tgtgcagatc cataggtttg cacccacacc aaagccgttt ttccgggatg aggtctcgtt   6720
ctgcgttggg cttaattcct atgctgtcgg gtcccagctt ccctgtgaac ctgagcccga   6780
cgcagacgta ttgaggtcca tgctaacaga tccgccccac atcacggcgg agactgcggc   6840
gcggcgcttg gcacggggat cacctccatc tgaggcgagc tcctcagtga gccagctatc   6900
agcaccgtcg ctgcgggcca cctgcaccac ccacagcaac acctatgacg tggacatggt   6960
cgatgccaac ctgctcatgg agggcggtgt ggctcagaca gagcctgagt ccagggtgcc   7020
cgttctggac tttctcgagc caatggccga ggaagagagc gaccttgagc cctcaatacc   7080
atcggagtgc atgctcccca ggagcgggtt tccacgggcc ttaccggctt gggcacggcc   7140
tgactacaac ccgccgctcg tggaatcgtg gaggaggcca gattaccaac cgcccaccgt   7200
tgctggttgt gctctccccc cccccaagaa ggccccgacg cctcccccaa ggagacgccg   7260
gacagtgggt ctgagcgaga gcaccatatc agaagccctc cagcaactgg ccatcaagac   7320
ctttggccag cccccctcga gcggtgatgc aggctcgtcc acgggggcgg gcgccgccga   7380
atccggcggt ccgacgtccc ctggtgagcc ggccccctca gagacaggtt ccgcctcctc   7440
tatgcccccc ctcgaggggg agcctggaga tccggacctg gagtctgatc aggtagagct   7500
tcaacctccc ccccaggggg gggggtagc tcccggttcg ggctcggggt cttggtctac   7560
ttgctccgag gaggacgata ccaccgtgtg ctgctccatg tcatactcct ggaccggggc   7620
tctaataact ccctgtagcc ccgaagagga aaagttgcca atcaaccctt tgagtaactc   7680
gctgttgcga taccataaca aggtgtactg tacaacatca aagagcgcct cacagagggc   7740
taaaaaggta acttttgaca ggacgcaagt gctcgacgcc cattatgact cagtcttaaa   7800
ggacatcaag ctagcggctt ccaaggtcag cgcaaggctc ctcaccttgg aggaggcgtg   7860
ccagttgact ccaccccatt ctgcaagatc caagtatgga ttcggggcca aggaggtccg   7920
cagcttgtcc gggagggccg ttaaccacat caagtccgtg tggaaggacc tcctggaaga   7980
cccacaaaca ccaattccca caaccatcat ggccaaaaat gaggtgttct gcgtggaccc   8040
```

```
cgccaagggg ggtaagaaac cagctcgcct catcgtttac cctgacctcg gcgtccgggt   8100

ctgcgagaaa atggccctct atgacattac acaaaagctt cctcaggcgg taatgggagc   8160

ttcctatggc ttccagtact cccctgccca acgggtggag tatctcttga aagcatgggc   8220

ggaaaagaag gaccccatgg gtttttcgta tgatacccga tgcttcgact caaccgtcac   8280

tgagagagac atcaggaccg aggagtccat ataccaggcc tgctccctgc ccgaggaggc   8340

ccgcactgcc atacactcgc tgactgagag actttacgta ggagggccca tgttcaacag   8400

caagggtcaa acctgcggtt acagacgttg ccgcgccagc ggggtgctaa ccactagcat   8460

gggtaacacc atcacatgct atgtgaaagc cctagcggcc tgcaaggctg cggggatagt   8520

tgcgcccaca atgctggtat gcggcgatga cctagtagtc atctcagaaa gccaggggac   8580

tgaggaggac gagcggaacc tgagagcctt cacggaggcc atgaccaggt actctgcccc   8640

tcctggtgat ccccccagac cggaatatga cctggagcta ataacatcct gttcctcaaa   8700

tgtgtctgtg gcgttgggcc cgcggggccg ccgcagatac tacctgacca gagacccaac   8760

cactccactc gcccgggctg cctgggaaac agttagacac tcccctatca attcatggct   8820

gggaaacatc atccagtatg ctccaaccat atgggttcgc atggtcctaa tgacacactt   8880

cttctccatt ctcatggtcc aagacaccct ggaccagaac ctcaactttg agatgtatgg   8940

atcagtatac tccgtgaatc ctttggacct tccagccata attgagaggt tacacgggct   9000

tgacgccttt tctatgcaca catactctca ccacgaactg acgcgggtgg cttcagccct   9060

cagaaaactt ggggcgccac ccctcagggt gtggaagagt cgggctcgcg cagtcagggc   9120

gtccctcatc tcccgtggag ggaaagcggc cgtttgcggc cgatatctct tcaattgggc   9180

ggtgaagacc aagctcaaac tcactccatt gccggaggcg cgcctactgg acttatccag   9240

ttggttcacc gtcggcgccg gcgggggcga catttttcac agcgtgtcgc gcgcccgacc   9300

ccgctcatta ctcttcggcc tactcctact tttcgtaggg gtaggcctct tcctactccc   9360

cgctcggtag agcggcacac actaggtaca ctccatagct aactgttcct ttttttttt    9420

ttttttttt ttttttttt ttttttttt ttctttttt tttttttccc tctttcttcc       9480

cttctcatct tattctactt tctttcttgg tggctccatc ttagccctag tcacggctag   9540

ctgtgaaagg tccgtgagcc gcatgactgc agagagtgcc gtaactggtc tctctgcaga   9600

tcatgt                                                              9606
```

<210> SEQ ID NO 13
<211> LENGTH: 3002
<212> TYPE: PRT
<213> ORGANISM: Hepatitis C virus

<400> SEQUENCE: 13

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
```

-continued

```
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg Arg Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Leu Phe Ala Gly Val Asp Ala Ile
    370                 375                 380

Gln Leu Ile Asn Thr Asn Gly Ser Trp His Ile Asn Ser Thr Ala Leu
385                 390                 395                 400

Asn Cys Asn Glu Ser Leu Asn Thr Gly Trp Leu Ala Gly Leu Phe Tyr
                405                 410                 415

Arg His Lys Phe Asn Ser Ser Gly Cys Pro Glu Arg Leu Ala Ser Cys
            420                 425                 430

Arg Arg Leu Thr Asp Phe Ala Gln Gly Trp Gly Pro Ile Ser Tyr Ala
        435                 440                 445

Asn Gly Ser Gly Leu Asp Glu Arg Pro Tyr Cys Trp His Tyr Pro Pro
    450                 455                 460

Arg Pro Cys Gly Ile Val Pro Ala Lys Ser Val Cys Gly Pro Val Tyr
465                 470                 475                 480

Cys Phe Thr Pro Ser Pro Val Val Val Gly Thr Thr Asp Arg Ser Gly
                485                 490                 495

Ala Pro Thr Tyr Ser Trp Gly Ala Asn Asp Thr Asp Val Phe Val Leu
            500                 505                 510
```

```
Asn Asn Thr Arg Pro Pro Leu Gly Asn Trp Phe Gly Cys Thr Trp Met
        515                 520                 525

Asn Ser Thr Gly Phe Thr Lys Val Cys Gly Ala Pro Pro Cys Val Ile
    530                 535                 540

Gly Gly Val Gly Asn Asn Thr Leu Leu Cys Pro Thr Asp Cys Phe Arg
545                 550                 555                 560

Lys His Pro Glu Ala Thr Tyr Ser Arg Cys Gly Ser Gly Pro Trp Ile
                565                 570                 575

Thr Pro Arg Cys Met Val Asp Tyr Pro Tyr Arg Leu Trp His Tyr Pro
            580                 585                 590

Cys Thr Ile Asn Tyr Thr Ile Phe Lys Val Arg Met Tyr Val Gly Gly
        595                 600                 605

Val Glu His Arg Leu Glu Ala Ala Cys Asn Trp Thr Arg Gly Glu Arg
    610                 615                 620

Cys Asp Leu Glu Asp Arg Asp Arg Ser Glu Leu Ser Pro Leu Leu Leu
625                 630                 635                 640

Ser Thr Thr Gln Trp Gln Val Leu Pro Cys Ser Phe Thr Thr Leu Pro
                645                 650                 655

Ala Leu Ser Thr Gly Leu Ile His Leu His Gln Asn Ile Val Asp Val
            660                 665                 670

Gln Tyr Leu Tyr Gly Val Gly Ser Ser Ile Ala Ser Trp Ala Ile Lys
        675                 680                 685

Trp Glu Tyr Val Val Leu Leu Phe Leu Leu Leu Ala Asp Ala Arg Val
    690                 695                 700

Cys Ser Cys Leu Trp Met Met Leu Leu Ile Ser Gln Ala Glu Ala Ala
705                 710                 715                 720

Leu Glu Asn Leu Val Ile Leu Asn Ala Ala Ser Leu Ala Gly Thr His
                725                 730                 735

Gly Leu Val Ser Phe Leu Val Phe Phe Cys Phe Ala Trp Tyr Leu Lys
            740                 745                 750

Gly Arg Trp Val Pro Gly Ala Ala Tyr Ala Leu Tyr Gly Met Trp Pro
        755                 760                 765

Leu Leu Leu Leu Leu Leu Ala Leu Pro Gln Arg Ala Tyr Ala Leu Asp
    770                 775                 780

Thr Glu Val Ala Ala Ser Cys Gly Gly Val Val Leu Val Gly Leu Met
785                 790                 795                 800

Ala Leu Thr Leu Ser Pro Tyr Tyr Lys Arg Tyr Ile Ser Trp Cys Met
                805                 810                 815

Trp Trp Leu Gln Tyr Phe Leu Thr Arg Val Glu Ala Gln Leu His Val
            820                 825                 830

Trp Val Pro Pro Leu Asn Val Arg Gly Gly Arg Asp Ala Val Ile Leu
        835                 840                 845

Leu Met Cys Val Val His Pro Thr Leu Val Phe Asp Ile Thr Lys Leu
    850                 855                 860

Leu Leu Ala Ile Phe Gly Pro Leu Trp Ile Leu Gln Ala Ser Leu Leu
865                 870                 875                 880

Lys Val Pro Tyr Phe Val Arg Val Gln Gly Leu Leu Arg Ile Cys Ala
                885                 890                 895

Leu Ala Arg Lys Ile Ala Gly Gly His Tyr Val Gln Met Ala Ile Ile
            900                 905                 910

Lys Leu Gly Ala Leu Thr Gly Thr Tyr Val Tyr Asn His Leu Thr Pro
        915                 920                 925
```

-continued

```
Leu Arg Asp Trp Ala His Asn Gly Leu Arg Asp Leu Ala Val Ala Val
    930                 935                 940

Glu Pro Val Val Phe Ser Arg Met Glu Thr Lys Leu Ile Thr Trp Gly
945                 950                 955                 960

Ala Asp Thr Ala Ala Cys Gly Asp Ile Ile Asn Gly Leu Pro Val Ser
                965                 970                 975

Ala Arg Arg Gly Gln Glu Ile Leu Leu Gly Pro Ala Asp Gly Met Val
            980                 985                 990

Ser Lys Gly Trp Arg Leu Leu Ala  Pro Ile Thr Ala Tyr  Ala Gln Gln
        995                 1000                1005

Thr Arg  Gly Leu Leu Gly Ala  Ile Val Val Ser Met  Thr Gly Arg
    1010                 1015                 1020

Asp Arg  Thr Glu Gln Ala Gly  Glu Val Gln Ile Leu  Ser Thr Val
    1025                 1030                 1035

Ser Gln  Ser Phe Leu Gly Thr  Thr Ile Ser Gly Val  Leu Trp Thr
    1040                 1045                 1050

Val Tyr  His Gly Ala Gly Asn  Lys Thr Leu Ala Gly  Leu Arg Gly
    1055                 1060                 1065

Pro Val  Thr Gln Met Tyr Ser  Ser Ala Glu Gly Asp  Leu Val Gly
    1070                 1075                 1080

Trp Pro  Ser Pro Pro Gly Thr  Lys Ser Leu Glu Pro  Cys Lys Cys
    1085                 1090                 1095

Gly Ala  Val Asp Leu Tyr Leu  Val Thr Arg Asn Ala  Asp Val Ile
    1100                 1105                 1110

Pro Ala  Arg Arg Arg Gly Asp  Lys Arg Gly Ala Leu  Leu Ser Pro
    1115                 1120                 1125

Arg Pro  Ile Ser Thr Leu Lys  Gly Ser Ser Gly Gly  Pro Val Leu
    1130                 1135                 1140

Cys Pro  Arg Gly His Val Val  Gly Leu Phe Arg Ala  Ala Val Cys
    1145                 1150                 1155

Ser Arg  Gly Val Ala Lys Ser  Ile Asp Phe Ile Pro  Val Glu Thr
    1160                 1165                 1170

Leu Asp  Val Val Thr Arg Ser  Pro Thr Phe Ser Asp  Asn Ser Thr
    1175                 1180                 1185

Pro Pro  Ala Val Pro Gln Thr  Tyr Gln Val Gly Tyr  Leu His Ala
    1190                 1195                 1200

Pro Thr  Gly Ser Gly Lys Ser  Thr Lys Val Pro Val  Ala Tyr Ala
    1205                 1210                 1215

Ala Leu  Gly Tyr Lys Val Leu  Val Leu Asn Pro Ser  Val Ala Ala
    1220                 1225                 1230

Thr Leu  Gly Phe Gly Ala Tyr  Leu Ser Lys Ala His  Gly Ile Asn
    1235                 1240                 1245

Pro Asn  Ile Arg Thr Gly Val  Arg Thr Val Met Thr  Gly Glu Ala
    1250                 1255                 1260

Ile Thr  Tyr Ser Thr Tyr Gly  Lys Phe Leu Ala Asp  Gly Gly Cys
    1265                 1270                 1275

Ala Ser  Gly Ala Tyr Asp Ile  Ile Ile Cys Asp Glu  Cys His Ala
    1280                 1285                 1290

Val Asp  Ala Thr Ser Ile Leu  Gly Ile Gly Thr Val  Leu Asp Gln
    1295                 1300                 1305

Ala Glu  Thr Ala Gly Val Arg  Leu Thr Val Leu Ala  Thr Ala Thr
    1310                 1315                 1320

Pro Pro  Gly Ser Val Thr Thr  Pro His Pro Asp Ile  Glu Glu Val
```

```
    1325                1330                1335

Gly Leu  Gly Arg Glu Gly Glu  Ile Pro Phe Tyr Gly  Arg Ala Ile
    1340                1345                1350

Pro Leu  Ser Cys Ile Lys Gly  Gly Arg His Leu Ile  Phe Cys His
    1355                1360                1365

Ser Lys  Lys Lys Cys Asp Glu  Leu Ala Ala Ala Leu  Arg Gly Met
    1370                1375                1380

Gly Leu  Asn Ala Val Ala Tyr  Tyr Arg Gly Leu Asp  Val Ser Ile
    1385                1390                1395

Ile Pro  Ala Gln Gly Asp Val  Val Val Val Ala Thr  Asp Ala Leu
    1400                1405                1410

Met Thr  Gly Tyr Thr Gly Asp  Phe Asp Ser Val Ile  Asp Cys Asn
    1415                1420                1425

Val Ala  Val Thr Gln Ala Val  Asp Phe Ser Leu Asp  Pro Thr Phe
    1430                1435                1440

Thr Ile  Thr Thr Gln Thr Val  Pro Gln Asp Ala Val  Ser Arg Ser
    1445                1450                1455

Gln Arg  Arg Gly Arg Thr Gly  Arg Gly Arg Gln Gly  Thr Tyr Arg
    1460                1465                1470

Tyr Val  Ser Thr Gly Glu Arg  Ala Ser Gly Met Phe  Asp Ser Val
    1475                1480                1485

Val Leu  Cys Glu Cys Tyr Asp  Ala Gly Ala Ala Trp  Tyr Asp Leu
    1490                1495                1500

Thr Pro  Ala Glu Thr Thr Val  Arg Leu Arg Ala Tyr  Phe Asn Thr
    1505                1510                1515

Pro Gly  Leu Pro Val Cys Gln  Asp His Leu Glu Phe  Trp Glu Ala
    1520                1525                1530

Val Phe  Thr Gly Leu Thr His  Ile Asp Ala His Phe  Leu Ser Gln
    1535                1540                1545

Thr Lys  Gln Ala Gly Glu Asn  Phe Ala Tyr Leu Val  Ala Tyr Gln
    1550                1555                1560

Ala Thr  Val Cys Ala Arg Ala  Lys Ala Pro Pro Pro  Ser Trp Asp
    1565                1570                1575

Ala Met  Trp Lys Cys Leu Ala  Arg Leu Lys Pro Thr  Leu Ala Gly
    1580                1585                1590

Pro Thr  Pro Leu Leu Tyr Arg  Leu Gly Pro Ile Thr  Asn Glu Val
    1595                1600                1605

Thr Leu  Thr His Pro Gly Thr  Lys Tyr Ile Ala Thr  Cys Met Gln
    1610                1615                1620

Ala Asp  Leu Glu Val Met Thr  Ser Thr Trp Val Leu  Ala Gly Gly
    1625                1630                1635

Val Leu  Ala Ala Val Ala Ala  Tyr Cys Leu Ala Thr  Gly Cys Val
    1640                1645                1650

Ser Ile  Ile Gly Arg Leu His  Val Asn Gln Arg Val  Val Val Ala
    1655                1660                1665

Pro Asp  Lys Glu Val Leu Tyr  Glu Ala Phe Asp Glu  Met Glu Glu
    1670                1675                1680

Cys Ala  Ser Arg Ala Ala Leu  Ile Glu Glu Gly Gln  Arg Ile Ala
    1685                1690                1695

Glu Met  Leu Lys Ser Lys Ile  Gln Gly Leu Leu Gln  Gln Ala Ser
    1700                1705                1710

Lys Gln  Ala Gln Asp Ile Gln  Pro Ala Met Gln Ala  Ser Trp Pro
    1715                1720                1725
```

```
Lys Val Glu Gln Phe Trp Ala Arg His Met Trp Asn Phe Ile Ser
    1730                1735                1740

Gly Ile Gln Tyr Leu Ala Gly Leu Ser Thr Leu Pro Gly Asn Pro
    1745                1750                1755

Ala Val Ala Ser Met Met Ala Phe Ser Ala Ala Leu Thr Ser Pro
    1760                1765                1770

Leu Ser Thr Ser Thr Thr Ile Leu Leu Asn Ile Met Gly Gly Trp
    1775                1780                1785

Leu Ala Ser Gln Ile Ala Pro Pro Ala Gly Ala Thr Gly Phe Val
    1790                1795                1800

Val Ser Gly Leu Val Gly Ala Ala Val Gly Ser Ile Gly Leu Gly
    1805                1810                1815

Lys Val Leu Val Asp Ile Leu Ala Gly Tyr Gly Ala Gly Ile Ser
    1820                1825                1830

Gly Ala Leu Val Ala Phe Lys Ile Met Ser Gly Glu Lys Pro Ser
    1835                1840                1845

Met Glu Asp Val Ile Asn Leu Leu Pro Gly Ile Leu Ser Pro Gly
    1850                1855                1860

Ala Leu Val Val Gly Val Ile Cys Ala Ala Ile Leu Arg Arg His
    1865                1870                1875

Val Gly Pro Gly Glu Gly Ala Val Gln Trp Met Asn Arg Leu Ile
    1880                1885                1890

Ala Phe Ala Ser Arg Gly Asn His Val Ala Pro Thr His Tyr Val
    1895                1900                1905

Thr Glu Ser Asp Ala Ser Gln Arg Val Thr Gln Leu Leu Gly Ser
    1910                1915                1920

Leu Thr Ile Thr Ser Leu Leu Arg Arg Leu His Asn Trp Ile Thr
    1925                1930                1935

Glu Asp Cys Pro Ile Pro Cys Ser Gly Ser Trp Leu Arg Asp Val
    1940                1945                1950

Trp Asp Trp Val Cys Thr Ile Leu Thr Asp Phe Lys Asn Trp Leu
    1955                1960                1965

Thr Ser Lys Leu Phe Pro Lys Leu Pro Gly Leu Pro Phe Ile Ser
    1970                1975                1980

Cys Gln Lys Gly Tyr Lys Gly Val Trp Ala Gly Thr Gly Ile Met
    1985                1990                1995

Thr Thr Arg Cys Pro Cys Gly Ala Asn Ile Ser Gly Asn Val Arg
    2000                2005                2010

Leu Gly Ser Met Arg Ile Thr Gly Pro Lys Thr Cys Met Asn Thr
    2015                2020                2025

Trp Gln Gly Thr Phe Pro Ile Asn Cys Tyr Thr Glu Gly Gln Cys
    2030                2035                2040

Ala Pro Lys Pro Pro Thr Asn Tyr Lys Thr Ala Ile Trp Arg Val
    2045                2050                2055

Ala Ala Ser Glu Tyr Ala Glu Val Thr Gln His Gly Ser Tyr Ser
    2060                2065                2070

Tyr Val Thr Gly Leu Thr Thr Asp Asn Leu Lys Ile Pro Cys Gln
    2075                2080                2085

Leu Pro Ser Pro Glu Phe Phe Ser Trp Val Asp Gly Val Gln Ile
    2090                2095                2100

His Arg Phe Ala Pro Thr Pro Lys Pro Phe Phe Arg Asp Glu Val
    2105                2110                2115
```

-continued

Ser Phe Cys Val Gly Leu Asn Ser Tyr Ala Val Gly Ser Gln Leu
2120 2125 2130

Pro Cys Glu Pro Glu Pro Asp Ala Asp Val Leu Arg Ser Met Leu
2135 2140 2145

Thr Asp Pro Pro His Ile Thr Ala Glu Thr Ala Ala Arg Arg Leu
2150 2155 2160

Ala Arg Gly Ser Pro Pro Ser Glu Ala Ser Ser Ser Val Ser Gln
2165 2170 2175

Leu Ser Ala Pro Ser Leu Arg Ala Thr Cys Thr Thr His Ser Asn
2180 2185 2190

Thr Tyr Asp Val Asp Met Val Asp Ala Asn Leu Leu Met Glu Gly
2195 2200 2205

Gly Val Ala Gln Thr Glu Pro Glu Ser Arg Val Pro Val Leu Asp
2210 2215 2220

Phe Leu Glu Pro Met Ala Glu Glu Glu Ser Asp Leu Glu Pro Ser
2225 2230 2235

Ile Pro Ser Glu Cys Met Leu Pro Arg Ser Gly Phe Pro Arg Ala
2240 2245 2250

Leu Pro Ala Trp Ala Arg Pro Asp Tyr Asn Pro Pro Leu Val Glu
2255 2260 2265

Ser Trp Arg Arg Pro Asp Tyr Gln Pro Pro Thr Val Ala Gly Cys
2270 2275 2280

Ala Leu Pro Pro Pro Lys Lys Ala Pro Thr Pro Pro Pro Arg Arg
2285 2290 2295

Arg Arg Thr Val Gly Leu Ser Glu Ser Thr Ile Ser Glu Ala Leu
2300 2305 2310

Gln Gln Leu Ala Ile Lys Thr Phe Gly Gln Pro Pro Ser Ser Gly
2315 2320 2325

Asp Ala Gly Ser Ser Thr Gly Ala Gly Ala Ala Glu Ser Gly Gly
2330 2335 2340

Pro Thr Ser Pro Gly Glu Pro Ala Pro Ser Glu Thr Gly Ser Ala
2345 2350 2355

Ser Ser Met Pro Pro Leu Glu Gly Glu Pro Gly Asp Pro Asp Leu
2360 2365 2370

Glu Ser Asp Gln Val Glu Leu Gln Pro Pro Pro Gln Gly Gly Gly
2375 2380 2385

Val Ala Pro Gly Ser Gly Ser Gly Ser Trp Ser Thr Cys Ser Glu
2390 2395 2400

Glu Asp Asp Thr Thr Val Cys Cys Ser Met Ser Tyr Ser Trp Thr
2405 2410 2415

Gly Ala Leu Ile Thr Pro Cys Ser Pro Glu Glu Glu Lys Leu Pro
2420 2425 2430

Ile Asn Pro Leu Ser Asn Ser Leu Leu Arg Tyr His Asn Lys Val
2435 2440 2445

Tyr Cys Thr Thr Ser Lys Ser Ala Ser Gln Arg Ala Lys Lys Val
2450 2455 2460

Thr Phe Asp Arg Thr Gln Val Leu Asp Ala His Tyr Asp Ser Val
2465 2470 2475

Leu Lys Asp Ile Lys Leu Ala Ala Ser Lys Val Ser Ala Arg Leu
2480 2485 2490

Leu Thr Leu Glu Glu Ala Cys Gln Leu Thr Pro Pro His Ser Ala
2495 2500 2505

Arg Ser Lys Tyr Gly Phe Gly Ala Lys Glu Val Arg Ser Leu Ser

```
    2510                2515                2520

Gly Arg  Ala Val Asn His Ile  Lys Ser Val Trp Lys  Asp Leu Leu
    2525                2530                2535

Glu Asp  Pro Gln Thr Pro Ile  Pro Thr Thr Ile Met  Ala Lys Asn
    2540                2545                2550

Glu Val  Phe Cys Val Asp Pro  Ala Lys Gly Gly Lys  Lys Pro Ala
    2555                2560                2565

Arg Leu  Ile Val Tyr Pro Asp  Leu Gly Val Arg Val  Cys Glu Lys
    2570                2575                2580

Met Ala  Leu Tyr Asp Ile Thr  Gln Lys Leu Pro Gln  Ala Val Met
    2585                2590                2595

Gly Ala  Ser Tyr Gly Phe Gln  Tyr Ser Pro Ala Gln  Arg Val Glu
    2600                2605                2610

Tyr Leu  Leu Lys Ala Trp Ala  Glu Lys Lys Asp Pro  Met Gly Phe
    2615                2620                2625

Ser Tyr  Asp Thr Arg Cys Phe  Asp Ser Thr Val Thr  Glu Arg Asp
    2630                2635                2640

Ile Arg  Thr Glu Glu Ser Ile  Tyr Gln Ala Cys Ser  Leu Pro Glu
    2645                2650                2655

Glu Ala  Arg Thr Ala Ile His  Ser Leu Thr Glu Arg  Leu Tyr Val
    2660                2665                2670

Gly Gly  Pro Met Phe Asn Ser  Lys Gly Gln Thr Cys  Gly Tyr Arg
    2675                2680                2685

Arg Cys  Arg Ala Ser Gly Val  Leu Thr Thr Ser Met  Gly Asn Thr
    2690                2695                2700

Ile Thr  Cys Tyr Val Lys Ala  Leu Ala Ala Cys Lys  Ala Ala Gly
    2705                2710                2715

Ile Val  Ala Pro Thr Met Leu  Val Cys Gly Asp Asp  Leu Val Val
    2720                2725                2730

Ile Ser  Glu Ser Gln Gly Thr  Glu Glu Asp Glu Arg  Asn Leu Arg
    2735                2740                2745

Ala Phe  Thr Glu Ala Met Thr  Arg Tyr Ser Ala Pro  Pro Gly Asp
    2750                2755                2760

Pro Pro  Arg Pro Glu Tyr Asp  Leu Glu Leu Ile Thr  Ser Cys Ser
    2765                2770                2775

Ser Asn  Val Ser Val Ala Leu  Gly Pro Arg Gly Arg  Arg Arg Tyr
    2780                2785                2790

Tyr Leu  Thr Arg Asp Pro Thr  Thr Pro Leu Ala Arg  Ala Ala Trp
    2795                2800                2805

Glu Thr  Val Arg His Ser Pro  Ile Asn Ser Trp Leu  Gly Asn Ile
    2810                2815                2820

Ile Gln  Tyr Ala Pro Thr Ile  Trp Val Arg Met Val  Leu Met Thr
    2825                2830                2835

His Phe  Phe Ser Ile Leu Met  Val Gln Asp Thr Leu  Asp Gln Asn
    2840                2845                2850

Leu Asn  Phe Glu Met Tyr Gly  Ser Val Tyr Ser Val  Asn Pro Leu
    2855                2860                2865

Asp Leu  Pro Ala Ile Ile Glu  Arg Leu His Gly Leu  Asp Ala Phe
    2870                2875                2880

Ser Met  His Thr Tyr Ser His  His Glu Leu Thr Arg  Val Ala Ser
    2885                2890                2895

Ala Leu  Arg Lys Leu Gly Ala  Pro Pro Leu Arg Val  Trp Lys Ser
    2900                2905                2910
```

Arg Ala Arg Ala Val Arg Ala Ser Leu Ile Ser Arg Gly Gly Lys
2915 2920 2925

Ala Ala Val Cys Gly Arg Tyr Leu Phe Asn Trp Ala Val Lys Thr
2930 2935 2940

Lys Leu Lys Leu Thr Pro Leu Pro Glu Ala Arg Leu Leu Asp Leu
2945 2950 2955

Ser Ser Trp Phe Thr Val Gly Ala Gly Gly Gly Asp Ile Phe His
2960 2965 2970

Ser Val Ser Arg Ala Arg Pro Arg Ser Leu Leu Phe Gly Leu Leu
2975 2980 2985

Leu Leu Phe Val Gly Val Gly Leu Phe Leu Leu Pro Ala Arg
2990 2995 3000

<210> SEQ ID NO 14
<211> LENGTH: 3002
<212> TYPE: PRT
<213> ORGANISM: Hepatitis C virus

<400> SEQUENCE: 14

Met Ser Thr Asn Pro Lys Pro Gln Arg Lys Thr Lys Arg Asn Thr Asn
1 5 10 15

Arg Arg Pro Gln Asp Val Lys Phe Pro Gly Gly Gly Gln Ile Val Gly
20 25 30

Gly Val Tyr Leu Leu Pro Arg Arg Gly Pro Arg Leu Gly Val Arg Ala
35 40 45

Thr Arg Lys Thr Ser Glu Arg Ser Gln Pro Arg Gly Arg Arg Gln Pro
50 55 60

Ile Pro Lys Ala Arg Arg Pro Glu Gly Arg Thr Trp Ala Gln Pro Gly
65 70 75 80

Tyr Pro Trp Pro Leu Tyr Gly Asn Glu Gly Cys Gly Trp Ala Gly Trp
85 90 95

Leu Leu Ser Pro Arg Gly Ser Arg Pro Ser Trp Gly Pro Thr Asp Pro
100 105 110

Arg Arg Arg Ser Arg Asn Leu Gly Lys Val Ile Asp Thr Leu Thr Cys
115 120 125

Gly Phe Ala Asp Leu Met Gly Tyr Ile Pro Leu Val Gly Ala Pro Leu
130 135 140

Gly Gly Ala Ala Arg Ala Leu Ala His Gly Val Arg Val Leu Glu Asp
145 150 155 160

Gly Val Asn Tyr Ala Thr Gly Asn Leu Pro Gly Cys Ser Phe Ser Ile
165 170 175

Phe Leu Leu Ala Leu Leu Ser Cys Leu Thr Val Pro Ala Ser Ala Tyr
180 185 190

Gln Val Arg Asn Ser Ser Gly Leu Tyr His Val Thr Asn Asp Cys Pro
195 200 205

Asn Ser Ser Ile Val Tyr Glu Ala Ala Asp Ala Ile Leu His Thr Pro
210 215 220

Gly Cys Val Pro Cys Val Arg Glu Gly Asn Ala Ser Arg Cys Trp Val
225 230 235 240

Ala Val Thr Pro Thr Val Ala Thr Arg Asp Gly Lys Leu Pro Thr Thr
245 250 255

Gln Leu Arg Arg His Ile Asp Leu Leu Val Gly Ser Ala Thr Leu Cys
260 265 270

Ser Ala Leu Tyr Val Gly Asp Leu Cys Gly Ser Val Phe Leu Val Gly

```
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Leu Phe Ala Gly Val Asp Ala Ile
    370                 375                 380

Gln Leu Ile Asn Thr Asn Gly Ser Trp His Ile Asn Ser Thr Ala Leu
385                 390                 395                 400

Asn Cys Asn Glu Ser Leu Asn Thr Gly Trp Leu Ala Gly Leu Phe Tyr
                405                 410                 415

Gln His Lys Phe Asn Ser Ser Gly Cys Pro Glu Arg Leu Ala Ser Cys
            420                 425                 430

Arg Arg Leu Thr Asp Phe Ala Gln Gly Trp Gly Pro Ile Ser Tyr Ala
        435                 440                 445

Asp Gly Ser Gly Leu Asp Glu Arg Pro Tyr Cys Trp His Tyr Pro Pro
    450                 455                 460

Arg Pro Cys Gly Ile Val Pro Ala Lys Ser Val Cys Gly Pro Val Tyr
465                 470                 475                 480

Cys Phe Thr Pro Ser Pro Val Val Val Gly Thr Thr Asp Arg Ser Gly
                485                 490                 495

Ala Pro Thr Tyr Ser Trp Gly Ala Asn Asp Thr Asp Val Phe Val Leu
            500                 505                 510

Asn Asn Thr Arg Pro Pro Leu Gly Asn Trp Phe Gly Cys Thr Trp Met
        515                 520                 525

Asn Ser Thr Gly Phe Thr Lys Val Cys Gly Ala Pro Pro Cys Val Ile
    530                 535                 540

Gly Gly Val Gly Asn Asn Thr Leu Leu Cys Pro Thr Asp Cys Phe Arg
545                 550                 555                 560

Lys His Pro Glu Ala Thr Tyr Ser Arg Cys Gly Ser Gly Pro Trp Ile
                565                 570                 575

Thr Pro Arg Cys Met Val Asp Tyr Pro Tyr Arg Leu Trp His Tyr Pro
            580                 585                 590

Cys Thr Ile Asn Tyr Thr Ile Phe Lys Val Arg Met Tyr Val Gly Gly
        595                 600                 605

Val Glu His Arg Leu Glu Ala Ala Cys Asn Trp Thr Arg Gly Glu Arg
    610                 615                 620

Cys Asp Leu Glu Asp Arg Asp Arg Ser Glu Leu Ser Pro Leu Leu Leu
625                 630                 635                 640

Ser Thr Thr Gln Trp Gln Val Leu Pro Cys Ser Phe Thr Thr Leu Pro
                645                 650                 655

Ala Leu Ser Thr Gly Leu Ile His Leu His Gln Asn Ile Val Asp Val
            660                 665                 670

Gln Tyr Leu Tyr Gly Val Gly Ser Ser Ile Ala Ser Trp Ala Ile Lys
        675                 680                 685

Trp Glu Tyr Val Val Leu Leu Phe Leu Leu Leu Ala Asp Ala Arg Val
    690                 695                 700
```

-continued

```
Cys Phe Cys Leu Trp Met Met Leu Leu Ile Ser Gln Ala Glu Ala Ala
705                 710                 715                 720

Leu Glu Asn Leu Val Ile Leu Asn Ala Ala Ser Leu Ala Gly Thr His
                725                 730                 735

Gly Leu Val Ser Phe Leu Val Phe Phe Cys Phe Ala Trp Tyr Leu Lys
            740                 745                 750

Gly Arg Trp Val Pro Gly Ala Ala Tyr Ala Leu Tyr Gly Met Trp Pro
        755                 760                 765

Leu Leu Leu Leu Leu Leu Ala Leu Pro Gln Arg Ala Tyr Ala Leu Asp
    770                 775                 780

Thr Glu Val Ala Ala Ser Cys Gly Gly Val Val Leu Val Gly Leu Met
785                 790                 795                 800

Ala Leu Thr Leu Ser Pro Tyr Tyr Lys Arg Tyr Ile Ser Trp Cys Met
                805                 810                 815

Trp Trp Leu Gln Tyr Phe Leu Thr Arg Val Glu Ala Gln Leu His Val
            820                 825                 830

Trp Val Pro Pro Leu Asn Val Arg Gly Gly Arg Asp Ala Val Ile Leu
        835                 840                 845

Leu Met Cys Val Val His Pro Thr Leu Val Phe Asp Ile Thr Lys Leu
    850                 855                 860

Leu Leu Ala Ile Phe Gly Pro Leu Trp Ile Leu Gln Ala Ser Leu Leu
865                 870                 875                 880

Lys Val Pro Tyr Phe Val Arg Val Gln Gly Leu Leu Arg Ile Cys Ala
                885                 890                 895

Leu Ala Arg Lys Ile Ala Gly Gly His Tyr Val Gln Met Ala Ile Ile
            900                 905                 910

Lys Leu Gly Ala Leu Thr Gly Thr Tyr Val Tyr Asn His Leu Thr Pro
        915                 920                 925

Leu Arg Asp Trp Ala His Asn Gly Leu Arg Asp Leu Ala Val Ala Val
    930                 935                 940

Glu Pro Val Val Phe Ser Arg Met Glu Thr Lys Leu Ile Thr Trp Gly
945                 950                 955                 960

Ala Asp Thr Ala Ala Cys Gly Asp Ile Ile Asn Gly Leu Pro Val Ser
                965                 970                 975

Ala Arg Arg Gly Gln Glu Ile Leu Leu Gly Pro Ala Asp Gly Met Val
            980                 985                 990

Ser Lys Gly Trp Arg Leu Leu Ala  Pro Ile Thr Ala Tyr  Ala Gln Gln
        995                 1000                1005

Thr Arg  Gly Leu Leu Gly Ala  Ile Val Val Ser Met  Thr Gly Arg
    1010                1015                1020

Asp Arg  Thr Glu Gln Ala Gly  Glu Val Gln Ile Leu  Ser Thr Val
    1025                1030                1035

Ser Gln  Ser Phe Leu Gly Thr  Thr Ile Ser Gly Val  Leu Trp Thr
    1040                1045                1050

Val Tyr  His Gly Ala Gly Asn  Lys Thr Leu Ala Gly  Leu Arg Gly
    1055                1060                1065

Pro Val  Thr Gln Met Tyr Ser  Ser Ala Glu Gly Asp  Leu Val Gly
    1070                1075                1080

Trp Pro  Ser Pro Pro Gly Thr  Lys Ser Leu Glu Pro  Cys Lys Cys
    1085                1090                1095

Gly Ala  Val Asp Leu Tyr Leu  Val Thr Arg Asn Ala  Asp Val Ile
    1100                1105                1110
```

```
Pro Ala Arg Arg Arg Gly Asp Lys Arg Gly Ala Leu Leu Ser Pro
    1115                1120                1125

Arg Pro Ile Ser Thr Leu Lys Gly Ser Ser Gly Gly Pro Val Leu
    1130                1135                1140

Cys Pro Arg Gly His Val Val Gly Leu Phe Arg Ala Ala Val Cys
    1145                1150                1155

Ser Arg Gly Val Ala Lys Ser Ile Asp Phe Ile Pro Val Glu Thr
    1160                1165                1170

Leu Asp Val Val Thr Arg Ser Pro Thr Phe Ser Asp Asn Ser Thr
    1175                1180                1185

Pro Pro Ala Val Pro Gln Thr Tyr Gln Val Gly Tyr Leu His Ala
    1190                1195                1200

Pro Thr Gly Ser Gly Lys Ser Thr Lys Val Pro Val Ala Tyr Ala
    1205                1210                1215

Ala Leu Gly Tyr Lys Val Leu Val Leu Asn Pro Ser Val Ala Ala
    1220                1225                1230

Thr Leu Gly Phe Gly Ala Tyr Leu Ser Lys Ala His Gly Ile Asn
    1235                1240                1245

Pro Asn Ile Arg Thr Gly Val Arg Thr Val Met Thr Gly Glu Ala
    1250                1255                1260

Ile Thr Tyr Ser Thr Tyr Gly Lys Phe Leu Ala Asp Gly Gly Cys
    1265                1270                1275

Ala Ser Gly Ala Tyr Asp Ile Ile Ile Cys Asp Glu Cys His Ala
    1280                1285                1290

Val Asp Ala Thr Ser Ile Leu Gly Ile Gly Thr Val Leu Asp Gln
    1295                1300                1305

Ala Glu Thr Ala Gly Val Arg Leu Thr Val Leu Ala Thr Ala Thr
    1310                1315                1320

Pro Pro Gly Ser Val Thr Thr Pro His Pro Asp Ile Glu Glu Val
    1325                1330                1335

Gly Leu Gly Arg Glu Gly Glu Ile Pro Phe Tyr Gly Arg Ala Ile
    1340                1345                1350

Pro Leu Ser Cys Ile Lys Gly Gly Arg His Leu Ile Phe Cys His
    1355                1360                1365

Ser Lys Lys Lys Cys Asp Glu Leu Ala Ala Ala Leu Arg Gly Met
    1370                1375                1380

Gly Leu Asn Ala Val Ala Tyr Tyr Arg Gly Leu Asp Val Ser Ile
    1385                1390                1395

Ile Pro Ala Gln Gly Asp Val Val Val Val Ala Thr Asp Ala Leu
    1400                1405                1410

Met Thr Gly Tyr Thr Gly Asp Phe Asp Ser Val Ile Asp Cys Asn
    1415                1420                1425

Val Ala Val Thr Gln Ala Val Asp Phe Ser Leu Asp Pro Thr Phe
    1430                1435                1440

Thr Ile Thr Thr Gln Thr Val Pro Gln Asp Ala Val Ser Arg Ser
    1445                1450                1455

Gln Arg Arg Gly Arg Thr Gly Arg Gly Arg Gln Gly Thr Tyr Arg
    1460                1465                1470

Tyr Val Ser Thr Gly Glu Arg Ala Ser Gly Met Phe Asp Ser Val
    1475                1480                1485

Val Leu Cys Glu Cys Tyr Asp Ala Gly Ala Ala Trp Tyr Asp Leu
    1490                1495                1500

Thr Pro Ala Glu Thr Thr Val Arg Leu Arg Ala Tyr Phe Asn Thr
```

-continued

```
    1505                1510                1515

Pro Gly  Leu Pro Val Cys Gln  Asp His Leu Glu Phe  Trp Glu Ala
    1520                1525                1530

Val Phe  Thr Gly Leu Thr His  Ile Asp Ala His Phe  Leu Ser Gln
    1535                1540                1545

Thr Lys  Gln Ala Gly Glu Asn  Phe Ala Tyr Leu Val  Ala Tyr Gln
    1550                1555                1560

Ala Thr  Val Cys Ala Arg Ala  Lys Ala Pro Pro Pro  Ser Trp Asp
    1565                1570                1575

Ala Met  Trp Lys Cys Leu Ala  Arg Leu Lys Pro Thr  Leu Ala Gly
    1580                1585                1590

Pro Thr  Pro Leu Leu Tyr Arg  Leu Gly Pro Ile Thr  Asn Glu Val
    1595                1600                1605

Thr Leu  Thr His Pro Gly Thr  Lys Tyr Ile Ala Thr  Cys Met Gln
    1610                1615                1620

Ala Asp  Leu Glu Val Met Thr  Ser Thr Trp Val Leu  Ala Gly Gly
    1625                1630                1635

Val Leu  Ala Ala Val Ala Ala  Tyr Cys Leu Ala Thr  Gly Cys Val
    1640                1645                1650

Ser Ile  Ile Gly Arg Leu His  Val Asn Gln Arg Val  Val Val Ala
    1655                1660                1665

Pro Asp  Lys Glu Val Leu Tyr  Glu Ala Phe Asp Glu  Met Glu Glu
    1670                1675                1680

Cys Ala  Ser Arg Ala Ala Leu  Ile Glu Glu Gly Gln  Arg Ile Ala
    1685                1690                1695

Glu Met  Leu Lys Ser Lys Ile  Gln Gly Leu Leu Gln  Gln Ala Ser
    1700                1705                1710

Lys Gln  Ala Gln Asp Ile Gln  Pro Ala Met Gln Ala  Ser Trp Pro
    1715                1720                1725

Lys Val  Glu Gln Phe Trp Ala  Arg His Met Trp Asn  Phe Ile Ser
    1730                1735                1740

Gly Ile  Gln Tyr Leu Ala Gly  Leu Ser Thr Leu Pro  Gly Asn Pro
    1745                1750                1755

Ala Val  Ala Ser Met Met Ala  Phe Ser Ala Ala Leu  Thr Ser Pro
    1760                1765                1770

Leu Ser  Thr Ser Thr Thr Ile  Leu Leu Asn Ile Met  Gly Gly Trp
    1775                1780                1785

Leu Ala  Ser Gln Ile Ala Pro  Pro Ala Gly Ala Thr  Gly Phe Val
    1790                1795                1800

Val Ser  Gly Leu Val Gly Ala  Ala Val Gly Ser Ile  Gly Leu Gly
    1805                1810                1815

Lys Val  Leu Val Asp Ile Leu  Ala Gly Tyr Gly Ala  Gly Ile Ser
    1820                1825                1830

Gly Ala  Leu Val Ala Phe Lys  Ile Met Ser Gly Glu  Lys Pro Ser
    1835                1840                1845

Met Glu  Asp Val Ile Asn Leu  Leu Pro Gly Ile Leu  Ser Pro Gly
    1850                1855                1860

Ala Leu  Val Val Gly Val Ile  Cys Ala Ala Ile Leu  Arg Arg His
    1865                1870                1875

Val Gly  Pro Gly Glu Gly Ala  Val Gln Trp Met Asn  Arg Leu Ile
    1880                1885                1890

Ala Phe  Ala Ser Arg Gly Asn  His Val Ala Pro Thr  His Tyr Val
    1895                1900                1905
```

-continued

```
Thr Glu  Ser Asp Ala Ser Gln  Arg Val Thr Gln Leu  Leu Gly Ser
    1910                 1915                 1920

Leu Thr  Ile Thr Ser Leu Leu  Arg Arg Leu His Asn  Trp Ile Thr
    1925                 1930                 1935

Glu Asp  Cys Pro Ile Pro Cys  Ser Gly Ser Trp Leu  Arg Asp Val
    1940                 1945                 1950

Trp Asp  Trp Val Cys Thr Ile  Leu Thr Asp Phe Lys  Asn Trp Leu
    1955                 1960                 1965

Thr Ser  Lys Leu Phe Pro Lys  Leu Pro Gly Leu Pro  Phe Ile Ser
    1970                 1975                 1980

Cys Gln  Lys Gly Tyr Lys Gly  Val Trp Ala Gly Thr  Gly Ile Met
    1985                 1990                 1995

Thr Thr  Arg Cys Pro Cys Gly  Ala Asn Ile Ser Gly  Asn Val Arg
    2000                 2005                 2010

Leu Gly  Ser Met Arg Ile Thr  Gly Pro Lys Thr Cys  Met Asn Thr
    2015                 2020                 2025

Trp Gln  Gly Thr Phe Pro Ile  Asn Cys Tyr Thr Glu  Gly Gln Cys
    2030                 2035                 2040

Ala Pro  Lys Pro Pro Thr Asn  Tyr Lys Thr Ala Ile  Trp Arg Val
    2045                 2050                 2055

Ala Ala  Ser Glu Tyr Ala Glu  Val Thr Gln His Gly  Ser Tyr Ser
    2060                 2065                 2070

Tyr Val  Thr Gly Leu Thr Thr  Asp Asn Leu Lys Ile  Pro Cys Gln
    2075                 2080                 2085

Leu Pro  Ser Pro Glu Phe Phe  Ser Trp Val Asp Gly  Val Gln Ile
    2090                 2095                 2100

His Arg  Phe Ala Pro Thr Pro  Lys Pro Phe Phe Arg  Asp Glu Val
    2105                 2110                 2115

Ser Phe  Cys Val Gly Leu Asn  Ser Tyr Ala Val Gly  Ser Gln Leu
    2120                 2125                 2130

Pro Cys  Glu Pro Glu Pro Asp  Ala Asp Val Leu Arg  Ser Met Leu
    2135                 2140                 2145

Thr Asp  Pro Pro His Ile Thr  Ala Glu Thr Ala Ala  Arg Arg Leu
    2150                 2155                 2160

Ala Arg  Gly Ser Pro Pro Ser  Glu Ala Ser Ser Ser  Val Ser Gln
    2165                 2170                 2175

Leu Ser  Ala Pro Ser Leu Arg  Ala Thr Cys Thr Thr  His Ser Asn
    2180                 2185                 2190

Thr Tyr  Asp Val Asp Met Val  Asp Ala Asn Leu Leu  Met Glu Gly
    2195                 2200                 2205

Gly Val  Ala Gln Thr Glu Pro  Glu Ser Arg Val Pro  Val Leu Asp
    2210                 2215                 2220

Phe Leu  Glu Pro Met Ala Glu  Glu Glu Ser Asp Leu  Glu Pro Ser
    2225                 2230                 2235

Ile Pro  Ser Glu Cys Met Leu  Pro Arg Ser Gly Phe  Pro Arg Ala
    2240                 2245                 2250

Leu Pro  Ala Trp Ala Arg Pro  Asp Tyr Asn Pro Pro  Leu Val Glu
    2255                 2260                 2265

Ser Trp  Arg Arg Pro Asp Tyr  Gln Pro Pro Thr Val  Ala Gly Cys
    2270                 2275                 2280

Ala Leu  Pro Pro Pro Lys Lys  Ala Pro Thr Pro Pro  Pro Arg Arg
    2285                 2290                 2295
```

```
Arg Arg  Thr Val Gly Leu Ser  Glu Ser Thr Ile Ser  Glu Ala Leu
    2300                 2305                 2310

Gln Gln  Leu Ala Ile Lys Thr  Phe Gly Gln Pro Pro  Ser Ser Gly
    2315                 2320                 2325

Asp Ala  Gly Ser Ser Thr Gly  Ala Gly Ala Ala Glu  Ser Gly Gly
    2330                 2335                 2340

Pro Thr  Ser Pro Gly Glu Pro  Ala Pro Ser Glu Thr  Gly Ser Ala
    2345                 2350                 2355

Ser Ser  Met Pro Pro Leu Glu  Gly Glu Pro Gly Asp  Pro Asp Leu
    2360                 2365                 2370

Glu Ser  Asp Gln Val Glu Leu  Gln Pro Pro Pro Gln  Gly Gly Gly
    2375                 2380                 2385

Val Ala  Pro Gly Ser Gly Ser  Gly Ser Trp Ser Thr  Cys Ser Glu
    2390                 2395                 2400

Glu Asp  Asp Thr Thr Val Cys  Cys Ser Met Ser Tyr  Ser Trp Thr
    2405                 2410                 2415

Gly Ala  Leu Ile Thr Pro Cys  Ser Pro Glu Glu Glu  Lys Leu Pro
    2420                 2425                 2430

Ile Asn  Pro Leu Ser Asn Ser  Leu Leu Arg Tyr His  Asn Lys Val
    2435                 2440                 2445

Tyr Cys  Thr Thr Ser Lys Ser  Ala Ser Gln Arg Ala  Lys Lys Val
    2450                 2455                 2460

Thr Phe  Asp Arg Thr Gln Val  Leu Asp Ala His Tyr  Asp Ser Val
    2465                 2470                 2475

Leu Lys  Asp Ile Lys Leu Ala  Ala Ser Lys Val Ser  Ala Arg Leu
    2480                 2485                 2490

Leu Thr  Leu Glu Glu Ala Cys  Gln Leu Thr Pro Pro  His Ser Ala
    2495                 2500                 2505

Arg Ser  Lys Tyr Gly Phe Gly  Ala Lys Glu Val Arg  Ser Leu Ser
    2510                 2515                 2520

Gly Arg  Ala Val Asn His Ile  Lys Ser Val Trp Lys  Asp Leu Leu
    2525                 2530                 2535

Glu Asp  Pro Gln Thr Pro Ile  Pro Thr Thr Ile Met  Ala Lys Asn
    2540                 2545                 2550

Glu Val  Phe Cys Val Asp Pro  Ala Lys Gly Gly Lys  Lys Pro Ala
    2555                 2560                 2565

Arg Leu  Ile Val Tyr Pro Asp  Leu Gly Val Arg Val  Cys Glu Lys
    2570                 2575                 2580

Met Ala  Leu Tyr Asp Ile Thr  Gln Lys Leu Pro Gln  Ala Val Met
    2585                 2590                 2595

Gly Ala  Ser Tyr Gly Phe Gln  Tyr Ser Pro Ala Gln  Arg Val Glu
    2600                 2605                 2610

Tyr Leu  Leu Lys Ala Trp Ala  Glu Lys Lys Asp Pro  Met Gly Phe
    2615                 2620                 2625

Ser Tyr  Asp Thr Arg Cys Phe  Asp Ser Thr Val Thr  Glu Arg Asp
    2630                 2635                 2640

Ile Arg  Thr Glu Glu Ser Ile  Tyr Gln Ala Cys Ser  Leu Pro Glu
    2645                 2650                 2655

Glu Ala  Arg Thr Ala Ile His  Ser Leu Thr Glu Arg  Leu Tyr Val
    2660                 2665                 2670

Gly Gly  Pro Met Phe Asn Ser  Lys Gly Gln Thr Cys  Gly Tyr Arg
    2675                 2680                 2685

Arg Cys  Arg Ala Ser Gly Val  Leu Thr Thr Ser Met  Gly Asn Thr
```

```
    2690                2695                2700

Ile Thr  Cys Tyr Val Lys Ala  Leu Ala Ala Cys Lys  Ala Ala Gly
    2705                2710                2715

Ile Val  Ala Pro Thr Met Leu  Val Cys Gly Asp Asp  Leu Val Val
    2720                2725                2730

Ile Ser  Glu Ser Gln Gly Thr  Glu Glu Asp Glu Arg  Asn Leu Arg
    2735                2740                2745

Ala Phe  Thr Glu Ala Met Thr  Arg Tyr Ser Ala Pro  Pro Gly Asp
    2750                2755                2760

Pro Pro  Arg Pro Glu Tyr Asp  Leu Glu Leu Ile Thr  Ser Cys Ser
    2765                2770                2775

Ser Asn  Val Ser Val Ala Leu  Gly Pro Arg Gly Arg  Arg Arg Tyr
    2780                2785                2790

Tyr Leu  Thr Arg Asp Pro Thr  Thr Pro Leu Ala Arg  Ala Ala Trp
    2795                2800                2805

Glu Thr  Val Arg His Ser Pro  Ile Asn Ser Trp Leu  Gly Asn Ile
    2810                2815                2820

Ile Gln  Tyr Ala Pro Thr Ile  Trp Val Arg Met Val  Leu Met Thr
    2825                2830                2835

His Phe  Phe Ser Ile Leu Met  Val Gln Asp Thr Leu  Asp Gln Asn
    2840                2845                2850

Leu Asn  Phe Glu Met Tyr Gly  Ser Val Tyr Ser Val  Asn Pro Leu
    2855                2860                2865

Asp Leu  Pro Ala Ile Ile Glu  Arg Leu His Gly Leu  Asp Ala Phe
    2870                2875                2880

Ser Met  His Thr Tyr Ser His  His Glu Leu Thr Arg  Val Ala Ser
    2885                2890                2895

Ala Leu  Arg Lys Leu Gly Ala  Pro Pro Leu Arg Val  Trp Lys Ser
    2900                2905                2910

Arg Ala  Arg Ala Val Arg Ala  Ser Leu Ile Ser Arg  Gly Gly Lys
    2915                2920                2925

Ala Ala  Val Cys Gly Arg Tyr  Leu Phe Asn Trp Ala  Val Lys Thr
    2930                2935                2940

Lys Leu  Lys Leu Thr Pro Leu  Pro Glu Ala Arg Leu  Leu Asp Leu
    2945                2950                2955

Ser Ser  Trp Phe Thr Val Gly  Ala Gly Gly Gly Asp  Ile Phe His
    2960                2965                2970

Ser Val  Ser Arg Ala Arg Pro  Arg Ser Leu Leu Phe  Gly Leu Leu
    2975                2980                2985

Leu Leu  Phe Val Gly Val Gly  Leu Phe Leu Leu Pro  Ala Arg
    2990                2995                3000


<210> SEQ ID NO 15
<211> LENGTH: 3008
<212> TYPE: PRT
<213> ORGANISM: Hepatitis C virus

<400> SEQUENCE: 15

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45
```

```
Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Val His Pro Ala Ala Ser Leu
            180                 185                 190

Glu Trp Arg Asn Thr Ser Gly Leu Tyr Val Leu Thr Asn Asp Cys Ser
        195                 200                 205

Asn Ser Ser Ile Val Tyr Glu Ala Asp Asp Val Ile Leu His Thr Pro
    210                 215                 220

Gly Cys Val Pro Cys Val Gln Asp Asp Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Leu Cys
            260                 265                 270

Ser Ala Leu Tyr Val Gly Asp Met Cys Gly Ala Val Phe Leu Val Gly
        275                 280                 285

Gln Ala Phe Thr Phe Arg Pro Arg Arg His Gln Thr Val Gln Thr Cys
    290                 295                 300

Asn Cys Ser Leu Tyr Pro Gly His Val Ser Gly His Arg Met Ala Trp
305                 310                 315                 320

Asp Met Met Met Asn Trp Ser Pro Ala Val Gly Met Val Val Ala His
                325                 330                 335

Ile Leu Arg Leu Pro Gln Thr Leu Phe Asp Ile Leu Ala Gly Ala His
            340                 345                 350

Trp Gly Ile Leu Ala Gly Leu Ala Tyr Tyr Ser Met Gln Gly Asn Trp
        355                 360                 365

Val Lys Val Ala Ile Val Met Ile Met Phe Ser Gly Val Asp Ala Leu
    370                 375                 380

Gln Leu Val Asn Thr Asn Gly Ser Trp His Ile Asn Ser Thr Ala Leu
385                 390                 395                 400

Asn Cys Asn Glu Ser Ile Asn Thr Gly Phe Ile Ala Gly Leu Phe Tyr
                405                 410                 415

Tyr His Lys Phe Asn Ser Thr Gly Cys Pro Gln Arg Leu Ser Ser Cys
            420                 425                 430

Lys Pro Ile Ile Ser Phe Arg Gln Gly Trp Gly Pro Leu Thr Asp Ala
        435                 440                 445

Asn Ile Thr Gly Pro Ser Asp Asp Arg Pro Tyr Cys Trp His Tyr Ala
    450                 455                 460

Pro Arg Pro Cys Ser Val Val Pro Ala Ser Ser Val Cys Gly Pro Val
```

-continued

```
465                 470                 475                 480

Tyr Cys Phe Thr Pro Ser Pro Val Val Val Gly Thr Thr Asp Ile Lys
                485                 490                 495

Gly Lys Pro Thr Tyr Asn Trp Gly Glu Asn Glu Thr Asp Val Phe Leu
            500                 505                 510

Leu Glu Ser Leu Arg Pro Pro Ser Gly Arg Trp Phe Gly Cys Ala Trp
        515                 520                 525

Met Asn Ser Thr Gly Phe Leu Lys Thr Cys Gly Ala Pro Pro Cys Asn
    530                 535                 540

Ile Tyr Gly Gly Glu Gly Asp Pro Glu Asn Glu Thr Asp Leu Phe Cys
545                 550                 555                 560

Pro Thr Asp Cys Phe Arg Lys His Pro Glu Ala Thr Tyr Ser Arg Cys
                565                 570                 575

Gly Ala Gly Pro Trp Leu Thr Pro Arg Cys Met Val Asp Tyr Pro Tyr
            580                 585                 590

Arg Leu Trp His Tyr Pro Cys Thr Val Asn Phe Thr Leu Phe Lys Val
        595                 600                 605

Arg Met Phe Val Gly Gly Phe Glu His Arg Phe Thr Ala Ala Cys Asn
    610                 615                 620

Trp Thr Arg Gly Glu Arg Cys Asn Ile Glu Asp Arg Asp Arg Ser Glu
625                 630                 635                 640

Gln His Pro Leu Leu His Ser Thr Thr Glu Leu Ala Ile Leu Pro Cys
                645                 650                 655

Ser Phe Thr Pro Met Pro Ala Leu Ser Thr Gly Leu Ile His Leu His
            660                 665                 670

Gln Asn Ile Val Asp Val Gln Tyr Leu Tyr Gly Val Gly Ser Asp Met
        675                 680                 685

Val Gly Trp Ala Leu Lys Trp Glu Phe Val Ile Leu Val Phe Leu Leu
    690                 695                 700

Leu Ala Asp Ala Arg Val Cys Val Ala Leu Trp Leu Met Leu Met Val
705                 710                 715                 720

Ser Gln Ala Glu Ala Ala Leu Glu Asn Leu Val Thr Leu Asn Ala Val
                725                 730                 735

Ala Ala Ala Gly Thr His Gly Ile Gly Trp Tyr Leu Val Ala Phe Cys
            740                 745                 750

Ala Ala Trp Tyr Val Arg Gly Lys Leu Val Pro Leu Thr Ser Tyr Gly
        755                 760                 765

Leu Thr Gly Leu Trp Ser Leu Ala Leu Leu Val Leu Leu Leu Pro Gln
    770                 775                 780

Arg Ala Tyr Ala Trp Ser Gly Glu Asp Ser Ala Thr Leu Gly Ala Gly
785                 790                 795                 800

Val Leu Ala Leu Phe Gly Phe Phe Thr Leu Ser Pro Trp Tyr Lys His
                805                 810                 815

Trp Ile Gly Arg Leu Met Trp Trp Asn Gln Tyr Thr Ile Cys Arg Cys
            820                 825                 830

Glu Ala Ala Leu Gln Val Trp Val Pro Pro Leu Leu Ala Arg Gly Ser
        835                 840                 845

Arg Asp Gly Val Ile Leu Leu Thr Ser Leu Leu Tyr Pro Ser Leu Ile
    850                 855                 860

Phe Asp Ile Thr Lys Leu Leu Ile Ala Val Ile Gly Pro Leu Tyr Leu
865                 870                 875                 880

Ile Gln Ala Ala Ile Thr Thr Thr Pro Tyr Phe Val Arg Ala His Val
                885                 890                 895
```

-continued

```
Leu Val Arg Leu Cys Met Leu Val Arg Ser Val Met Gly Gly Lys Tyr
            900                 905                 910

Phe Gln Met Ala Ile Leu Ser Ile Gly Arg Trp Phe Asn Thr Tyr Leu
        915                 920                 925

Tyr Asp His Leu Ala Pro Met Gln His Trp Ala Ala Ala Gly Leu Lys
    930                 935                 940

Asp Leu Ala Val Ala Thr Glu Pro Val Ile Phe Ser Pro Met Glu Ile
945                 950                 955                 960

Lys Val Ile Thr Trp Gly Ala Asp Thr Ala Ala Cys Gly Asp Ile Leu
                965                 970                 975

Cys Gly Leu Pro Val Ser Ala Arg Leu Gly Arg Glu Val Leu Leu Gly
            980                 985                 990

Pro Ala Asp Asp Tyr Arg Glu Met  Gly Trp Arg Leu Leu  Ala Pro Ile
        995                 1000                1005

Thr Ala  Tyr Ala Gln Gln Thr  Arg Gly Leu Leu Gly  Ala Ile Val
    1010                1015                1020

Val Ser  Met Thr Gly Arg Asp  Arg Thr Glu Gln Ala  Gly Glu Val
    1025                1030                1035

Gln Ile  Leu Ser Thr Val Ser  Gln Ser Phe Leu Gly  Thr Thr Ile
    1040                1045                1050

Ser Gly  Val Leu Trp Thr Val  Tyr His Gly Ala Gly  Asn Lys Thr
    1055                1060                1065

Leu Ala  Gly Leu Arg Gly Pro  Val Thr Gln Met Tyr  Ser Ser Ala
    1070                1075                1080

Glu Gly  Asp Leu Val Gly Trp  Pro Ser Pro Pro Gly  Thr Lys Ser
    1085                1090                1095

Leu Glu  Pro Cys Lys Cys Gly  Ala Val Asp Leu Tyr  Leu Val Thr
    1100                1105                1110

Arg Asn  Ala Asp Val Ile Pro  Ala Arg Arg Arg Gly  Asp Lys Arg
    1115                1120                1125

Gly Ala  Leu Leu Ser Pro Arg  Pro Ile Ser Thr Leu  Lys Gly Ser
    1130                1135                1140

Ser Gly  Gly Pro Val Leu Cys  Pro Arg Gly His Val  Val Gly Leu
    1145                1150                1155

Phe Arg  Ala Ala Val Cys Ser  Arg Gly Val Ala Lys  Ser Ile Asp
    1160                1165                1170

Phe Ile  Pro Val Glu Thr Leu  Asp Val Val Thr Arg  Ser Pro Thr
    1175                1180                1185

Phe Ser  Asp Asn Ser Thr Pro  Pro Ala Val Pro Gln  Thr Tyr Gln
    1190                1195                1200

Val Gly  Tyr Leu His Ala Pro  Thr Gly Ser Gly Lys  Ser Thr Lys
    1205                1210                1215

Val Pro  Val Ala Tyr Ala Ala  Gln Gly Tyr Lys Val  Leu Val Leu
    1220                1225                1230

Asn Pro  Ser Val Ala Ala Thr  Leu Gly Phe Gly Ala  Tyr Leu Ser
    1235                1240                1245

Lys Ala  His Gly Ile Asn Pro  Asn Ile Arg Thr Gly  Val Arg Thr
    1250                1255                1260

Val Met  Thr Gly Glu Ala Ile  Thr Tyr Ser Thr Tyr  Gly Lys Phe
    1265                1270                1275

Leu Ala  Asp Gly Gly Cys Ala  Ser Gly Ala Tyr Asp  Ile Ile Ile
    1280                1285                1290
```

Cys Asp Glu Cys His Ala Val Asp Ala Thr Ser Ile Leu Gly Ile
1295 1300 1305

Gly Thr Val Leu Asp Gln Ala Glu Thr Ala Gly Val Arg Leu Thr
1310 1315 1320

Val Leu Ala Thr Ala Thr Pro Pro Gly Ser Val Thr Thr Pro His
1325 1330 1335

Pro Asp Ile Glu Glu Val Gly Leu Gly Arg Glu Gly Glu Ile Pro
1340 1345 1350

Phe Tyr Gly Arg Ala Ile Pro Leu Ser Cys Ile Lys Gly Gly Arg
1355 1360 1365

His Leu Ile Phe Cys His Ser Lys Lys Lys Cys Asp Glu Leu Ala
1370 1375 1380

Ala Ala Leu Arg Gly Met Gly Leu Asn Ala Val Ala Tyr Tyr Arg
1385 1390 1395

Gly Leu Asp Val Ser Ile Ile Pro Ala Gln Gly Asp Val Val Val
1400 1405 1410

Val Ala Thr Asp Ala Leu Met Thr Gly Tyr Thr Gly Asp Phe Asp
1415 1420 1425

Ser Val Ile Asp Cys Asn Val Ala Val Thr Gln Ala Val Asp Phe
1430 1435 1440

Ser Leu Asp Pro Thr Phe Thr Ile Thr Thr Gln Thr Val Pro Gln
1445 1450 1455

Asp Ala Val Ser Arg Ser Gln Arg Arg Gly Arg Thr Gly Arg Gly
1460 1465 1470

Arg Gln Gly Thr Tyr Arg Tyr Val Ser Thr Gly Glu Arg Ala Ser
1475 1480 1485

Gly Met Phe Asp Ser Val Val Leu Cys Glu Cys Tyr Asp Ala Gly
1490 1495 1500

Ala Ala Trp Tyr Asp Leu Thr Pro Ala Glu Thr Thr Val Arg Leu
1505 1510 1515

Arg Ala Tyr Phe Asn Thr Pro Gly Leu Pro Val Cys Gln Asp His
1520 1525 1530

Leu Glu Phe Trp Glu Ala Val Phe Thr Gly Leu Thr His Ile Asp
1535 1540 1545

Ala His Phe Leu Ser Gln Thr Lys Gln Ala Gly Glu Asn Phe Ala
1550 1555 1560

Tyr Leu Val Ala Tyr Gln Ala Thr Val Cys Ala Arg Ala Lys Ala
1565 1570 1575

Pro Pro Pro Ser Trp Asp Ala Met Trp Lys Cys Leu Ala Arg Leu
1580 1585 1590

Lys Pro Thr Leu Ala Gly Pro Thr Pro Leu Leu Tyr Arg Leu Gly
1595 1600 1605

Pro Ile Thr Asn Glu Val Thr Leu Thr His Pro Gly Thr Lys Tyr
1610 1615 1620

Ile Ala Thr Cys Met Gln Ala Asp Leu Glu Val Met Thr Ser Thr
1625 1630 1635

Trp Val Leu Ala Gly Gly Val Leu Ala Ala Val Ala Ala Tyr Cys
1640 1645 1650

Leu Ala Thr Gly Cys Val Ser Ile Ile Gly Arg Leu His Val Asn
1655 1660 1665

Gln Arg Val Val Val Ala Pro Asp Lys Glu Val Leu Tyr Glu Ala
1670 1675 1680

Phe Asp Glu Met Glu Glu Cys Ala Ser Arg Ala Ala Leu Ile Glu 1685 1690 1695

Glu Gly Gln Arg Ile Ala Glu Met Leu Lys Ser Lys Ile Gln Gly
1700 1705 1710

Leu Leu Gln Gln Ala Ser Lys Gln Ala Gln Asp Ile Gln Pro Ala
1715 1720 1725

Met Gln Ala Ser Trp Pro Lys Val Glu Gln Phe Trp Ala Arg His
1730 1735 1740

Met Trp Asn Phe Ile Ser Gly Ile Gln Tyr Leu Ala Gly Leu Ser
1745 1750 1755

Thr Leu Pro Gly Asn Pro Ala Val Ala Ser Met Met Ala Phe Ser
1760 1765 1770

Ala Ala Leu Thr Ser Pro Leu Ser Thr Ser Thr Thr Ile Leu Leu
1775 1780 1785

Asn Ile Met Gly Gly Trp Leu Ala Ser Gln Ile Ala Pro Pro Ala
1790 1795 1800

Gly Ala Thr Gly Phe Val Val Ser Gly Leu Val Gly Ala Ala Val
1805 1810 1815

Gly Ser Ile Gly Leu Gly Lys Val Leu Val Asp Ile Leu Ala Gly
1820 1825 1830

Tyr Gly Ala Gly Ile Ser Gly Ala Leu Val Ala Phe Lys Ile Met
1835 1840 1845

Ser Gly Glu Lys Pro Ser Met Glu Asp Val Ile Asn Leu Leu Pro
1850 1855 1860

Gly Ile Leu Ser Pro Gly Ala Leu Val Val Gly Val Ile Cys Ala
1865 1870 1875

Ala Ile Leu Arg Arg His Val Gly Pro Gly Glu Gly Ala Val Gln
1880 1885 1890

Trp Met Asn Arg Leu Ile Ala Phe Ala Ser Arg Gly Asn His Val
1895 1900 1905

Ala Pro Thr His Tyr Val Thr Glu Ser Asp Ala Ser Gln Arg Val
1910 1915 1920

Thr Gln Leu Leu Gly Ser Leu Thr Ile Thr Ser Leu Leu Arg Arg
1925 1930 1935

Leu His Asn Trp Ile Thr Glu Asp Cys Pro Ile Pro Cys Ser Gly
1940 1945 1950

Ser Trp Leu Arg Asp Val Trp Asp Trp Val Cys Thr Ile Leu Thr
1955 1960 1965

Asp Phe Lys Asn Trp Leu Thr Ser Lys Leu Phe Pro Lys Leu Pro
1970 1975 1980

Gly Leu Pro Phe Ile Ser Cys Gln Lys Gly Tyr Lys Gly Val Trp
1985 1990 1995

Ala Gly Thr Gly Ile Met Thr Thr Arg Cys Pro Cys Gly Ala Asn
2000 2005 2010

Ile Ser Gly Asn Val Arg Leu Gly Ser Met Arg Ile Thr Gly Pro
2015 2020 2025

Lys Thr Cys Met Asn Thr Trp Gln Gly Thr Phe Pro Ile Asn Cys
2030 2035 2040

Tyr Thr Glu Gly Gln Cys Ala Pro Lys Pro Pro Thr Asn Tyr Lys
2045 2050 2055

Thr Ala Ile Trp Arg Val Ala Ala Ser Glu Tyr Ala Glu Val Thr
2060 2065 2070

Gln His Gly Ser Tyr Ser Tyr Val Thr Gly Leu Thr Thr Asp Asn
2075 2080 2085

```
Leu Lys  Ile Pro Cys Gln Leu  Pro Ser Pro Glu Phe  Phe Ser Trp
    2090                 2095                 2100

Val Asp  Gly Val Gln Ile His  Arg Phe Ala Pro Thr  Pro Lys Pro
    2105                 2110                 2115

Phe Phe  Arg Asp Glu Val Ser  Phe Cys Val Gly Leu  Asn Ser Tyr
    2120                 2125                 2130

Ala Val  Gly Ser Gln Leu Pro  Cys Glu Pro Glu Pro  Asp Ala Asp
    2135                 2140                 2145

Val Leu  Arg Ser Met Leu Thr  Asp Pro Pro His Ile  Thr Ala Glu
    2150                 2155                 2160

Thr Ala  Ala Arg Arg Leu Ala  Arg Gly Ser Pro Pro  Ser Glu Ala
    2165                 2170                 2175

Ser Ser  Ser Val Ser Gln Leu  Ser Ala Pro Ser Leu  Arg Ala Thr
    2180                 2185                 2190

Cys Thr  Thr His Ser Asn Thr  Tyr Asp Val Asp Met  Val Asp Ala
    2195                 2200                 2205

Asn Leu  Leu Met Glu Gly Gly  Val Ala Gln Thr Glu  Pro Glu Ser
    2210                 2215                 2220

Arg Val  Pro Val Leu Asp Phe  Leu Glu Pro Met Ala  Glu Glu Glu
    2225                 2230                 2235

Ser Asp  Leu Glu Pro Ser Ile  Pro Pro Glu Cys Met  Leu Pro Arg
    2240                 2245                 2250

Ser Gly  Phe Pro Arg Ala Leu  Pro Ala Trp Ala Arg  Pro Asp Tyr
    2255                 2260                 2265

Asn Pro  Pro Leu Val Glu Ser  Trp Arg Arg Pro Asp  Tyr Gln Pro
    2270                 2275                 2280

Pro Thr  Val Ala Gly Cys Ala  Leu Pro Pro Pro Lys  Lys Ala Pro
    2285                 2290                 2295

Thr Pro  Pro Pro Arg Arg Arg  Arg Thr Val Gly Leu  Ser Glu Ser
    2300                 2305                 2310

Thr Ile  Ser Glu Ala Leu Gln  Gln Leu Ala Ile Lys  Thr Phe Gly
    2315                 2320                 2325

Gln Pro  Pro Ser Ser Gly Asp  Ala Gly Ser Ser Thr  Gly Ala Gly
    2330                 2335                 2340

Ala Ala  Glu Ser Gly Gly Pro  Thr Ser Pro Gly Glu  Pro Ala Pro
    2345                 2350                 2355

Ser Glu  Thr Gly Ser Ala Ser  Ser Met Pro Pro Leu  Glu Gly Glu
    2360                 2365                 2370

Pro Gly  Asp Pro Asp Leu Glu  Ser Asp Gln Val Glu  Leu Gln Pro
    2375                 2380                 2385

Pro Pro  Gln Gly Gly Gly Val  Ala Pro Gly Ser Gly  Ser Gly Ser
    2390                 2395                 2400

Trp Ser  Thr Cys Ser Glu Glu  Asp Asp Thr Thr Val  Cys Cys Ser
    2405                 2410                 2415

Met Ser  Tyr Ser Trp Thr Gly  Ala Leu Ile Thr Pro  Cys Ser Pro
    2420                 2425                 2430

Glu Glu  Glu Lys Leu Pro Ile  Asn Pro Leu Ser Asn  Ser Leu Leu
    2435                 2440                 2445

Arg Tyr  His Asn Lys Val Tyr  Cys Thr Thr Ser Lys  Ser Ala Ser
    2450                 2455                 2460

Gln Arg  Ala Lys Lys Val Thr  Phe Asp Arg Thr Gln  Val Leu Asp
    2465                 2470                 2475
```

```
Ala His Tyr Asp Ser Val Leu Lys Asp Ile Lys Leu Ala Ala Ser
    2480                2485                2490

Lys Val Ser Ala Arg Leu Leu Thr Leu Glu Glu Ala Cys Gln Leu
    2495                2500                2505

Thr Pro Pro His Ser Ala Arg Ser Lys Tyr Gly Phe Gly Ala Lys
    2510                2515                2520

Glu Val Arg Ser Leu Ser Gly Arg Ala Val Asn His Ile Lys Ser
    2525                2530                2535

Val Trp Lys Asp Leu Leu Glu Asp Pro Gln Thr Pro Ile Pro Thr
    2540                2545                2550

Thr Ile Met Ala Lys Asn Glu Val Phe Cys Val Asp Pro Ala Lys
    2555                2560                2565

Gly Gly Lys Lys Pro Ala Arg Leu Ile Val Tyr Pro Asp Leu Gly
    2570                2575                2580

Val Arg Val Cys Glu Lys Met Ala Leu Tyr Asp Ile Thr Gln Lys
    2585                2590                2595

Leu Pro Gln Ala Val Met Gly Ala Ser Tyr Gly Phe Gln Tyr Ser
    2600                2605                2610

Pro Ala Gln Arg Val Glu Tyr Leu Leu Lys Ala Trp Ala Glu Lys
    2615                2620                2625

Lys Asp Pro Met Gly Phe Ser Tyr Asp Thr Arg Cys Phe Asp Ser
    2630                2635                2640

Thr Val Thr Glu Arg Asp Ile Arg Thr Glu Glu Ser Ile Tyr Gln
    2645                2650                2655

Ala Cys Ser Leu Pro Glu Glu Ala Arg Thr Ala Ile His Ser Leu
    2660                2665                2670

Thr Glu Arg Leu Tyr Val Gly Gly Pro Met Phe Asn Ser Lys Gly
    2675                2680                2685

Gln Thr Cys Gly Tyr Arg Arg Cys Arg Ala Ser Gly Val Leu Thr
    2690                2695                2700

Thr Ser Met Gly Asn Thr Ile Thr Cys Tyr Val Lys Ala Leu Ala
    2705                2710                2715

Ala Cys Lys Ala Ala Gly Ile Val Ala Pro Thr Met Leu Val Cys
    2720                2725                2730

Gly Asp Asp Leu Val Val Ile Ser Glu Ser Gln Gly Thr Glu Glu
    2735                2740                2745

Asp Glu Arg Asn Leu Arg Ala Phe Thr Glu Ala Met Thr Arg Tyr
    2750                2755                2760

Ser Ala Pro Pro Gly Asp Pro Pro Arg Pro Glu Tyr Asp Leu Glu
    2765                2770                2775

Leu Ile Thr Ser Cys Ser Ser Asn Val Ser Val Ala Leu Gly Pro
    2780                2785                2790

Arg Gly Arg Arg Arg Tyr Tyr Leu Thr Arg Asp Pro Thr Thr Pro
    2795                2800                2805

Leu Ala Arg Ala Ala Trp Glu Thr Val Arg His Ser Pro Ile Asn
    2810                2815                2820

Ser Trp Leu Gly Asn Ile Ile Gln Tyr Ala Pro Thr Ile Trp Val
    2825                2830                2835

Arg Met Val Leu Met Thr His Phe Phe Ser Ile Leu Met Val Gln
    2840                2845                2850

Asp Thr Leu Asp Gln Asn Leu Asn Phe Glu Met Tyr Gly Ser Val
    2855                2860                2865

Tyr Ser Val Asn Pro Leu Asp Leu Pro Ala Ile Ile Glu Arg Leu
```

-continued 2870 2875 2880

His Gly Leu Asp Ala Phe Ser Met His Thr Tyr Ser His His Glu
2885 2890 2895

Leu Thr Arg Val Ala Ser Ala Leu Arg Lys Leu Gly Ala Pro Pro
2900 2905 2910

Leu Arg Val Trp Lys Ser Arg Ala Arg Ala Val Arg Ala Ser Leu
2915 2920 2925

Ile Ser Arg Gly Gly Lys Ala Ala Val Cys Gly Arg Tyr Leu Phe
2930 2935 2940

Asn Trp Ala Val Lys Thr Lys Leu Lys Leu Thr Pro Leu Pro Glu
2945 2950 2955

Ala Arg Leu Leu Asp Leu Ser Ser Trp Phe Thr Val Gly Ala Gly
2960 2965 2970

Gly Gly Asp Ile Phe His Ser Val Ser Arg Ala Arg Pro Arg Ser
2975 2980 2985

Leu Leu Phe Gly Leu Leu Leu Leu Phe Val Gly Val Gly Leu Phe
2990 2995 3000

Leu Leu Pro Ala Arg
3005

<210> SEQ ID NO 16
<211> LENGTH: 9585
<212> TYPE: DNA
<213> ORGANISM: Hepatitis C virus

<400> SEQUENCE: 16
acctgcccct aataggggcg acactccgcc atgaatcact cccctgtgag gaactactgt 60
cttcacgcag aaagcgccta gccatggcgt tagtatgagt gtcgtacagc ctccaggccc 120
ccccctcccg ggagagccat agtggtctgc ggaaccggtg agtacaccgg aattgccggg 180
aagactgggt cctttcttgg ataaacccac tctatgcccg gccatttggg cgtgcccccg 240
caagactgct agccgagtag cgttgggttg cgaaaggcct tgtggtactg cctgataggg 300
cgcttgcgag tgccccggga ggtctcgtag accgtgcacc atgagcacga atcctaaacc 360
tcaaagaaaa accaaacgta acaccaaccg tcgcccacag gacgtcaagt tcccgggtgg 420
cggtcagatc gttggtggag tttacttgtt gccgcgcagg ggccctagat tgggtgtgcg 480
cgcgacgagg aagacttccg agcggtcgca acctcgaggt agacgtcagc ctatccccaa 540
ggcacgtcgg cccgagggca ggacctgggc tcagcccggg taccccttggc ccctctatgg 600 caatgagggt tgcgggtggg cgggatggct cctgtctccc cgtggctctc ggcctagctg 660
gggccccaca gacccccggc gtaggtcgcg caatttgggt aaggtcatcg ataccccttac 720 gtgcggcttc gccgacctca tggggtacat accgctcgtc ggcgcccctc ttggaggcgc 780
tgccagggcc ctggcgcatg gcgtccgggt tctggaagac ggcgtgaact atgcaacagg 840
gaaccttcct ggttgctctt tctctatctt ccttctggcc ctgctctctt gcctgactgt 900
gcccgcttca gcctaccaag tgcgcaattc ctcggggctt taccatgtca ccaatgattg 960
ccctaactcg agtattgtgt acgaggcggc cgatgccatc ctgcacactc cggggtgtgt 1020
cccttgcgtt cgcgagggta acgcctcgag gtgttgggtg gcggtgaccc ccacggtggc 1080
caccagggac ggcaaactcc ccacaacgca gcttcgacgt cgtatcgatc tgcttgtcgg 1140
gagcgccacc ctctgctcgg ccctctacgt gggggacctg tgcgggtctg tctttcttgt 1200
tggtcaactg tttaccttct ctcccaggcg ccactggacg acgcaagact gcaattgttc 1260

-continued

```
tatctatccc ggccatataa cgggtcatcg catggcatgg gatatgatga tgaactggtc   1320
ccctacggca gcgttggtgg tagctcagct gctccggatc ccacaagcca tcatggacat   1380
gatcgctggt gctcactggg gagtcctggc gggcatagcg tatttctcca tggtggggaa   1440
ctgggcgaag gtcctggtag tgctgctgct atttgccggc gtcgacgcga tccaactgat   1500
caacaccaac ggcagttggc acatcaatag cacggccttg aattgcaatg aaagccttaa   1560
caccggctgg ttagcagggc tcttctatcg acacaaattc aactcttcag gctgtcctga   1620
gaggttggcc agctgccgac gccttaccga ttttgcccag ggctggggtc ctatcagtta   1680
tgccaacgga agcggcctcg acgaacgccc ctactgctgg cactaccctc caagaccttg   1740
tggcattgtg cccgcaaaga gcgtgtgtgg cccggtatat tgcttcactc ccagccccgt   1800
ggtggtggga acgaccgaca ggtcgggcgc gcctacctac agctggggtg caaatgatac   1860
ggatgtcttc gtccttaaca acaccaggcc accgctgggc aattggttcg gttgtacctg   1920
gatgaactca actggattca ccaaagtgtg cggagcgccc ccttgtgtca tcggaggggt   1980
gggcaacaac accttgctct gccccactga ttgcttccgc aaacatccgg aagccacata   2040
ctctcggtgc ggctccggtc cctggattac acccaggtgc atggtcgact acccgtatag   2100
gctttggcac tatccttgta ccatcaatta caccatattc aaagtcagga tgtacgtggg   2160
aggggtcgag cacaggctgg aagcggcctg caactggacg cggggcgaac gctgtgatct   2220
ggaagacagg gacaggtccg agctcagccc gttgctgctg tccaccacac agtggcaggt   2280
ccttccgtgt tctttcacga ccctgccagc cttgtccacc ggcctcatcc acctccacca   2340
gaacattgtg gacgtgcagt acttgtacgg ggtagggtca agcatcgcgt cctgggccat   2400
taagtgggag tacgtcgttc tcctgttcct tctgcttgca gacgcgcgcg tctgctcctg   2460
cttgtggatg atgttactca tatcccaagc ggaggcggct ttggagaacc tcgtaatact   2520
caatgcagca tccctggccg ggacgcacgg tcttgtgtcc ttcctcgtgt tcttctgctt   2580
tgcgtggtat ctgaagggta ggtgggtgcc cggagcggcc tacgccctct acgggatgtg   2640
gcctctcctc ctgctcctgc tggcgttgcc tcagcgggca tacgcactgg acacggaggt   2700
ggccgcgtcg tgtggcggcg ttgttcttgt cgggttaatg gcgctgactc tgtcgccata   2760
ttacaagcgc tatatcagct ggtgcatgtg gtggcttcag tattttctga ccagagtaga   2820
agcgcaactg cacgtgtggg ttcccccccct caacgtccgg ggggggcgcg atgccgtcat   2880
cttactcatg tgtgtagtac acccgaccct ggtatttgac atcaccaaac tactcctggc   2940
catcttcgga cccctttgga ttcttcaagc cagtttgctt aaagtcccct acttcgtgcg   3000
cgttcaaggc cttctccgga tctgcgcgct agcgcggaag atagccggag gtcattacgt   3060
gcaaatggcc atcatcaagt taggggcgct tactggcacc tatgtgtata accatctcac   3120
ccctcttcga gactgggcgc acaacggcct gcgagatctg gccgtggctg tggaaccagt   3180
cgtcttctcc cgaatggaga ccaagctcat cacgtggggg gcagataccg ccgcgtgcgg   3240
tgacatcatc aacggcttgc ccgtctctgc ccgtaggggc caggagatac tgcttgggcc   3300
agccgacgga atggtctcca aggggtggag gttgctggct cccatcactg cttatgccca   3360
gcaaacacga ggcctcctgg gcgccatagt ggtgagtatg acggggcgtg acaggacaga   3420
acaggccggg gaagtccaaa tcctgtccac agtctctcag tccttcctcg gaacaaccat   3480
ctcgggggtt ttgtggactg tttaccacgg agctggcaac aagactctag ccggcttacg   3540
gggtccggtc acgcagatgt actcgagtgc tgagggggac ttggtaggct ggcccagccc   3600
ccctgggacc aagtctttgg agccgtgcaa gtgtggagcc gtcgacctat atctggtcac   3660
```

```
gcggaacgct gatgtcatcc cggctcggag acgcggggac aagcggggag cattgctctc   3720
cccgagaccc atttcgacct tgaaggggtc ctcggggggg ccggtgctct gccctagggg   3780
ccacgtcgtt gggctcttcc gagcagctgt gtgctctcgg ggcgtggcca aatccatcga   3840
tttcatcccc gttgagacac tcgacgttgt tacaaggtct cccactttca gtgacaacag   3900
cacgccaccg gctgtgcccc agacctatca ggtcgggtac ttgcatgctc caactggcag   3960
tggaaagagc accaaggtcc ctgtcgcgta tgccgccctg ggtacaaag tactagtgct   4020
taacccctcg gtagctgcca ccctggggtt tggggcgtac ctatccaagg cacatggcat   4080
caatcccaac attaggactg gagtcaggac cgtgatgacc ggggaggcca tcacgtactc   4140
cacatatggc aaatttctcg ccgatggggg ctgcgctagc ggcgcctatg acatcatcat   4200
atgcgatgaa tgccacgctg tggatgctac ctccattctc ggcatcggaa cggtccttga   4260
tcaagcagag acagccgggg tcagactaac tgtgctggct acggccacac cccccgggtc   4320
agtgacaacc ccccatcccg atatagaaga ggtaggcctc gggcgggagg gtgagatccc   4380
cttctatggg agggcgattc ccctatcctg catcaaggga gggagacacc tgattttctg   4440
ccactcaaag aaaaagtgtg acgagctcgc ggcggccctt cggggcatgg gcttgaatgc   4500
cgtggcatac tatagagggt tggacgtctc cataatacca gctcagggag atgtggtggt   4560
cgtcgccacc gacgccctca tgacggggta cactggagac tttgactccg tgatcgactg   4620
caatgtagcg gtcacccaag ctgtcgactt cagcctggac cccaccttca ctataaccac   4680
acagactgtc ccacaagacg ctgtctcacg cagtcagcgc cgcgggcgca caggtagagg   4740
aagacagggc acttataggt atgtttccac tggtgaacga gcctcaggaa tgtttgacag   4800
tgtagtgctt tgtgagtgct acgacgcagg ggctgcgtgg tacgatctca caccagcgga   4860
gaccaccgtc aggcttagag cgtatttcaa cacgcccggc ctacccgtgt gtcaagacca   4920
tcttgaattt tgggaggcag ttttcaccgg cctcacacac atagacgccc acttcctctc   4980
ccaaacaaag caagcggggg agaacttcgc gtacctagta gcctaccaag ctacggtgtg   5040
cgccagagcc aaggcccctc ccccgtcctg ggacgccatg tggaagtgcc tggcccgact   5100
caagcctacg cttgcgggcc ccacacctct cctgtaccgt ttgggcccta ttaccaatga   5160
ggtcaccctc acacaccctg ggacgaagta catcgccaca tgcatgcaag ctgaccttga   5220
ggtcatgacc agcacgtggg tcctagctgg aggagtcctg gcagccgtcg ccgcatattg   5280
cctggcgact ggatgcgttt ccatcatcgg ccgcttgcac gtcaaccagc gagtcgtcgt   5340
tgcgccggat aaggaggtcc tgtatgaggc ttttgatgag atggaggaat gcgcctctag   5400
ggcggctctc atcgaagagg ggcagcggat agccgagatg ttgaagtcca agatccaagg   5460
cttgctgcag caggcctcta agcaggccca ggacatacaa cccgctatgc aggcttcatg   5520
gcccaaagtg gaacaatttt gggccagaca catgtggaac ttcattagcg gcatccaata   5580
cctcgcagga ttgtcaacac tgccagggaa ccccgcggtg gcttccatga tggcattcag   5640
tgccgccctc accagtccgt tgtcgaccag taccaccatc cttctcaaca tcatgggagg   5700
ctggttagcg tcccagatcg caccacccgc gggggccacc ggctttgtcg tcagtggcct   5760
ggtgggggct gccgtgggca gcataggcct gggtaaggtg ctggtggaca tcctggcagg   5820
atatggtgcg ggcatttcgg gggccctcgt cgcattcaag atcatgtctg gcgagaagcc   5880
ctctatggaa gatgtcatca atctactgcc tgggatcctg tctccgggag ccctggtggt   5940
gggggtcatc tgcgcggcca ttctgcgccg ccacgtggga ccgggggagg gcgcggtcca   6000
```

-continued

```
atggatgaac aggcttattg cctttgcttc cagaggaaac cacgtcgccc ctactcacta   6060
cgtgacggag tcggatgcgt cgcagcgtgt gacccaacta cttggctctc ttactataac   6120
cagcctactc agaagactcc acaattggat aactgaggac tgccccatcc catgctccgg   6180
atcctggctc cgcgacgtgt gggactgggt ttgcaccatc ttgacagact tcaaaaattg   6240
gctgacctct aaattgttcc ccaagctgcc cggcctcccc ttcatctctt gtcaaaaggg   6300
gtacaagggt gtgtgggccg gcactggcat catgaccacg cgctgccctt gcggcgccaa   6360
catctctggc aatgtccgcc tgggctctat gaggatcaca gggcctaaaa cctgcatgaa   6420
cacctggcag gggacctttc ctatcaattg ctacacggag ggccagtgcg cgccgaaacc   6480
ccccacgaac tacaagaccg ccatctggag ggtggcggcc tcggagtacg cggaggtgac   6540
gcagcatggg tcgtactcct atgtaacagg actgaccact gacaatctga aaattccttg   6600
ccaactacct tctccagagt tttctcctg ggtggacggt gtgcagatcc ataggtttgc   6660
acccacacca aagccgtttt tccgggatga ggtctcgttc tgcgttgggc ttaattccta   6720
tgctgtcggg tcccagcttc cctgtgaacc tgagcccgac gcagacgtat tgaggtccat   6780
gctaacagat ccgccccaca tcacggcgga gactgcggcg cggcgcttgg cacggggatc   6840
acctccatct gaggcgagct cctcagtgag ccagctatca gcaccgtcgc tgcgggccac   6900
ctgcaccacc cacagcaaca cctatgacgt ggacatggtc gatgccaacc tgctcatgga   6960
gggcggtgtg gctcagacag agcctgagtc cagggtgccc gttctggact ttctcgagcc   7020
aatggccgag gaagagagcg accttgagcc ctcaatacca tcggagtgca tgctccccag   7080
gagcgggttt ccacgggcct taccggcttg ggcacggcct gactacaacc cgccgctcgt   7140
ggaatcgtgg aggaggccag attaccaacc gcccaccgtt gctggttgtg ctctcccccc   7200
ccccaagaag gccccgacgc ctcccccaag gagacgccgg acagtgggtc tgagcgagag   7260
caccatatca gaagccctcc agcaactggc catcaagacc tttggccagc ccccctcgag   7320
cggtgatgca ggctcgtcca cgggggcggg cgccgccgaa tccggcggtc cgacgtcccc   7380
tggtgagccg gccccctcag agacaggttc cgcctcctct atgcccccc tcgaggggga   7440
gcctggagat ccggacctgg agtctgatca ggtagagctt caacctcccc cccagggggg   7500
gggggtagct cccggttcgg gctcggggtc ttggtctact tgctccgagg aggacgatac   7560
caccgtgtgc tgctccatgt catactcctg gaccggggct ctaataactc cctgtagccc   7620
cgaagaggaa aagttgccaa tcaacccttt gagtaactcg ctgttgcgat accataacaa   7680
ggtgtactgt acaacatcaa agagcgcctc acagagggct aaaaaggtaa cttttgacag   7740
gacgcaagtg ctcgacgccc attatgactc agtcttaaag gacatcaagc tagcggcttc   7800
caaggtcagc gcaaggctcc tcaccttgga ggaggcgtgc cagttgactc caccccattc   7860
tgcaagatcc aagtatggat tcggggccaa ggaggtccgc agcttgtccg ggagggccgt   7920
taaccacatc aagtccgtgt ggaaggacct cctggaagac ccacaaacac caattcccac   7980
aaccatcatg gccaaaaatg aggtgttctg cgtggacccc gccaaggggg gtaagaaacc   8040
agctcgcctc atcgtttacc ctgacctcgg cgtccgggtc tgcgagaaaa tggccctcta   8100
tgacattaca caaaagcttc ctcaggcggt aatgggagct tcctatggct tccagtactc   8160
ccctgcccaa cgggtggagt atctcttgaa agcatgggcg gaaaagaagg accccatggg   8220
tttttcgtat gatacccgat gcttcgactc aaccgtcact gagagagaca tcaggaccga   8280
ggagtccata taccaggcct gctccctgcc cgaggaggcc cgcactgcca tacactcgct   8340
gactgagaga ctttacgtag gagggcccat gttcaacagc aagggtcaaa cctgcggtta   8400
```

```
cagacgttgc cgcgccagcg gggtgctaac cactagcatg ggtaacacca tcacatgcta   8460

tgtgaaagcc ctagcggcct gcaaggctgc ggggatagtt gcgcccacaa tgctggtatg   8520

cggcgatgac ctagtagtca tctcagaaag ccaggggact gaggaggacg agcggaacct   8580

gagagccttc acggaggcca tgaccaggta ctctgcccct cctggtgatc cccccagacc   8640

ggaatatgac ctggagctaa taacatcctg ttcctcaaat gtgtctgtgg cgttgggccc   8700

gcggggccgc cgcagatact acctgaccag agacccaacc actccactcg cccgggctgc   8760

ctgggaaaca gttagacact cccctatcaa ttcatggctg ggaaacatca tccagtatgc   8820

tccaaccata tgggttcgca tggtcctaat gacacacttc ttctccattc tcatggtcca   8880

agacaccctg gaccagaacc tcaactttga gatgtatgga tcagtatact ccgtgaatcc   8940

tttggacctt ccagccataa ttgagaggtt acacgggctt gacgcctttt ctatgcacac   9000

atactctcac cacgaactga cgcgggtggc ttcagccctc agaaaacttg gggcgccacc   9060

cctcagggtg tggaagagtc gggctcgcgc agtcagggcg tccctcatct cccgtggagg   9120

gaaagcggcc gtttgcggcc gatatctctt caattgggcg gtgaagacca agctcaaact   9180

cactccattg ccggaggcgc gcctactgga cttatccagt tggttcaccg tcggcgccgg   9240

cgggggcgac atttttcaca gcgtgtcgcg cgcccgaccc cgctcattac tcttcggcct   9300

actcctactt ttcgtagggg taggcctctt cctactcccc gctcggtaga gcggcacaca   9360

ctaggtacac tccatagcta actgttcctt tttttttttt tttttttttt tttttttttt   9420

tttttttttt tctttttttt ttttttccct ctttcttccc ttctcatctt attctacttt   9480

ctttcttggt ggctccatct tagccctagt cacggctagc tgtgaaaggt ccgtgagccg   9540

catgactgca gagagtgccg taactggtct ctctgcagat catgt                   9585
```

<210> SEQ ID NO 17
<211> LENGTH: 9585
<212> TYPE: DNA
<213> ORGANISM: Hepatitis C virus

<400> SEQUENCE: 17

```
acctgcccct aatagggggcg acactccgcc atgaatcact cccctgtgag gaactactgt     60

cttcacgcag aaagcgccta gccatggcgt tagtatgagt gtcgtacagc ctccaggccc    120

ccccctcccg ggagagccat agtggtctgc ggaaccggtg agtacaccgg aattgccggg    180

aagactgggt cctttcttgg ataaacccac tctatgcccg gccatttggg cgtgcccccg    240

caagactgct agccgagtag cgttgggttg cgaaaggcct tgtggtactg cctgataggg    300

cgcttgcgag tgccccggga ggtctcgtag accgtgcacc atgagcacga atcctaaacc    360

tcaaagaaaa accaaacgta acaccaaccg tcgcccacag gacgtcaagt tcccgggtgg    420

cggtcagatc gttggtggag tttacttgtt gccgcgcagg ggccctagat tgggtgtgcg    480

cgcgacgagg aagacttccg agcggtcgca acctcgaggt agacgtcagc ctatccccaa    540

ggcacgtcgg cccgagggca ggacctgggc tcagcccggg taccccttggc ccctctatgg    600

caatgagggt tgcgggtggg cgggatggct cctgtctccc cgtggctctc ggcctagctg    660

gggccccaca gacccccggc gtaggtcgcg caatttgggt aaggtcatcg ataccccttac    720

gtgcggcttc gccgacctca tggggtacat accgctcgtc ggcgcccctc ttggaggcgc    780

tgccagggcc ctggcgcatg gcgtccgggt tctggaagac ggcgtgaact atgcaacagg    840

gaaccttcct ggttgctctt tctctatctt ccttctggcc ctgctctctt gcctgactgt    900
```

gcccgcttca gcctaccaag tgcgcaattc ctcggggctt taccatgtca ccaatgattg 960
ccctaactcg agtattgtgt acgaggcggc cgatgccatc ctgcacactc cggggtgtgt 1020
cccttgcgtt cgcgagggta acgcctcgag gtgttgggtg gcggtgaccc ccacggtggc 1080
caccagggac ggcaaactcc ccacaacgca gcttcgacgt catatcgatc tgcttgtcgg 1140
gagcgccacc ctctgctcgg ccctctacgt gggggacctg tgcgggtctg tctttcttgt 1200
tggtcaactg tttaccttct ctcccaggcg ccactggacg acgcaagact gcaattgttc 1260
tatctatccc ggccatataa cgggtcatcg catggcatgg gatatgatga tgaactggtc 1320
ccctacggca gcgttggtgg tagctcagct gctccggatc ccacaagcca tcatggacat 1380
gatcgctggt gctcactggg gagtcctggc gggcatagcg tatttctcca tggtggggaa 1440
ctgggcgaag gtcctggtag tgctgctgct atttgccggc gtcgacgcga tccaactgat 1500
caacaccaac ggcagttggc acatcaatag cacggccttg aattgcaatg aaagccttaa 1560
caccggctgg ttagcagggc tcttctatca acacaaattc aactcttcag gctgtcctga 1620
gaggttggcc agctgccgac gccttaccga ttttgcccag ggctggggtc ctatcagtta 1680
tgccgacgga agcggcctcg acgaacgccc ctactgctgg cactaccctc caagaccttg 1740
tggcattgtg cccgcaaaga gcgtgtgtgg cccggtatat tgcttcactc ccagccccgt 1800
ggtggtggga acgaccgaca ggtcgggcgc gcctacctac agctggggtg caaatgatac 1860
ggatgtcttc gtccttaaca acaccaggcc accgctgggc aattggttcg gttgtacctg 1920
gatgaactca actggattca ccaaagtgtg cggagcgccc ccttgtgtca tcggaggggt 1980
gggcaacaac accttgctct gccccactga ttgcttccgc aaacatccgg aagccacata 2040
ctctcggtgc ggctccggtc cctggattac acccaggtgc atggtcgact acccgtatag 2100
gctttggcac tatccttgta ccatcaatta caccatattc aaagtcagga tgtacgtggg 2160
aggggtcgag cacaggctgg aagcggcctg caactggacg cggggcgaac gctgtgatct 2220
ggaagacagg gacaggtccg agctcagccc gttgctgctg tccaccacac agtggcaggt 2280
ccttccgtgt tctttcacga ccctgccagc cttgtccacc ggcctcatcc acctccacca 2340
gaacattgtg gacgtgcagt acttgtacgg ggtagggtca agcatcgcgt cctgggccat 2400
taagtgggag tacgtcgttc tcctgttcct tctgcttgca gacgcgcgcg tctgcttctg 2460
cttgtggatg atgttactca tatcccaagc ggaggcggct ttggagaacc tcgtaatact 2520
caatgcagca tccctggccg ggacgcacgg tcttgtgtcc ttcctcgtgt tcttctgctt 2580
tgcgtggtat ctgaagggta ggtgggtgcc cggagcggcc tacgccctct acgggatgtg 2640
gcctctcctc ctgctcctgc tggcgttgcc tcagcgggca tacgcactgg acacggaggt 2700
ggccgcgtcg tgtggcggcg ttgttcttgt cgggttaatg gcgctgactc tgtcgccata 2760
ttacaagcgc tatatcagct ggtgcatgtg gtggcttcag tattttctga ccagagtaga 2820
agcgcaactg cacgtgtggg ttcccccccct caacgtccgg ggggggcgcg atgccgtcat 2880
cttactcatg tgtgtagtac acccgaccct ggtatttgac atcaccaaac tactcctggc 2940
catcttcgga cccctttgga ttcttcaagc cagtttgctt aaagtcccct acttcgtgcg 3000
cgttcaaggc cttctccgga tctgcgcgct agcgcggaag atagccggag gtcattacgt 3060
gcaaatggcc atcatcaagt taggggcgct tactggcacc tatgtgtata accatctcac 3120
ccctcttcga gactgggcgc acaacggcct gcgagatctg gccgtggctg tggaaccagt 3180
cgtcttctcc cgaatggaga ccaagctcat cacgtggggg gcagataccg ccgcgtgcgg 3240
tgacatcatc aacggcttgc ccgtctctgc ccgtaggggc caggagatac tgcttgggcc 3300
agccgacgga atggtctcca aggggtggag gttgctggct cccatcactg cttatgccca 3360
gcaaacacga ggcctcctgg gcgccatagt ggtgagtatg acggggcgtg acaggacaga 3420
acaggccggg gaagtccaaa tcctgtccac agtctctcag tccttcctcg gaacaaccat 3480 ctcggggggtt ttgtggactg tttaccacgg agctggcaac aagactctag ccggcttacg 3540
gggtccggtc acgcagatgt actcgagtgc tgagggggac ttggtaggct ggcccagccc 3600
ccctgggacc aagtctttgg agccgtgcaa gtgtggagcc gtcgacctat atctggtcac 3660
gcggaacgct gatgtcatcc cggctcggag acgcggggac aagcggggag cattgctctc 3720
cccgagaccc atttcgacct tgaaggggtc ctcgggggggg ccggtgctct gccctagggg 3780
ccacgtcgtt gggctcttcc gagcagctgt gtgctctcgg ggcgtggcca aatccatcga 3840
tttcatcccc gttgagacac tcgacgttgt tacaaggtct cccactttca gtgacaacag 3900
cacgccaccg gctgtgcccc agacctatca ggtcgggtac ttgcatgctc caactggcag 3960
tggaaagagc accaaggtcc ctgtcgcgta tgccgccctg ggtacaaag tactagtgct 4020 taacccctcg gtagctgcca ccctggggtt tggggcgtac ctatccaagg cacatggcat 4080
caatcccaac attaggactg gagtcaggac cgtgatgacc ggggaggcca tcacgtactc 4140
cacatatggc aaatttctcg ccgatggggg ctgcgctagc ggcgcctatg acatcatcat 4200
atgcgatgaa tgccacgctg tggatgctac ctccattctc ggcatcggaa cggtccttga 4260
tcaagcagag acagccgggg tcagactaac tgtgctggct acggccacac cccccgggtc 4320
agtgacaacc ccccatcccg atatagaaga ggtaggcctc gggcgggagg gtgagatccc 4380
cttctatggg agggcgattc ccctatcctg catcaaggga gggagacacc tgattttctg 4440
ccactcaaag aaaaagtgtg acgagctcgc ggcggccctt cggggcatgg gcttgaatgc 4500
cgtggcatac tatagagggt tggacgtctc cataatacca gctcagggag atgtggtggt 4560
cgtcgccacc gacgccctca tgacggggta cactggagac tttgactccg tgatcgactg 4620
caatgtagcg gtcacccaag ctgtcgactt cagcctggac cccaccttca ctataaccac 4680
acagactgtc ccacaagacg ctgtctcacg cagtcagcgc cgcgggcgca caggtagagg 4740
aagacagggc acttataggt atgtttccac tggtgaacga gcctcaggaa tgtttgacag 4800
tgtagtgctt tgtgagtgct acgacgcagg ggctgcgtgg tacgatctca caccagcgga 4860
gaccaccgtc aggcttagag cgtatttcaa cacgcccggc ctacccgtgt gtcaagacca 4920
tcttgaattt tgggaggcag ttttcaccgg cctcacacac atagacgccc acttcctctc 4980
ccaaacaaag caagcggggg agaacttcgc gtacctagta gcctaccaag ctacggtgtg 5040
cgccagagcc aaggcccctc ccccgtcctg ggacgccatg tggaagtgcc tggcccgact 5100
caagcctacg cttgcgggcc ccacacctct cctgtaccgt ttgggcccta ttaccaatga 5160
ggtcaccctc acacaccctg ggacgaagta catcgccaca tgcatgcaag ctgaccttga 5220
ggtcatgacc agcacgtggg tcctagctgg aggagtcctg gcagccgtcg ccgcatattg 5280
cctggcgact ggatgcgttt ccatcatcgg ccgcttgcac gtcaaccagc gagtcgtcgt 5340
tgcgccggat aaggaggtcc tgtatgaggc ttttgatgag atggaggaat gcgcctctag 5400
ggcggctctc atcgaagagg ggcagcggat agccgagatg ttgaagtcca agatccaagg 5460
cttgctgcag caggcctcta agcaggccca ggacatacaa cccgctatgc aggcttcatg 5520
gcccaaagtg gaacaatttt gggccagaca catgtggaac ttcattagcg gcatccaata 5580
cctcgcagga ttgtcaacac tgccagggaa ccccgcggtg gcttccatga tggcattcag 5640

-continued

```
tgccgccctc accagtccgt tgtcgaccag taccaccatc cttctcaaca tcatgggagg   5700
ctggttagcg tcccagatcg caccacccgc gggggccacc ggctttgtcg tcagtggcct   5760
ggtgggggct gccgtgggca gcataggcct gggtaaggtg ctggtggaca tcctggcagg   5820
atatggtgcg ggcatttcgg gggccctcgt cgcattcaag atcatgtctg gcgagaagcc   5880
ctctatggaa gatgtcatca atctactgcc tgggatcctg tctccgggag ccctggtggt   5940
gggggtcatc tgcgcggcca ttctgcgccg ccacgtggga ccgggggagg gcgcggtcca   6000
atggatgaac aggcttattg cctttgcttc cagaggaaac cacgtcgccc ctactcacta   6060
cgtgacggag tcggatgcgt cgcagcgtgt gacccaacta cttggctctc ttactataac   6120
cagcctactc agaagactcc acaattggat aactgaggac tgccccatcc catgctccgg   6180
atcctggctc cgcgacgtgt gggactgggt ttgcaccatc ttgacagact tcaaaaattg   6240
gctgacctct aaattgttcc ccaagctgcc cggcctcccc ttcatctctt gtcaaaaggg   6300
gtacaagggt gtgtgggccg gcactggcat catgaccacg cgctgccctt gcggcgccaa   6360
catctctggc aatgtccgcc tgggctctat gaggatcaca gggcctaaaa cctgcatgaa   6420
cacctggcag gggacctttc ctatcaattg ctacacggag ggccagtgcg cgccgaaacc   6480
ccccacgaac tacaagaccg ccatctggag ggtggcggcc tcggagtacg cggaggtgac   6540
gcagcatggg tcgtactcct atgtaacagg actgaccact gacaatctga aaattccttg   6600
ccaactacct tctccagagt ttttctcctg ggtggacggt gtgcagatcc ataggtttgc   6660
acccacacca aagccgtttt tccgggatga ggtctcgttc tgcgttgggc ttaattccta   6720
tgctgtcggg tcccagcttc cctgtgaacc tgagcccgac gcagacgtat tgaggtccat   6780
gctaacagat ccgccccaca tcacggcgga gactgcggcg cggcgcttgg cacggggatc   6840
acctccatct gaggcgagct cctcagtgag ccagctatca gcaccgtcgc tgcgggccac   6900
ctgcaccacc cacagcaaca cctatgacgt ggacatggtc gatgccaacc tgctcatgga   6960
gggcggtgtg gctcagacag agcctgagtc cagggtgccc gttctggact ttctcgagcc   7020
aatggccgag gaagagagcg accttgagcc ctcaatacca tcggagtgca tgctccccag   7080
gagcgggttt ccacgggcct taccggcttg ggcacggcct gactacaacc cgccgctcgt   7140
ggaatcgtgg aggaggccag attaccaacc gcccaccgtt gctggttgtg ctctcccccc   7200
ccccaagaag gccccgacgc ctcccccaag gagacgccgg acagtgggtc tgagcgagag   7260
caccatatca gaagccctcc agcaactggc catcaagacc tttggccagc ccccctcgag   7320
cggtgatgca ggctcgtcca cgggggcggg cgccgccgaa tccggcggtc cgacgtcccc   7380
tggtgagccg gccccctcag agacaggttc cgcctcctct atgccccccc tcgaggggga   7440
gcctggagat ccggacctgg agtctgatca ggtagagctt caacctcccc cccagggggg   7500
gggggtagct cccggttcgg gctcggggtc ttggtctact tgctccgagg aggacgatac   7560
caccgtgtgc tgctccatgt catactcctg gaccggggct ctaataactc cctgtagccc   7620
cgaagaggaa aagttgccaa tcaacccttt gagtaactcg ctgttgcgat accataacaa   7680
ggtgtactgt acaacatcaa agagcgcctc acagagggct aaaaaggtaa cttttgacag   7740
gacgcaagtg ctcgacgccc attatgactc agtcttaaag gacatcaagc tagcggcttc   7800
caaggtcagc gcaaggctcc tcaccttgga ggaggcgtgc cagttgactc caccccattc   7860
tgcaagatcc aagtatggat tcggggccaa ggaggtccgc agcttgtccg ggagggccgt   7920
taaccacatc aagtccgtgt ggaaggacct cctggaagac ccacaaacac caattcccac   7980
aaccatcatg gccaaaaatg aggtgttctg cgtggacccc gccaaggggg gtaagaaacc   8040
```

agctcgcctc atcgtttacc ctgacctcgg cgtccgggtc tgcgagaaaa tggccctcta 8100
tgacattaca caaaagcttc ctcaggcggt aatgggagct tcctatggct tccagtactc 8160
ccctgcccaa cgggtggagt atctcttgaa agcatgggcg gaaaagaagg accccatggg 8220
tttttcgtat gatacccgat gcttcgactc aaccgtcact gagagagaca tcaggaccga 8280
ggagtccata taccaggcct gctccctgcc cgaggaggcc cgcactgcca tacactcgct 8340
gactgagaga ctttacgtag gagggcccat gttcaacagc aagggtcaaa cctgcggtta 8400
cagacgttgc cgcgccagcg gggtgctaac cactagcatg ggtaacacca tcacatgcta 8460
tgtgaaagcc ctagcggcct gcaaggctgc ggggatagtt gcgcccacaa tgctggtatg 8520
cggcgatgac ctagtagtca tctcagaaag ccaggggact gaggaggacg agcggaacct 8580
gagagccttc acggaggcca tgaccaggta ctctgcccct cctggtgatc cccccagacc 8640
ggaatatgac ctggagctaa taacatcctg ttcctcaaat gtgtctgtgg cgttgggccc 8700
gcggggccgc cgcagatact acctgaccag agacccaacc actccactcg cccgggctgc 8760
ctgggaaaca gttagacact cccctatcaa ttcatggctg ggaaacatca tccagtatgc 8820
tccaaccata tgggttcgca tggtcctaat gacacacttc ttctccattc tcatggtcca 8880
agacaccctg gaccagaacc tcaactttga gatgtatgga tcagtatact ccgtgaatcc 8940
tttggacctt ccagccataa ttgagaggtt acacgggctt gacgcctttt ctatgcacac 9000
atactctcac cacgaactga cgcgggtggc ttcagccctc agaaaacttg ggcgccacc 9060 cctcagggtg tggaagagtc gggctcgcgc agtcagggcg tccctcatct cccgtggagg 9120
gaaagcggcc gtttgcggcc gatatctctt caattgggcg gtgaagacca agctcaaact 9180
cactccattg ccggaggcgc gcctactgga cttatccagt tggttcaccg tcggcgccgg 9240
cgggggcgac atttttcaca gcgtgtcgcg cgcccgaccc cgctcattac tcttcggcct 9300
actcctactt ttcgtagggg taggcctctt cctactcccc gctcggtaga gcggcacaca 9360
ctaggtacac tccatagcta actgttcctt tttttttttt tttttttttt tttttttttt 9420
tttttttttt tcttttttttt tttttccct ctttcttccc ttctcatctt attctacttt 9480
ctttcttggt ggctccatct tagccctagt cacggctagc tgtgaaaggt ccgtgagccg 9540
catgactgca gagagtgccg taactggtct ctctgcagat catgt 9585

<210> SEQ ID NO 18
<211> LENGTH: 9603
<212> TYPE: DNA
<213> ORGANISM: Hepatitis C virus

<400> SEQUENCE: 18
acctgcccct aatagggcg acactccgcc atgaatcact cccctgtgag gaactactgt 60
cttcacgcag aaagcgccta gccatggcgt tagtatgagt gtcgtacagc ctccaggccc 120
ccccctcccg ggagagccat agtggtctgc ggaaccggtg agtacaccgg aattgccggg 180
aagactgggt cctttcttgg ataaacccac tctatgcccg gccatttggg cgtgcccccg 240
caagactgct agccgagtag cgttgggttg cgaaaggcct tgtggtactg cctgataggg 300
tgcttgcgag tgccccggga ggtctcgtag accgtgcacc atgagcacac ttcctaaacc 360
tcaaagaaaa accaaaagaa acaccatccg tcgcccacag gacgttaagt tcccgggtgg 420
cggacagatc gttggtggag tatacgtgtt gccgcgcagg ggcccacgat tgggtgtgcg 480
cgcgacgcgt aaaacttctg aacggtcaca gcctcgcgga cgacgacagc ctatccccaa 540

-continued

```
ggcgcgtcgg agcgaaggcc ggtcctgggc tcagcccggg taccccttggc ccctctatgg    600
taatgagggc tgcgggtggg cagggtggct cctgtccccg cgcggctccc gtccatcttg    660
gggcccaaac gacccccggc ggaggtcccg caatttgggt aaagtcatcg ataccccttac    720
gtgcggattc gccgacctca tggggtacat cccgctcgtc ggcgctcccg taggaggcgt    780
cgcaagagcc ctcgcgcatg gcgtgagggc ccttgaagac gggataaatt ttgcaacagg    840
gaacttgccc ggttgctcct tttctatctt ccttcttgct ctgttctcct gcttagttca    900
tcctgcagct agtcttgagt ggcggaatac gtctggcctc tatgtcctta ccaacgactg    960
ttccaatagc agtattgtgt atgaggccga tgacgtcatt ctgcacacac ccggctgtgt   1020
accttgtgtt caggacgaca atacatccac gtgctggacc ccagtgacac ctacggtggc   1080
agtcaggtac gtcggagcaa ccaccgcttc gatacgcagt catgtggacc tattagtggg   1140
cgcggccacg ctgtgctctg cgctctatgt gggtgatatg tgtggggccg tctttctcgt   1200
gggacaagcc ttcacgttca gacctcgtcg ccatcaaacg gtccagacct gtaactgctc   1260
gctgtaccca ggccatgttt caggacatcg aatggcttgg gatatgatga tgaattggtc   1320
ccccgctgtg ggtatggtgg tggcgcacat cctgcgattg ccccagacct tgtttgacat   1380
actggccggg gcccattggg gcatcttggc gggcctagcc tattattcta tgcagggcaa   1440
ctgggtcaag gtcgctattg tcatgattat gttttcaggg gtcgatgctc tgcaattggt   1500
caacaccaat ggctcgtggc acatcaacag tactgccctg aactgcaatg agtccataaa   1560
caccgggttc atagctgggt tgttttatta ccataagttc aactctactg gatgtcctca   1620
aaggcttagc agctgcaagc ccatcatttc cttcaggcag ggtggggcc ccttgacaga   1680
tgctaacatc accggtcctt ctgatgatag accgtattgc tggcactacg cacctagacc   1740
ttgtagtgtt gtcccggcat caagtgtctg cggccctgtg tactgcttca caccatcgcc   1800
agtggtcgta ggcactactg atatcaaagg caagccgacc tacaactggg gtgagaatga   1860
gacagatgtg ttcctgctgg agtccctgcg gcctcccagt ggccggtggt ttggatgcgc   1920
gtggatgaac tccacggggt tcctcaagac gtgtggagct ccccccttgta acatctatgg   1980
gggtgagggg gatcccgaaa atgagacaga cctcttctgc ccccaccgact gcttcaggaa   2040
acatcctgag gccacataca gccggtgtgg tgcggggccc tggttgacac ctcgctgcat   2100
ggtcgactat ccataccggc tttggcatta cccatgtaca gtcaatttca cattgttcaa   2160
ggtgaggatg tttgtgggcg gatttgaaca ccggtttacc gccgcttgta actggaccag   2220
gggggagcgc tgcaatatcg aggatcgtga tcgcagcgag caacatccgc tgctgcattc   2280
aacaactgag cttgctatac tgccttgctc tttcacgccc atgcctgcat tgtcaacagg   2340
tctaatacac ctccaccaaa atatcgtgga tgtccaatac ctttatggtg ttggatctga   2400
catggtggga tgggcgctga aatgggagtt cgtcatcctc gttttcctcc tcctggcaga   2460
cgcacgcgtg tgcgttgccc tttggctgat gctgatggta tcacaagcag aagcagcctt   2520
ggagaacctt gtcacgctga acgccgtcgc tgctgctggg acacatggta ttggttggta   2580
cctggtagcc ttttgcgcgg cgtggtacgt gcggggtaaa cttgtcccgc tgacgagcta   2640
cggcctgacg ggtctttggt ccctagcatt gcttgtcctc ttgctccccc aacgggcgta   2700
tgcttggtcg ggtgaagaca gcgctactct cggcgctggg gtcttggccc tcttcggctt   2760
ctttacctta tcaccctggt acaagcattg gatcggccgc ctcatgtggt ggaaccagta   2820
cactatatgt agatgcgagg ccgcccttca agtgtgggtc ccccccttac ttgcacgcgg   2880
gagtagggac ggtgtcatcc tgctaacaag cttgctttat ccatccttaa tttttgacat   2940
```

cactaagctg ctgatagcag taataggccc attatactta atacaggctg ccatcactac 3000 cacccctac tttgtgcgcg cacatgtact ggtccgcctt tgcatgctcg tgcgctccgt 3060
gatgggggga aagtacttcc agatggccat actgagcatt ggcagatggt tcaacaccta 3120
cctatatgac cacctagcgc caatgcaaca ttgggccgca gctggcctca aagacctagc 3180
agtggccact gaacctgtaa tatttagtcc catggaaatt aaggtcatca cctggggcgc 3240
ggacacagcg gcttgcggag atattctttg cgggctgccg gtctccgcgc gattaggccg 3300
tgaggtattg ttgggacctg ctgatgatta tcgggaaatg ggttggcgtc tgttggctcc 3360
catcactgct tatgcccagc aaacacgagg cctcctgggc gccatagtgg tgagtatgac 3420
ggggcgtgac aggacagaac aggccgggga agtccaaatc ctgtccacag tctctcagtc 3480
cttcctcgga acaaccatct cgggggtttt gtggactgtt taccacggag ctggcaacaa 3540
gactctagcc ggcttacggg gtccggtcac gcagatgtac tcgagtgctg agggggactt 3600
ggtaggctgg cccagccccc ctgggaccaa gtctttggag ccgtgcaagt gtggagccgt 3660
cgacctatat ctggtcacgc ggaacgctga tgtcatcccg gctcggagac gcggggacaa 3720
gcggggagca ttgctctccc cgagacccat ttcgaccttg aaggggtcct cggggggggcc 3780 ggtgctctgc cctaggggcc acgtcgttgg gctcttccga gcagctgtgt gctctcgggg 3840
cgtggccaaa tccatcgatt tcatccccgt tgagacactc gacgttgtta caaggtctcc 3900
cactttcagt gacaacagca cgccaccggc tgtgccccag acctatcagg tcgggtactt 3960
gcatgctcca actggcagtg gaaagagcac caaggtccct gtcgcgtatg ccgcccaggg 4020
gtacaaagta ctagtgctta acccctcggt agctgccacc ctggggtttg ggcgtacct 4080 atccaaggca catggcatca atcccaacat taggactgga gtcaggaccg tgatgaccgg 4140
ggaggccatc acgtactcca catatggcaa atttctcgcc gatgggggct gcgctagcgg 4200
cgcctatgac atcatcatat gcgatgaatg ccacgctgtg gatgctacct ccattctcgg 4260
catcggaacg gtccttgatc aagcagagac agccggggtc agactaactg tgctggctac 4320
ggccacaccc cccgggtcag tgacaacccc ccatcccgat atagaagagg taggcctcgg 4380
gcgggagggt gagatcccct tctatgggag ggcgattccc ctatcctgca tcaagggagg 4440
gagacacctg attttctgcc actcaaagaa aaagtgtgac gagctcgcgg cggcccttcg 4500
gggcatgggc ttgaatgccg tggcatacta tagagggttg gacgtctcca taataccagc 4560
tcagggagat gtggtggtcg tcgccaccga cgccctcatg acggggtaca ctggagactt 4620
tgactccgtg atcgactgca atgtagcggt cacccaagct gtcgacttca gcctggaccc 4680
caccttcact ataaccacac agactgtccc acaagacgct gtctcacgca gtcagcgccg 4740
cgggcgcaca ggtagaggaa gacagggcac ttataggtat gtttccactg gtgaacgagc 4800
ctcaggaatg tttgacagtg tagtgctttg tgagtgctac gacgcagggg ctgcgtggta 4860
cgatctcaca ccagcggaga ccaccgtcag gcttagagcg tatttcaaca cgcccggcct 4920
acccgtgtgt caagaccatc ttgaattttg ggaggcagtt ttcaccggcc tcacacacat 4980
agacgcccac ttcctctccc aaacaaagca agcgggggag aacttcgcgt acctagtagc 5040
ctaccaagct acggtgtgcg ccagagccaa ggcccctccc ccgtcctggg acgccatgtg 5100
gaagtgcctg gcccgactca agcctacgct tgcgggcccc acacctctcc tgtaccgttt 5160
gggccctatt accaatgagg tcaccctcac acaccctggg acgaagtaca tcgccacatg 5220
catgcaagct gaccttgagg tcatgaccag cacgtgggtc ctagctggag gagtcctggc 5280

-continued agccgtcgcc gcatattgcc tggcgactgg atgcgtttcc atcatcggcc gcttgcacgt 5340
caaccagcga gtcgtcgttg cgccggataa ggaggtcctg tatgaggctt ttgatgagat 5400
ggaggaatgc gcctctaggg cggctctcat cgaagagggg cagcggatag ccgagatgtt 5460
gaagtccaag atccaaggct tgctgcagca ggcctctaag caggcccagg acatacaacc 5520
cgctatgcag gcttcatggc ccaaagtgga acaattttgg gccagacaca tgtggaactt 5580
cattagcggc atccaatacc tcgcaggatt gtcaacactg ccagggaacc ccgcggtggc 5640
ttccatgatg gcattcagtg ccgccctcac cagtccgttg tcgaccagta ccaccatcct 5700
tctcaacatc atgggaggct ggttagcgtc ccagatcgca ccacccgcgg gggccaccgg 5760
ctttgtcgtc agtggcctgg tgggggctgc cgtgggcagc ataggcctgg gtaaggtgct 5820
ggtggacatc ctggcaggat atggtgcggg catttcgggg gccctcgtcg cattcaagat 5880
catgtctggc gagaagccct ctatggaaga tgtcatcaat ctactgcctg ggatcctgtc 5940
tccgggagcc ctggtggtgg gggtcatctg cgcggccatt ctgcgccgcc acgtgggacc 6000
gggggagggc gcggtccaat ggatgaacag gcttattgcc tttgcttcca gaggaaacca 6060
cgtcgcccct actcactacg tgacggagtc ggatgcgtcg cagcgtgtga cccaactact 6120
tggctctctt actataacca gcctactcag aagactccac aattggataa ctgaggactg 6180
ccccatccca tgctccggat cctggctccg cgacgtgtgg gactgggttt gcaccatctt 6240
gacagacttc aaaaattggc tgacctctaa attgttcccc aagctgcccg gcctcccctt 6300
catctcttgt caaaaggggt acaagggtgt gtgggccggc actggcatca tgaccacgcg 6360
ctgcccttgc ggcgccaaca tctctggcaa tgtccgcctg ggctctatga ggatcacagg 6420
gcctaaaacc tgcatgaaca cctggcaggg gacctttcct atcaattgct acacggaggg 6480
ccagtgcgcg ccgaaacccc ccacgaacta caagaccgcc atctggaggg tggcggcctc 6540
ggagtacgcg gaggtgacgc agcatgggtc gtactcctat gtaacaggac tgaccactga 6600
caatctgaaa attccttgcc aactaccttc tccagagttt ttctcctggg tggacggtgt 6660
gcagatccat aggtttgcac ccacaccaaa gccgtttttc cgggatgagg tctcgttctg 6720
cgttgggctt aattcctatg ctgtcgggtc ccagcttccc tgtgaacctg agcccgacgc 6780
agacgtattg aggtccatgc taacagatcc gccccacatc acggcggaga ctgcggcgcg 6840
gcgcttggca cggggatcac ctccatctga ggcgagctcc tcagtgagcc agctatcagc 6900
accgtcgctg cgggccacct gcaccaccca cagcaacacc tatgacgtgg acatggtcga 6960
tgccaacctg ctcatggagg gcggtgtggc tcagacagag cctgagtcca gggtgcccgt 7020
tctggacttt ctcgagccaa tggccgagga agagagcgac cttgagccct caataccacc 7080
ggagtgcatg ctccccagga gcgggtttcc acgggcctta ccggcttggg cacggcctga 7140
ctacaacccg ccgctcgtgg aatcgtggag gaggccagat taccaaccgc ccaccgttgc 7200
tggttgtgct ctcccccccc ccaagaaggc cccgacgcct cccccaagga gacgccggac 7260
agtgggtctg agcgagagca ccatatcaga agccctccag caactggcca tcaagacctt 7320
tggccagccc ccctcgagcg gtgatgcagg ctcgtccacg gggcgggcg ccgccgaatc 7380 cggcggtccg acgtcccctg gtgagccggc cccctcagag acaggttccg cctcctctat 7440 gcccccccctc gagggggagc ctggagatcc ggacctggag tctgatcagg tagagcttca 7500
acctcccccc cagggggggg gggtagctcc cggttcgggc tcggggtctt ggtctacttg 7560
ctccgaggag gacgatacca ccgtgtgctg ctccatgtca tactcctgga ccggggctct 7620
aataactccc tgtagccccg aagaggaaaa gttgccaatc aaccctttga gtaactcgct 7680

-continued gttgcgatac cataacaagg tgtactgtac aacatcaaag agcgcctcac agagggctaa 7740
aaaggtaact tttgacagga cgcaagtgct cgacgcccat tatgactcag tcttaaagga 7800
catcaagcta gcggcttcca aggtcagcgc aaggctcctc accttggagg aggcgtgcca 7860
gttgactcca ccccattctg caagatccaa gtatggattc ggggccaagg aggtccgcag 7920
cttgtccggg agggccgtta accacatcaa gtccgtgtgg aaggacctcc tggaagaccc 7980
acaaacacca attcccacaa ccatcatggc caaaaatgag gtgttctgcg tggaccccgc 8040 caagggggt aagaaaccag ctcgcctcat cgtttaccct gacctcggcg tccgggtctg 8100
cgagaaaatg gccctctatg acattacaca aaagcttcct caggcggtaa tgggagcttc 8160
ctatggcttc cagtactccc ctgcccaacg ggtggagtat ctcttgaaag catgggcgga 8220
aaagaaggac cccatgggtt tttcgtatga tacccgatgc ttcgactcaa ccgtcactga 8280
gagagacatc aggaccgagg agtccatata ccaggcctgc tccctgcccg aggaggcccg 8340
cactgccata cactcgctga ctgagagact ttacgtagga gggcccatgt tcaacagcaa 8400
gggtcaaacc tgcggttaca gacgttgccg cgccagcggg gtgctaacca ctagcatggg 8460
taacaccatc acatgctatg tgaaagccct agcggcctgc aaggctgcgg ggatagttgc 8520
gcccacaatg ctggtatgcg gcgatgacct agtagtcatc tcagaaagcc aggggactga 8580
ggaggacgag cggaacctga gagccttcac ggaggccatg accaggtact ctgcccctcc 8640
tggtgatccc cccagaccgg aatatgacct ggagctaata acatcctgtt cctcaaatgt 8700
gtctgtggcg ttgggcccgc ggggccgccg cagatactac ctgaccagag acccaaccac 8760
tccactcgcc cggctgcct gggaaacagt tagacactcc cctatcaatt catggctggg 8820
aaacatcatc cagtatgctc caaccatatg ggttcgcatg gtcctaatga cacacttctt 8880
ctccattctc atggtccaag acaccctgga ccagaacctc aactttgaga tgtatggatc 8940
agtatactcc gtgaatcctt tggaccttcc agccataatt gagaggttac acgggcttga 9000
cgccttttct atgcacacat actctcacca cgaactgacg cgggtggctt cagccctcag 9060
aaaacttggg gcgccacccc tcagggtgtg gaagagtcgg gctcgcgcag tcagggcgtc 9120
cctcatctcc cgtggaggga aagcggccgt ttgcggccga tatctcttca attgggcggt 9180
gaagaccaag ctcaaactca ctccattgcc ggaggcgcgc ctactggact tatccagttg 9240
gttcaccgtc ggcgccggcg gggcgacat ttttcacagc gtgtcgcgcg cccgaccccg 9300
ctcattactc ttcggcctac tcctactttt cgtaggggta ggcctcttcc tactccccgc 9360
tcggtagagc ggcacacact aggtacactc catagctaac tgttcctttt tttttttttt 9420
tttttttttt tttttttttt tttttttttc tttttttttt ttttccctct ttcttccctt 9480
ctcatcttat tctactttct ttcttggtgg ctccatctta gccctagtca cggctagctg 9540
tgaaaggtcc gtgagccgca tgactgcaga gagtgccgta actggtctct ctgcagatca 9600
tgt 9603

<210> SEQ ID NO 19
<211> LENGTH: 9585
<212> TYPE: DNA
<213> ORGANISM: Hepatitis C virus

<400> SEQUENCE: 19
acctgcccct aataggggcg acactccgcc atgaatcact cccctgtgag gaactactgt 60
cttcacgcag aaagcgccta gccatggcgt tagtatgagt gtcgtacagc ctccaggccc 120

-continued

```
ccccctcccg ggagagccat agtggtctgc ggaaccggtg agtacaccgg aattgccggg    180
aagactgggt cctttcttgg ataaacccac tctatgcccg gccatttggg cgtgcccccg    240
caagactgct agccgagtag cgttgggttg cgaaaggcct tgtggtactg cctgataggg    300
cgcttgcgag tgccccggga ggtctcgtag accgtgcacc atgagcacga atcctaaacc    360
tcaaagaaaa accaaacgta acaccaaccg ccgcccacag gacgtcaagt tcccgggcgg    420
tggtcagatc gttggtggag tttacctgtt gccgcgcagg ggccccaggt tgggtgtgcg    480
cgcgactagg aaggcttccg agcggtcgca acctcgtgga aggcgacaac ctatcccaaa    540
ggctcgccga cccgagggca gggcctgggc tcagcccggg tacccttggc ccctctatgg    600
caatgagggc ctggggtggg caggatggct cctgtcaccc cgcggctccc ggcctagttg    660
gggccccacg gacccccggc gtaggtcgcg taacttgggt aaggtcatcg atacccttac    720
atgcggcttc gccgatctca tggggtacat tccgctcgtc ggcgcccccc taggggggcgc   780
tgccagggcc ttggcacacg gtgtccgggt tctggaggac ggcgtgaact atgcaacagg    840
gaacttgccc ggttgctctt tctctatctt cctcttggct ctgctgtcct gtttgaccat    900
cccagcttcc gcttatgaag tgcgcaacgt gtccgggata taccatgtca cgaacgactg    960
ctccaactca agcattgtgt atgaggcagc ggacgtgatc atgcatactc ccgggtgcgt   1020
gccctgtgtt caggagggta acagctcccg ttgctgggta gcgctcactc ccacgctcgc   1080
ggccaggaat gccagcgtcc ccactacgac aatacgacgc cacgtcgact tgctcgttgg   1140
gacggctgct ttctgctccg ctatgtacgt gggggatctc tgcggatcta ttttcctcgt   1200
ctcccagctg ttcaccttct cgcctcgccg gcatgagaca gtgcaggact gcaactgctc   1260
aatctatccc ggccatgtat caggtcaccg catggcttgg gatatgatga tgaactggtc   1320
acctacaaca gccctagtgg tgtcgcagtt gctccggatc ccacaagctg tcgtggacat   1380
ggtggcgggg gcccactggg gagtcctggc gggccttgcc tactattcca tggtagggaa   1440
ctgggctaag gttctgattg tggcgctact ctttgccggc gttgacggga tccagcttgt   1500
gaataccaac ggcagctggc acatcaacag gactgcccta aattgcaatg actccctcca   1560
aactgggttc tttgccgcgc tgttttacgc acacaagttc aactcgtccg ggtgcccgga   1620
gcgcatggcc agctgccgcc ccattgactg gttcgcccag gggtggggcc ccatcaccta   1680
tactaagcct aacagctcgg atcagaggcc ttattgctgg cattacgcgc ctcgaccgtg   1740
tggtgtcgta cccgcgtcgc aggtgtgtgg tccagtgtat tgtttcaccc caagccctgt   1800
tgtggtgggg accaccgatc gttccggtgt ccctacgtat agctgggggg agaatgagac   1860
agacgtgatg ctcctcaaca acacgcgtcc gccacaaggc aactggttcg gctgtacatg   1920
gatgaatagt actgggttca ctaagacgtg cggaggtccc ccgtgtaaca tcgggggggt   1980
cggtaaccgc accttgatct gccccacgga ctgcttccgg aagcaccccg aggctactta   2040
cacaaaatgt ggctcggggc cctggttgac acctaggtgc ctagtagact acccatacag   2100
gctttggcac taccccctgca ctctcaattt ttccatcttt aaggttagga tgtatgtggg  2160
gggcgtggag cacaggctca atgccgcatg caattggact cgaggagagc gctgtaactt   2220
ggaggacagg gataggtcag aactcagccc gctgctgctg tctacaacag agtggcagat   2280
actgccctgt gctttcacca ccctaccggc tttatccact ggtttgatcc atctccatca   2340
gaacatcgtg gacgtgcaat acctgtacgg tgtagggtca gcgtttgtct cctttgcaat   2400
caaatgggag tacatcctgt tgcttttcct tctcctggca gacgcgcgcg tgtgtgcctg   2460
cttgtggatg atgctgctga tagcccaggc tgaggccgcc ttagagaact tggtggtcct   2520
```

caatgcggcg tccgtggccg gagcgcatgg tattctctcc tttcttgtgt tcttctgcgc 2580
cgcctggtac attaagggca ggctggctcc tggggcggcg tatgcttttt atggcgtatg 2640
gccgctgctc ctgctcctac tggcgttacc accacgagct tacgccttgg accgggagat 2700
ggctgcatcg tgcgggggtg cggttcttgt aggtctggta ttcttgacct tgtcaccata 2760
ctacaaagtg tttctcacta ggctcatatg gtggttacaa tactttatca ccagagccga 2820
ggcgcacatg caagtgtggg tcccccccct caacgttcgg ggaggccgcg atgccatcat 2880
cctcctcacg tgtgcggttc atccagagtt aattcttgac atcaccaaac tcctgctcgc 2940
catactcggc ccgctcatgg tgctccaggc tggcataacg agagtgccgt acttcgtgcg 3000
cgctcaaggg ctcattcgtg catgcatgtt agtgcgaaaa gtcgccgggg gtcattatgt 3060
ccaaatggtc ttcatgaagc tgggcgcgct gacaggtacg tacgtttata accatcttac 3120
cccactgcgg gactgggccc acgcgggcct acgagacctt gcggtggcgg tagagcccgt 3180
cgtcttctcc gccatggaga ccaaggtcat cacctgggga gcagacaccg ctgcgtgtgg 3240
ggacatcatc ttgggtctac ccgtctccgc ccgaaggggg aaggagatat ttttgggacc 3300
ggctgatagt ctcgaagggc aagggtggcg actccttgct cccatcactg cttatgccca 3360
gcaaacacga ggcctcctgg gcgccatagt ggtgagtatg acggggcgtg acaggacaga 3420
acaggccggg gaagtccaaa tcctgtccac agtctctcag tccttcctcg gaacaaccat 3480
ctcggggggtt ttgtggactg tttaccacgg agctggcaac aagactctag ccggcttacg 3540
gggtccggtc acgcagatgt actcgagtgc tgagggggac ttggtaggct ggcccagccc 3600
ccctgggacc aagtctttgg agccgtgcaa gtgtggagcc gtcgacctat atctggtcac 3660
gcggaacgct gatgtcatcc cggctcggag acgcggggac aagcggggag cattgctctc 3720
cccgagaccc atttcgacct tgaaggggtc ctcggggggg ccggtgctct gccctagggg 3780
ccacgtcgtt gggctcttcc gagcagctgt gtgctctcgg ggcgtggcca aatccatcga 3840
tttcatcccc gttgagacac tcgacgttgt tacaaggtct cccactttca gtgacaacag 3900
cacgccaccg gctgtgcccc agacctatca ggtcgggtac ttgcatgctc caactggcag 3960
tggaaagagc accaaggtcc ctgtcgcgta tgccgcccag gggtacaaag tactagtgct 4020
taacccctcg gtagctgcca ccctggggtt tggggcgtac ctatccaagg cacatggcat 4080
caatcccaac attaggactg gagtcaggac cgtgatgacc ggggaggcca tcacgtactc 4140
cacatatggc aaatttctcg ccgatggggg ctgcgctagc ggcgcctatg acatcatcat 4200
atgcgatgaa tgccacgctg tggatgctac ctccattctc ggcatcggaa cggtccttga 4260
tcaagcagag acagccgggg tcagactaac tgtgctggct acggccacac cccccgggtc 4320
agtgacaacc ccccatcccg atatagaaga ggtaggcctc gggcgggagg gtgagatccc 4380
cttctatggg agggcgattc ccctatcctg catcaaggga gggagacacc tgattttctg 4440
ccactcaaag aaaaagtgtg acgagctcgc ggcggccctt cggggcatgg gcttgaatgc 4500
cgtggcatac tatagagggt tggacgtctc cataatacca gctcagggag atgtggtggt 4560
cgtcgccacc gacgccctca tgacggggta cactggagac tttgactccg tgatcgactg 4620
caatgtagcg gtcacccaag ctgtcgactt cagcctggac cccaccttca ctataaccac 4680
acagactgtc ccacaagacg ctgtctcacg cagtcagcgc cgcgggcgca caggtagagg 4740
aagactgggc acttataggt atgtttccac tggtgaacga gcctcaggaa tgtttgacag 4800
tgtagtgctt tgtgagtgct acgacgcagg ggctgcgtgg tacgatctca caccagcgga 4860

-continued

```
gaccaccgtc aggcttagag cgtatttcaa cacgcccggc ctacccgtgt gtcaagacca   4920
tcttgaattt tgggaggcag ttttcaccgg cctcacacac atagacgccc acttcctctc   4980
ccaaacaaag caagcggggg agaacttcgc gtacctagta gcctaccaag ctacggtgtg   5040
cgccagagcc aaggcccctc ccccgtcctg ggacgccatg tggaagtgcc tggcccgact   5100
caagcctacg cttgcgggcc ccacacctct cctgtaccgt ttgggcccta ttaccaatga   5160
ggtcaccctc acacaccctg ggacgaagta catcgccaca tgcatgcaag ctgaccttga   5220
ggtcatgacc agcacgtggg tcctagctgg aggagtcctg gcagccgtcg ccgcatattg   5280
cctggcgact ggatgcgttt ccatcatcgg ccgcttgcac gtcaaccagc gagtcgtcgt   5340
tgcgccggat aaggaggtcc tgtatgaggc ttttgatgag atggaggaat gcgcctctag   5400
ggcggctctc atcgaagagg ggcagcggat agccgagatg ttgaagtcca agatccaagg   5460
cttgctgcag caggcctcta agcaggccca ggacatacaa cccgctatgc aggcttcatg   5520
gcccaaagtg gaacaatttt gggccagaca catgtggaac ttcattagcg gcatccaata   5580
cctcgcagga ttgtcaacac tgccagggaa ccccgcggtg gcttccatga tggcattcag   5640
tgccgccctc accagtccgt tgtcgaccag taccaccatc cttctcaaca tcatgggagg   5700
ctggttagcg tcccagatcg caccacccgc gggggccacc ggctttgtcg tcagtggcct   5760
ggtgggggct gccgtgggca gcataggcct gggtaaggtg ctggtggaca tcctggcagg   5820
atatggtgcg ggcatttcgg gggccctcgt cgcattcaag atcatgtctg gcgagaagcc   5880
ctctatggaa gatgtcatca atctactgcc tgggatcctg tctccgggag ccctggtggt   5940
gggggtcatc tgcgcggcca ttctgcgccg ccacgtggga ccgggggagg gcgcggtcca   6000
atggatgaac aggcttattg cctttgcttc cagaggaaac cacgtcgccc ctactcacta   6060
cgtgacggag tcggatgcgt cgcagcgtgt gacccaacta cttggctctc ttactataac   6120
cagcctactc agaagactcc acaattggat aactgaggac tgccccatcc catgctccgg   6180
atcctggctc cgcgacgtgt gggactgggt ttgcaccatc ttgacagact tcaaaaattg   6240
gctgacctct aaattgttcc ccaagctgcc cggcctcccc ttcatctctt gtcaaaaggg   6300
gtacaagggt gtgtgggccg gcactggcat catgaccacg cgctgccctt gcggcgccaa   6360
catctctggc aatgtccgcc tgggctctat gaggatcaca gggcctaaaa cctgcatgaa   6420
cacctggcag gggacctttc ctatcaattg ctacacggag ggccagtgcg cgccgaaacc   6480
ccccacgaac tacaagaccg ccatctggag ggtggcggcc tcggagtacg cggaggtgac   6540
gcagcatggg tcgtactcct atgtaacagg actgaccact gacaatctga aaattccttg   6600
ccaactacct tctccagagt ttttctcctg ggtggacggt gtgcagatcc ataggtttgc   6660
acccacacca aagccgtttt tccgggatga ggtctcgttc tgcgttgggc ttaattccta   6720
tgctgtcggg tcccagcttc cctgtgaacc tgagcccgac gcagacgtat tgaggtccat   6780
gctaacagat ccgccccaca tcacggcgga gactgcggcg cggcgcttgg cacggggatc   6840
acctccatct gaggcgagct cctcagtgag ccagctatca gcaccgtcgc tgcgggccac   6900
ctgcaccacc cacagcaaca cctatgacgt ggacatggtc gatgccaacc tgctcatgga   6960
gggcggtgtg gctcagacag agcctgagtc cagggtgccc gttctggact ttctcgagcc   7020
aatggccgag gaagagagcg accttgagcc ctcaatacca tcggagtgca tgctccccag   7080
gagcgggttt ccacgggcct taccggcttg ggcacggcct gactacaacc cgccgctcgt   7140
ggaatcgtgg aggaggccag attaccaacc gcccaccgtt gctggttgtg ctctcccccc   7200
ccccaagaag gccccgacgc ctcccccaag gagacgccgg acagtgggtc tgagcgagag   7260
```

-continued caccatatca gaagccctcc agcaactggc catcaagacc tttggccagc ccccctcgag 7320
cggtgatgca ggctcgtcca cgggggcggg cgccgccgaa tccggcggtc cgacgtcccc 7380
tggtgagccg gccccctcag agacaggttc cgcctcctct atgccccccc tcgaggggga 7440
gcctggagat ccggacctgg agtctgatca ggtagagctt caacctcccc cccagggggg 7500
gggggtagct cccggttcgg gctcggggtc ttggtctact tgctccgagg aggacgatac 7560
caccgtgtgc tgctccatgt catactcctg gaccggggct ctaataactc cctgtagccc 7620
cgaagaggaa aagttgccaa tcaacccttt gagtaactcg ctgttgcgat accataacaa 7680
ggtgtactgt acaacatcaa agagcgcctc acagagggct aaaaaggtaa cttttgacag 7740
gacgcaagtg ctcgacgccc attatgactc agtcttaaag gacatcaagc tagcggcttc 7800
caaggtcagc gcaaggctcc tcaccttgga ggaggcgtgc cagttgactc caccccattc 7860
tgcaagatcc aagtatggat tcggggccaa ggaggtccgc agcttgtccg ggagggccgt 7920
taaccacatc aagtccgtgt ggaaggacct cctggaagac ccacaaacac caattcccac 7980
aaccatcatg gccaaaaatg aggtgttctg cgtggacccc gccaaggggg gtaagaaacc 8040
agctcgcctc atcgtttacc ctgacctcgg cgtccgggtc tgcgagaaaa tggccctcta 8100
tgacattaca caaaagcttc ctcaggcggt aatgggagct tcctatggct tccagtactc 8160
ccctgcccaa cgggtggagt atctcttgaa agcatgggcg gaaaagaagg accccatggg 8220
tttttcgtat gatacccgat gcttcgactc aaccgtcact gagagagaca tcaggaccga 8280
ggagtccata taccaggcct gctccctgcc cgaggaggcc cgcactgcca tacactcgct 8340
gactgagaga ctttacgtag gagggcccat gttcaacagc aagggtcaaa cctgcggtta 8400
cagacgttgc cgcgccagcg gggtgctaac cactagcatg ggtaacacca tcacatgcta 8460
tgtgaaagcc ctagcggcct gcaaggctgc ggggatagtt gcgcccacaa tgctggtatg 8520
cggcgatgac ctagtagtca tctcagaaag ccaggggact gaggaggacg agcggaacct 8580
gagagccttc acggaggcca tgaccaggta ctctgcccct cctggtgatc cccccagacc 8640
ggaatatgac ctggagctaa taacatcctg ttcctcaaat gtgtctgtgg cgttgggccc 8700
gcggggccgc cgcagatact acctgaccag agacccaacc actccactcg cccgggctgc 8760
ctgggaaaca gttagacact cccctatcaa ttcatggctg ggaaacatca tccagtatgc 8820
tccaaccata tgggttcgca tggtcctaat gacacacttc ttctccattc tcatggtcca 8880
agacaccctg gaccagaacc tcaactttga gatgtatgga tcagtatact ccgtgaatcc 8940
tttggacctt ccagccataa ttgagaggtt acacgggctt gacgcctttt ctatgcacac 9000
atactctcac cacgaactga cgcgggtggc ttcagccctc agaaaacttg ggcgcccacc 9060
cctcagggtg tggaagagtc gggctcgcgc agtcagggcg tccctcatct cccgtggagg 9120
gaaagcggcc gtttgcggcc gatatctctt caattgggcg gtgaagacca agctcaaact 9180
cactccattg ccggaggcgc gcctactgga cttatccagt tggttcaccg tcggcgccgg 9240
cgggggcgac atttttcaca gcgtgtcgcg cgcccgaccc cgctcattac tcttcggcct 9300
actcctactt ttcgtagggg taggcctctt cctactcccc gctcggtaga gcggcacaca 9360
ctaggtacac tccatagcta actgttcctt tttttttttt tttttttttt tttttttttt 9420
tttttttttt tctttttttt tttttccct ctttcttccc ttctcatctt attctacttt 9480
ctttcttggt ggctccatct tagccctagt cacggctagc tgtgaaaggt ccgtgagccg 9540
catgactgca gagagtgccg taactggtct ctctgcagat catgt 9585

<210> SEQ ID NO 20
<211> LENGTH: 9597
<212> TYPE: DNA
<213> ORGANISM: Hepatitis C virus

<400> SEQUENCE: 20

```
acctgcccct aataggggcg acactccgcc atgaatcact cccctgtgag gaactactgt     60
cttcacgcag aaagcgccta gccatggcgt tagtatgagt gtcgtacagc ctccaggccc    120
ccccctcccg ggagagccat agtggtctgc ggaaccggtg agtacaccgg aattgccggg    180
aagactgggt cctttcttgg ataaacccac tctatgcccg gccatttggg cgtgcccccg    240
caagactgct agccgagtag cgttgggttg cgaaaggcct tgtggtactg cctgataggg    300
tgcttgcgag tgccccggga ggtctcgtag accgtgcacc atgagcacaa atcctaaacc    360
tcaaagaaaa accaaaagaa acacaaaccg ccgcccacag gacgttaagt tcccgggtgg    420
cggtcagatc gttggcggag tttacttgct gccgcgcagg ggccccaggt tgggtgtgcg    480
cgcgacaagg aagacttctg agcgatccca gccgcgtgga cgacgccagc ccatcccgaa    540
agatcggcgc tccaccggca agtcctgggg aaagccagga tatccttggc ccctgtacgg    600
aaacgagggt tgcggctggg cgggttggct cctgtccccc cgcgggtctc gtcctacttg    660
gggccccacc gacccccggc atagatcacg caatttgggc agagtcatcg ataccattac    720
gtgtggtttt gccgacctca tggggtacat ccctgtcgtt ggcgccccgg ttggaggcgt    780
cgccagagct ctggcacacg gtgttagggt cctggaggac gggataaatt acgcaacagg    840
gaatttaccc ggttgctctt tttctatctt tttgcttgct cttctgtcat gcgtcacagt    900
gccagtgtct gcagtggaag tcaggaacat tagttctagc tactacgcca ctaatgattg    960
ctcaaacaac agcatcacct ggcagctcac tgacgcagtt ctccatcttc ctggatgcgt   1020
cccatgtgag aatgataatg gcaccttgca ttgctggata caagtaacac ccaacgtggc   1080
tgtgaaacac cgcggtgcgc tcactcgtag cctgcgaaca cacgtcgaca tgatcgtaat   1140
ggcagctacg gcctgctcgg ccttgtatgt gggagatgtg tgcggggccg tgatgattct   1200
atcgcaggct ttcatggtat caccacaacg ccacaacttc acccaagagt gcaactgttc   1260
catctaccaa ggtcacatca ccggccatcg catggcatgg gacatgatgc tgaactggtc   1320
tccaactctt gccatgatcc tcgcctacgc cgctcgtgtt cccgagatgg tcctcgaaat   1380
tattttcggc ggccattggg gtgtggtgtt tggcttggcc tacttctcca tgcaaggagc   1440
gtgggccaaa gtcattgcca tcctccttct tgttgcggga gtggatgcac tctatttaat   1500
caacaccaat ggcagctggc acataaaccg gactgccctc aattgcaatg acagcttaca   1560
gacgggtttc atggcttccc tgttttacac ccacaggttc aacagctctg gctgccccga   1620
gcgcttgtct tcctgccgcg ggctggacga ttttcgcatc ggctggggaa ccttggaata   1680
cgaaacccac gtcaccaacg atgaggacat gaggccgtac tgctggcatt accctccgag   1740
gccttgcggc atcgtcccgg ctagaacggt ttgcggaccg gtctattgtt tcacccctag   1800
ccctgttgtc gtgggcacca ctgacaagca gggcgtaccc acctacacct gggggggaaaa   1860
cgagaccgat gtcttcctgc tgaatagcac aagacccccg cgaggagctt ggttcggctg   1920
cacttggatg aacgggactg ggttcactaa gacatgcggt gcaccacctt gccgcattag   1980
gaaagactac aacagcacta tcgatttatt gtgccccaca gactgtttta ggaagcaccc   2040
cgatgctacc tatcttaagt gtggagcagg gccttggtta actcccaggt gcctggtaga   2100
ctacccttat agactgtggc attatccgtg cactgtaaac ttcaccatct ttaaggcgcg   2160
```

-continued gatgtatgta ggaggggtgg agcatcgatt ctccgcagca tgcaacttca cgcgcggaga 2220
tcgctgcaga ctggaagata gggatagggg tcagcagagt ccactgctgc attccactac 2280
tgagtgggcg gtgctcccat gctccttctc tgacctacca gcactatcca ctggcctatt 2340
gcacctccac caaaacatcg tggacgtgca gtacctttac ggactttctc cggctctgac 2400
aagatacatc gtgaagtggg agtgggtgat cctccttttc ttgttgttgg cagacgccag 2460
gatctgtgca tgcctttgga tgctcatcat actgggccaa gccgaagcgg cgcttgagaa 2520
gctcatcatc ttgcactccg ctagtgctgc tagtgccaat ggtccgctgt ggtttttcat 2580
cttctttaca gcggcctggt acttaaaggg cagggtggtc cccgtggcca cgtactctgt 2640
tctcggctta tggtccttcc tcctcctagt cctggcctta ccacagcagg cttatgcctt 2700
ggacgctgct gaacaagggg aactggggct ggccatatta gtaattatat ccatctttac 2760
tcttacccca gcatacaaga tcctcctgag ccgttcagtg tggtggctgt cctacatgct 2820
ggtcttggcc gaggcccaga ttcagcaatg ggttcccccc ctggaggtcc gaggggggcg 2880
tgacggaatc atctgggtgg ctgtcattct acacccacgc cttgtgtttg aggtcacgaa 2940
atggttgtta gcaatcctgg ggcctgccta cctccttaaa gcgtctctgc tacggatacc 3000
gtactttgtg agggcccacg ctttgctacg agtgtgtacc ctggtgaaac acctcgcggg 3060
ggctaggtac atccagatgc tgttgatcac cataggcaga tggaccggca cttacatcta 3120
cgaccacctc tccccttat caacttgggc ggcccagggt ttgcgggacc tggcaatcgc 3180
cgtggagcct gtggtgttca gcccaatgga gaagaaggtc attgtgtggg gggctgagac 3240
agtggcgtgt ggagacatcc tgcatggcct cccggtctcc gcgaggctag gtagggaggt 3300
tctgctcggc cctgccgacg gctacacctc caaggggtgg aagctcctag ctcccatcac 3360
tgcttatgcc cagcaaacac gaggcctcct gggcgccata gtggtgagta tgacggggcg 3420
tgacaggaca gaacaggccg gggaagtcca aatcctgtcc acagtctctc agtccttcct 3480
cggaacaacc atctcggggg ttttgtggac tgtttaccac ggagctggca acaagactct 3540
agccggctta cggggtccgg tcacgcagat gtactcgagt gctgaggggg acttggtagg 3600
ctggcccagc ccccctggga ccaagtcttt ggagccgtgc aagtgtggag ccgtcgacct 3660
atatctggtc acgcggaacg ctgatgtcat cccggctcgg agacgcgggg acaagcgggg 3720
agcattgctc tccccgagac ccatttcgac cttgaagggg tcctcggggg ggccggtgct 3780
ctgccctagg ggccacgtcg ttgggctctt ccgagcagct gtgtgctctc ggggcgtggc 3840
caaatccatc gatttcatcc ccgttgagac actcgacgtt gttacaaggt ctcccacttt 3900
cagtgacaac agcacgccac cggctgtgcc ccagacctat caggtcgggt acttgcatgc 3960
tccaactggc agtggaaaga gcaccaaggt ccctgtcgcg tatgccgccc aggggtacaa 4020
agtactagtg cttaacccct cggtagctgc caccctgggg tttggggcgt acctatccaa 4080
ggcacatggc atcaatccca acattaggac tggagtcagg accgtgatga ccggggaggc 4140
catcacgtac tccacatatg gcaaatttct cgccgatggg ggctgcgcta gcggcgccta 4200
tgacatcatc atatgcgatg aatgccacgc tgtggatgct acctccattc tcggcatcgg 4260
aacggtcctt gatcaagcag agacagccgg ggtcagacta actgtgctgg ctacggccac 4320
accccccggg tcagtgacaa ccccccatcc cgatatagaa gaggtaggcc tcgggcggga 4380
gggtgagatc cccttctatg ggagggcgat tcccctatcc tgcatcaagg gagggagaca 4440
cctgattttc tgccactcaa agaaaaagtg tgacgagctc gcggcggccc ttcggggcat 4500

-continued

```
gggcttgaat gccgtggcat actatagagg gttggacgtc tccataatac cagctcaggg   4560
agatgtggtg gtcgtcgcca ccgacgccct catgacgggg tacactggag actttgactc   4620
cgtgatcgac tgcaatgtag cggtcaccca agctgtcgac ttcagcctgg accccacctt   4680
cactataacc acacagactg tcccacaaga cgctgtctca cgcagtcagc gccgcgggcg   4740
cacaggtaga ggaagacagg gcacttatag gtatgtttcc actggtgaac gagcctcagg   4800
aatgtttgac agtgtagtgc tttgtgagtg ctacgacgca ggggctgcgt ggtacgatct   4860
cacaccagcg gagaccaccg tcaggcttag agcgtatttc aacacgcccg gcctacccgt   4920
gtgtcaagac catcttgaat tttgggaggc agttttcacc ggcctcacac acatagacgc   4980
ccacttcctc tcccaaacaa agcaagcggg ggagaacttc gcgtacctag tagcctacca   5040
agctacggtg tgcgccagag ccaaggcccc tcccccgtcc tgggacgcca tgtggaagtg   5100
cctggcccga ctcaagccta cgcttgcggg ccccacacct ctcctgtacc gtttgggccc   5160
tattaccaat gaggtcaccc tcacacaccc tgggacgaag tacatcgcca catgcatgca   5220
agctgacctt gaggtcatga ccagcacgtg ggtcctagct ggaggagtcc tggcagccgt   5280
cgccgcatat tgcctggcga ctggatgcgt ttccatcatc ggccgcttgc acgtcaacca   5340
gcgagtcgtc gttgcgccgg ataaggaggt cctgtatgag gcttttgatg agatggagga   5400
atgcgcctct agggcggctc tcatcgaaga ggggcagcgg atagccgaga tgttgaagtc   5460
caagatccaa ggcttgctgc agcaggcctc taagcaggcc caggacatac aacccgctat   5520
gcaggcttca tggcccaaag tggaacaatt ttgggccaga cacatgtgga acttcattag   5580
cggcatccaa tacctcgcag gattgtcaac actgccaggg aaccccgcgg tggcttccat   5640
gatggcattc agtgccgccc tcaccagtcc gttgtcgacc agtaccacca tccttctcaa   5700
catcatggga ggctggttag cgtcccagat cgcaccaccc gcgggggcca ccggctttgt   5760
cgtcagtggc ctggtggggg ctgccgtggg cagcataggc ctgggtaagg tgctggtgga   5820
catcctggca ggatatggtg cgggcatttc gggggccctc gtcgcattca agatcatgtc   5880
tggcgagaag ccctctatgg aagatgtcat caatctactg cctgggatcc tgtctccggg   5940
agccctggtg gtgggggtca tctgcgcggc cattctgcgc cgccacgtgg gaccggggga   6000
gggcgcggtc caatggatga acaggcttat tgcctttgct tccagaggaa accacgtcgc   6060
ccctactcac tacgtgacgg agtcggatgc gtcgcagcgt gtgacccaac tacttggctc   6120
tcttactata accagcctac tcagaagact ccacaattgg ataactgagg actgccccat   6180
cccatgctcc ggatcctggc tccgcgacgt gtgggactgg gtttgcacca tcttgacaga   6240
cttcaaaaat tggctgacct ctaaattgtt ccccaagctg cccggcctcc ccttcatctc   6300
ttgtcaaaag gggtacaagg gtgtgtgggc cggcactggc atcatgacca cgcgctgccc   6360
ttgcggcgcc aacatctctg gcaatgtccg cctgggctct atgaggatca cagggcctaa   6420
aacctgcatg aacacctggc aggggacctt tcctatcaat tgctacacgg agggccagtg   6480
cgcgccgaaa ccccccacga actacaagac cgccatctgg agggtggcgg cctcggagta   6540
cgcggaggtg acgcagcatg ggtcgtactc ctatgtaaca ggactgacca ctgacaatct   6600
gaaaattcct tgccaactac cttctccaga gtttttctcc tgggtggacg gtgtgcagat   6660
ccataggttt gcacccacac caaagccgtt tttccgggat gaggtctcgt tctgcgttgg   6720
gcttaattcc tatgctgtcg ggtcccagct tccctgtgaa cctgagcccg acgcagacgt   6780
attgaggtcc atgctaacag atccgcccca catcacggcg gagactgcgg cgcggcgctt   6840
ggcacgggga tcacctccat ctgaggcgag ctcctcagtg agccagctat cagcaccgtc   6900
```

-continued

```
gctgcgggcc acctgcacca cccacagcaa cacctatgac gtggacatgg tcgatgccaa   6960
cctgctcatg gagggcggtg tggctcagac agagcctgag tccagggtgc ccgttctgga   7020
ctttctcgag ccaatggccg aggaagagag cgaccttgag ccctcaatac catcggagtg   7080
catgctcccc aggagcgggt ttccacgggc cttaccggct tgggcacggc ctgactacaa   7140
cccgccgctc gtggaatcgt ggaggaggcc agattaccaa ccgcccaccg ttgctggttg   7200
tgctctcccc ccccccaaga aggccccgac gcctccccca aggagacgcc ggacagtggg   7260
tctgagcgag agcaccatat cagaagccct ccagcaactg gccatcaaga cctttggcca   7320
gccccccctcg agcggtgatg caggctcgtc cacgggggcg ggcgccgccg aatccggcgg   7380
tccgacgtcc cctggtgagc cggcccccctc agagacaggt tccgcctcct ctatgccccc   7440
cctcgagggg gagcctggag atccggacct ggagtctgat caggtagagc ttcaacctcc   7500
cccccagggg ggggggtag ctcccggttc gggctcgggg tcttggtcta cttgctccga   7560
ggaggacgat accaccgtgt gctgctccat gtcatactcc tggaccgggg ctctaataac   7620
tccctgtagc cccgaagagg aaaagttgcc aatcaaccct ttgagtaact cgctgttgcg   7680
ataccataac aaggtgtact gtacaacatc aaagagcgcc tcacagaggg ctaaaaaggt   7740
aacttttgac aggacgcaag tgctcgacgc ccattatgac tcagtcttaa aggacatcaa   7800
gctagcggct tccaaggtca gcgcaaggct cctcaccttg gaggaggcgt gccagttgac   7860
tccaccccat tctgcaagat ccaagtatgg attcggggcc aaggaggtcc gcagcttgtc   7920
cgggagggcc gttaaccaca tcaagtccgt gtggaaggac ctcctggaag acccacaaac   7980
accaattccc acaaccatca tggccaaaaa tgaggtgttc tgcgtggacc ccgccaaggg   8040
gggtaagaaa ccagctcgcc tcatcgttta ccctgacctc ggcgtccggg tctgcgagaa   8100
aatggccctc tatgacatta cacaaaagct tcctcaggcg gtaatgggag cttcctatgg   8160
cttccagtac tcccctgccc aacgggtgga gtatctcttg aaagcatggg cggaaaagaa   8220
ggaccccatg ggtttttcgt atgatacccg atgcttcgac tcaaccgtca ctgagagaga   8280
catcaggacc gaggagtcca tataccaggc ctgctccctg cccgaggagg cccgcactgc   8340
catacactcg ctgactgaga gactttacgt aggagggccc atgttcaaca gcaagggtca   8400
aacctgcggt tacagacgtt gccgcgccag cggggtgcta accactagca tgggtaacac   8460
catcacatgc tatgtgaaag ccctagcggc ctgcaaggct gcggggatag ttgcgcccac   8520
aatgctggta tgcggcgatg acctagtagt catctcagaa agccagggga ctgaggagga   8580
cgagcggaac ctgagagcct tcacggaggc catgaccagg tactctgccc ctcctggtga   8640
tccccccaga ccggaatatg acctggagct aataacatcc tgttcctcaa atgtgtctgt   8700
ggcgttgggc ccgcggggcc gccgcagata ctacctgacc agagacccaa ccactccact   8760
cgcccgggct gcctgggaaa cagttagaca ctcccctatc aattcatggc tgggaaacat   8820
catccagtat gctccaacca tatgggttcg catggtccta atgacacact tcttctccat   8880
tctcatggtc caagacaccc tggaccagaa cctcaacttt gagatgtatg gatcagtata   8940
ctccgtgaat cctttggacc ttccagccat aattgagagg ttacacgggc ttgacgcctt   9000
ttctatgcac acatactctc accacgaact gacgcgggtg gcttcagccc tcagaaaact   9060
tggggcgcca cccctcaggg tgtggaagag tcgggctcgc gcagtcaggg cgtccctcat   9120
ctcccgtgga gggaaagcgg ccgtttgcgg ccgatatctc ttcaattggg cggtgaagac   9180
caagctcaaa ctcactccat tgccggaggc gcgcctactg gacttatcca gttggttcac   9240
```

-continued

```
cgtcggcgcc ggcgggggcg acatttttca cagcgtgtcg cgcgcccgac cccgctcatt   9300

actcttcggc ctactcctac ttttcgtagg ggtaggcctc ttcctactcc ccgctcggta   9360

gagcggcaca cactaggtac actccatagc taactgttcc tttttttttt tttttttttt   9420

tttttttttt tttttttttt tttcttttt ttttttttcc ctctttcttc ccttctcatc   9480

ttattctact ttctttcttg gtggctccat cttagcccta gtcacggcta gctgtgaaag   9540

gtccgtgagc cgcatgactg cagagagtgc cgtaactggt ctctctgcag atcatgt     9597
```

<210> SEQ ID NO 21
<211> LENGTH: 9597
<212> TYPE: DNA
<213> ORGANISM: Hepatitis C virus

<400> SEQUENCE: 21

```
acctgcccct aatagggggcg acactccgcc atgaatcact cccctgtgag gaactactgt     60

cttcacgcag aaagcgccta gccatggcgt tagtatgagt gtcgtacagc ctccaggccc    120

ccccctcccg ggagagccat agtggtctgc ggaaccggtg agtacaccgg aattgccggg    180

aagactgggt cctttcttgg ataaacccac tctatgcccg gccatttggg cgtgcccccg    240

caagactgct agccgagtag cgttgggttg cgaaaggcct tgtggtactg cctgataggg    300

tgcttgcgag tgccccggga ggtctcgtag accgtgcacc atgagcacaa atcctaaacc    360

tcaaagaaaa accaaaagaa acacaaaccg ccgcccacag gacgttaagt tcccgggtgg    420

cggtcagatc gttggcggag tttacttgct gccgcgcagg ggccccaggt tgggtgtgcg    480

cgcgacaagg aagacttctg agcgatccca gccgcgtgga cgacgccagc ccatcccgaa    540

agatcggcgc tccaccggca agtcctgggg aaagccagga tatccttggc ccctgtacgg    600

aaacgagggt tgcggctggg cgggttggct cctgtccccc cgcgggtctc gtcctacttg    660

gggccccacc gacccccggc atagatcacg caatttgggc agagtcatcg ataccattac    720

gtgtggtttt gccgacctca tggggtacat ccctgtcgtt ggcgccccgg ttggaggcgt    780

cgccagagct ctggcacacg gtgttagggt cctggaggac gggataaatt acgcaacagg    840

gaatttaccc ggttgctctt tttctatctt tttgcttgct cttctgtcat gcgtcacagt    900

gccagtgtct gcagtggaag tcaggaacat tagttctagc tactacgcca ctaatgattg    960

ctcaaacaac agcatcacct ggcagctcac tgacgcagtt ctccatcttc ctggatgcgt   1020

cccatgtgag aatgataatg gcaccttgca ttgctggata caagtaacac ccaacgtggc   1080

tgtgaaacac cgcggtgcgc tcactcgtag cctgcgaaca cacgtcgaca tgatcgtaat   1140

ggcagctacg gcctgctcgg ccttgtatgt gggagatgtg tgcggggccg tgatgattct   1200

atcgcaggct ttcatggtat caccacaacg ccacaacttc acccaagagt gcaactgttc   1260

catctaccaa ggtcacatca ccggccatcg catggcatgg gacatgatgc tgaactggtc   1320

tccaactctt gccatgatcc tcgcctacgc cgctcgtgtt cccgagatgg tcctcgaaat   1380

tattttcggc ggccattggg gtgtggtgtt tggcttggcc tacttctcca tgcaaggagc   1440

gtgggccaaa gtcattgcca tcctccttct tgttgcggga gtggatgcac tcaatttaat   1500

caacaccaat ggcagctggc acataaaccg gactgccctc aattgcaatg acagcttaca   1560

gacgggtttc atggcttccc tgttttacac ccacaggttc aacagctctg gctgccccga   1620

gcgcttgtct tcctgccgcg ggctggacga ttttcgcatc ggctggggaa ccttggaata   1680

cgaaacccac gtcaccaacg atgaggacat gaggccgtac tgctggcatt accctccgag   1740

gccttgcggc atcgtcccgg ctagaacggt ttgcggaccg gtctattgtt tcacccctag   1800
```

```
ccctgttgtc gtgggcacca ctgacaagca gggcgtaccc acctacacct ggggggaaaa   1860
cgagaccgat gtcttcctgc tgaatagcac aagacccccg cgaggagctt ggttcggctg   1920
cacttggatg aacgggactg ggttcactaa gacatgcggt gcaccacctt gccgcattag   1980
gaaagactac aacagcacta tcgatttatt gtgccccaca gactgtttta ggaagcaccc   2040
cgatgctacc tatcttaagt gtggagcagg gccttggtta actcccaggt gcctggtaga   2100
ctacccttat agactgtggc attatccgtg cactgtaaac ttcaccatct ttaaggcgcg   2160
gatgtatgta ggaggggtgg agcatcgatt ctccgcagca tgcaacttca cgcgcggaga   2220
tcgctgcaga ctggaagata gggatagggg tcagcagagt ccactgctgc attccactac   2280
tgagtgggcg gtgctcccat gctccttctc tgacctacca gcactatcca ctggcctatt   2340
gcacctccac caaaacatcg tggacgtgca gtacctttac ggactttctc cggctctgac   2400
aagatacatc gtgaagtggg agtgggtgat cctccttttc ttgttgttgg cagacgccag   2460
gatctgtgca tgcctttgga tgctcatcat actgggccaa gccgaagcgg cgcttgagaa   2520
gctcatcatc ttgcactccg ctagtgctgc tagtgccaat ggtccgctgt ggtttttcat   2580
cttctttaca gcggcctggt acttaaaggg cagggtggtc cccgtggcca cgtactctgt   2640
tctcggctta tggtccttcc tcctcctagt cctggcctta ccacagcagg cttatgcctt   2700
ggacgctgct gaacaagggg aactggggct ggccatatta gtaattatat ccatctttac   2760
tcttacccca gcatacaaga tcctcctgag ccgttcagtg tggtggctgt cctacatgct   2820
ggtcttggcc gaggcccaga ttcagcaatg ggttcccccc ctggaggtcc gagggggggcg  2880
tgacggaatc atctgggtgg ctgtcattct acacccacgc cttgtgtttg aggtcacgaa   2940
atggttgtta gcaatcctgg ggcctgccta cctccttaaa gcgtctctgc tacggatacc   3000
gtactttgtg agggcccacg ctttgctacg agtgtgtacc ctggtgaaac acctcgcggg   3060
ggctaggtac atccagatgc tgttgatcac cataggcaga tggaccggca cttacatcta   3120
cgaccacctc tcccctttat caacttgggc ggcccagggt ttgcgggacc tggcaatcgc   3180
cgtggagcct gtggtgttca gcccaatgga gaagaaggtc attgtgtggg gggctgagac   3240
agtggcgtgt ggagacatcc tgcatggcct cccggtctcc gcgaggctag gtagggaggt   3300
tctgctcggc cctgccgacg gctacacctc caaggggtgg aagctcctag ctcccatcac   3360
tgcttatgcc cagcaaacac gaggcctcct gggcgccata gtggtgagta tgacggggcg   3420
tgacaggaca gaacaggccg gggaagtcca aatcctgtcc acagtctctc agtccttcct   3480
cggaacaacc atctcggggg ttttgtggac tgtttaccac ggagctggca acaagactct   3540
agccggctta cggggtccgg tcacgcagat gtactcgagt gctgaggggg acttggtagg   3600
ctggcccagc ccccctggga ccaagtcttt ggagccgtgc aagtgtggag ccgtcgacct   3660
atatctggtc acgcggaacg ctgatgtcat cccggctcgg agacgcgggg acaagcgggg   3720
agcattgctc tccccgagac ccatttcgac cttgaagggg tcctcggggg ggccggtgct   3780
ctgccctagg ggccacgtcg ttgggctctt ccgagcagct gtgtgctctc ggggcgtggc   3840
caaatccatc gatttcatcc ccgttgagac actcgacgtt gttacaaggt ctcccacttt   3900
cagtgacaac agcacgccac cggctgtgcc ccagacctat caggtcgggt acttgcatgc   3960
tccaactggc agtggaaaga gcaccaaggt ccctgtcgcg tatgccgccc aggggtacaa   4020
agtactagtg cttaacccct cggtagctgc caccctgggg tttggggcgt acctatccaa   4080
ggcacatggc atcaatccca acattaggac tggagtcagg accgtgatga ccggggaggc   4140
```

-continued

```
catcacgtac tccacatatg gcaaatttct cgccgatggg ggctgcgcta gcggcgccta   4200
tgacatcatc atatgcgatg aatgccacgc tgtggatgct acctccattc tcggcatcgg   4260
aacggtcctt gatcaagcag agacagccgg ggtcagacta actgtgctgg ctacggccac   4320
accccccggg tcagtgacaa ccccccatcc cgatatagaa gaggtaggcc tcgggcggga   4380
gggtgagatc cccttctatg ggagggcgat tcccctatcc tgcatcaagg gagggagaca   4440
cctgattttc tgccactcaa agaaaaagtg tgacgagctc gcggcggccc ttcggggcat   4500
gggcttgaat gccgtggcat actatagagg gttggacgtc tccataatac cagctcaggg   4560
agatgtggtg gtcgtcgcca ccgacgccct catgacgggg tacactggag actttgactc   4620
cgtgatcgac tgcaatgtag cggtcaccca agctgtcgac ttcagcctgg accccacctt   4680
cactataacc acacagactg tcccacaaga cgctgtctca cgcagtcagc gccgcgggcg   4740
cacaggtaga ggaagacagg gcacttatag gtatgtttcc actggtgaac gagcctcagg   4800
aatgtttgac agtgtagtgc tttgtgagtg ctacgacgca ggggctgcgt ggtacgatct   4860
cacaccagcg gagaccaccg tcaggcttag agcgtatttc aacacgcccg gcctacccgt   4920
gtgtcaagac catcttgaat tttgggaggc agttttcacc ggcctcacac acatagacgc   4980
ccacttcctc tcccaaacaa agcaagcggg ggagaacttc gcgtacctag tagcctacca   5040
agctacggtg tgcgccagag ccaaggcccc tcccccgtcc tgggacgcca tgtggaagtg   5100
cctggcccga ctcaagccta cgcttgcggg ccccacacct ctcctgtacc gtttgggccc   5160
tattaccaat gaggtcaccc tcacacaccc tgggacgaag tacatcgcca catgcatgca   5220
agctgacctt gaggtcatga ccagcacgtg ggtcctagct ggaggagtcc tggcagccgt   5280
cgccgcatat tgcctggcga ctggatgcgt ttccatcatc ggccgcttgc acgtcaacca   5340
gcgagtcgtc gttgcgccgg ataaggaggt cctgtatgag gcttttgatg agatggagga   5400
atgcgcctct agggcggctc tcatcgaaga ggggcagcgg atagccgaga tgttgaagtc   5460
caagatccaa ggcttgctgc agcaggcctc taagcaggcc caggacatac aacccgctat   5520
gcaggcttca tggcccaaag tggaacaatt ttgggccaga cacatgtgga acttcattag   5580
cggcatccaa tacctcgcag gattgtcaac actgccaggg aaccccgcgg tggcttccat   5640
gatggcattc agtgccgccc tcaccagtcc gttgtcgacc agtaccacca tccttctcaa   5700
catcatggga ggctggttag cgtcccagat cgcaccaccc gcgggggcca ccggctttgt   5760
cgtcagtggc ctggtggggg ctgccgtggg cagcataggc ctgggtaagg tgctggtgga   5820
catcctggca ggatatggtg cgggcatttc gggggccctc gtcgcattca agatcatgtc   5880
tggcgagaag ccctctatgg aagatgtcat caatctactg cctgggatcc tgtctccggg   5940
agccctggtg gtgggggtca tctgcgcggc cattctgcgc cgccacgtgg gaccggggga   6000
gggcgcggtc caatggatga acaggcttat tgcctttgct tccagaggaa accacgtcgc   6060
ccctactcac tacgtgacgg agtcggatgc gtcgcagcgt gtgacccaac tacttggctc   6120
tcttactata accagcctac tcagaagact ccacaattgg ataactgagg actgccccat   6180
cccatgctcc ggatcctggc tccgcgacgt gtgggactgg gtttgcacca tcttgacaga   6240
cttcaaaaat tggctgacct ctaaattgtt ccccaagctg cccggcctcc ccttcatctc   6300
ttgtcaaaag ggtacaaggg gtgtgtgggc cggcactggc atcatgacca cgcgctgccc   6360
ttgcggcgcc aacatctctg gcaatgtccg cctgggctct atgaggatca cagggcctaa   6420
aacctgcatg aacacctggc aggggacctt tcctatcaat tgctacacgg agggccagtg   6480
cgcgccgaaa ccccccacga actacaagac cgccatctgg agggtggcgg cctcggagta   6540
```

```
cgcggaggtg acgcagcatg ggtcgtactc ctatgtaaca ggactgacca ctgacaatct   6600
gaaaattcct tgccaactac cttctccaga gtttttctcc tgggtggacg gtgtgcagat   6660
ccataggttt gcacccacac caaagccgtt tttccgggat gaggtctcgt tctgcgttgg   6720
gcttaattcc tatgctgtcg ggtcccagct tccctgtgaa cctgagcccg acgcagacgt   6780
attgaggtcc atgctaacag atccgcccca catcacggcg gagactgcgg cgcggcgctt   6840
ggcacgggga tcacctccat ctgaggcgag ctcctcagtg agccagctat cagcaccgtc   6900
gctgcgggcc acctgcacca cccacagcaa cacctatgac gtggacatgg tcgatgccaa   6960
cctgctcatg gagggcggtg tggctcagac agagcctgag tccagggtgc ccgttctgga   7020
ctttctcgag ccaatggccg aggaagagag cgaccttgag ccctcaatac catcggagtg   7080
catgctcccc aggagcgggt ttccacgggc cttaccggct tgggcacggc ctgactacaa   7140
cccgccgctc gtggaatcgt ggaggaggcc agattaccaa ccgcccaccg ttgctggttg   7200
tgctctcccc ccccccaaga aggccccgac gcctccccca aggagacgcc ggacagtggg   7260
tctgagcgag agcaccatat cagaagccct ccagcaactg gccatcaaga cctttggcca   7320
gccccccctcg agcggtgatg caggctcgtc cacgggggcg ggcgccgccg aatccggcgg   7380
tccgacgtcc cctggtgagc cggccccctc agagacaggt tccgcctcct ctatgccccc   7440
cctcgagggg gagcctggag atccggacct ggagtctgat caggtagagc ttcaacctcc   7500
cccccagggg gggggggtag ctcccggttc gggctcgggg tcttggtcta cttgctccga   7560
ggaggacgat accaccgtgt gctgctccat gtcatactcc tggaccgggg ctctaataac   7620
tccctgtagc cccgaagagg aaaagttgcc aatcaaccct ttgagtaact cgctgttgcg   7680
ataccataac aaggtgtact gtacaacatc aaagagcgcc tcacagaggg ctaaaaaggt   7740
aacttttgac aggacgcaag tgctcgacgc ccattatgac tcagtcttaa aggacatcaa   7800
gctagcggct tccaaggtca gcgcaaggct cctcaccttg gaggaggcgt gccagttgac   7860
tccaccccat tctgcaagat ccaagtatgg attcggggcc aaggaggtcc gcagcttgtc   7920
cgggagggcc gttaaccaca tcaagtccgt gtggaaggac ctcctggaag acccacaaac   7980
accaattccc acaaccatca tggccaaaaa tgaggtgttc tgcgtggacc ccgccaaggg   8040
gggtaagaaa ccagctcgcc tcatcgttta ccctgacctc ggcgtccggg tctgcgagaa   8100
aatggccctc tatgacatta cacaaaagct tcctcaggcg gtaatgggag cttcctatgg   8160
cttccagtac tcccctgccc aacgggtgga gtatctcttg aaagcatggg cggaaaagaa   8220
ggaccccatg ggtttttcgt atgatacccg atgcttcgac tcaaccgtca ctgagagaga   8280
catcaggacc gaggagtcca tataccaggc ctgctccctg cccgaggagg cccgcactgc   8340
catacactcg ctgactgaga gactttacgt aggagggccc atgttcaaca gcaagggtca   8400
aacctgcggt tacagacgtt gccgcgccag cggggtgcta accactagca tgggtaacac   8460
catcacatgc tatgtgaaag ccctagcggc ctgcaaggct gcggggatag ttgcgcccac   8520
aatgctggta tgcggcgatg acctagtagt catctcagaa agccagggga ctgaggagga   8580
cgagcggaac ctgagagcct tcacggaggc catgaccagg tactctgccc ctcctggtga   8640
tccccccaga ccggaatatg acctggagct aataacatcc tgttcctcaa atgtgtctgt   8700
ggcgttgggc ccgcggggcc gccgcagata ctacctgacc agagacccaa ccactccact   8760
cgcccgggct gcctgggaaa cagttagaca ctcccctatc aattcatggc tgggaaacat   8820
catccagtat gctccaacca tatgggttcg catggtccta atgacacact tcttctccat   8880
```

-continued

```
tctcatggtc caagacaccc tggaccagaa cctcaacttt gagatgtatg gatcagtata    8940
ctccgtgaat cctttggacc ttccagccat aattgagagg ttacacgggc ttgacgcctt    9000
ttctatgcac acatactctc accacgaact gacgcgggtg gcttcagccc tcagaaaact    9060
tggggcgcca cccctcaggg tgtggaagag tcgggctcgc gcagtcaggg cgtccctcat    9120
ctcccgtgga gggaaagcgg ccgtttgcgg ccgatatctc ttcaattggg cggtgaagac    9180
caagctcaaa ctcactccat tgccggaggc gcgcctactg gacttatcca gttggttcac    9240
cgtcggcgcc ggcgggggcg acattttttca cagcgtgtcg cgcgcccgac cccgctcatt    9300
actcttcggc ctactcctac ttttcgtagg ggtaggcctc ttcctactcc ccgctcggta    9360
gagcggcaca cactaggtac actccatagc taactgttcc ttttttttttt tttttttttt    9420
tttttttttt tttttttttt ttctttttttt ttttttttcc ctctttcttc ccttctcatc    9480
ttattctact ttctttcttg gtggctccat cttagcccta gtcacggcta gctgtgaaag    9540
gtccgtgagc cgcatgactg cagagagtgc cgtaactggt ctctctgcag atcatgt      9597
```

<210> SEQ ID NO 22
<211> LENGTH: 3002
<212> TYPE: PRT
<213> ORGANISM: Hepatitis C virus

<400> SEQUENCE: 22

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Ala Ser Glu Arg Ser Gln Pro Arg Gly Arg Arg Gln Pro
    50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Ile Tyr His Val Thr Asn Asp Cys Ser
        195                 200                 205

Asn Ser Ser Ile Val Tyr Glu Ala Ala Asp Val Ile Met His Thr Pro
    210                 215                 220

Gly Cys Val Pro Cys Val Gln Glu Gly Asn Ser Ser Arg Cys Trp Val
225                 230                 235                 240

Ala Leu Thr Pro Thr Leu Ala Ala Arg Asn Ala Ser Val Pro Thr Thr
                245                 250                 255
```

```
Thr Ile Arg Arg His Val Asp Leu Leu Val Gly Thr Ala Ala Phe Cys
            260                 265                 270

Ser Ala Met Tyr Val Gly Asp Leu Cys Gly Ser Ile Phe Leu Val Ser
        275                 280                 285

Gln Leu Phe Thr Phe Ser Pro Arg Arg His Glu Thr Val Gln Asp Cys
    290                 295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Val Gly Asn Trp
        355                 360                 365

Ala Lys Val Leu Ile Val Ala Leu Leu Phe Ala Gly Val Asp Gly Ile
    370                 375                 380

Gln Leu Val Asn Thr Asn Gly Ser Trp His Ile Asn Arg Thr Ala Leu
385                 390                 395                 400

Asn Cys Asn Asp Ser Leu Gln Thr Gly Phe Phe Ala Ala Leu Phe Tyr
                405                 410                 415

Ala His Lys Phe Asn Ser Ser Gly Cys Pro Glu Arg Met Ala Ser Cys
            420                 425                 430

Arg Pro Ile Asp Trp Phe Ala Gln Gly Trp Gly Pro Ile Thr Tyr Thr
        435                 440                 445

Lys Pro Asn Ser Ser Asp Gln Arg Pro Tyr Cys Trp His Tyr Ala Pro
    450                 455                 460

Arg Pro Cys Gly Val Val Pro Ala Ser Gln Val Cys Gly Pro Val Tyr
465                 470                 475                 480

Cys Phe Thr Pro Ser Pro Val Val Val Gly Thr Thr Asp Arg Ser Gly
                485                 490                 495

Val Pro Thr Tyr Ser Trp Gly Glu Asn Glu Thr Asp Val Met Leu Leu
            500                 505                 510

Asn Asn Thr Arg Pro Pro Gln Gly Asn Trp Phe Gly Cys Thr Trp Met
        515                 520                 525

Asn Ser Thr Gly Phe Thr Lys Thr Cys Gly Gly Pro Pro Cys Asn Ile
    530                 535                 540

Gly Gly Val Gly Asn Arg Thr Leu Ile Cys Pro Thr Asp Cys Phe Arg
545                 550                 555                 560

Lys His Pro Glu Ala Thr Tyr Thr Lys Cys Gly Ser Gly Pro Trp Leu
                565                 570                 575

Thr Pro Arg Cys Leu Val Asp Tyr Pro Tyr Arg Leu Trp His Tyr Pro
            580                 585                 590

Cys Thr Leu Asn Phe Ser Ile Phe Lys Val Arg Met Tyr Val Gly Gly
        595                 600                 605

Val Glu His Arg Leu Asn Ala Ala Cys Asn Trp Thr Arg Gly Glu Arg
    610                 615                 620

Cys Asn Leu Glu Asp Arg Asp Arg Ser Glu Leu Ser Pro Leu Leu Leu
625                 630                 635                 640

Ser Thr Thr Glu Trp Gln Ile Leu Pro Cys Ala Phe Thr Thr Leu Pro
                645                 650                 655

Ala Leu Ser Thr Gly Leu Ile His Leu His Gln Asn Ile Val Asp Val
            660                 665                 670
```

```
Gln Tyr Leu Tyr Gly Val Gly Ser Ala Phe Val Ser Phe Ala Ile Lys
        675                 680                 685

Trp Glu Tyr Ile Leu Leu Leu Phe Leu Leu Leu Ala Asp Ala Arg Val
    690                 695                 700

Cys Ala Cys Leu Trp Met Met Leu Leu Ile Ala Gln Ala Glu Ala Ala
705                 710                 715                 720

Leu Glu Asn Leu Val Val Leu Asn Ala Ala Ser Val Ala Gly Ala His
                725                 730                 735

Gly Ile Leu Ser Phe Leu Val Phe Phe Cys Ala Ala Trp Tyr Ile Lys
            740                 745                 750

Gly Arg Leu Ala Pro Gly Ala Ala Tyr Ala Phe Tyr Gly Val Trp Pro
        755                 760                 765

Leu Leu Leu Leu Leu Leu Ala Leu Pro Pro Arg Ala Tyr Ala Leu Asp
    770                 775                 780

Arg Glu Met Ala Ala Ser Cys Gly Gly Ala Val Leu Val Gly Leu Val
785                 790                 795                 800

Phe Leu Thr Leu Ser Pro Tyr Tyr Lys Val Phe Leu Thr Arg Leu Ile
                805                 810                 815

Trp Trp Leu Gln Tyr Phe Ile Thr Arg Ala Glu Ala His Met Gln Val
            820                 825                 830

Trp Val Pro Pro Leu Asn Val Arg Gly Gly Arg Asp Ala Ile Ile Leu
        835                 840                 845

Leu Thr Cys Ala Val His Pro Glu Leu Ile Leu Asp Ile Thr Lys Leu
    850                 855                 860

Leu Leu Ala Ile Leu Gly Pro Leu Met Val Leu Gln Ala Gly Ile Thr
865                 870                 875                 880

Arg Val Pro Tyr Phe Val Arg Ala Gln Gly Leu Ile Arg Ala Cys Met
                885                 890                 895

Leu Val Arg Lys Val Ala Gly Gly His Tyr Val Gln Met Val Phe Met
            900                 905                 910

Lys Leu Gly Ala Leu Thr Gly Thr Tyr Val Tyr Asn His Leu Thr Pro
        915                 920                 925

Leu Arg Asp Trp Ala His Ala Gly Leu Arg Asp Leu Ala Val Ala Val
    930                 935                 940

Glu Pro Val Val Phe Ser Ala Met Glu Thr Lys Val Ile Thr Trp Gly
945                 950                 955                 960

Ala Asp Thr Ala Ala Cys Gly Asp Ile Ile Leu Gly Leu Pro Val Ser
                965                 970                 975

Ala Arg Arg Gly Lys Glu Ile Phe Leu Gly Pro Ala Asp Ser Leu Glu
            980                 985                 990

Gly Gln Gly Trp Arg Leu Leu Ala  Pro Ile Thr Ala Tyr  Ala Gln Gln
        995                 1000                1005

Thr Arg  Gly Leu Leu Gly Ala  Ile Val Val Ser Met  Thr Gly Arg
    1010                1015                1020

Asp Arg  Thr Glu Gln Ala Gly  Glu Val Gln Ile Leu  Ser Thr Val
    1025                1030                1035

Ser Gln  Ser Phe Leu Gly Thr  Thr Ile Ser Gly Val  Leu Trp Thr
    1040                1045                1050

Val Tyr  His Gly Ala Gly Asn  Lys Thr Leu Ala Gly  Leu Arg Gly
    1055                1060                1065

Pro Val  Thr Gln Met Tyr Ser  Ser Ala Glu Gly Asp  Leu Val Gly
    1070                1075                1080

Trp Pro  Ser Pro Pro Gly Thr  Lys Ser Leu Glu Pro  Cys Lys Cys
```

```
    1085                1090                1095

Gly Ala  Val Asp Leu Tyr Leu  Val Thr Arg Asn Ala  Asp Val Ile
    1100                1105                1110

Pro Ala  Arg Arg Arg Gly Asp  Lys Arg Gly Ala Leu  Leu Ser Pro
    1115                1120                1125

Arg Pro  Ile Ser Thr Leu Lys  Gly Ser Ser Gly Gly  Pro Val Leu
    1130                1135                1140

Cys Pro  Arg Gly His Val Val  Gly Leu Phe Arg Ala  Ala Val Cys
    1145                1150                1155

Ser Arg  Gly Val Ala Lys Ser  Ile Asp Phe Ile Pro  Val Glu Thr
    1160                1165                1170

Leu Asp  Val Val Thr Arg Ser  Pro Thr Phe Ser Asp  Asn Ser Thr
    1175                1180                1185

Pro Pro  Ala Val Pro Gln Thr  Tyr Gln Val Gly Tyr  Leu His Ala
    1190                1195                1200

Pro Thr  Gly Ser Gly Lys Ser  Thr Lys Val Pro Val  Ala Tyr Ala
    1205                1210                1215

Ala Gln  Gly Tyr Lys Val Leu  Val Leu Asn Pro Ser  Val Ala Ala
    1220                1225                1230

Thr Leu  Gly Phe Gly Ala Tyr  Leu Ser Lys Ala His  Gly Ile Asn
    1235                1240                1245

Pro Asn  Ile Arg Thr Gly Val  Arg Thr Val Met Thr  Gly Glu Ala
    1250                1255                1260

Ile Thr  Tyr Ser Thr Tyr Gly  Lys Phe Leu Ala Asp  Gly Gly Cys
    1265                1270                1275

Ala Ser  Gly Ala Tyr Asp Ile  Ile Ile Cys Asp Glu  Cys His Ala
    1280                1285                1290

Val Asp  Ala Thr Ser Ile Leu  Gly Ile Gly Thr Val  Leu Asp Gln
    1295                1300                1305

Ala Glu  Thr Ala Gly Val Arg  Leu Thr Val Leu Ala  Thr Ala Thr
    1310                1315                1320

Pro Pro  Gly Ser Val Thr Thr  Pro His Pro Asp Ile  Glu Glu Val
    1325                1330                1335

Gly Leu  Gly Arg Glu Gly Glu  Ile Pro Phe Tyr Gly  Arg Ala Ile
    1340                1345                1350

Pro Leu  Ser Cys Ile Lys Gly  Gly Arg His Leu Ile  Phe Cys His
    1355                1360                1365

Ser Lys  Lys Lys Cys Asp Glu  Leu Ala Ala Ala Leu  Arg Gly Met
    1370                1375                1380

Gly Leu  Asn Ala Val Ala Tyr  Tyr Arg Gly Leu Asp  Val Ser Ile
    1385                1390                1395

Ile Pro  Ala Gln Gly Asp Val  Val Val Val Ala Thr  Asp Ala Leu
    1400                1405                1410

Met Thr  Gly Tyr Thr Gly Asp  Phe Asp Ser Val Ile  Asp Cys Asn
    1415                1420                1425

Val Ala  Val Thr Gln Ala Val  Asp Phe Ser Leu Asp  Pro Thr Phe
    1430                1435                1440

Thr Ile  Thr Thr Gln Thr Val  Pro Gln Asp Ala Val  Ser Arg Ser
    1445                1450                1455

Gln Arg  Arg Gly Arg Thr Gly  Arg Gly Arg Leu Gly  Thr Tyr Arg
    1460                1465                1470

Tyr Val  Ser Thr Gly Glu Arg  Ala Ser Gly Met Phe  Asp Ser Val
    1475                1480                1485
```

```
Val Leu Cys Glu Cys Tyr Asp Ala Gly Ala Ala Trp Tyr Asp Leu
    1490                1495                1500

Thr Pro Ala Glu Thr Thr Val Arg Leu Arg Ala Tyr Phe Asn Thr
    1505                1510                1515

Pro Gly Leu Pro Val Cys Gln Asp His Leu Glu Phe Trp Glu Ala
    1520                1525                1530

Val Phe Thr Gly Leu Thr His Ile Asp Ala His Phe Leu Ser Gln
    1535                1540                1545

Thr Lys Gln Ala Gly Glu Asn Phe Ala Tyr Leu Val Ala Tyr Gln
    1550                1555                1560

Ala Thr Val Cys Ala Arg Ala Lys Ala Pro Pro Pro Ser Trp Asp
    1565                1570                1575

Ala Met Trp Lys Cys Leu Ala Arg Leu Lys Pro Thr Leu Ala Gly
    1580                1585                1590

Pro Thr Pro Leu Leu Tyr Arg Leu Gly Pro Ile Thr Asn Glu Val
    1595                1600                1605

Thr Leu Thr His Pro Gly Thr Lys Tyr Ile Ala Thr Cys Met Gln
    1610                1615                1620

Ala Asp Leu Glu Val Met Thr Ser Thr Trp Val Leu Ala Gly Gly
    1625                1630                1635

Val Leu Ala Ala Val Ala Ala Tyr Cys Leu Ala Thr Gly Cys Val
    1640                1645                1650

Ser Ile Ile Gly Arg Leu His Val Asn Gln Arg Val Val Val Ala
    1655                1660                1665

Pro Asp Lys Glu Val Leu Tyr Glu Ala Phe Asp Glu Met Glu Glu
    1670                1675                1680

Cys Ala Ser Arg Ala Ala Leu Ile Glu Glu Gly Gln Arg Ile Ala
    1685                1690                1695

Glu Met Leu Lys Ser Lys Ile Gln Gly Leu Leu Gln Gln Ala Ser
    1700                1705                1710

Lys Gln Ala Gln Asp Ile Gln Pro Ala Met Gln Ala Ser Trp Pro
    1715                1720                1725

Lys Val Glu Gln Phe Trp Ala Arg His Met Trp Asn Phe Ile Ser
    1730                1735                1740

Gly Ile Gln Tyr Leu Ala Gly Leu Ser Thr Leu Pro Gly Asn Pro
    1745                1750                1755

Ala Val Ala Ser Met Met Ala Phe Ser Ala Ala Leu Thr Ser Pro
    1760                1765                1770

Leu Ser Thr Ser Thr Thr Ile Leu Leu Asn Ile Met Gly Gly Trp
    1775                1780                1785

Leu Ala Ser Gln Ile Ala Pro Pro Ala Gly Ala Thr Gly Phe Val
    1790                1795                1800

Val Ser Gly Leu Val Gly Ala Ala Val Gly Ser Ile Gly Leu Gly
    1805                1810                1815

Lys Val Leu Val Asp Ile Leu Ala Gly Tyr Gly Ala Gly Ile Ser
    1820                1825                1830

Gly Ala Leu Val Ala Phe Lys Ile Met Ser Gly Glu Lys Pro Ser
    1835                1840                1845

Met Glu Asp Val Ile Asn Leu Leu Pro Gly Ile Leu Ser Pro Gly
    1850                1855                1860

Ala Leu Val Val Gly Val Ile Cys Ala Ala Ile Leu Arg Arg His
    1865                1870                1875
```

```
Val Gly  Pro Gly Glu Gly Ala  Val Gln Trp Met Asn  Arg Leu Ile
    1880                 1885                 1890

Ala Phe  Ala Ser Arg Gly Asn  His Val Ala Pro Thr  His Tyr Val
    1895                 1900                 1905

Thr Glu  Ser Asp Ala Ser Gln  Arg Val Thr Gln Leu  Leu Gly Ser
    1910                 1915                 1920

Leu Thr  Ile Thr Ser Leu Leu  Arg Arg Leu His Asn  Trp Ile Thr
    1925                 1930                 1935

Glu Asp  Cys Pro Ile Pro Cys  Ser Gly Ser Trp Leu  Arg Asp Val
    1940                 1945                 1950

Trp Asp  Trp Val Cys Thr Ile  Leu Thr Asp Phe Lys  Asn Trp Leu
    1955                 1960                 1965

Thr Ser  Lys Leu Phe Pro Lys  Leu Pro Gly Leu Pro  Phe Ile Ser
    1970                 1975                 1980

Cys Gln  Lys Gly Tyr Lys Gly  Val Trp Ala Gly Thr  Gly Ile Met
    1985                 1990                 1995

Thr Thr  Arg Cys Pro Cys Gly  Ala Asn Ile Ser Gly  Asn Val Arg
    2000                 2005                 2010

Leu Gly  Ser Met Arg Ile Thr  Gly Pro Lys Thr Cys  Met Asn Thr
    2015                 2020                 2025

Trp Gln  Gly Thr Phe Pro Ile  Asn Cys Tyr Thr Glu  Gly Gln Cys
    2030                 2035                 2040

Ala Pro  Lys Pro Pro Thr Asn  Tyr Lys Thr Ala Ile  Trp Arg Val
    2045                 2050                 2055

Ala Ala  Ser Glu Tyr Ala Glu  Val Thr Gln His Gly  Ser Tyr Ser
    2060                 2065                 2070

Tyr Val  Thr Gly Leu Thr Thr  Asp Asn Leu Lys Ile  Pro Cys Gln
    2075                 2080                 2085

Leu Pro  Ser Pro Glu Phe Phe  Ser Trp Val Asp Gly  Val Gln Ile
    2090                 2095                 2100

His Arg  Phe Ala Pro Thr Pro  Lys Pro Phe Phe Arg  Asp Glu Val
    2105                 2110                 2115

Ser Phe  Cys Val Gly Leu Asn  Ser Tyr Ala Val Gly  Ser Gln Leu
    2120                 2125                 2130

Pro Cys  Glu Pro Glu Pro Asp  Ala Asp Val Leu Arg  Ser Met Leu
    2135                 2140                 2145

Thr Asp  Pro Pro His Ile Thr  Ala Glu Thr Ala Ala  Arg Arg Leu
    2150                 2155                 2160

Ala Arg  Gly Ser Pro Pro Ser  Glu Ala Ser Ser Ser  Val Ser Gln
    2165                 2170                 2175

Leu Ser  Ala Pro Ser Leu Arg  Ala Thr Cys Thr Thr  His Ser Asn
    2180                 2185                 2190

Thr Tyr  Asp Val Asp Met Val  Asp Ala Asn Leu Leu  Met Glu Gly
    2195                 2200                 2205

Gly Val  Ala Gln Thr Glu Pro  Glu Ser Arg Val Pro  Val Leu Asp
    2210                 2215                 2220

Phe Leu  Glu Pro Met Ala Glu  Glu Glu Ser Asp Leu  Glu Pro Ser
    2225                 2230                 2235

Ile Pro  Ser Glu Cys Met Leu  Pro Arg Ser Gly Phe  Pro Arg Ala
    2240                 2245                 2250

Leu Pro  Ala Trp Ala Arg Pro  Asp Tyr Asn Pro Pro  Leu Val Glu
    2255                 2260                 2265

Ser Trp  Arg Arg Pro Asp Tyr  Gln Pro Pro Thr Val  Ala Gly Cys
```

```
    2270                2275                2280

Ala Leu  Pro Pro Pro Lys Lys  Ala Pro Thr Pro Pro  Pro Arg Arg
    2285                2290                2295

Arg Arg  Thr Val Gly Leu Ser  Glu Ser Thr Ile Ser  Glu Ala Leu
    2300                2305                2310

Gln Gln  Leu Ala Ile Lys Thr  Phe Gly Gln Pro Pro  Ser Ser Gly
    2315                2320                2325

Asp Ala  Gly Ser Ser Thr Gly  Ala Gly Ala Ala Glu  Ser Gly Gly
    2330                2335                2340

Pro Thr  Ser Pro Gly Glu Pro  Ala Pro Ser Glu Thr  Gly Ser Ala
    2345                2350                2355

Ser Ser  Met Pro Pro Leu Glu  Gly Glu Pro Gly Asp  Pro Asp Leu
    2360                2365                2370

Glu Ser  Asp Gln Val Glu Leu  Gln Pro Pro Pro Gln  Gly Gly Gly
    2375                2380                2385

Val Ala  Pro Gly Ser Gly Ser  Gly Ser Trp Ser Thr  Cys Ser Glu
    2390                2395                2400

Glu Asp  Asp Thr Thr Val Cys  Cys Ser Met Ser Tyr  Ser Trp Thr
    2405                2410                2415

Gly Ala  Leu Ile Thr Pro Cys  Ser Pro Glu Glu Glu  Lys Leu Pro
    2420                2425                2430

Ile Asn  Pro Leu Ser Asn Ser  Leu Leu Arg Tyr His  Asn Lys Val
    2435                2440                2445

Tyr Cys  Thr Thr Ser Lys Ser  Ala Ser Gln Arg Ala  Lys Lys Val
    2450                2455                2460

Thr Phe  Asp Arg Thr Gln Val  Leu Asp Ala His Tyr  Asp Ser Val
    2465                2470                2475

Leu Lys  Asp Ile Lys Leu Ala  Ala Ser Lys Val Ser  Ala Arg Leu
    2480                2485                2490

Leu Thr  Leu Glu Glu Ala Cys  Gln Leu Thr Pro Pro  His Ser Ala
    2495                2500                2505

Arg Ser  Lys Tyr Gly Phe Gly  Ala Lys Glu Val Arg  Ser Leu Ser
    2510                2515                2520

Gly Arg  Ala Val Asn His Ile  Lys Ser Val Trp Lys  Asp Leu Leu
    2525                2530                2535

Glu Asp  Pro Gln Thr Pro Ile  Pro Thr Thr Ile Met  Ala Lys Asn
    2540                2545                2550

Glu Val  Phe Cys Val Asp Pro  Ala Lys Gly Gly Lys  Lys Pro Ala
    2555                2560                2565

Arg Leu  Ile Val Tyr Pro Asp  Leu Gly Val Arg Val  Cys Glu Lys
    2570                2575                2580

Met Ala  Leu Tyr Asp Ile Thr  Gln Lys Leu Pro Gln  Ala Val Met
    2585                2590                2595

Gly Ala  Ser Tyr Gly Phe Gln  Tyr Ser Pro Ala Gln  Arg Val Glu
    2600                2605                2610

Tyr Leu  Leu Lys Ala Trp Ala  Glu Lys Lys Asp Pro  Met Gly Phe
    2615                2620                2625

Ser Tyr  Asp Thr Arg Cys Phe  Asp Ser Thr Val Thr  Glu Arg Asp
    2630                2635                2640

Ile Arg  Thr Glu Glu Ser Ile  Tyr Gln Ala Cys Ser  Leu Pro Glu
    2645                2650                2655

Glu Ala  Arg Thr Ala Ile His  Ser Leu Thr Glu Arg  Leu Tyr Val
    2660                2665                2670
```

Gly Gly Pro Met Phe Asn Ser Lys Gly Gln Thr Cys Gly Tyr Arg
2675 2680 2685

Arg Cys Arg Ala Ser Gly Val Leu Thr Thr Ser Met Gly Asn Thr
2690 2695 2700

Ile Thr Cys Tyr Val Lys Ala Leu Ala Ala Cys Lys Ala Ala Gly
2705 2710 2715

Ile Val Ala Pro Thr Met Leu Val Cys Gly Asp Asp Leu Val Val
2720 2725 2730

Ile Ser Glu Ser Gln Gly Thr Glu Glu Asp Glu Arg Asn Leu Arg
2735 2740 2745

Ala Phe Thr Glu Ala Met Thr Arg Tyr Ser Ala Pro Pro Gly Asp
2750 2755 2760

Pro Pro Arg Pro Glu Tyr Asp Leu Glu Leu Ile Thr Ser Cys Ser
2765 2770 2775

Ser Asn Val Ser Val Ala Leu Gly Pro Arg Gly Arg Arg Arg Tyr
2780 2785 2790

Tyr Leu Thr Arg Asp Pro Thr Thr Pro Leu Ala Arg Ala Ala Trp
2795 2800 2805

Glu Thr Val Arg His Ser Pro Ile Asn Ser Trp Leu Gly Asn Ile
2810 2815 2820

Ile Gln Tyr Ala Pro Thr Ile Trp Val Arg Met Val Leu Met Thr
2825 2830 2835

His Phe Phe Ser Ile Leu Met Val Gln Asp Thr Leu Asp Gln Asn
2840 2845 2850

Leu Asn Phe Glu Met Tyr Gly Ser Val Tyr Ser Val Asn Pro Leu
2855 2860 2865

Asp Leu Pro Ala Ile Ile Glu Arg Leu His Gly Leu Asp Ala Phe
2870 2875 2880

Ser Met His Thr Tyr Ser His His Glu Leu Thr Arg Val Ala Ser
2885 2890 2895

Ala Leu Arg Lys Leu Gly Ala Pro Pro Leu Arg Val Trp Lys Ser
2900 2905 2910

Arg Ala Arg Ala Val Arg Ala Ser Leu Ile Ser Arg Gly Gly Lys
2915 2920 2925

Ala Ala Val Cys Gly Arg Tyr Leu Phe Asn Trp Ala Val Lys Thr
2930 2935 2940

Lys Leu Lys Leu Thr Pro Leu Pro Glu Ala Arg Leu Leu Asp Leu
2945 2950 2955

Ser Ser Trp Phe Thr Val Gly Ala Gly Gly Gly Asp Ile Phe His
2960 2965 2970

Ser Val Ser Arg Ala Arg Pro Arg Ser Leu Leu Phe Gly Leu Leu
2975 2980 2985

Leu Leu Phe Val Gly Val Gly Leu Phe Leu Leu Pro Ala Arg
2990 2995 3000

<210> SEQ ID NO 23
<211> LENGTH: 3006
<212> TYPE: PRT
<213> ORGANISM: Hepatitis C virus

<400> SEQUENCE: 23

Met Ser Thr Asn Pro Lys Pro Gln Arg Lys Thr Lys Arg Asn Thr Asn
1 5 10 15

Arg Arg Pro Gln Asp Val Lys Phe Pro Gly Gly Gly Gln Ile Val Gly

-continued

```
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Arg Val Ile Asp Thr Ile Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Val Thr Val Pro Val Ser Ala Val
            180                 185                 190

Glu Val Arg Asn Ile Ser Ser Ser Tyr Tyr Ala Thr Asn Asp Cys Ser
        195                 200                 205

Asn Asn Ser Ile Thr Trp Gln Leu Thr Asp Ala Val Leu His Leu Pro
    210                 215                 220

Gly Cys Val Pro Cys Glu Asn Asp Asn Gly Thr Leu His Cys Trp Ile
225                 230                 235                 240

Gln Val Thr Pro Asn Val Ala Val Lys His Arg Gly Ala Leu Thr Arg
                245                 250                 255

Ser Leu Arg Thr His Val Asp Met Ile Val Met Ala Ala Thr Ala Cys
            260                 265                 270

Ser Ala Leu Tyr Val Gly Asp Val Cys Gly Ala Val Met Ile Leu Ser
        275                 280                 285

Gln Ala Phe Met Val Ser Pro Gln Arg His Asn Phe Thr Gln Glu Cys
    290                 295                 300

Asn Cys Ser Ile Tyr Gln Gly His Ile Thr Gly His Arg Met Ala Trp
305                 310                 315                 320

Asp Met Met Leu Asn Trp Ser Pro Thr Leu Ala Met Ile Leu Ala Tyr
                325                 330                 335

Ala Ala Arg Val Pro Glu Met Val Leu Glu Ile Ile Phe Gly Gly His
            340                 345                 350

Trp Gly Val Val Phe Gly Leu Ala Tyr Phe Ser Met Gln Gly Ala Trp
        355                 360                 365

Ala Lys Val Ile Ala Ile Leu Leu Leu Val Ala Gly Val Asp Ala Leu
    370                 375                 380

Tyr Leu Ile Asn Thr Asn Gly Ser Trp His Ile Asn Arg Thr Ala Leu
385                 390                 395                 400

Asn Cys Asn Asp Ser Leu Gln Thr Gly Phe Met Ala Ser Leu Phe Tyr
                405                 410                 415

Thr His Arg Phe Asn Ser Ser Gly Cys Pro Glu Arg Leu Ser Ser Cys
            420                 425                 430

Arg Gly Leu Asp Asp Phe Arg Ile Gly Trp Gly Thr Leu Glu Tyr Glu
        435                 440                 445
```

-continued

```
Thr His Val Thr Asn Asp Glu Asp Met Arg Pro Tyr Cys Trp His Tyr
    450                 455                 460

Pro Pro Arg Pro Cys Gly Ile Val Pro Ala Arg Thr Val Cys Gly Pro
465                 470                 475                 480

Val Tyr Cys Phe Thr Pro Ser Pro Val Val Val Gly Thr Thr Asp Lys
                485                 490                 495

Gln Gly Val Pro Thr Tyr Thr Trp Gly Glu Asn Glu Thr Asp Val Phe
            500                 505                 510

Leu Leu Asn Ser Thr Arg Pro Pro Arg Gly Ala Trp Phe Gly Cys Thr
        515                 520                 525

Trp Met Asn Gly Thr Gly Phe Thr Lys Thr Cys Gly Ala Pro Pro Cys
    530                 535                 540

Arg Ile Arg Lys Asp Tyr Asn Ser Thr Ile Asp Leu Leu Cys Pro Thr
545                 550                 555                 560

Asp Cys Phe Arg Lys His Pro Asp Ala Thr Tyr Leu Lys Cys Gly Ala
                565                 570                 575

Gly Pro Trp Leu Thr Pro Arg Cys Leu Val Asp Tyr Pro Tyr Arg Leu
            580                 585                 590

Trp His Tyr Pro Cys Thr Val Asn Phe Thr Ile Phe Lys Ala Arg Met
        595                 600                 605

Tyr Val Gly Gly Val Glu His Arg Phe Ser Ala Ala Cys Asn Phe Thr
    610                 615                 620

Arg Gly Asp Arg Cys Arg Leu Glu Asp Arg Asp Arg Gly Gln Gln Ser
625                 630                 635                 640

Pro Leu Leu His Ser Thr Thr Glu Trp Ala Val Leu Pro Cys Ser Phe
                645                 650                 655

Ser Asp Leu Pro Ala Leu Ser Thr Gly Leu Leu His Leu His Gln Asn
            660                 665                 670

Ile Val Asp Val Gln Tyr Leu Tyr Gly Leu Ser Pro Ala Leu Thr Arg
        675                 680                 685

Tyr Ile Val Lys Trp Glu Trp Val Ile Leu Leu Phe Leu Leu Leu Ala
    690                 695                 700

Asp Ala Arg Ile Cys Ala Cys Leu Trp Met Leu Ile Ile Leu Gly Gln
705                 710                 715                 720

Ala Glu Ala Ala Leu Glu Lys Leu Ile Ile Leu His Ser Ala Ser Ala
                725                 730                 735

Ala Ser Ala Asn Gly Pro Leu Trp Phe Phe Ile Phe Phe Thr Ala Ala
            740                 745                 750

Trp Tyr Leu Lys Gly Arg Val Val Pro Val Ala Thr Tyr Ser Val Leu
        755                 760                 765

Gly Leu Trp Ser Phe Leu Leu Leu Val Leu Ala Leu Pro Gln Gln Ala
    770                 775                 780

Tyr Ala Leu Asp Ala Ala Glu Gln Gly Glu Leu Gly Leu Ala Ile Leu
785                 790                 795                 800

Val Ile Ile Ser Ile Phe Thr Leu Thr Pro Ala Tyr Lys Ile Leu Leu
                805                 810                 815

Ser Arg Ser Val Trp Trp Leu Ser Tyr Met Leu Val Leu Ala Glu Ala
            820                 825                 830

Gln Ile Gln Gln Trp Val Pro Pro Leu Glu Val Arg Gly Gly Arg Asp
        835                 840                 845

Gly Ile Ile Trp Val Ala Val Ile Leu His Pro Arg Leu Val Phe Glu
    850                 855                 860
```

-continued

```
Val Thr Lys Trp Leu Leu Ala Ile Leu Gly Pro Ala Tyr Leu Leu Lys
865                 870                 875                 880

Ala Ser Leu Leu Arg Ile Pro Tyr Phe Val Arg Ala His Ala Leu Leu
                885                 890                 895

Arg Val Cys Thr Leu Val Lys His Leu Ala Gly Ala Arg Tyr Ile Gln
            900                 905                 910

Met Leu Leu Ile Thr Ile Gly Arg Trp Thr Gly Thr Tyr Ile Tyr Asp
        915                 920                 925

His Leu Ser Pro Leu Ser Thr Trp Ala Ala Gln Gly Leu Arg Asp Leu
    930                 935                 940

Ala Ile Ala Val Glu Pro Val Val Phe Ser Pro Met Glu Lys Lys Val
945                 950                 955                 960

Ile Val Trp Gly Ala Glu Thr Val Ala Cys Gly Asp Ile Leu His Gly
                965                 970                 975

Leu Pro Val Ser Ala Arg Leu Gly Arg Glu Val Leu Leu Gly Pro Ala
            980                 985                 990

Asp Gly Tyr Thr Ser Lys Gly Trp  Lys Leu Leu Ala Pro  Ile Thr Ala
        995                 1000                 1005

Tyr Ala  Gln Gln Thr Arg Gly  Leu Leu Gly Ala Ile  Val Val Ser
    1010                 1015                 1020

Met Thr  Gly Arg Asp Arg Thr  Glu Gln Ala Gly Glu  Val Gln Ile
    1025                 1030                 1035

Leu Ser  Thr Val Ser Gln Ser  Phe Leu Gly Thr Thr  Ile Ser Gly
    1040                 1045                 1050

Val Leu  Trp Thr Val Tyr His  Gly Ala Gly Asn Lys  Thr Leu Ala
    1055                 1060                 1065

Gly Leu  Arg Gly Pro Val Thr  Gln Met Tyr Ser Ser  Ala Glu Gly
    1070                 1075                 1080

Asp Leu  Val Gly Trp Pro Ser  Pro Pro Gly Thr Lys  Ser Leu Glu
    1085                 1090                 1095

Pro Cys  Lys Cys Gly Ala Val  Asp Leu Tyr Leu Val  Thr Arg Asn
    1100                 1105                 1110

Ala Asp  Val Ile Pro Ala Arg  Arg Arg Gly Asp Lys  Arg Gly Ala
    1115                 1120                 1125

Leu Leu  Ser Pro Arg Pro Ile  Ser Thr Leu Lys Gly  Ser Ser Gly
    1130                 1135                 1140

Gly Pro  Val Leu Cys Pro Arg  Gly His Val Val Gly  Leu Phe Arg
    1145                 1150                 1155

Ala Ala  Val Cys Ser Arg Gly  Val Ala Lys Ser Ile  Asp Phe Ile
    1160                 1165                 1170

Pro Val  Glu Thr Leu Asp Val  Val Thr Arg Ser Pro  Thr Phe Ser
    1175                 1180                 1185

Asp Asn  Ser Thr Pro Pro Ala  Val Pro Gln Thr Tyr  Gln Val Gly
    1190                 1195                 1200

Tyr Leu  His Ala Pro Thr Gly  Ser Gly Lys Ser Thr  Lys Val Pro
    1205                 1210                 1215

Val Ala  Tyr Ala Ala Gln Gly  Tyr Lys Val Leu Val  Leu Asn Pro
    1220                 1225                 1230

Ser Val  Ala Ala Thr Leu Gly  Phe Gly Ala Tyr Leu  Ser Lys Ala
    1235                 1240                 1245

His Gly  Ile Asn Pro Asn Ile  Arg Thr Gly Val Arg  Thr Val Met
    1250                 1255                 1260

Thr Gly  Glu Ala Ile Thr Tyr  Ser Thr Tyr Gly Lys  Phe Leu Ala
```

```
    1265                1270                1275

Asp Gly  Gly Cys Ala Ser Gly  Ala Tyr Asp Ile Ile  Ile Cys Asp
    1280                1285                1290

Glu Cys  His Ala Val Asp Ala  Thr Ser Ile Leu Gly  Ile Gly Thr
    1295                1300                1305

Val Leu  Asp Gln Ala Glu Thr  Ala Gly Val Arg Leu  Thr Val Leu
    1310                1315                1320

Ala Thr  Ala Thr Pro Pro Gly  Ser Val Thr Thr Pro  His Pro Asp
    1325                1330                1335

Ile Glu  Glu Val Gly Leu Gly  Arg Glu Gly Glu Ile  Pro Phe Tyr
    1340                1345                1350

Gly Arg  Ala Ile Pro Leu Ser  Cys Ile Lys Gly Gly  Arg His Leu
    1355                1360                1365

Ile Phe  Cys His Ser Lys Lys  Lys Cys Asp Glu Leu  Ala Ala Ala
    1370                1375                1380

Leu Arg  Gly Met Gly Leu Asn  Ala Val Ala Tyr Tyr  Arg Gly Leu
    1385                1390                1395

Asp Val  Ser Ile Ile Pro Ala  Gln Gly Asp Val Val  Val Val Ala
    1400                1405                1410

Thr Asp  Ala Leu Met Thr Gly  Tyr Thr Gly Asp Phe  Asp Ser Val
    1415                1420                1425

Ile Asp  Cys Asn Val Ala Val  Thr Gln Ala Val Asp  Phe Ser Leu
    1430                1435                1440

Asp Pro  Thr Phe Thr Ile Thr  Thr Gln Thr Val Pro  Gln Asp Ala
    1445                1450                1455

Val Ser  Arg Ser Gln Arg Arg  Gly Arg Thr Gly Arg  Gly Arg Gln
    1460                1465                1470

Gly Thr  Tyr Arg Tyr Val Ser  Thr Gly Glu Arg Ala  Ser Gly Met
    1475                1480                1485

Phe Asp  Ser Val Val Leu Cys  Glu Cys Tyr Asp Ala  Gly Ala Ala
    1490                1495                1500

Trp Tyr  Asp Leu Thr Pro Ala  Glu Thr Thr Val Arg  Leu Arg Ala
    1505                1510                1515

Tyr Phe  Asn Thr Pro Gly Leu  Pro Val Cys Gln Asp  His Leu Glu
    1520                1525                1530

Phe Trp  Glu Ala Val Phe Thr  Gly Leu Thr His Ile  Asp Ala His
    1535                1540                1545

Phe Leu  Ser Gln Thr Lys Gln  Ala Gly Glu Asn Phe  Ala Tyr Leu
    1550                1555                1560

Val Ala  Tyr Gln Ala Thr Val  Cys Ala Arg Ala Lys  Ala Pro Pro
    1565                1570                1575

Pro Ser  Trp Asp Ala Met Trp  Lys Cys Leu Ala Arg  Leu Lys Pro
    1580                1585                1590

Thr Leu  Ala Gly Pro Thr Pro  Leu Leu Tyr Arg Leu  Gly Pro Ile
    1595                1600                1605

Thr Asn  Glu Val Thr Leu Thr  His Pro Gly Thr Lys  Tyr Ile Ala
    1610                1615                1620

Thr Cys  Met Gln Ala Asp Leu  Glu Val Met Thr Ser  Thr Trp Val
    1625                1630                1635

Leu Ala  Gly Gly Val Leu Ala  Ala Val Ala Ala Tyr  Cys Leu Ala
    1640                1645                1650

Thr Gly  Cys Val Ser Ile Ile  Gly Arg Leu His Val  Asn Gln Arg
    1655                1660                1665
```

Val Val Val Ala Pro Asp Lys Glu Val Leu Tyr Glu Ala Phe Asp
1670 1675 1680

Glu Met Glu Glu Cys Ala Ser Arg Ala Ala Leu Ile Glu Glu Gly
1685 1690 1695

Gln Arg Ile Ala Glu Met Leu Lys Ser Lys Ile Gln Gly Leu Leu
1700 1705 1710

Gln Gln Ala Ser Lys Gln Ala Gln Asp Ile Gln Pro Ala Met Gln
1715 1720 1725

Ala Ser Trp Pro Lys Val Glu Gln Phe Trp Ala Arg His Met Trp
1730 1735 1740

Asn Phe Ile Ser Gly Ile Gln Tyr Leu Ala Gly Leu Ser Thr Leu
1745 1750 1755

Pro Gly Asn Pro Ala Val Ala Ser Met Met Ala Phe Ser Ala Ala
1760 1765 1770

Leu Thr Ser Pro Leu Ser Thr Ser Thr Thr Ile Leu Leu Asn Ile
1775 1780 1785

Met Gly Gly Trp Leu Ala Ser Gln Ile Ala Pro Pro Ala Gly Ala
1790 1795 1800

Thr Gly Phe Val Val Ser Gly Leu Val Gly Ala Ala Val Gly Ser
1805 1810 1815

Ile Gly Leu Gly Lys Val Leu Val Asp Ile Leu Ala Gly Tyr Gly
1820 1825 1830

Ala Gly Ile Ser Gly Ala Leu Val Ala Phe Lys Ile Met Ser Gly
1835 1840 1845

Glu Lys Pro Ser Met Glu Asp Val Ile Asn Leu Leu Pro Gly Ile
1850 1855 1860

Leu Ser Pro Gly Ala Leu Val Val Gly Val Ile Cys Ala Ala Ile
1865 1870 1875

Leu Arg Arg His Val Gly Pro Gly Glu Gly Ala Val Gln Trp Met
1880 1885 1890

Asn Arg Leu Ile Ala Phe Ala Ser Arg Gly Asn His Val Ala Pro
1895 1900 1905

Thr His Tyr Val Thr Glu Ser Asp Ala Ser Gln Arg Val Thr Gln
1910 1915 1920

Leu Leu Gly Ser Leu Thr Ile Thr Ser Leu Leu Arg Arg Leu His
1925 1930 1935

Asn Trp Ile Thr Glu Asp Cys Pro Ile Pro Cys Ser Gly Ser Trp
1940 1945 1950

Leu Arg Asp Val Trp Asp Trp Val Cys Thr Ile Leu Thr Asp Phe
1955 1960 1965

Lys Asn Trp Leu Thr Ser Lys Leu Phe Pro Lys Leu Pro Gly Leu
1970 1975 1980

Pro Phe Ile Ser Cys Gln Lys Gly Tyr Lys Gly Val Trp Ala Gly
1985 1990 1995

Thr Gly Ile Met Thr Thr Arg Cys Pro Cys Gly Ala Asn Ile Ser
2000 2005 2010

Gly Asn Val Arg Leu Gly Ser Met Arg Ile Thr Gly Pro Lys Thr
2015 2020 2025

Cys Met Asn Thr Trp Gln Gly Thr Phe Pro Ile Asn Cys Tyr Thr
2030 2035 2040

Glu Gly Gln Cys Ala Pro Lys Pro Pro Thr Asn Tyr Lys Thr Ala
2045 2050 2055

```
Ile Trp  Arg Val Ala Ala Ser  Glu Tyr Ala Glu Val  Thr Gln His
    2060                 2065                 2070

Gly Ser  Tyr Ser Tyr Val Thr  Gly Leu Thr Thr Asp  Asn Leu Lys
    2075                 2080                 2085

Ile Pro  Cys Gln Leu Pro Ser  Pro Glu Phe Phe Ser  Trp Val Asp
    2090                 2095                 2100

Gly Val  Gln Ile His Arg Phe  Ala Pro Thr Pro Lys  Pro Phe Phe
    2105                 2110                 2115

Arg Asp  Glu Val Ser Phe Cys  Val Gly Leu Asn Ser  Tyr Ala Val
    2120                 2125                 2130

Gly Ser  Gln Leu Pro Cys Glu  Pro Glu Pro Asp Ala  Asp Val Leu
    2135                 2140                 2145

Arg Ser  Met Leu Thr Asp Pro  Pro His Ile Thr Ala  Glu Thr Ala
    2150                 2155                 2160

Ala Arg  Arg Leu Ala Arg Gly  Ser Pro Pro Ser Glu  Ala Ser Ser
    2165                 2170                 2175

Ser Val  Ser Gln Leu Ser Ala  Pro Ser Leu Arg Ala  Thr Cys Thr
    2180                 2185                 2190

Thr His  Ser Asn Thr Tyr Asp  Val Asp Met Val Asp  Ala Asn Leu
    2195                 2200                 2205

Leu Met  Glu Gly Gly Val Ala  Gln Thr Glu Pro Glu  Ser Arg Val
    2210                 2215                 2220

Pro Val  Leu Asp Phe Leu Glu  Pro Met Ala Glu Glu  Glu Ser Asp
    2225                 2230                 2235

Leu Glu  Pro Ser Ile Pro Ser  Glu Cys Met Leu Pro  Arg Ser Gly
    2240                 2245                 2250

Phe Pro  Arg Ala Leu Pro Ala  Trp Ala Arg Pro Asp  Tyr Asn Pro
    2255                 2260                 2265

Pro Leu  Val Glu Ser Trp Arg  Arg Pro Asp Tyr Gln  Pro Pro Thr
    2270                 2275                 2280

Val Ala  Gly Cys Ala Leu Pro  Pro Pro Lys Lys Ala  Pro Thr Pro
    2285                 2290                 2295

Pro Pro  Arg Arg Arg Arg Thr  Val Gly Leu Ser Glu  Ser Thr Ile
    2300                 2305                 2310

Ser Glu  Ala Leu Gln Gln Leu  Ala Ile Lys Thr Phe  Gly Gln Pro
    2315                 2320                 2325

Pro Ser  Ser Gly Asp Ala Gly  Ser Ser Thr Gly Ala  Gly Ala Ala
    2330                 2335                 2340

Glu Ser  Gly Gly Pro Thr Ser  Pro Gly Glu Pro Ala  Pro Ser Glu
    2345                 2350                 2355

Thr Gly  Ser Ala Ser Ser Met  Pro Pro Leu Glu Gly  Glu Pro Gly
    2360                 2365                 2370

Asp Pro  Asp Leu Glu Ser Asp  Gln Val Glu Leu Gln  Pro Pro Pro
    2375                 2380                 2385

Gln Gly  Gly Gly Val Ala Pro  Gly Ser Gly Ser Gly  Ser Trp Ser
    2390                 2395                 2400

Thr Cys  Ser Glu Glu Asp Asp  Thr Thr Val Cys Cys  Ser Met Ser
    2405                 2410                 2415

Tyr Ser  Trp Thr Gly Ala Leu  Ile Thr Pro Cys Ser  Pro Glu Glu
    2420                 2425                 2430

Glu Lys  Leu Pro Ile Asn Pro  Leu Ser Asn Ser Leu  Leu Arg Tyr
    2435                 2440                 2445

His Asn  Lys Val Tyr Cys Thr  Thr Ser Lys Ser Ala  Ser Gln Arg
```

```
    2450                 2455                 2460

Ala Lys  Lys Val Thr Phe Asp  Arg Thr Gln Val Leu  Asp Ala His
    2465                 2470                 2475

Tyr Asp  Ser Val Leu Lys Asp  Ile Lys Leu Ala Ala  Ser Lys Val
    2480                 2485                 2490

Ser Ala  Arg Leu Leu Thr Leu  Glu Glu Ala Cys Gln  Leu Thr Pro
    2495                 2500                 2505

Pro His  Ser Ala Arg Ser Lys  Tyr Gly Phe Gly Ala  Lys Glu Val
    2510                 2515                 2520

Arg Ser  Leu Ser Gly Arg Ala  Val Asn His Ile Lys  Ser Val Trp
    2525                 2530                 2535

Lys Asp  Leu Leu Glu Asp Pro  Gln Thr Pro Ile Pro  Thr Thr Ile
    2540                 2545                 2550

Met Ala  Lys Asn Glu Val Phe  Cys Val Asp Pro Ala  Lys Gly Gly
    2555                 2560                 2565

Lys Lys  Pro Ala Arg Leu Ile  Val Tyr Pro Asp Leu  Gly Val Arg
    2570                 2575                 2580

Val Cys  Glu Lys Met Ala Leu  Tyr Asp Ile Thr Gln  Lys Leu Pro
    2585                 2590                 2595

Gln Ala  Val Met Gly Ala Ser  Tyr Gly Phe Gln Tyr  Ser Pro Ala
    2600                 2605                 2610

Gln Arg  Val Glu Tyr Leu Leu  Lys Ala Trp Ala Glu  Lys Lys Asp
    2615                 2620                 2625

Pro Met  Gly Phe Ser Tyr Asp  Thr Arg Cys Phe Asp  Ser Thr Val
    2630                 2635                 2640

Thr Glu  Arg Asp Ile Arg Thr  Glu Glu Ser Ile Tyr  Gln Ala Cys
    2645                 2650                 2655

Ser Leu  Pro Glu Glu Ala Arg  Thr Ala Ile His Ser  Leu Thr Glu
    2660                 2665                 2670

Arg Leu  Tyr Val Gly Gly Pro  Met Phe Asn Ser Lys  Gly Gln Thr
    2675                 2680                 2685

Cys Gly  Tyr Arg Arg Cys Arg  Ala Ser Gly Val Leu  Thr Thr Ser
    2690                 2695                 2700

Met Gly  Asn Thr Ile Thr Cys  Tyr Val Lys Ala Leu  Ala Ala Cys
    2705                 2710                 2715

Lys Ala  Ala Gly Ile Val Ala  Pro Thr Met Leu Val  Cys Gly Asp
    2720                 2725                 2730

Asp Leu  Val Val Ile Ser Glu  Ser Gln Gly Thr Glu  Glu Asp Glu
    2735                 2740                 2745

Arg Asn  Leu Arg Ala Phe Thr  Glu Ala Met Thr Arg  Tyr Ser Ala
    2750                 2755                 2760

Pro Pro  Gly Asp Pro Pro Arg  Pro Glu Tyr Asp Leu  Glu Leu Ile
    2765                 2770                 2775

Thr Ser  Cys Ser Ser Asn Val  Ser Val Ala Leu Gly  Pro Arg Gly
    2780                 2785                 2790

Arg Arg  Arg Tyr Tyr Leu Thr  Arg Asp Pro Thr Thr  Pro Leu Ala
    2795                 2800                 2805

Arg Ala  Ala Trp Glu Thr Val  Arg His Ser Pro Ile  Asn Ser Trp
    2810                 2815                 2820

Leu Gly  Asn Ile Ile Gln Tyr  Ala Pro Thr Ile Trp  Val Arg Met
    2825                 2830                 2835

Val Leu  Met Thr His Phe Phe  Ser Ile Leu Met Val  Gln Asp Thr
    2840                 2845                 2850
```

Leu Asp Gln Asn Leu Asn Phe Glu Met Tyr Gly Ser Val Tyr Ser
2855 2860 2865

Val Asn Pro Leu Asp Leu Pro Ala Ile Ile Glu Arg Leu His Gly
2870 2875 2880

Leu Asp Ala Phe Ser Met His Thr Tyr Ser His His Glu Leu Thr
2885 2890 2895

Arg Val Ala Ser Ala Leu Arg Lys Leu Gly Ala Pro Pro Leu Arg
2900 2905 2910

Val Trp Lys Ser Arg Ala Arg Ala Val Arg Ala Ser Leu Ile Ser
2915 2920 2925

Arg Gly Gly Lys Ala Ala Val Cys Gly Arg Tyr Leu Phe Asn Trp
2930 2935 2940

Ala Val Lys Thr Lys Leu Lys Leu Thr Pro Leu Pro Glu Ala Arg
2945 2950 2955

Leu Leu Asp Leu Ser Ser Trp Phe Thr Val Gly Ala Gly Gly Gly
2960 2965 2970

Asp Ile Phe His Ser Val Ser Arg Ala Arg Pro Arg Ser Leu Leu
2975 2980 2985

Phe Gly Leu Leu Leu Leu Phe Val Gly Val Gly Leu Phe Leu Leu
2990 2995 3000

Pro Ala Arg
3005

<210> SEQ ID NO 24
<211> LENGTH: 3006
<212> TYPE: PRT
<213> ORGANISM: Hepatitis C virus

<400> SEQUENCE: 24

Met Ser Thr Asn Pro Lys Pro Gln Arg Lys Thr Lys Arg Asn Thr Asn
1 5 10 15

Arg Arg Pro Gln Asp Val Lys Phe Pro Gly Gly Gly Gln Ile Val Gly
20 25 30

Gly Val Tyr Leu Leu Pro Arg Arg Gly Pro Arg Leu Gly Val Arg Ala
35 40 45

Thr Arg Lys Thr Ser Glu Arg Ser Gln Pro Arg Gly Arg Arg Gln Pro
50 55 60

Ile Pro Lys Asp Arg Arg Ser Thr Gly Lys Ser Trp Gly Lys Pro Gly
65 70 75 80

Tyr Pro Trp Pro Leu Tyr Gly Asn Glu Gly Cys Gly Trp Ala Gly Trp
85 90 95

Leu Leu Ser Pro Arg Gly Ser Arg Pro Thr Trp Gly Pro Thr Asp Pro
100 105 110

Arg His Arg Ser Arg Asn Leu Gly Arg Val Ile Asp Thr Ile Thr Cys
115 120 125

Gly Phe Ala Asp Leu Met Gly Tyr Ile Pro Val Val Gly Ala Pro Val
130 135 140

Gly Gly Val Ala Arg Ala Leu Ala His Gly Val Arg Val Leu Glu Asp
145 150 155 160

Gly Ile Asn Tyr Ala Thr Gly Asn Leu Pro Gly Cys Ser Phe Ser Ile
165 170 175

Phe Leu Leu Ala Leu Leu Ser Cys Val Thr Val Pro Val Ser Ala Val
180 185 190

Glu Val Arg Asn Ile Ser Ser Ser Tyr Tyr Ala Thr Asn Asp Cys Ser

```
        195                 200                 205

Asn Asn Ser Ile Thr Trp Gln Leu Thr Asp Ala Val Leu His Leu Pro
    210                 215                 220

Gly Cys Val Pro Cys Glu Asn Asp Asn Gly Thr Leu His Cys Trp Ile
225                 230                 235                 240

Gln Val Thr Pro Asn Val Ala Val Lys His Arg Gly Ala Leu Thr Arg
                245                 250                 255

Ser Leu Arg Thr His Val Asp Met Ile Val Met Ala Ala Thr Ala Cys
            260                 265                 270

Ser Ala Leu Tyr Val Gly Asp Val Cys Gly Ala Val Met Ile Leu Ser
        275                 280                 285

Gln Ala Phe Met Val Ser Pro Gln Arg His Asn Phe Thr Gln Glu Cys
    290                 295                 300

Asn Cys Ser Ile Tyr Gln Gly His Ile Thr Gly His Arg Met Ala Trp
305                 310                 315                 320

Asp Met Met Leu Asn Trp Ser Pro Thr Leu Ala Met Ile Leu Ala Tyr
                325                 330                 335

Ala Ala Arg Val Pro Glu Met Val Leu Glu Ile Ile Phe Gly Gly His
            340                 345                 350

Trp Gly Val Val Phe Gly Leu Ala Tyr Phe Ser Met Gln Gly Ala Trp
        355                 360                 365

Ala Lys Val Ile Ala Ile Leu Leu Leu Val Ala Gly Val Asp Ala Leu
    370                 375                 380

Asn Leu Ile Asn Thr Asn Gly Ser Trp His Ile Asn Arg Thr Ala Leu
385                 390                 395                 400

Asn Cys Asn Asp Ser Leu Gln Thr Gly Phe Met Ala Ser Leu Phe Tyr
                405                 410                 415

Thr His Arg Phe Asn Ser Ser Gly Cys Pro Glu Arg Leu Ser Ser Cys
            420                 425                 430

Arg Gly Leu Asp Asp Phe Arg Ile Gly Trp Gly Thr Leu Glu Tyr Glu
        435                 440                 445

Thr His Val Thr Asn Asp Glu Asp Met Arg Pro Tyr Cys Trp His Tyr
    450                 455                 460

Pro Pro Arg Pro Cys Gly Ile Val Pro Ala Arg Thr Val Cys Gly Pro
465                 470                 475                 480

Val Tyr Cys Phe Thr Pro Ser Pro Val Val Val Gly Thr Thr Asp Lys
                485                 490                 495

Gln Gly Val Pro Thr Tyr Thr Trp Gly Glu Asn Glu Thr Asp Val Phe
            500                 505                 510

Leu Leu Asn Ser Thr Arg Pro Pro Arg Gly Ala Trp Phe Gly Cys Thr
        515                 520                 525

Trp Met Asn Gly Thr Gly Phe Thr Lys Thr Cys Gly Ala Pro Pro Cys
    530                 535                 540

Arg Ile Arg Lys Asp Tyr Asn Ser Thr Ile Asp Leu Leu Cys Pro Thr
545                 550                 555                 560

Asp Cys Phe Arg Lys His Pro Asp Ala Thr Tyr Leu Lys Cys Gly Ala
                565                 570                 575

Gly Pro Trp Leu Thr Pro Arg Cys Leu Val Asp Tyr Pro Tyr Arg Leu
            580                 585                 590

Trp His Tyr Pro Cys Thr Val Asn Phe Thr Ile Phe Lys Ala Arg Met
        595                 600                 605

Tyr Val Gly Gly Val Glu His Arg Phe Ser Ala Ala Cys Asn Phe Thr
    610                 615                 620
```

```
Arg Gly Asp Arg Cys Arg Leu Glu Asp Arg Asp Arg Gly Gln Gln Ser
625                 630                 635                 640

Pro Leu Leu His Ser Thr Thr Glu Trp Ala Val Leu Pro Cys Ser Phe
                645                 650                 655

Ser Asp Leu Pro Ala Leu Ser Thr Gly Leu Leu His Leu His Gln Asn
            660                 665                 670

Ile Val Asp Val Gln Tyr Leu Tyr Gly Leu Ser Pro Ala Leu Thr Arg
        675                 680                 685

Tyr Ile Val Lys Trp Glu Trp Val Ile Leu Leu Phe Leu Leu Leu Ala
    690                 695                 700

Asp Ala Arg Ile Cys Ala Cys Leu Trp Met Leu Ile Ile Leu Gly Gln
705                 710                 715                 720

Ala Glu Ala Ala Leu Glu Lys Leu Ile Ile Leu His Ser Ala Ser Ala
                725                 730                 735

Ala Ser Ala Asn Gly Pro Leu Trp Phe Phe Ile Phe Phe Thr Ala Ala
            740                 745                 750

Trp Tyr Leu Lys Gly Arg Val Val Pro Val Ala Thr Tyr Ser Val Leu
        755                 760                 765

Gly Leu Trp Ser Phe Leu Leu Leu Val Leu Ala Leu Pro Gln Gln Ala
    770                 775                 780

Tyr Ala Leu Asp Ala Ala Glu Gln Gly Glu Leu Gly Leu Ala Ile Leu
785                 790                 795                 800

Val Ile Ile Ser Ile Phe Thr Leu Thr Pro Ala Tyr Lys Ile Leu Leu
                805                 810                 815

Ser Arg Ser Val Trp Trp Leu Ser Tyr Met Leu Val Leu Ala Glu Ala
            820                 825                 830

Gln Ile Gln Gln Trp Val Pro Pro Leu Glu Val Arg Gly Gly Arg Asp
        835                 840                 845

Gly Ile Ile Trp Val Ala Val Ile Leu His Pro Arg Leu Val Phe Glu
    850                 855                 860

Val Thr Lys Trp Leu Leu Ala Ile Leu Gly Pro Ala Tyr Leu Leu Lys
865                 870                 875                 880

Ala Ser Leu Leu Arg Ile Pro Tyr Phe Val Arg Ala His Ala Leu Leu
                885                 890                 895

Arg Val Cys Thr Leu Val Lys His Leu Ala Gly Ala Arg Tyr Ile Gln
            900                 905                 910

Met Leu Leu Ile Thr Ile Gly Arg Trp Thr Gly Thr Tyr Ile Tyr Asp
        915                 920                 925

His Leu Ser Pro Leu Ser Thr Trp Ala Ala Gln Gly Leu Arg Asp Leu
    930                 935                 940

Ala Ile Ala Val Glu Pro Val Val Phe Ser Pro Met Glu Lys Lys Val
945                 950                 955                 960

Ile Val Trp Gly Ala Glu Thr Val Ala Cys Gly Asp Ile Leu His Gly
                965                 970                 975

Leu Pro Val Ser Ala Arg Leu Gly Arg Glu Val Leu Leu Gly Pro Ala
            980                 985                 990

Asp Gly Tyr Thr Ser Lys Gly Trp  Lys Leu Leu Ala Pro  Ile Thr Ala
        995                 1000                1005

Tyr Ala  Gln Gln Thr Arg Gly  Leu Leu Gly Ala Ile  Val Val Ser
    1010                 1015                 1020

Met Thr  Gly Arg Asp Arg Thr  Glu Gln Ala Gly Glu  Val Gln Ile
    1025                 1030                 1035
```

```
Leu Ser  Thr Val Ser Gln Ser  Phe Leu Gly Thr Thr  Ile Ser Gly
    1040                 1045                 1050

Val Leu  Trp Thr Val Tyr His  Gly Ala Gly Asn Lys  Thr Leu Ala
    1055                 1060                 1065

Gly Leu  Arg Gly Pro Val Thr  Gln Met Tyr Ser Ser  Ala Glu Gly
    1070                 1075                 1080

Asp Leu  Val Gly Trp Pro Ser  Pro Pro Gly Thr Lys  Ser Leu Glu
    1085                 1090                 1095

Pro Cys  Lys Cys Gly Ala Val  Asp Leu Tyr Leu Val  Thr Arg Asn
    1100                 1105                 1110

Ala Asp  Val Ile Pro Ala Arg  Arg Arg Gly Asp Lys  Arg Gly Ala
    1115                 1120                 1125

Leu Leu  Ser Pro Arg Pro Ile  Ser Thr Leu Lys Gly  Ser Ser Gly
    1130                 1135                 1140

Gly Pro  Val Leu Cys Pro Arg  Gly His Val Val Gly  Leu Phe Arg
    1145                 1150                 1155

Ala Ala  Val Cys Ser Arg Gly  Val Ala Lys Ser Ile  Asp Phe Ile
    1160                 1165                 1170

Pro Val  Glu Thr Leu Asp Val  Val Thr Arg Ser Pro  Thr Phe Ser
    1175                 1180                 1185

Asp Asn  Ser Thr Pro Pro Ala  Val Pro Gln Thr Tyr  Gln Val Gly
    1190                 1195                 1200

Tyr Leu  His Ala Pro Thr Gly  Ser Gly Lys Ser Thr  Lys Val Pro
    1205                 1210                 1215

Val Ala  Tyr Ala Ala Gln Gly  Tyr Lys Val Leu Val  Leu Asn Pro
    1220                 1225                 1230

Ser Val  Ala Ala Thr Leu Gly  Phe Gly Ala Tyr Leu  Ser Lys Ala
    1235                 1240                 1245

His Gly  Ile Asn Pro Asn Ile  Arg Thr Gly Val Arg  Thr Val Met
    1250                 1255                 1260

Thr Gly  Glu Ala Ile Thr Tyr  Ser Thr Tyr Gly Lys  Phe Leu Ala
    1265                 1270                 1275

Asp Gly  Gly Cys Ala Ser Gly  Ala Tyr Asp Ile Ile  Ile Cys Asp
    1280                 1285                 1290

Glu Cys  His Ala Val Asp Ala  Thr Ser Ile Leu Gly  Ile Gly Thr
    1295                 1300                 1305

Val Leu  Asp Gln Ala Glu Thr  Ala Gly Val Arg Leu  Thr Val Leu
    1310                 1315                 1320

Ala Thr  Ala Thr Pro Pro Gly  Ser Val Thr Thr Pro  His Pro Asp
    1325                 1330                 1335

Ile Glu  Glu Val Gly Leu Gly  Arg Glu Gly Glu Ile  Pro Phe Tyr
    1340                 1345                 1350

Gly Arg  Ala Ile Pro Leu Ser  Cys Ile Lys Gly Gly  Arg His Leu
    1355                 1360                 1365

Ile Phe  Cys His Ser Lys Lys  Lys Cys Asp Glu Leu  Ala Ala Ala
    1370                 1375                 1380

Leu Arg  Gly Met Gly Leu Asn  Ala Val Ala Tyr Tyr  Arg Gly Leu
    1385                 1390                 1395

Asp Val  Ser Ile Ile Pro Ala  Gln Gly Asp Val Val  Val Val Ala
    1400                 1405                 1410

Thr Asp  Ala Leu Met Thr Gly  Tyr Thr Gly Asp Phe  Asp Ser Val
    1415                 1420                 1425

Ile Asp  Cys Asn Val Ala Val  Thr Gln Ala Val Asp  Phe Ser Leu
```

```
    1430                 1435                 1440

Asp Pro  Thr Phe Thr Ile Thr  Thr Gln Thr Val Pro  Gln Asp Ala
    1445                 1450                 1455

Val Ser  Arg Ser Gln Arg Arg  Gly Arg Thr Gly Arg  Gly Arg Gln
    1460                 1465                 1470

Gly Thr  Tyr Arg Tyr Val Ser  Thr Gly Glu Arg Ala  Ser Gly Met
    1475                 1480                 1485

Phe Asp  Ser Val Val Leu Cys  Glu Cys Tyr Asp Ala  Gly Ala Ala
    1490                 1495                 1500

Trp Tyr  Asp Leu Thr Pro Ala  Glu Thr Thr Val Arg  Leu Arg Ala
    1505                 1510                 1515

Tyr Phe  Asn Thr Pro Gly Leu  Pro Val Cys Gln Asp  His Leu Glu
    1520                 1525                 1530

Phe Trp  Glu Ala Val Phe Thr  Gly Leu Thr His Ile  Asp Ala His
    1535                 1540                 1545

Phe Leu  Ser Gln Thr Lys Gln  Ala Gly Glu Asn Phe  Ala Tyr Leu
    1550                 1555                 1560

Val Ala  Tyr Gln Ala Thr Val  Cys Ala Arg Ala Lys  Ala Pro Pro
    1565                 1570                 1575

Pro Ser  Trp Asp Ala Met Trp  Lys Cys Leu Ala Arg  Leu Lys Pro
    1580                 1585                 1590

Thr Leu  Ala Gly Pro Thr Pro  Leu Leu Tyr Arg Leu  Gly Pro Ile
    1595                 1600                 1605

Thr Asn  Glu Val Thr Leu Thr  His Pro Gly Thr Lys  Tyr Ile Ala
    1610                 1615                 1620

Thr Cys  Met Gln Ala Asp Leu  Glu Val Met Thr Ser  Thr Trp Val
    1625                 1630                 1635

Leu Ala  Gly Gly Val Leu Ala  Ala Val Ala Ala Tyr  Cys Leu Ala
    1640                 1645                 1650

Thr Gly  Cys Val Ser Ile Ile  Gly Arg Leu His Val  Asn Gln Arg
    1655                 1660                 1665

Val Val  Val Ala Pro Asp Lys  Glu Val Leu Tyr Glu  Ala Phe Asp
    1670                 1675                 1680

Glu Met  Glu Glu Cys Ala Ser  Arg Ala Ala Leu Ile  Glu Glu Gly
    1685                 1690                 1695

Gln Arg  Ile Ala Glu Met Leu  Lys Ser Lys Ile Gln  Gly Leu Leu
    1700                 1705                 1710

Gln Gln  Ala Ser Lys Gln Ala  Gln Asp Ile Gln Pro  Ala Met Gln
    1715                 1720                 1725

Ala Ser  Trp Pro Lys Val Glu  Gln Phe Trp Ala Arg  His Met Trp
    1730                 1735                 1740

Asn Phe  Ile Ser Gly Ile Gln  Tyr Leu Ala Gly Leu  Ser Thr Leu
    1745                 1750                 1755

Pro Gly  Asn Pro Ala Val Ala  Ser Met Met Ala Phe  Ser Ala Ala
    1760                 1765                 1770

Leu Thr  Ser Pro Leu Ser Thr  Ser Thr Thr Ile Leu  Leu Asn Ile
    1775                 1780                 1785

Met Gly  Gly Trp Leu Ala Ser  Gln Ile Ala Pro Pro  Ala Gly Ala
    1790                 1795                 1800

Thr Gly  Phe Val Val Ser Gly  Leu Val Gly Ala Ala  Val Gly Ser
    1805                 1810                 1815

Ile Gly  Leu Gly Lys Val Leu  Val Asp Ile Leu Ala  Gly Tyr Gly
    1820                 1825                 1830
```

```
Ala Gly  Ile Ser Gly Ala Leu  Val Ala Phe Lys Ile  Met Ser Gly
    1835                 1840                 1845

Glu Lys  Pro Ser Met Glu Asp  Val Ile Asn Leu Leu  Pro Gly Ile
    1850                 1855                 1860

Leu Ser  Pro Gly Ala Leu Val  Val Gly Val Ile Cys  Ala Ala Ile
    1865                 1870                 1875

Leu Arg  Arg His Val Gly Pro  Gly Glu Gly Ala Val  Gln Trp Met
    1880                 1885                 1890

Asn Arg  Leu Ile Ala Phe Ala  Ser Arg Gly Asn His  Val Ala Pro
    1895                 1900                 1905

Thr His  Tyr Val Thr Glu Ser  Asp Ala Ser Gln Arg  Val Thr Gln
    1910                 1915                 1920

Leu Leu  Gly Ser Leu Thr Ile  Thr Ser Leu Leu Arg  Arg Leu His
    1925                 1930                 1935

Asn Trp  Ile Thr Glu Asp Cys  Pro Ile Pro Cys Ser  Gly Ser Trp
    1940                 1945                 1950

Leu Arg  Asp Val Trp Asp Trp  Val Cys Thr Ile Leu  Thr Asp Phe
    1955                 1960                 1965

Lys Asn  Trp Leu Thr Ser Lys  Leu Phe Pro Lys Leu  Pro Gly Leu
    1970                 1975                 1980

Pro Phe  Ile Ser Cys Gln Lys  Gly Tyr Lys Gly Val  Trp Ala Gly
    1985                 1990                 1995

Thr Gly  Ile Met Thr Thr Arg  Cys Pro Cys Gly Ala  Asn Ile Ser
    2000                 2005                 2010

Gly Asn  Val Arg Leu Gly Ser  Met Arg Ile Thr Gly  Pro Lys Thr
    2015                 2020                 2025

Cys Met  Asn Thr Trp Gln Gly  Thr Phe Pro Ile Asn  Cys Tyr Thr
    2030                 2035                 2040

Glu Gly  Gln Cys Ala Pro Lys  Pro Pro Thr Asn Tyr  Lys Thr Ala
    2045                 2050                 2055

Ile Trp  Arg Val Ala Ala Ser  Glu Tyr Ala Glu Val  Thr Gln His
    2060                 2065                 2070

Gly Ser  Tyr Ser Tyr Val Thr  Gly Leu Thr Thr Asp  Asn Leu Lys
    2075                 2080                 2085

Ile Pro  Cys Gln Leu Pro Ser  Pro Glu Phe Phe Ser  Trp Val Asp
    2090                 2095                 2100

Gly Val  Gln Ile His Arg Phe  Ala Pro Thr Pro Lys  Pro Phe Phe
    2105                 2110                 2115

Arg Asp  Glu Val Ser Phe Cys  Val Gly Leu Asn Ser  Tyr Ala Val
    2120                 2125                 2130

Gly Ser  Gln Leu Pro Cys Glu  Pro Glu Pro Asp Ala  Asp Val Leu
    2135                 2140                 2145

Arg Ser  Met Leu Thr Asp Pro  Pro His Ile Thr Ala  Glu Thr Ala
    2150                 2155                 2160

Ala Arg  Arg Leu Ala Arg Gly  Ser Pro Pro Ser Glu  Ala Ser Ser
    2165                 2170                 2175

Ser Val  Ser Gln Leu Ser Ala  Pro Ser Leu Arg Ala  Thr Cys Thr
    2180                 2185                 2190

Thr His  Ser Asn Thr Tyr Asp  Val Asp Met Val Asp  Ala Asn Leu
    2195                 2200                 2205

Leu Met  Glu Gly Gly Val Ala  Gln Thr Glu Pro Glu  Ser Arg Val
    2210                 2215                 2220
```

```
Pro Val  Leu Asp Phe Leu Glu  Pro Met Ala Glu Glu  Glu Ser Asp
    2225                 2230                 2235

Leu Glu  Pro Ser Ile Pro Ser  Glu Cys Met Leu Pro  Arg Ser Gly
    2240                 2245                 2250

Phe Pro  Arg Ala Leu Pro Ala  Trp Ala Arg Pro Asp  Tyr Asn Pro
    2255                 2260                 2265

Pro Leu  Val Glu Ser Trp Arg  Arg Pro Asp Tyr Gln  Pro Pro Thr
    2270                 2275                 2280

Val Ala  Gly Cys Ala Leu Pro  Pro Pro Lys Lys Ala  Pro Thr Pro
    2285                 2290                 2295

Pro Pro  Arg Arg Arg Arg Thr  Val Gly Leu Ser Glu  Ser Thr Ile
    2300                 2305                 2310

Ser Glu  Ala Leu Gln Gln Leu  Ala Ile Lys Thr Phe  Gly Gln Pro
    2315                 2320                 2325

Pro Ser  Ser Gly Asp Ala Gly  Ser Ser Thr Gly Ala  Gly Ala Ala
    2330                 2335                 2340

Glu Ser  Gly Gly Pro Thr Ser  Pro Gly Glu Pro Ala  Pro Ser Glu
    2345                 2350                 2355

Thr Gly  Ser Ala Ser Ser Met  Pro Pro Leu Glu Gly  Glu Pro Gly
    2360                 2365                 2370

Asp Pro  Asp Leu Glu Ser Asp  Gln Val Glu Leu Gln  Pro Pro Pro
    2375                 2380                 2385

Gln Gly  Gly Gly Val Ala Pro  Gly Ser Gly Ser Gly  Ser Trp Ser
    2390                 2395                 2400

Thr Cys  Ser Glu Glu Asp Asp  Thr Thr Val Cys Cys  Ser Met Ser
    2405                 2410                 2415

Tyr Ser  Trp Thr Gly Ala Leu  Ile Thr Pro Cys Ser  Pro Glu Glu
    2420                 2425                 2430

Glu Lys  Leu Pro Ile Asn Pro  Leu Ser Asn Ser Leu  Leu Arg Tyr
    2435                 2440                 2445

His Asn  Lys Val Tyr Cys Thr  Thr Ser Lys Ser Ala  Ser Gln Arg
    2450                 2455                 2460

Ala Lys  Lys Val Thr Phe Asp  Arg Thr Gln Val Leu  Asp Ala His
    2465                 2470                 2475

Tyr Asp  Ser Val Leu Lys Asp  Ile Lys Leu Ala Ala  Ser Lys Val
    2480                 2485                 2490

Ser Ala  Arg Leu Leu Thr Leu  Glu Glu Ala Cys Gln  Leu Thr Pro
    2495                 2500                 2505

Pro His  Ser Ala Arg Ser Lys  Tyr Gly Phe Gly Ala  Lys Glu Val
    2510                 2515                 2520

Arg Ser  Leu Ser Gly Arg Ala  Val Asn His Ile Lys  Ser Val Trp
    2525                 2530                 2535

Lys Asp  Leu Leu Glu Asp Pro  Gln Thr Pro Ile Pro  Thr Thr Ile
    2540                 2545                 2550

Met Ala  Lys Asn Glu Val Phe  Cys Val Asp Pro Ala  Lys Gly Gly
    2555                 2560                 2565

Lys Lys  Pro Ala Arg Leu Ile  Val Tyr Pro Asp Leu  Gly Val Arg
    2570                 2575                 2580

Val Cys  Glu Lys Met Ala Leu  Tyr Asp Ile Thr Gln  Lys Leu Pro
    2585                 2590                 2595

Gln Ala  Val Met Gly Ala Ser  Tyr Gly Phe Gln Tyr  Ser Pro Ala
    2600                 2605                 2610

Gln Arg  Val Glu Tyr Leu Leu  Lys Ala Trp Ala Glu  Lys Lys Asp
```

-continued

```
    2615                2620                2625

Pro Met  Gly Phe Ser Tyr Asp  Thr Arg Cys Phe Asp  Ser Thr Val
    2630                2635                2640

Thr Glu  Arg Asp Ile Arg Thr  Glu Glu Ser Ile Tyr  Gln Ala Cys
    2645                2650                2655

Ser Leu  Pro Glu Glu Ala Arg  Thr Ala Ile His Ser  Leu Thr Glu
    2660                2665                2670

Arg Leu  Tyr Val Gly Gly Pro  Met Phe Asn Ser Lys  Gly Gln Thr
    2675                2680                2685

Cys Gly  Tyr Arg Arg Cys Arg  Ala Ser Gly Val Leu  Thr Thr Ser
    2690                2695                2700

Met Gly  Asn Thr Ile Thr Cys  Tyr Val Lys Ala Leu  Ala Ala Cys
    2705                2710                2715

Lys Ala  Ala Gly Ile Val Ala  Pro Thr Met Leu Val  Cys Gly Asp
    2720                2725                2730

Asp Leu  Val Val Ile Ser Glu  Ser Gln Gly Thr Glu  Glu Asp Glu
    2735                2740                2745

Arg Asn  Leu Arg Ala Phe Thr  Glu Ala Met Thr Arg  Tyr Ser Ala
    2750                2755                2760

Pro Pro  Gly Asp Pro Pro Arg  Pro Glu Tyr Asp Leu  Glu Leu Ile
    2765                2770                2775

Thr Ser  Cys Ser Ser Asn Val  Ser Val Ala Leu Gly  Pro Arg Gly
    2780                2785                2790

Arg Arg  Arg Tyr Tyr Leu Thr  Arg Asp Pro Thr Thr  Pro Leu Ala
    2795                2800                2805

Arg Ala  Ala Trp Glu Thr Val  Arg His Ser Pro Ile  Asn Ser Trp
    2810                2815                2820

Leu Gly  Asn Ile Ile Gln Tyr  Ala Pro Thr Ile Trp  Val Arg Met
    2825                2830                2835

Val Leu  Met Thr His Phe Phe  Ser Ile Leu Met Val  Gln Asp Thr
    2840                2845                2850

Leu Asp  Gln Asn Leu Asn Phe  Glu Met Tyr Gly Ser  Val Tyr Ser
    2855                2860                2865

Val Asn  Pro Leu Asp Leu Pro  Ala Ile Ile Glu Arg  Leu His Gly
    2870                2875                2880

Leu Asp  Ala Phe Ser Met His  Thr Tyr Ser His His  Glu Leu Thr
    2885                2890                2895

Arg Val  Ala Ser Ala Leu Arg  Lys Leu Gly Ala Pro  Pro Leu Arg
    2900                2905                2910

Val Trp  Lys Ser Arg Ala Arg  Ala Val Arg Ala Ser  Leu Ile Ser
    2915                2920                2925

Arg Gly  Gly Lys Ala Ala Val  Cys Gly Arg Tyr Leu  Phe Asn Trp
    2930                2935                2940

Ala Val  Lys Thr Lys Leu Lys  Leu Thr Pro Leu Pro  Glu Ala Arg
    2945                2950                2955

Leu Leu  Asp Leu Ser Ser Trp  Phe Thr Val Gly Ala  Gly Gly Gly
    2960                2965                2970
```

-continued

```
Asp Ile  Phe His Ser Val Ser  Arg Ala Arg Pro Arg  Ser Leu Leu
    2975                 2980                 2985

Phe Gly  Leu Leu Leu Leu Phe  Val Gly Val Gly Leu  Phe Leu Leu
    2990                 2995                 3000

Pro Ala  Arg
    3005
```